(12) United States Patent
Glinskii

(10) Patent No.: US 8,349,555 B2
(45) Date of Patent: Jan. 8, 2013

(54) METHODS AND COMPOSITIONS FOR PREDICTING DEATH FROM CANCER AND PROSTATE CANCER SURVIVAL USING GENE EXPRESSION SIGNATURES

(75) Inventor: Gennadi V. Glinskii, La Jolla, CA (US)

(73) Assignee: Gennadi V. Glinsky, La Jolla, CA (US)

( * ) Notice: Subject to any disclaimer, the term of this patent is extended or adjusted under 35 U.S.C. 154(b) by 887 days.

(21) Appl. No.: 11/908,775

(22) PCT Filed: Mar. 16, 2006

(86) PCT No.: PCT/US2006/009870
§ 371 (c)(1),
(2), (4) Date: Jun. 23, 2008

(87) PCT Pub. No.: WO2006/110264
PCT Pub. Date: Oct. 19, 2006

(65) Prior Publication Data
US 2009/0233279 A1  Sep. 17, 2009

Related U.S. Application Data

(60) Provisional application No. 60/663,014, filed on Mar. 16, 2005.

(51) Int. Cl.
*C12Q 1/68* (2006.01)
(52) U.S. Cl. .......................................... 435/6; 536/23.1
(58) Field of Classification Search ........................ None
See application file for complete search history.

(56) References Cited

U.S. PATENT DOCUMENTS

| | | | |
|---|---|---|---|
| 6,203,987 B1 | 3/2001 | Friend et al. | |
| 6,218,122 B1 | 4/2001 | Friend et al. | |
| 7,514,209 B2 | 4/2009 | Dai et al. | |
| 2005/0208500 A1 | 9/2005 | Erlander et al. | |
| 2006/0074565 A1 | 4/2006 | Miller et al. | |
| 2006/0160169 A1 | 7/2006 | Marcotte et al. | |
| 2009/0098538 A1 | 4/2009 | Glinsky | |
| 2009/0170715 A1 | 7/2009 | Glinsky | |

FOREIGN PATENT DOCUMENTS

| | | |
|---|---|---|
| WO | WO-0153834 A2 | 7/2001 |
| WO | WO-03060164 A1 | 7/2003 |

OTHER PUBLICATIONS

Glinsky et al. in "Microarray analysis identifies a death-from-cancer signature predicting therapy failure in patients with multiple types of cancer" (J. Clin. Invest. Jun. 2005, vol. 115: pp. 1503-1521).*
International Search Report and Written Opinion, PCT/US06/09870, Nov. 2, 2006, 10 pages.
"Affymetrix GeneChip Human Genome U133 Array Set HG-U133A", NCBI, GEO, Mar. 11, 2002, 16 pages.
European Search Report, European Patent Application No. 06748441.0, Nov. 11, 2008, 14 pages.
Cheung et al. "Mapping Determinants of Human Gene Expression by Regional and Genome-Wide Association." *Nature.* 437(2005):1365-1369.
Cheung et al. "Natural Variation in Human Gene Expression Assessed in Lymphoblastoid Cells." *Nature Gen.* 33(2003):422-425.
Edgar et al. "Gene Expression Omnibus: NCBI Gene Expression and Hybridization Array Data Repository." *Nucl. Acids Res.* 30.1(2002):207-210.
Glinsky et al. "Classification of Human Breast Cancer Using Gene Expression Profiling as a Component of the Survival Predictor Algorithm." *Clin. Cancer Res.* 10(2004):2272-2283.
Glinsky et al. "Gene Expression Profiling Predicts Clinical Outcome of Prostate Cancer." *J. Clin. Invest.* 113.6(2004):913-923.
Glinsky et al. "Microarray Analysis Identifies a Death-From-Cancer Signature Predicting Therapy Failure in Patients With Multiple Types of Cancer." *J. Clin. Invest.* 115.6(2005):1503-1521.
Glinsky et al. "Microarray Analysis of Xenograft-Derived Cancer Cell Lines Representing Multiple Experimental Models of Human Prostate Cancer." *Mol. Carcinogenesis.* 37(2003):209-221.
Glinsky. "Death-From-Cancer Signatures and Stem Cell Contribution to Metastatic Cancer." *Cell Cycle.* 4.9(2005):1171-1175.
Khan et al. "Classification and Diagnostic Prediction of Cancers Using Gene Expression Profiling and Artificial Neural Networks." *Nature Med.* 7.6(2001):673-679.
LaTulippe et al. "Comprehensive Gene Expression Analysis of Prostate Cancer Reveals Distinct Transcriptional Programs Associated With Metastatic Disease." *Cancer Res.* 62(2002):4499-4506.
Varambally et al. "Integrative Genomic and Proteomic Analysis of Prostate Cancer Reveals Signatures of Metastatic Progression." *Cancer Cell.* 8(2005):393-406.
Veer et al. "Gene Expression Profiling Predicts Clinical Outcome of Breast Cancer." *Nature.* 415(2002):530-536.

* cited by examiner

*Primary Examiner* — Nancy Vogel
*Assistant Examiner* — Catherine Hibbert
(74) *Attorney, Agent, or Firm* — Mintz Levin Cohn Ferris Glovsky and Popeo, P.C.; Ivor R. Elrifi; Muriel Liberto, Esq.

(57) ABSTRACT

The emerging concept of cancer stem cells suggests that activation in transformed cells of "stemness" genetic pathways (e.g., normal stem cells' self-renewal pathways) may contribute to the survival life cycle of cancer stem cells, and to tumor progression and metastasis of the malignancy. Thus, activation of "stemness" genes in cancer cells may be associated with aggressive clinical behavior and increased likelihood of therapy failure. General methods and kits associated with prediction of clinical outcome for a disease state of a subject based on gene expression analysis are described. The invention includes determining expression of at least three genes selected from the group consisting of GBX2, MKI67, CCNB1, BUB1, KNTC2, USP22, HCFC1, RNF2, ANK3, FGFR2, and CES1, and mouse homologs thereof.

3 Claims, 12 Drawing Sheets

Survival of prostate cancer patients with early stage disease and distinct expression profiles of the 11-gene MTTS/PNS signature Relapse-free survival of prostate cancer patients (11-gene Q-RT-PCR assay-based recurrence score)

Metastasis-free survival of breast cancer patients with early stage disease and distinct expression profiles of the 11-gene MTTS/PNS signature (all patients)

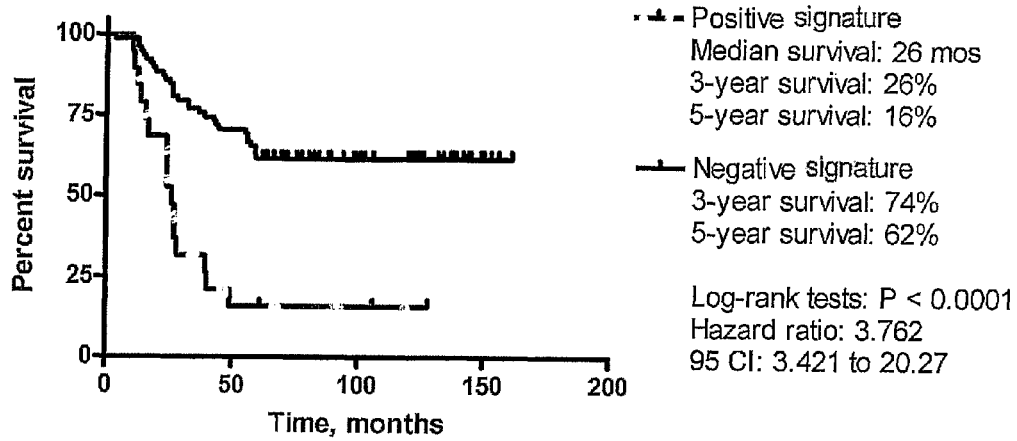

- - - Positive signature
Median survival: 26 mos
3-year survival: 26%
5-year survival: 16%

— Negative signature
3-year survival: 74%
5-year survival: 62%

Log-rank tests: P < 0.0001
Hazard ratio: 3.762
95 CI: 3.421 to 20.27

FIGURE 9

Survival of lung cancer patients with distinct expression profiles of the 11-gene MTTS/PNS signature (all patients)

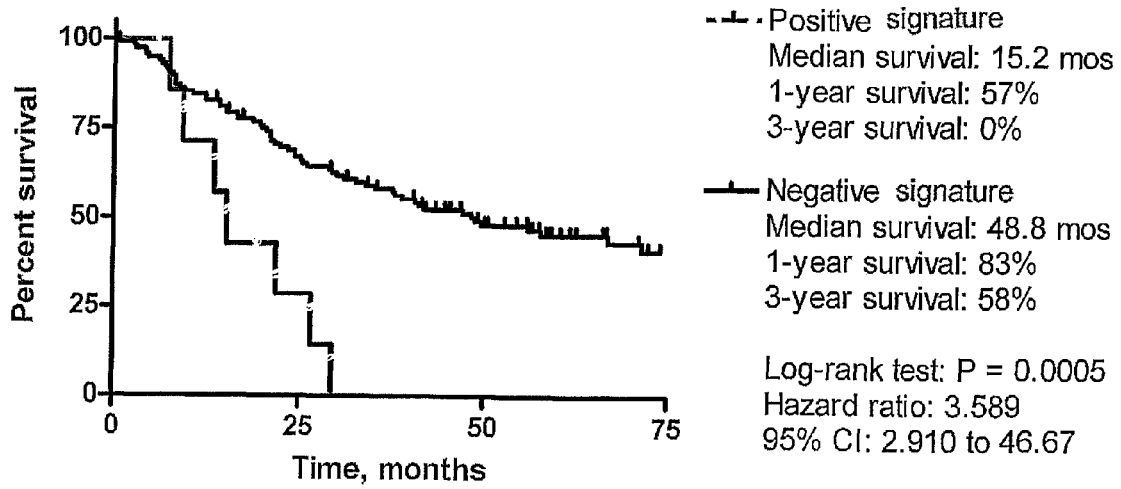

- - - Positive signature
Median survival: 15.2 mos
1-year survival: 57%
3-year survival: 0%

— Negative signature
Median survival: 48.8 mos
1-year survival: 83%
3-year survival: 58%

Log-rank test: P = 0.0005
Hazard ratio: 3.589
95% CI: 2.910 to 46.67

FIGURE 10

Survival of lymphoma patients with distinct expression profiles of the MTTS/PNS signature Expression profiles of the 23-gene "stemness" signature in highly metastatic PC3MLN4 orthotopic xenografts and prostate tumors from patients with recurrent disease

METHODS AND COMPOSITIONS FOR PREDICTING DEATH FROM CANCER AND PROSTATE CANCER SURVIVAL USING GENE EXPRESSION SIGNATURES

CROSS REFERENCE TO RELATED APPLICATIONS

This application is the National Stage of International Application No. PCT/US2006/009870, published in English under PCT Article 21(2), filed Mar. 16, 2006, which claims priority to 60/663,014, filed Mar. 16, 2005, both of which are incorporated by reference in their entirety, including any appendices or attachments thereof, for all purposes.

STATEMENT REGARDING FEDERALLY SPONSORED RESEARCH OR DEVELOPMENT

The U.S. Government has certain rights in this invention pursuant to Grant No. 5RO1 CA89827 awarded by the National Institutes of Health (National Cancer Institute).

FIELD OF THE INVENTION

The present invention relates to predicting clinical outcome of patients by detecting gene expression patterns relating to molecular signatures.

BACKGROUND OF THE INVENTION

Studies regarding the genetic basis of human cancer progression have allowed many advances toward finding effective treatments for this disease. Beyond providing an effective treatment for cancer, genetic analyses can provide other essential information about progression of the disease. Cancer patients in the early stages of the disease, for example, would typically greatly benefit from simply knowing more about the aggressiveness that their cancer is likely to exhibit, how their cancer is likely to progress, whether it is likely to metastasize, whether it is likely to recur after therapy (and how quickly it might recur), and so forth. With this type of knowledge in hand, physicians could respond by applying more aggressive therapies for patients with cancers that will likely exhibit particularly aggressive malignant behavior. Treatments could be properly tailored to the patient based on prognosis for that patient's particular disease state.

Recent studies suggest that more aggressive cancers may have some recognizable and measurable characteristics that distinguish them from the less aggressive types. Studies suggest that some types of cancers include a small number of cells in tumors with significant biological resemblance to stem cells, which are unspecialized, precursor cells with the ability to quickly divide and differentiate to give rise to specific specialized cells (Al-Hajj, M., Wicha, M. S., et al., M. F. Prospective identification of tumorigenic breast cancer cells. Proc. Natl. Acad. Sci. USA 2003, 100:3983-3988; Pardal, R., Clarke, M. F., Morrison, S. J. Applying the principle of stem-cell biology to cancer. Nature Review Cancer 2003, 3:895-902; Smalley, M. and Ashworth, A. Stem cells and breast cancer: a field in transit. Nature Review Cancer 2003, 3:832-844, each incorporated herein by reference). For a pluripotent stem cell-like phenotype, self-renewal ability is an essential defining property distinguishing stem cells from other cell types (Dick, J. E. Self-renewal writ in blood. Nature 2003, 423:231-233, incorporated herein by reference). Similarly, in cancer stem cells, this self-renewal ability can play an important role in tumor development, especially in more aggressive cancers. This small population of cancer stem cells within tumors can allow replication that seeds the growth of additional cancer cells. The presence of a rare stem-cell resembling population of cancer cells among the heterogeneous mix of cells comprising a tumor appears to be essential for sustained tumor growth and may contribute to the emergence of metastatic cancer cells during tumor progression (Pardal, R., Clarke, M. F., Morrison, S. J. Applying the principle of stem-cell biology to cancer. Nature Review Cancer 2003, 3:895-902; Al-Hajj, M., et al., Prospective identification of tumorigenic breast cancer cells. Proc. Natl. Acad. Sci. USA 2003, 100:3983-3988; Smalley, M. and Ashworth, A. Stem cells and breast cancer: a field in transit. Nature Review Cancer 2003, 3:832-844, incorporated herein by reference).

This concept of cancer stem cells further implies that common genetic pathways might define critical stem cell-like functions in neoplastic stem cells, as well as in normal stem cells (Lessard, J. and Sauvageau, G. BMI-1 determines the proliferative capacity of normal and leukaemic stem cells. Nature 2003, 423:255-260; Pardal, R., Clarke, M. F., Morrison, S. J. Applying the principle of stem-cell biology to cancer. Nature Review Cancer 2003, 3:895-902, incorporated herein by reference). In colorectal cancer, for example, constitutive activation of the β-catenin/TCF-4 pathway imposes a crypt progenitor phenotype on colorectal cancer cells, suggesting that analysis of normal stem cells and cancer cells may reveal common stem cell-like pathways engaged in malignant cells (van den Wetering, M., Sancho, E., Verweij, C., et al. The β-catenin/TCF-4 complex imposes a crypt progenitor phenotype on colorectal cancer cells. *Cell* 2002, 111: 241-250, incorporated herein by reference).

Specifically, genes associated with the potential of a stem cell to proliferate are likely to be of particular interest in cancer studies. As one example, recent studies indicate that the Polycomb group (PcG) gene BMI-1 determines the proliferative potential of normal and leukemic stem cells and is required for the self-renewal of hematopoietic and neural stem cells (Lessard, J. and Sauvageau, G. BMI-1 determines the proliferative capacity of normal and leukaemic stem cells. Nature 2003, 423:255-260; Park, I.-K., et al., BMI-1 is required for maintenance of adult self-renewing haematopoietic stem cells. Nature 2003, 423:302-305; Molofsky, A. V., et al., BMI-1 dependence distinguishes neural stem cell self-renewal from progenitor proliferation. Nature 2003, 425:962-967, each incorporated herein by reference). BMI-1 oncogene is expressed in all primary myeloid leukemia and leukemic cell lines that have been analyzed in various studies so far and over-expression of BMI-1 causes neoplastic transformation of lymphocytes (Lessard, J. and Sauvageau, G. BMI-1 determines the proliferative capacity of normal and leukaemic stem cells. Nature 2003, 423:255-260; Lessard, J., et al., Stage-specific expression of polycomb group genes in human bone marrow cells. Blood 1998, 91:1216-1224; Haupt, Y., et al., J. M. BMI-1 transgene induces lymphomas and collaborates with Myc in tumorigenesis. Oncogene 1993, 8:3161-3164; Alkema, M. J., et al., A. Perturbation of B and T cell development and predisposition to lymphomagenesis in Eμ-BMI-1 transgenic mice require the BMI-1 RING finger. Oncogene 1997, 15:899-910, each incorporated herein by reference), Recently, BMI-1 expression was reported in human non-small-cell lung cancer and breast cancer cell lines, suggesting an oncogenic role for BMI-1 activation in epithelial malignancies (Vonlanthen, S., et al. The BMI-1 oncoprotein is differentially expressed in non-small-cell lung cancer and correlates with INK4A-ARF locus expression. Br. J. Cancer 2001, 84:1372-1376; Dimri, G. P., et al., The BMI-1 oncogene induces telomerase activity and immortalizes human mammary epithelial cells. Cancer Res. 2002, 62:4736-4745; LaTulippe, E., et al., Comprehensive gene expression analysis of prostate cancer reveals distinct transcriptional programs associated with metastasis. Cancer Res. 2002, 62:4499-4506, each incorporated herein by reference).

These strong ties between neoplastic stem cells and normal stem cells, and the common genetic pathways defining critical stem cell-like functions in cancer cells, provide a useful opportunity for further analysis. Expression profiling of tumor samples using oligonucleotide or cDNA microarray technology is a powerful tool for revealing multiple gene expression signatures associated with various cancers. For example, comparative gene expression profiling analysis of normal stem cells and cancer cells may reveal gene expression signatures of "stemness" pathways engaged in malignant cells. These gene signatures identified to be associated with certain cancers and identified to have an association with stem cell-like properties could then be used prognostically to predict clinical outcome for a particular patient. Accuracy of different technologies using expression profiling for providing diagnosis and prognosis could be increased through identification of small signatures that are highly effective in providing information regarding likely clinical outcome for a cancer patient, even in the early stages of the cancer. These gene signatures could act as powerful predictors of distant metastasis, short interval to disease recurrence, death after therapy in cancer patients, and so forth, thus providing cancer patients with essential information before the cancer has had a chance to progress.

Thus, there exists in the art a need for improved methods of predicting the clinical outcome of disease states, such as cancer, through use of gene signatures associated with genes that are differentially expressed or regulated in biological samples, such as tumor and normal cell samples. The present invention addresses these and other shortcomings of the art.

SUMMARY OF THE INVENTION

Disclosed herein are kits and methods for predicting the clinical outcome for a disease state in a subject. Accordingly one aspect of the invention is a kit for predicting a clinical outcome for a disease state in a subject comprising a set of nucleic acid probes for determining expression level of a plurality of genes and instructions for use. The plurality of genes is selected from a group consisting of the genes of a gene set identified in Table 2 (described below). The set of nucleic acid probes is capable of hybridizing to RNA or cDNA species derived from the plurality of genes, and the probes allow quantification of the expression level and prediction of the clinical outcome based on said quantification.

Another aspect is a method for predicting a clinical outcome for a disease state in a subject comprising detecting expression level of a plurality of genes in said subject. The plurality of genes is selected from a group consisting of the genes of a gene set identified in Table 2. A set of nucleic acid probes capable of hybridizing to RNA or cDNA species derived from the plurality of genes allows quantification of the expression level and prediction of the clinical outcome based on said quantification.

In some embodiments of the kit and of the method, the plurality comprises all of the genes of the gene set identified in Table 2. In one embodiment, the plurality comprises the genes MKI67 and CCNB1. In an embodiment where the disease state is prostate cancer, the plurality includes at least two genes selected from the group consisting of MKI67, ANK3, FGFR2 and CES1. In an embodiment where the disease state is breast cancer, the plurality is selected from a group consisting of CCNB1, BUB1, and KNTC2. In still other embodiments, the plurality includes five or six of the genes identified in Table 2. In some embodiments, the invention further comprises analyzing a clinico-pathological feature selected from a group consisting of pre-RP Gleason sum, surgical margins, seminal vesicle invasion, age, and extracapsular extension.

In still another aspect of the invention, a kit is disclosed for predicting a clinical outcome for a disease state in a subject comprising a set of nucleic acid probes for determining expression level of a plurality of genes and instructions for use. The plurality of genes is selected from a group consisting of genes from gene set A identified in Table 9a, gene set B identified in Table 9b, gene set C identified in Table 9c, and gene set D identified in Table 9d (Tables described below). The set of nucleic acid probes is capable of hybridizing to RNA or cDNA species derived from the plurality of genes, and the probes allow quantification of the expression level and prediction of the clinical outcome based on said quantification. In certain embodiments, probes are directed to all genes from an identified gene set. In other embodiments, probes are directed to a subset of genes from an identified gene set.

Another aspect is a method for predicting a clinical outcome for a disease state in a subject comprising detecting expression level of a plurality of genes in said subject. The plurality of genes is selected from a group consisting of genes from gene set A identified in Table 9a, gene set B identified in Table 9b, gene set C identified in Table 9c, and gene set D identified in Table 9d. A set of nucleic acid probes capable of hybridizing to RNA or cDNA species derived from the plurality of genes allows quantification of the expression level and prediction of the clinical outcome based on said quantification. In certain embodiments, probes are directed to all genes from an identified gene set. In other embodiments, probes are directed to a subset of genes from an identified gene set.

In some embodiments of the methods, the genes are extracted from a tumor cell recovered from said subject. The tumor cell can be recovered from an organ selected from the group consisting of a prostate, a breast, a colon, a lung, a bladder, and an ovary.

In some embodiments, the methods further comprise performing a Kaplan-Meier survival analysis to determine probability that the subject will remain disease-free for a time period after therapy. In some embodiments, the methods further comprise calculating a Pearson correlation coefficient by comparing an expression profile for a tumor sample taken from the subject to a stem cell-associated expression profile.

In any one of the embodiments described above, the nucleic acid probes can be affixed to a solid support or the probes can comprise primers for nucleic acid amplification of a subset of genes. The primers can be selected from a group consisting of the primers identified in Table 5 and Table 6 (described below). Furthermore, in any of the embodiments described above, the disease state preferably is prostate cancer, breast cancer, lung cancer, ovarian cancer, bladder cancer, lymphoma, mantle cell lymphoma, mesothelioma, medulloblastoma, glioma, or acute myeloid leukemia. In addition, the prognosis can be selected from the group consisting of recurrence of the disease state after therapy, non-recurrence of the disease state after therapy, therapy failure, short interval to disease recurrence (e.g., less than two years, or less than one year, or less than six months), short interval to metastasis (e.g., less than two years, or less than one year, or less than six months), invasiveness, non-invasiveness, likelihood of metastasis, likelihood of distant metastasis, poor survival after therapy, death after therapy, and disease free survival.

Another aspect of the present invention is a kit for determining expression of at least three genes selected from the group consisting of GBX2, MKI67, CCNB1, BUB1, KNTC2, USP22, HCFC1, RNF2, ANK3, FGFR2, and CES1, and mouse homologs thereof. The kit comprises a set of probes to specifically detect expression of the at least three genes and that specifically do not detect expression of other genes. The set of probes are nucleic acids or antibodies (the term "antibodies" can include antibodies, antibody fragments, scFvs, etc.).

In some embodiments, the set of probes are nucleic acids capable of hybridizing under normal stringency conditions (e.g., conditions under which a compound of the invention will hybridize to its target sequence, but to a minimal number of other sequences, such as described in Korkola, et al., Optimizing Stringency for Expression Microarrays, Microarray Technologies 2003, 35:828-835 and in U.S. Pat. No. 7,005,500, filed Nov. 14, 2001, incorporated by reference) to RNA species transcribed from the at least three genes or to cDNA species derived from the RNA species. In some embodiments, the set of probes are PCR primers. Further, the PCR primers can be at least three pair of primers selected from the group consisting of SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14, SEQ. ID NO: 15, SEQ. ID NO: 16, SEQ. ID NO: 17, SEQ. ID NO: 18, SEQ. ID NO: 19, SEQ. ID NO: 20, SEQ. ID NO: 213, SEQ. ID NO: 22, SEQ. ID NO: 23, SEQ. ID NO: 24, SEQ. ID NO: 25, SEQ. ID NO: 26, SEQ. ID NO: 27, and SEQ. ID NO: 28.

In some embodiments, the kit comprises a solid phase. Further, in some embodiments, the set of probes consists of at least three probe sets selected from the group consisting of Affymetrix HG-U95Av2 probe set 33688_at, Affymetrix HG-U95Av2 probe set 418_at, Affymetrix HG-U95Av2 probe set 34736_at, Affymetrix HG-U95Av2 probe set 41081_at, Affymetrix HG-U95Av2 probe set 40041_at, Affymetrix HG-U95Av2 probe set 39866_at, Affymetrix HG-U95Av2 probe set 37910_at, Affymetrix HG-U95Av2 probe set 33484_at, Affymetrix HG-U95Av2 probe set 36967_g_at, Affymetrix HG-U95Av2 probe set 1143_s_at Affymetrix HG-U95Av2 probe set 37203_at, Affymetrix HG-U133A probe set 210560_at, Affymetrix HG-U133A probe set 212022_s_at, Affymetrix HG-U133A probe set 214710_s_at, Affymetrix HG-U133A probe set 216277_at, Affymetrix HG-U133A probe set 204162_at, Affymetrix HG-U133A probe set 216964_at, Affymetrix HG-U133A probe set 202473_x_at, Affymetrix HG-U133A probe set 205215_at, Affymetrix HG-U133A probe set 209442_x_at, Affymetrix HG-U133A probe set 208228_-s_at, Affymetrix HG-U133A probe set 209616_-s_at, Affymetrix MG-U74A probe set 94200_at, Affymetrix MG-U74A probe set 99457_at, Affymetrix MG-U74A probe set 160159_at, Affymetrix MG-U74A probe set 104097_at, Affymetrix MG-U74A probe set 93441_at, Affymetrix MG-U74A probe set 97960_at, Affymetrix MG-U74A probe set 100901_at, Affymetrix MG-U74A probe set 93164_at, Affymetrix MG-U74A probe set 98477_-s_at, Affymetrix MG-U74A probe set 93090_at, and Affymetrix MG-U74A probe set 101538_i_at.

In some embodiments of the invention, the at least three genes are CCNB1, BUB1, KNTC2, or the mouse homologs thereof. In other embodiments, the kit is a kit for determining expression of MKI67, ANK3, FGFR2, and CES1, or the mouse homologs thereof, and the set of probes specifically detects expression of MKI67, ANK3, FGFR2, and CES1, or the mouse homologs thereof. In still other embodiments, the kit is a kit for determining expression of GBX2, MKI67, CCNB1, BUB1, KNTC2, USP22, HCFC1, RNF2, ANK3, FGFR2, and CES1, or the mouse homologs thereof, and the set of probes specifically detects expression of GBX2, MKI67, CCNB1, BUB1, KNTC2, USP22, HCFC1, RNF2, ANK3, FGFR2, and CES1, or the mouse homologs thereof.

Another aspect of the present invention is a method for predicting a clinical outcome for a disease state in a subject. The method comprises obtaining a sample from said subject, and determining from the sample a set of gene expression measurements for at least three genes selected from the group consisting of GBX2, MKI67, CCNB1, BUB1, KNTC2, USP22, HCFC1, RNF2, ANK3, FGFR2, and CES1, or the mouse homologs thereof. The method further comprises determining a correlation coefficient between the set of gene expression measurements and a reference standard set of gene expression measurements obtained by comparing expression values from a stem cell and from a tumor cell for the set of genes. The sign of the correlation coefficient is predictive of the clinical outcome for the disease state.

In some embodiments, the stem cell is a peripheral nervous system neurosphere. In some embodiments, the tumor cell is a metastatic prostate tumor cell. In addition, in some embodiments, the disease state is cancer, and in some embodiments, the cancer is prostate cancer. The cancer can also be selected from the group consisting of prostate cancer, breast cancer, lung cancer, ovarian cancer, bladder cancer, lymphoma, mantle cell lymphoma, mesothelioma, medulloblastoma, glioma, and acute myeloid leukemia. In some embodiments, the clinical outcome is selected from the group consisting of recurrence, therapy failure, likelihood of metastasis, likelihood of distant metastasis, disease free survival, invasiveness, and likelihood of survival at a predetermined time period.

In some embodiments of the present invention, the at least three genes are CCNB1, BUB1, KNTC2, or the mouse homologs thereof. In other embodiments, the set of gene expression measurements are expression measurements of MKI67, ANK3, FGFR2, and CES1, or the mouse homologs thereof. In still other embodiments, the set of gene expression measurements are expression measurements of GBX2, MKI67, CCNB1, BUB1, KNTC2, USP22, HCFC1, RNF2, ANK3, FGFR2, and CES1, or the mouse homologs thereof.

In some embodiments, the method further comprises analyzing a clinico-pathological feature selected from the group consisting of a pre-radical prostatectomy Gleason sum, a surgical margin evaluation, a seminal vesicle invasion, an age, and an extra-capsular extension.

BRIEF DESCRIPTION OF THE SEVERAL VIEWS OF THE DRAWING

These and other features, aspects, and advantages of the present invention will become better understood with regard to the following description, and accompanying drawings, where:

FIG. 9 is a graph showing the Kaplan-Meier analysis of the probability that patients would remain metastasis-free or survive after therapy among 97 early stage breast cancer patients according to whether they had a good-prognosis or poor-prognosis signatures defined by the expression profiles of the 11-gene MTTS/PNS signature.

FIG. 10 is a graph showing the Kaplan-Meier analysis of the probability that patients would remain metastasis-free or survive after therapy among 125 lung adenocarcinoma patients of all stages according to whether they had a good-prognosis or poor-prognosis signatures defined by the expression profiles of the 11-gene MTTS/PNS signature.

DETAILED DESCRIPTION OF THE INVENTION

Definitions

Figure 1:
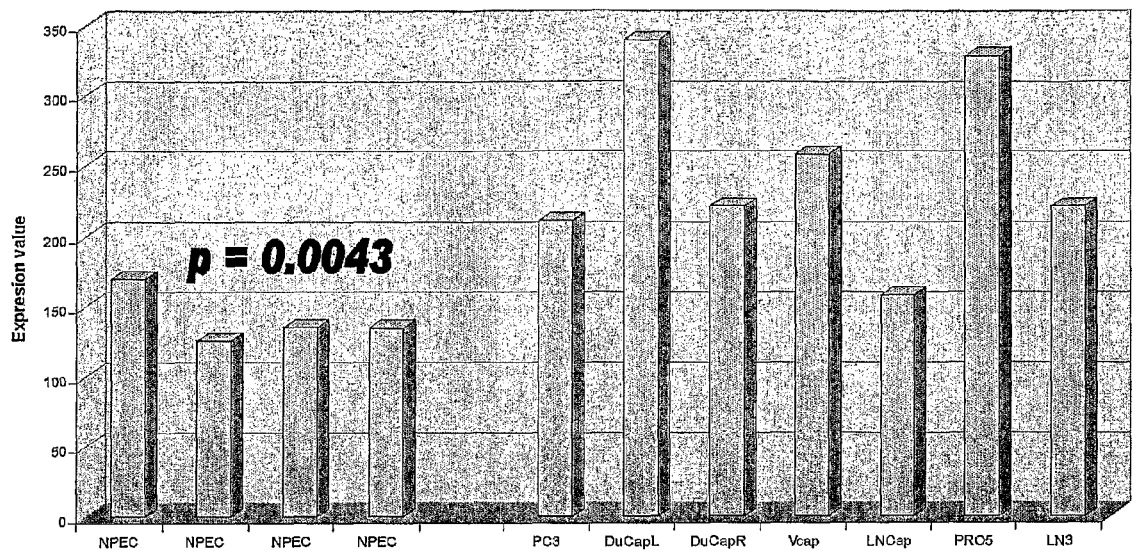
FIG. 1 is a graph showing microarray data-derived expression values of BMI-1 mRNA in multiple human prostate cancer cell lines established from metastatic tumors (PC-3, LNCap, DuCap, VCap, etc.) and normal human prostate epithelial cells, NPEC (normal prostate epithelial cells).

All terms, unless specifically defined below, are intended to have their ordinary meanings as understood by those of skill in the art. Claimed masses and volumes are intended to encompass variations in the stated quantities compatible with the practice of the invention. Such variations are contemplated to be within, e.g. about ±10-20 percent of the stated quantities. In case of conflict between the specific definitions contained in this section and the ordinary meanings as understood by those of skill in the art, the definitions supplied below are to control.

"Differentially expressed" refers to the existence of a difference in the expression level of a gene as compared between two sample classes. Differences in the expression levels of "differentially expressed" genes preferably are statistically significant.

"Tumor" is to be construed broadly to refer to any and all types of solid and diffuse malignant neoplasias including but not limited to sarcomas, carcinomas, leukemias, lymphomas, etc., and includes by way of example, but not limitation, tumors found within prostate, breast, colon, lung, and ovarian tissues.

A "tumor cell line" refers to a transformed cell line derived from a tumor sample. Usually, a "tumor cell line" is capable of generating a tumor upon explant into an appropriate host. A "tumor cell line" line usually retains, in vitro, properties in common with the tumor from which it is derived, including, e.g., loss of differentiation, loss of contact inhibition, and will undergo essentially unlimited cell divisions in vitro.

A "control cell line" refers to a non-transformed, usually primary culture of a normally differentiated cell type. In the practice of the invention, it is preferable to use a "control cell line" and a "tumor cell line" that are related with respect to the tissue of origin, to improve the likelihood that observed gene expression differences are related to gene expression changes underlying the transformation from control cell to tumor.

"Orthotopic" refers to the placement of cells in an organ or tissue of origin, and is intended to encompass placement within the same species or in a different species from which the cells are originally derived.

The term "in vivo" refers to processes that occur in a living organism.

It must be noted that, as used in the specification and the appended claims, the singular forms "a," "an" and "the" include plural referents unless the context clearly dictates otherwise.

Introduction

Recently, a global gene expression profiling approach was successfully utilized to identify molecular signatures associated with activation of oncogenic pathways, targeted genetic manipulations, or cellular responses to physiological stimuli, and to build robust transcriptional identifiers reliably recognizing the engagement of corresponding pathways within the high complexity patterns of gene expression in experimental and clinical samples (Lamb, J., Ramaswamy, S., et al., A mechanism of cyclin D1 action encoded in the patterns of gene expression in human cancer. Cell 2003, 114:323-334; Chang, H. Y., et al., Gene expression signature of fibroblast serum response predicts human cancer progression: Similarities between tumors and wounds. PLOS Biology 2004, 2:1-9; Raaphorst, F. M. et al., Poorly differentiated breast carcinoma is associated with increased expression of the human polycomb group EZH2 gene. Neoplasia 2003, 5:481-488, each incorporated herein by reference). The present invention uses techniques, such as microarray gene expression analysis, to determine whether invasive tumors, while actively seeding metastatic cancer cells as well as established distant metastatic lesions, have gene expression profiles similar to the transcriptional program of stem cells. This gene expression profiling approach was successfully utilized to identify molecular signatures associated with activation of oncogenic pathways and which consistently displayed a stem-cell resembling profile in distant metastatic lesions. Analyses of metastases and primary tumors from a transgenic mouse model of prostate cancer and from human cancer patients were conducted. The methods of the present invention were then used to estimate the prognostic power of the identified "stemness" signatures in predicting the clinical outcome for a cancer patient.

In some embodiments of the present invention, in identifying stem cell-like signatures that can be used in predicting clinical outcome (as applied to the analysis of tumor samples), gene expression data showing genes up-regulated or down-regulated in primary tumors and metastases is compared to data showing genes up- or down-regulated in certain stem cells (e.g., in neural stem cells, hematopoeitic stem cells, embryonic stem cells, etc.). Sets of differentially regulated transcripts can be identified for distant metastatic lesions and primary tumors versus the stem cell samples. One or more genes are selected that have met the screening criterion requiring that the genes be differentially expressed between tumor and control cell lines or between tumor and normal clinical samples. Molecular signatures can then be identified from these sets of transcripts exhibiting concordant expression changes between metastatic tumor and stem cell samples. A more detailed explanation of methods that can be used to identify and validate the outcome prediction capabilities of these signatures is provided in Glinsky, Gennadi V. et al, Microarray analysis identifies a death-from-cancer signature predicting therapy failure in patients with multiple types of cancer, J. Clin. Invest. 2005, 1:115(6):1503-1521 (incorporated by reference), and in pending U.S. patent application Ser. No. 10/861,003, filed Jun. 3, 2004 and pending U.S. patent application Ser. No. 10/660,434, filed Sep. 10, 2003, each of which is incorporated herein by reference in its entirety.

The molecular signatures can be used to predict the clinical outcome of a disease state (such as cancer) for patients. Although most of the description contained herein focuses primarily on prediction of clinical outcomes associated with cancer, the present invention can also be used for predicting clinical outcomes associated with other disease states (e.g., atherosclerosis, arthritis, etc.).

In a broad and general sense, as applied to the analysis of tumor samples, the method of the present invention includes specifically detecting the expression level of a plurality of genes in a patient, where the genes correspond to one or more gene signatures identified using the procedures described above. Examples of specific signatures identified include those shown in Tables 2, 9a, 9b, 9c, and 9d, described in a later section. The molecular signatures identified can vary in the number of interrogated genes. In some embodiments, the molecular signature used includes at least 5, 11, 14, 16, 23 genes, or other number of genes that is found to be effective as a set in predicting clinical outcome. In some embodiments, one or more of the genes contained in the gene set for each molecular signature is used for predicting clinical outcome for a patient. In some embodiments, at least two or more of the signatures identified in the Tables 2, 9a, 9b, 9c, or 9d are used in the methods or in a kit of the present invention to predict clinical outcome for a patient.

Specifically detecting expression would be understood by one of skill in art, in case of a nucleic acid probe, to include measuring the level of mRNA or a cDNA to which a probe has been engineered to bind, where the probe binds the intended species and provides a distinguishable signal. Exemplary methods for selecting PCR primers and/or hybridization probes are included in Innis et al., eds., 1990, PCR Protocols: A Guide to Methods and Applications, Academic Press Inc., San Diego, Calif.; Froehler et al., 1986, Nucleic Acid Res. 14:5399-5407; McBride et al., 1983, Tetrahedron Lett. 24:246-248, U.S. Pat. No. 7,013,221, filed Apr. 28, 2000, incorporated by reference. Preferably probes have length of at least 20 nucleotides which provides requisite specificity for detecting expression, although they may be shorter depending upon other species expected to be found in sample. Specifically detecting expression for measurement or determining protein expression levels can also be accomplished by using a specific binding reagent, such as an antibody, as described in more detail below.

In some embodiments, the kits and methods of the present invention can be used to predict various different types of clinical outcomes. For example, the invention can be used to predict recurrence of a disease state after therapy, non-recurrence of a disease state after therapy, therapy failure, short interval to disease recurrence, short interval to metastasis in cancer, invasiveness, non-invasiveness, likelihood of metastasis in cancer, likelihood of distant metastasis in cancer, poor survival after therapy, death after therapy, disease free survival, and so forth.

In some embodiments, a set of nucleic acid probes capable of hybridizing to RNA or cDNA species derived from plurality of genes making up the molecular signature allows quantification of the expression level and prediction of the outcome based on this quantification. In some embodiments, the probes are affixed to a solid support, such as a microarray (such as those provided by Affymetrix). Methods for creating microarrays and examples of microarrays used the present invention are described in more detail below. In other embodiments, the probes primers for nucleic acid amplification of set of genes. Methods for Q-RT-PCR used with the present invention are described in more detail below. In general, expression of the genes within the gene set of the molecular signature can be analyzed by any method now known or later developed to assess gene expression, including but not limited to measurements to the biological processes of nucleic acid amplification, transcription, RNA splicing, and translation. Thus, direct indirect measures of gene copy number (e.g., as by fluorescence in situ hybridization or other type of quantitative hybridization measurement, or by quantitative PCR), transcript concentration (e.g., as by Northern blotting, expression array measurements, quantitative RT-PCR, or comparative genomic hybridization, CGH as described in e.g., U.S. Pat. No. 6,335,167, incorporated by reference), and protein concentration (e.g., by quantitative 2-D gel electrophoresis, mass spectrometry, Western blotting, ELISA, or other method for determining protein concentration).

One of ordinary skill in the art would recognize that different affinity reagents could be used with present invention, such as one or more antibodies (e.g., monoclonal or polyclonal antibodies) and the invention can include using techniques, such as ELISA, for the analysis. Thus, specific antibodies (e.g., specific to the genes of the proteins encoded by the molecular signature of interest) can be used in a kit and in methods of the present invention for predicting clinical outcome based on expression analysis in a manner similar to the kits and methods described above. In the case of antibodies and related affinity reagents such as, e.g., antibody fragments, and engineered sequences such as single chain Fvs (scFvs), these reagents must specifically bind their intended target, i.e., a protein encoded by a gene included in the molecular signature of interest. Specific binding includes binding primarily or exclusively to an intended target. Specific binding is easily assessed using, e.g., a Western blot, where the reagent gives rise to a band at the expected molecular weight that is at least 2 or at least 10 or more times intense than other bands that might appear on the gel. For example, in a kit of this embodiment, the kit would include reagents and instructions for use, where the reagents are antibodies and the antibodies hybridize to the plurality of expression products of the gene set consisting of genes identified in Table 3 or the antibodies hybridize to the plurality of expression products selected from a group consisting of genes from gene set A identified in Table 9a, gene set B identified in Table 9b, gene set C identified in Table 9c, gene set D identified in Table 9d. It is well-known in the art the manner in which antibodies can be identified and obtained from a variety of sources, such as the MSRS catalog of antibodies (Aerie Corporation, Birmingham, Mich.), or can be prepared via conventional antibody-generation methods. Methods for preparation of polyclonal antisera are taught in, for example, Ausubel, F. M. et al., Current Protocols in Molecular Biology, Volume 2, 1997, pp. 11.12.1-11.12.9 (incorporated by reference). Preparation of monoclonal antibodies is taught in, for example, Ausubel, F. M. et al., Current Protocols in Molecular Biology, Volume 2, 1997, pp. 11.4.1-11.11.5 (incorporated by reference). Preparation of scFvs is taught in, e.g., U.S. Pat. Nos. 5,516,637 and 5,872,215, both of which are incorporated by reference.

Signatures identified (such as those exhibiting the most significant correlation of expression profiles in stem cells and cancer metastasis) can be used to discriminate between metastatic and primary prostate tumors in patients, and thus can be used in predicting clinical outcome for patients. In some embodiments, a survival prediction model based on a signature is validated by testing the prognostic performance of the model in multiple independent therapy outcome data sets representing disease states (e.g., epithelial and non-epithelial cancers). A prognosis discrimination cut-off value for a signature can be selected based on highest level of statistical significance in patient's stratification into poor and good prognosis groups as determined by a log-rank test (lowest P value and highest hazard ratio).

In some embodiments, to assess a potential diagnostic and prognostic relevance of the signatures, a Pearson correlation coefficient is calculated (e.g., using Microsoft Excel and the GraphPad Prism version 4.00 software) for each individual tumor sample by comparing the expression profiles of individual samples to the reference expression profile in stem cells. The Pearson correlation coefficient can be used to measure degree of resemblance of the transcript abundance rank order within a gene cluster between a sample and reference standard, which can be designated as a phenotype association index (PAI). Samples with stem cell-resembling expression profiles (stem cell-like PAI or SPAI) are expected to have positive values of Pearson correlation coefficients. Clinical samples with the Pearson correlation coefficient at or higher than the cut-off value can be identified as having the poor prognosis signature. Clinical samples with the coefficient lower than the cut-off value were identified as having the good prognosis signature. In some embodiments, the survival prediction model performance is confirmed using sample stratification approaches, such as terrain clustering, support vector machine classification, and weighted survival score algorithm.

In some embodiments, the potential clinical utility of a signature can be further validated by evaluating the prognostic power of the signature applied to samples obtained from cancer patients who developed recurrence after therapy and to other patients who remained disease-free. A Kaplan-Meier survival analysis can be used to determine if there is a highly significant difference in the probability that cancer patients would remain disease-free after therapy between groups with positive and negative SPAIs defined by the signature. An estimated hazard ratio for disease recurrence after therapy can be determined for patients with positive versus negative SPAIs defined by the signature.

In some embodiments, to ascertain the incremental statistical power of the individual covariates as predictors of therapy outcome and unfavorable prognosis, univariate and multivariate Cox proportional hazard survival analyses are performed. These analyses allow comparison of the prognostic performance of an entire stemness signature and of individual genes making up the signature or subsets of genes.

In some embodiments, a weighted survival score analysis is implemented to reflect the incremental statistical power of the individual covariates as predictors of therapy outcome based on a multi-component prognostic model. Final survival predictor score can comprise a sum of scores for individual genes of a signature and can reflect the relative contribution of each gene in the multivariate analysis. The negative weighting values imply that higher expression correlates with longer survival and favorable prognosis, whereas positive scores indicate that higher expression correlates with poor outcome and shorter survival. Application of this weighted survival predictor model based on cumulative score of weighted expression values of genes making up a signature can be used to confirm the prognostic power of the identified signature in stratification of cancer patients into sub-groups with statistically distinct probability of relapse-free survival after therapy.

Similar types of methods (e.g., Kaplan-Meier methods) can also be used to determine a signature's prediction capabilities of a short relapse survival after therapy in patients with an early stage disease, of metastatic recurrence, and of poor survival after therapy. In addition, Kaplan-Meier analysis can be used to determine the probability of developing distant metastases after therapy and higher risk of death after therapy. These analyses can be used to examine the predictive capabilities of signatures regarding numerous types of cancer, both epithelial and non-epithelial. Further detail regarding the Kaplan-Meier analysis and other methods is provided in Glinsky, Gennadi V. et al, Microarray analysis identifies a death-from-cancer signature predicting therapy failure in patients with multiple types of cancer, J. Clin. Invest. 2005, 1:115(6):1503-1521 (incorporated by reference).

More detailed information regarding the methods/kits of the present invention and how these methods are applied for detecting expression, including methods and kits involving an 11-gene signature in the first example and four other stemness signatures in the second example, is included below.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed*. (Plenum Press) Vols A and B (1992).

Materials and Methods

The materials and methods used with regard to the present invention are described in detail in Glinsky, Gennadi V. et al, Microarray analysis identifies a death-from-cancer signature predicting therapy failure in patients with multiple types of cancer, J. Clin. Invest. 2005, 1:115(6):1503-1521 (incorporated by reference), and some of the methods are also described in pending U.S. patent application Ser. No. 10/861,003, filed Jun. 3, 2004 and pending U.S. patent application Ser. No. 10/660,434, filed Sep. 10, 2003, each of which is incorporated herein by reference in its entirety. Specifically, the incorporated references describe the materials and methods associated with the use of clinical samples and cell cultures, anoikis assay, apotosis assay for identifying and quantifying apoptotic cells, use of flow cytometry, development of orthotopic xenografts of human prostate PC-3 cells and sublines, creation of the transgenic mouse model of prostate cancer, tissue processing for mRNA and RNA isolation, RNA and mRNA extraction, usage of Affymetrix arrays for mRNA quality control and gene expression analysis, and data analysis.

The detailed protocol of discovery of an 11-gene signature associated with the BMI-1 pathway in stem cells, including the steps for identification of differentially regulated transcripts in the TRAMP mouse model, PNS (peripheral nervous system) neurospheres, and CNS (central nervous system) neurospheres, identification of sub-sets of transcripts exhibiting concordant expression changes, selection of small gene clusters from the sub-sets (e.g., to obtain the 11-gene MTTS (metastatic TRAMP tumor sample)/PNS signature, the 11-gene MTTS/CNS signature, and the 14-gene MTTS/PNS/CNS signature), testing the three signatures for metastatic phenotype-discriminative power leading to selection of the best-performing 11-gene MTTS/PNS signature (also referred to as 11-gene signature or 11-gene BMI-1 pathway signature) for further validation analysis, are described in detail in Glinsky, Gennadi V. et al, Microarray analysis identifies a death-from-cancer signature predicting therapy failure in patients with multiple types of cancer, use of the SPAI Index, Cox analysis, random co-occurrence test, J. Clin. Invest. 2005, 1:115(6):1503-1521 (incorporated by reference). In addition, these methods are described with regard to the Examples below.

Validation of the 11-Gene Signature

SPAI Index

Definition of the Pearson correlation coefficient as a phenotype association index [stem cell-resembling phenotype association indices (SPAIs)] is based on highly concordant behavior of the 11-gene signature between neural stem cells in the state of PNS neurospheres and prostate cancer metastasis (r=0.9897; P<0.0001). A standard PNS neurosphere and TRAMP metastasis values were established as described in the signature discovery protocol. They were used as uniform reference standards for measurements of Pearson correlation coefficients for clinical samples consistently throughout the study.

A degree of resemblance of the transcript abundance rank order within a gene cluster between a test sample and reference standard is measured by a Pearson correlation coefficient and designated as a phenotype association index (PAI). Samples with stem cell-resembling expression profiles (stem cell-like PAI or SPAI) are expected to have positive values of Pearson correlation coefficients. The detailed prognostic signature identification and validation protocol are described below.

Step 1. Sets of differentially regulated transcripts were independently identified for distant metastatic lesions and primary prostate tumors versus age-matched control samples in a transgenic TRAMP mouse model of metastatic prostate cancer (MTTS signature) as well as PNS (PNS signature) and CNS (CNS signature) neurospheres in BMI-1+/+ versus BMI-1-/- backgrounds using the Affymetrix microarray processing and statistical analysis software package (Affymetrix Microarray Suite version 5.0, MicroDB version 3.0, and DMT version 3.0). Transcripts with negative signal-intensity values in both experimental and control sets were eliminated from further consideration. At least 2-fold changes of the mRNA abundance levels in experimental versus control samples for both upregulated and downregulated genes were required for inclusion in the lists of differentially regulated transcripts. Fold expression changes of the mRNA abundance levels for each transcript were calculated as ratios of the average intensity values for a given transcript in experimental versus control samples for both upregulated and downregulated genes and log 10-transformed for further analysis. Thus, this analytical step defined 3 large parent signatures: MTTS signature comprising 868 upregulated and 477 downregulated transcripts; PNS signature comprising 885 upregulated and 1,088 downregulated transcripts; and CNS signature comprising 769 upregulated and 778 downregulated transcripts.

Step 2. Subsets of transcripts exhibiting concordant expression changes in metastatic TRAMP tumor samples (MTTS signature) as well as PNS PNS signature) and CNS (CNS signature) neurospheres in BMI-1+/+ versus BMI-1−/− backgrounds were identified. Concordant lists of transcripts were obtained by intersecting the 2 lists each of upregulated and downregulated genes. Thus, 2 concordant subsets of transcripts were identified corresponding to each binary comparison of metastatic TRAMP tumors and neural stem cell samples in a state of PNS and CNS neurospheres (141 upregulated and 58 downregulated transcripts for PNS neurospheres [r=0.7593; P<0.0001] and 40 upregulated and 24 downregulated transcripts for CNS neurospheres [r=0.7679; P<0.0001]). A third concordant subset of 27 genes comprising 15 upregulated and 12 downregulated transcripts was selected for intersection common to all 3 signatures (r=0.8002; P<0.0001).

Step 3. Selection of small gene clusters was performed from subsets of genes exhibiting concordant changes of transcript-abundance behavior in metastatic TRAMP tumor samples and PNS and CNS neurospheres in BMI-1+/+ versus BMI-1−/− backgrounds. Expression profiles were presented as log 10 average fold changes for each transcript and processed for visualization and Pearson correlation analysis using Microsoft Excel software Microsoft Corp.). For the concordant differentially expressed genes, vectors of log 10 average fold change were determined for both experimental settings, and the correlation between 2 vectors was determined. Practical considerations essential for future development of genetic diagnostic tests prompted us to select from concordant gene sets small gene expression signatures comprising transcripts with a high level of expression correlation in metastatic cancer cells and stem cells. The concordant list of differentially expressed genes was reduced by removing those genes whose removal led to the largest increase in the correlation coefficient. The reduction in the signature transcript number was terminated when further elimination of a transcript did not increase the value of the Pearson correlation coefficient. The cutoff criterion for signature reduction was arbitrarily set to exceed a Pearson correlation coefficient of 0.95 (P<0.0001). Using this approach, a single candidate prognostic gene expression signature was selected for each intersection of the MTTS signature and parent stem cell signatures. Thus, 3 highly concordant small signatures were identified corresponding to 3 concordant subsets of genes defined in step 2 (a set of 11 genes comprising 8 upregulated and 3 downregulated transcripts for PNS neurospheres, i.e., the 11-gene MTTS/PNS signature; a set of 11 genes comprising 7 upregulated and 4 downregulated transcripts for CNS neurospheres, i.e., the 11-gene MTTS/CNS signature; and a set of 14 genes comprising 8 upregulated and 6 downregulated transcripts, i.e., the MTTS/PNS/CNS signature).

Figure 3:
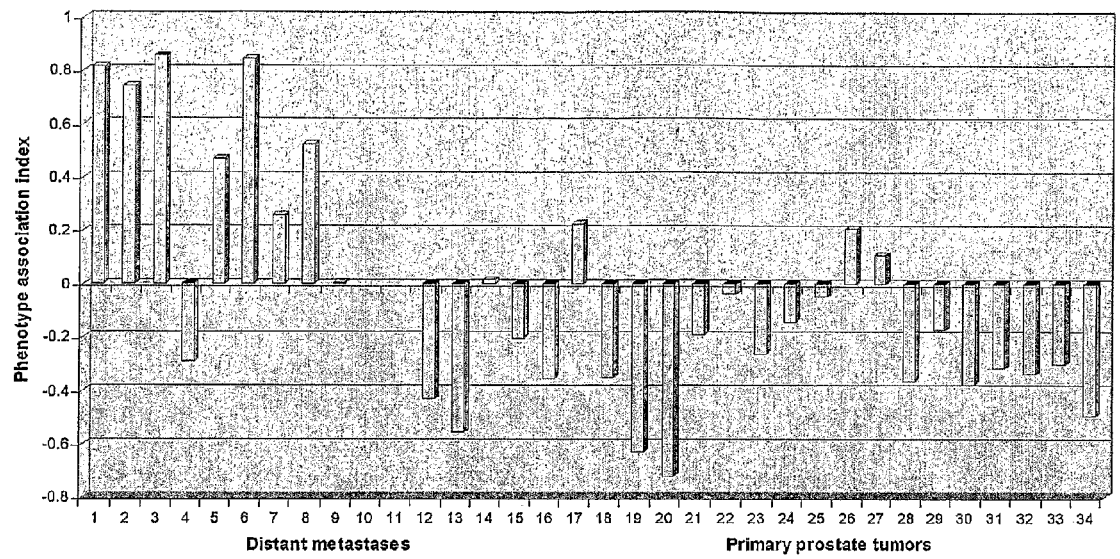
FIG. 3 is a graph showing an expression profile (depicted as a phenotype association index) of the 11-gene MTTS/PNS signature in metastatic lesions at multiple distant target organs and primary prostate carcinomas in human prostate cancer patients.
Figure 4:
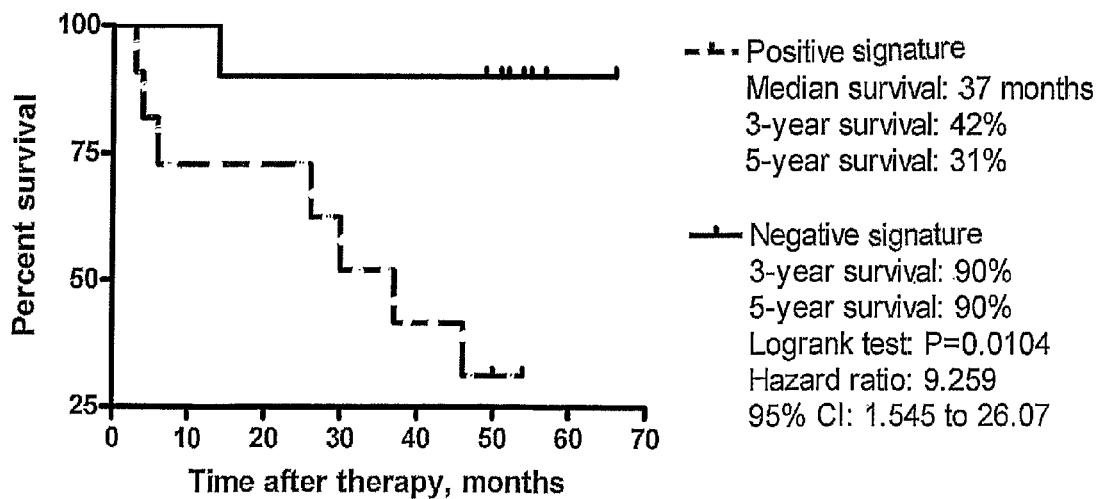
FIG. 4 is a graph showing Kaplan-Meier survival curves of prostate cancer patients with distinct expression profiles of the 11-gene MTTS/PNS signature.

Step 4. The small signatures identified in step 3 (one 11-gene signature for the PNS set, one 11-gene signature for the CNS set, and one 14-gene signature for the common PNS/CNS set) were tested for the power to discriminate the metastatic phenotype (using 1 mouse prostate cancer data set and 1 human prostate cancer data set comprising primary and metastatic tumors) and therapy-outcome classification performance (using human prostate cancer therapy outcome set 1). Three identified small signatures were evaluated for their ability to discriminate metastatic and primary prostate tumors in a TRAMP mouse model of prostate cancer, and clinical samples of 9 metastatic versus 23 primary prostate tumors as well as primary prostate tumors from 21 patients with distinct outcome after the therapy (8 recurrent and 13 nonrecurrent samples). To assess a potential diagnostic and prognostic relevance of small signatures, we calculated a Pearson correlation coefficient for each individual tumor sample by comparing the expression profiles of individual samples with the reference expression profile in either PNS or CNS neurospheres in BMI-1+/+ versus BMI-1−/− backgrounds. Fold expression changes in individual clinical samples were calculated for each gene as a ratio of the expression value in a given sample to the "average" expression value of the gene across the entire data set of clinical samples. For each data set, the vector (X) of average gene expression was determined, and then the relative expression vector (R) was determined for each sample (R=X/X). The relative expression vectors were log 10-transformed and correlated with the fixed vectors of gene expression determined in step 3. Negative expression values were treated as missing data. Based on the expected correlation of expression profiles of identified gene clusters with stem cell-like expression profiles, we named the corresponding correlation coefficients calculated for individual samples the SPAIs. We evaluated the prognostic power of identified small signatures based on their ability to discriminate metastatic versus primary tumors (criterion 1) and to segregate the patients with recurrent and nonrecurrent prostate tumors into distinct subgroups (criterion 2) and selected a single best-performing small signature for subsequent validation analysis (FIGS. 3 and 4). Based on diagnostic and prognostic classification performance, a single best-performing 11-gene MTTS/PNS signature was selected for further validation analysis.

Step 5. To assess the incremental statistical power of the individual genetic and clinical covariates as predictors of therapy outcome and unfavorable prognosis in prostate cancer patients, we performed both univariate and multivariate Cox proportional hazard survival analyses.

Step 6. To validate a survival prediction model based on the 11-gene MTTS/PNS signature, we tested the prognostic performance of the model in the multiple independent therapy-outcome data sets representing 5 epithelial and 5 nonepithelial cancers. We divided the patients within individual cohorts into a training set, which was used to select the cutoff threshold and to test the model, and a test set, which was used to evaluate the reproducibility of the classification performance. We used the training set to select the prognosis-discrimination cutoff value for a signature based on the highest level of statistical significance in patients' stratification into poor- and good-prognosis groups as determined by the log-rank test (lowest P value and highest hazard ratio in the training set). Clinical samples having the Pearson correlation coefficient at or higher than the cutoff value were identified as having the poor-prognosis signature. Clinical samples with the Pearson correlation coefficient below the cutoff value were identified as having the good-prognosis signature. Each training set was used to estimate a threshold of the correlation coefficients before a survival analysis was performed. The same discrimination cutoff value was then applied to evaluate the reproducibility of the prognostic performance in the test set of patients.

Lastly, we applied the model to the entire outcome set using the same cutoff threshold to confirm the classification performance. The average gene expression vectors were determined for each gene and applied separately on the training, test, and combined data sets. The training and test sets were balanced with respect to the total number of patients, negative and positive therapy outcomes, and the length of survival. For the breast cancer data set, we maintained the patients' distribution among training and test data sets described in the original publication. At this stage of the analysis, we did not carry out additional model training, development, or optimization steps, except for selection of a prognostic cutoff threshold in the training set. The same MTTS/PNS expression profile was consistently used throughout the study as a reference standard to quantify the Pearson correlation coefficients of the individual samples.

Step 7. We tested the model performance using various sample-stratification approaches, such as TRN clustering, SVM classification, and weighted survival score algorithm. We evaluated the therapy outcome-predictive power of the 11-gene model in a prostate cancer setting using a prognostic test based on an independent method of gene expression analysis, namely Q-RT-PCR.

Random Co-Occurrence Test.

We performed 10,000 permutations test to check how likely small 11-gene signatures derived from the large MTTS signature would display high discrimination power to assess the significance at the 0.1% level. We carried out 10,000 permutations of small 11-gene signatures derived from the large 1345-gene MTTS signature and compared their sample stratification power to the 11-gene MTTS/PNS signature. The classification performance cut-off p-values were established by applying two-tailed T-test to the 11-gene MTTS/PNS signature (p=0.0005 for metastasis versus primary prostate cancer data set and p=0.026 for recurrent versus non-recurrent prostate cancer data set). Random concordant gene sets comprising ~200 transcripts were generated using mouse transcriptome data set representing expression profiling data of ~12,000 transcripts across 45 normal tissues (55). Inter- and intra-species array to array probe set match was performed at 95% or greater identity level using the Affymetrix data base (www.affymetrix.com).

To assess discrimination of random 11-gene signatures derived from the 1345-gene MTTS signature two-tailed T-test was carried out for metastatic versus primary prostate cancer data set (32 samples) and recurrent versus non-recurrent prostate cancer data set (21 samples). The signatures were ranked based on p-values and ranking metrics of each random 11-gene signature were compared to the 11-gene MTTS/PNS signature p-values. We found that 10,000 permutations generated 7 random 11-gene signatures performing at sample classification level of the 11-gene MTTS/PNS signature.

Weighted Survival Predictor Score Algorithm

We implemented the weighted survival score analysis to reflect the incremental statistical power of the individual covariates as predictors of therapy outcome based on a multi-component prognostic model. Microarray-based or Q-RT-PCR-derived gene expression values were normalized and log-transformed. The log-transformed normalized expression values for each data set were analyzed in a multivariate Cox proportional hazards regression model, with overall survival or event-free survival as the dependent variable.

To calculate the survival/prognosis predictor score for each patient, we multiplied the log-transformed normalized gene expression value measured for each gene by a coefficient derived from the multivariate Cox proportional hazard regression analysis. The final survival predictor score comprises a sum of scores for individual genes and reflects the relative contribution of each of the eleven genes in the multivariate analysis. Negative weighting values indicate that higher expression correlates with longer survival and favorable prognosis, whereas positive weighting values indicate that higher expression correlates with poor outcome and shorter survival. Thus, the weighted survival predictor model is based on a cumulative score of the weighted expression values of eleven genes. Target siRNA SMART pools for BMI-1 and control luciferase siRNAs were purchased from Dharmacon Research, Inc. They were transfected into PC-3-32 human prostate carcinoma cells according to the manufacturer's protocols. Cell cultures were continuously monitored for growth and viability and assayed for mRNA expression levels of BMI-1 and selected set of genes using RT-PCR and Q-RT-PCR methods.

Quantitative RT-PCR Analysis

Real time PCR methods measure the accumulation of PCR products by a fluorescence detector system and allow for quantification of the amount of amplified PCR products in the log phase of the reaction. Total RNA was extracted using RNeasy mini-kit (Qiagen, Valencia, Calif., USA) following the manufacturer's instructions. A measure of 1 µg (tumor samples), or 2 µg and 4 µg (independent preparations of reference cDNA samples) of total RNA was used then as a template for cDNA synthesis with SuperScript II (Invitrogen, Carlsbad, Calif., USA). QPCR primer sequences were selected for each cDNA with the aid of Primer Express™ software (Applied Biosystems, Foster City, Calif., USA). PCR amplification was performed with the gene-specific primers listed in Tables 5 and 6 (described in detail below).

Q-PCR reactions and measurements were performed with the SYBR-Green and ROX as a passive reference, using the ABI 7900 HT Sequence Detection System (Applied Biosystems, Foster City, Calif., USA). Conditions for the PCR were as follows: one cycle of 10 min at 95° C.; 40 cycles of 0.20 min at 94° C.; 0.20 min at 60° C. and 0.30 min at 72° C. The results were normalized to the relative amount of expression of an endogenous control gene GAPDH.

Expression of messenger RNA (mRNA) for eleven genes and an endogenous control gene (GAPDH) was measured in twenty specimens of primary prostate cancer obtained from patients with documented PSA recurrence within five years after RP (radial prostatectomy) and patients who remained disease-free for at least five years after RP (ten patients in each group) by real-time PCR method on an ABI PRISM 7900 HT Sequence Detection System (Applied Biosystems). For each gene at least two sets of primers were tested and the set-up with highest amplification efficiency was selected for the assay used in this study. Specificity of the assay for mRNA measurements was confirmed by the absence of the expected PCR products when genomic DNA was used as a template. Glyceraldehyde-3-phosphate dehydrogenase (GAPDH: 5'-CCCTCAACGACCACTTTGTCA-3' (SEQ ID NO: 1) and 5'-TTCCTCTTGTGCTCTTGCTGG-3' (SEQ ID NO: 2)) was used as the endogenous RNA and cDNA quantity normalization control. For calibration and generation of standard curves, we used several reference cDNAs: cDNA prepared from primary in vitro cultures of normal human prostate epithelial cells (NPEC), cDNA derived from the PC-3M human prostate carcinoma cell line, and cDNA prepared from normal human prostate (NHP) (Glinsky, G. V., et al., Microarray analysis of xenograft-derived cancer cell lines representing multiple experimental models of human prostate cancer.

Molecular Carcinogenesis 200337:209-221 (Magee, J. A., et al., Expression profiling reveals hepsin overexpression in prostate cancer. Cancer Res. 2001, 61:5692-5696, incorporated by reference).

Expression analysis of all genes was assessed in two independent experiments using reference cDNAs to control for variations among different Q-RT-PCR experiments. Prior to statistical analysis, the normalized gene expression values were log-transformed similarly to the transformation of the array-based gene expression data.

Survival Analysis

Kaplan-Meier survival analysis was carried out using GraphPad Prism version 4.00 software (GraphPad Software, Diego, Calif.). The end point for survival analysis in prostate cancer was the biochemical recurrence defined by serum PSA increase after therapy. Disease-free interval (DFI) was defined as the time period between of radical prostatectomy (RP) and the date of PSA relapse (recurrence group) or date of last follow-up (non-recurrence group). Statistical significance of the difference between the survival curves for different groups of patients was assessed using Chi square and Log-rank tests. To evaluate the incremental statistical power of the individual covariates as predictors of therapy outcome and unfavorable prognosis, we performed both univariate and multivariate Cox proportional survival analyses.

Validation of Stemness Signatures in Predicting Clinical Outcome

Clinical Samples

We utilized in our experiments three independent sets of human primary prostate tumors and distant metastases comprising 132 tissue samples. Microarray analysis and associated clinical information for 32 clinical samples (23 primary tumors and 9 distant metastatic lesions) was utilized to delineate the expression profiles of human prostate cancer metastases were reported previously (11). Two clinical outcome sets comprising 21 (outcome set 1) and 79 (outcome set 2) were utilized for discovery and validation of the gene expression-based recurrence predictor algorithm. Original expression profiles of the 21 clinical samples (outcome set 1) analyzed in this study were reported elsewhere (Glinsky, al. Microarray analysis of xenograft-derived cancer cell lines representing multiple experimental models of human cancer. Molecular Carcinogenesis 2003, 37:209-221, incorporated herein by reference). Further detail regarding clinical samples and cell cultures used can be found in Glinsky, Gennadi V. et al, Microarray analysis identifies a death-from-cancer signature predicting therapy failure in patients with multiple types of cancer, J. Clin. Invest. 2005, 1:115(6):1503-1521 (incorporated by reference).

Orthotopic Xenografts

Orthotopic xenografts of human prostate PC-3 cells and sublines used in this study were developed by surgical orthotopic implantation as previously described (13). Briefly, $2 \times 10^6$ cultured PC3 cells, PC3M or PC3MLN4 sublines were injected subcutaneously into male athymic mice, and allowed to develop into firm palpable and visible tumors over the course of 2-4 weeks. Intact tissue was harvested from a single subcutaneous tumor and surgically implanted in the ventral lateral lobes of the prostate gland in a series of six athymic mice per cell line subtype. The mice were examined periodically for suprapubic masses, which appeared for all subline cell types, in the order PC3MLN4>PC3M>>PC3. Tumor-bearing mice were sacrificed by CO2 inhalation over dry ice and necropsy was carried out in a 2-4° C. cold room. Typically, bilaterally symmetric prostate gland tumors in the shape of greatly distended prostate glands were apparent. Prostate tumor tissue was excised and snap frozen in liquid nitrogen. The elapsed time from sacrifice to snap freezing was <5 min. A systematic gross and microscopic post mortem examination was carried out. Further detail regarding creation of the transgenic mouse model of prostate cancer, tissue processing for mRNA and RNA isolation, RNA and mRNA extraction, usage of Affymetrix arrays for mRNA quality control and gene expression, data analysis and survival analysis can be found in Glinsky, Gennadi V. et al, Microarray analysis identifies a death-from-cancer signature predicting therapy failure in patients with multiple types of cancer, J. Clin. Invest. 2005, 1:115(6):1503-1521 (incorporated by reference).

Data Analysis

Detailed protocols for data analysis and documentation of the sensitivity, reproducibility and other aspects of the quantitative statistical microarray analysis using Affymetrix technology have been reported (Baron, V., et al., Inhibition of Egr-1 expression reverses transformation of prostate cancer cells in vitro and in vivo. Oncogene 2003, 22:4194-4204, incorporated by reference). 40-50% of the surveyed genes were called present by the Affymetrix Microarray Suite 5.0 software in these experiments. The concordance analysis of differential gene expression across the data sets was performed using Affymetrix MicroDB v. 3.0 and DMT v.3.0 software as described earlier (11, 13). We processed the microarray data using the Affymetrix Microarray Suite v.5.0 software and performed statistical analysis of expression data set using the Affymetrix MicroDB and Affymetrix DMT software. This analysis identified a set of 218 genes (91 up-regulated and 127 down-regulated transcripts) differentially regulated in tumors from patients with recurrent versus non-recurrent prostate cancer at the statistically significant level ($p<0.05$) defined by both T-test and Mann-Whitney test. The concordance analysis of differential gene expression across the clinical and experimental data sets was performed using Affymetrix MicroDB v. 3.0 and DMT v.3.0 software as described earlier. See Id. The Pearson correlation coefficient for individual test samples and appropriate reference standard was determined using the Microsoft Excel and the GraphPad Prism version 4.00 software. We calculated the significance of the overlap between the lists of "stemness" and prostate cancer-associated genes by using the hypergeometrical distribution tests.

Example 1

11-Gene Signature for Predicting Clinical Outcome in Patients

BMI-1 Oncogene Expression is Elevated in Prostate Cancer

Recent experimental observations documented an increased BMI-1 expression in human non-small-cell lung cancer, human breast carcinomas, and established breast cancer cell lines, suggesting that an oncogenic role of the BMI-1 activation may be extended beyond the leukemia and, perhaps, may affect progression of the epithelial malignancies as well (Vonlanthen, S., et al. The BMI-1 oncoprotein is differentially expressed in non-small-cell lung cancer and correlates with INK4A-ARF locus expression. Br. J. Cancer 2001, 84:1372-1376; Dimri, G. P., et al. The BMI-1 oncogene induces telomerase activity and immortalizes human mammary epithelial cells. Cancer Res. 2002, 62:4736-4745; LaTulippe, E., et al., Comprehensive gene expression analysis of prostate cancer reveals distinct transcriptional programs associated with metastasis. Cancer Res. 2002, 62:4499-4506; Gingrich, J. R., et al., Metastatic prostate cancer in a transgenic mouse. Cancer Res. 1996, 56:4096-4102). Microarray gene expression analysis of established cancer cell lines representing multiple experimental models of human prostate cancer revealed that BMI-1 expression seems to be consistently elevated in human prostate cancer cell lines established from metastatic tumors (carcinoma cell lines used in this example were PC-3, DuCapL, DuCapR, Vcap, LNCap, PRO5, and LN3) compared to the primary cultures of human normal prostate epithelial cells (NPEC), as illustrated in FIG. 1 (Magee, J. A., et al., Expression profiling reveals hepsin overexpression in prostate cancer. Cancer Res. 2001, 61:5692-5696, incorporated by reference). To validate the results of the microarray experiments, quantitative reverse transcription-polymerase chain reaction (Q-RT-PCR) analysis of BMI-1 mRNA expression was used, as shown in Table 1 below (showing the carcinoma cell lines for which expression was analyzed, and the average expression value, standard deviation, and P values for each).

TABLE 1

Q-RT-PCR analysis of the BMI-1 mRNA expression in human prostate carcinoma cell lines

| Cell line | Average Expression Value[1] | STDEV | P value[2] |
| --- | --- | --- | --- |
| NPEC | 0.090656645 | 0.0154152 | |
| LNCap | 0.216610094 | 0.0311867 | 0.0013481 |
| LNCapPro5 | 0.292913482 | 0.0222714 | 1.472E−05 |
| LNCapLN3 | 0.235569094 | 0.0429103 | 0.0038571 |
| PC-3 | 1.030811318 | 0.1271548 | 0.000586 |
| PC-3LN4 | 0.635668126 | 0.0892679 | 0.0009314 |
| PC-3Pro4 | 1.424229109 | 0.1758348 | 0.0005788 |
| VCAP | 0.192483261 | 0.012621 | 6.494E−05 |
| DUCAP | 0.128637764 | 0.012266 | 0.0092371 |

[1]Normalized average expression value from four measurements
[2]Two-tailed T-test compared to the NPEC Thus, results of expression profiling experiments appear to support the notion that transcriptional activation of the BMI-1 gene is frequently associated with human prostate cancer.

Interestingly, microarray analysis shows markedly higher BMI-1 expression levels in lymph node metastases and highly metastatic orthotopic xenografts of human prostate carcinoma in nude mice compared to the less metastatic counterparts, implying that BMI-1 activation might be associated with aggressive malignant behavior of prostate carcinoma cells. To test this hypothesis, expression profiling analysis of ~12,000 transcripts in a transgenic mouse model of metastatic prostate cancer was carried out. Microarray experiments detected increased levels of the BMI-1 mRNA expression in late-stage invasive primary tumors and multiple distant metastatic lesions in the TRAMP transgenic mouse model of prostate cancer, thus, lending more credence to the idea linking the activation of BMI-1-associated pathway with prostate cancer metastasis.

Identification of a BMI-1 Pathway Signature with Concordant Expression Profiles in Normal Stem Cells and Distant Metastatic Lesions in a Transgenic Mouse Model of Prostate Cancer Recent experiments established that the BMI-1 gene is required for self-renewal of hematopoietic and neural stem cells and identified BMI-1-regulated genes in neural stem cells that are presumably engaged in an execution of self-renewal programs in a state of both central nervous system (CNS) and peripheral nervous system (PNS) neurospheres (Lessard, J. and Sauvageau, G. BMI-1 determines the proliferative capacity of normal and leukaemic stem cells. Nature 2003, 423:255-260; Park, I.-K., et al., BMI-1 is required for maintenance of adult self-renewing haematopoietic stem cells. Nature 2003, 423:302-305; Molofsky, A. V., et al., BMI-1 dependence distinguishes neural stem cell self-renewal from progenitor proliferation, Nature 2003, 425:962-967, each incorporated herein by reference). It was hypothesized that molecular signatures associated with activation of a normal stem cells' self-renewal program in metastatic cancer cells might be possible to detect by looking for genes manifesting concordant patterns of regulation in metastasis and normal stem cells in BMI-1$^{+/+}$ versus BMI-1$^{-/-}$ genetic backgrounds. Therefore, a determination was made regarding whether expression profiles of transcripts activated and suppressed in prostate cancer metastases would recapitulate the expression profile of the BMI-1-regulated genes in normal stem cells by comparing the sets of differentially regulated genes in search for union/intersections of lists for both up- and down-regulated transcripts. This analysis identified genes exhibiting highly concordant profiles of transcript abundance behavior in prostate cancer metastases and BMI-1$^{+/+}$ versus BMI-1$^{-/-}$ PNS neurospheres, suggesting the presence of a conserved BMI-1-regulated pathway(s) similarly engaged in both normal stem cells and distant metastatic lesions of prostate carcinoma.

1) Identification of Parent Signatures

Transgenic mouse models of prostate cancer (TRAMP) were used in these experiments. The metastatic TRAMP tumor samples (MTTS) signature is likely to be enriched for genes discriminative for the metastatic phenotype. It is reasonable to assume that many of the gene expression patterns wired into the MTTS signature would manifest metastatic phenotype discriminative power and would have no relation to the transcriptional program of normal stem cells. These features of the MTTS signature were used for identification of the gene expression components of a stem cell transcriptome that are coordinately expressed in metastatic cancer cells and might manifest discriminative diagnostic power for the malignant phenotype. Sets of differentially regulated transcripts were independently identified for distant metastatic lesions and primary prostate tumors versus age-matched control samples in a transgenic TRAMP mouse model of metastatic prostate cancer (MTTS signature) as well as PNS (PNS signature) and CNS(CNS signature) neurospheres in BMI-1$^{+/+}$ versus BMI-1$^{-/-}$ backgrounds. This analytical step defined three large parent signatures: MTTS signature comprising 868 up-regulated and 477 down-regulated transcripts; PNS signature comprising 885 up-regulated and 1088 down-regulated transcripts; and CNS signature comprising 769 up-regulated and 778 down-regulated transcripts.

2) Identification of Concordant Sub-Sets of Genes (Child Signatures)

The MTSS signature was intersected with the stem cell signatures in the state of PNS and CNS neurospheres to identify concordant sets of genes and define the stem cell signatures embedded into MTSS signature. Sub-sets of transcripts exhibiting concordant expression changes in metastatic TRAMP tumor samples (MTTS signature) as well as PNS (PNS signature) and CNS(CNS signature) neurospheres in BMI-1$^{+/+}$ versus BMI-1$^{-/-}$ backgrounds were identified. Thus, two concordant sub-sets of transcripts were identified corresponding to each binary comparison of metastatic TRAMP tumors and neural stem cell samples in a state of PNS and CNS neurospheres [141 up-regulated and 58 down-regulated transcripts for PNS neurospheres (r=0.7593; P<0.0001) and 40 up-regulated and 24 down-regulated for CNS neurospheres (r=0.7679; P<0.0001)]. A third concordant sub-set of 27 genes comprising 15 up-regulated and 12 down-regulated transcripts was selected for intersection common for all three signatures (r=0.8002; P<0.0001). Thus, three concordant sub-sets of genes were identified.

This analysis also identified a stem cell-like expression profile for transcripts coordinately expressed in metastatic cancer cells and normal stem cells which can be used as a consistent reference standard to interrogate independent data sets for possible presence of a stem cell-like expression signature. From these concordant gene sets, we selected smaller gene expression signatures (e.g., 11 or 14 gene sets) comprising transcripts with high level of expression correlation in metastatic cancer cells and stem cells (the selection threshold for smaller signatures was arbitrarily set at Pearson correlation coefficients>0.95). The reduction in the signature transcript number was terminated when further elimination of a transcript did not increase the value of the Pearson correlation coefficient. Using this approach a single candidate prognostic gene expression signature was selected for each binary intersection of the MTTS signature and parent stem cell signatures. The smaller child signatures (one 11-gene signature for the PNS set, one 11-gene signature for the CNS set, and one 14-gene signature for common PNS/CNS set) were tested for metastatic phenotype discriminative power and therapy outcome classification performance. As one example, the gene set for the 11-gene signature for the PNS set (the 11-gene MTTS/PNS signature) is shown below in Table 2.

TABLE 2

The 11-gene MTTS/PNS signature

| GENE | Affymetrix HG-U95Av2 probe set | Affymetrix HG-U133A probe set | Affymetrix MG-U74A probe set | UniGene (*Homo sapiens*) | Unigene (*Mus Musculus*) | GenBank | SEQ ID NO: (nucleotide) | SEQ ID NO: (nucleotide) |
|---|---|---|---|---|---|---|---|---|
| GBX2 | 33688_at | 210560_at | 94200_at | Hs.184945 | Mm.2047308 | Z48800 | 33 (*Home sapiens*) 35 (*Mus musculus*) | 34 (*Home sapiens*) 36 (*Mus musculus*) |
| MKI67 | 418_at | 212022_s_at | 99457_at | Hs.80976 | Mm.4078 | X82786 | 37 (*Home sapiens*) 39 (*Mus musculus*) | 38 (*Home sapiens*) 40 (*Mus musculus*) |
| CCNB1 | 34736_at | 214710_s_at | 160159_at | Hs.23960 | Mm.379450 | X64713 | 41 (*Home sapiens*) 43 (*Mus musculus*) | 42 (*Home sapiens*) 44 (*Mus musculus*) |
| BUB1 | 41081_at | 216277_at | 104097_at | Hs.469649 | Mm.2185 | AF002823 | 45 (*Home sapiens*) 47 (*Mus musculus*) | 46 (*Home sapiens*) 48 (*Mus musculus*) |
| KNTC2 | 40041_at | 204162_at | 93441_at | Hs.414407 | Mm.225956 | AI595322 | 49 (*Home sapiens*) 51 (*Mus musculus*) | 50 (*Home sapiens*) 52 (*Mus musculus*) |
| USP22 | 39866_at | 216964_at | 97960_at | Hs.462492 | Mm.30602 | AW125800 | 53 (*Home sapiens*) 55(*Mus musculus*) | 54 (*Home sapiens*) 56 (*Mus musculus*) |
| HCFC1 | 37910_at | 202473_x_at | 100901_at | Hs.83634 | Mm.248353 | U80821 | 57 (*Home sapiens*) 59 (*Mus musculus*) | 58 (*Home sapiens*) 60 (*Mus musculus*) |
| RNF2 | 33484_at | 205215_at | 93164_at | Hs.124186 | Mm.31512 | Y12783 | 61 (*Home sapiens*) 63 (*Mus musculus*) | 62 (*Home sapiens*) 64 (*Mus musculus*) |
| ANK3 | 36967_g_at | 209442_x_at | 98477_s_at | Hs.499725 | Mm.235960 | L40632 | 65 (*Home sapiens*) 67 (*Mus musculus*) | 66 (*Home sapiens*) 68 (*Mus musculus*) |
| FGFR2 | 1143_s_at | 208228_s_at | 93090_at | Hs.533683 | Mm.16340 | M23362 | 69 (*Home sapiens*) 71 (*Mus musculus*) | 70 (*Home sapiens*) 72 (*Mus musculus*) |
| CES1 | 37203_at | 209616_s_at | 101538_i_at | Hs.558865 | Mm.22720 | AW226939 | 73 (*Home sapiens*) 75 (*Mus musculus*) | 74 (*Home sapiens*) 76 (*Mus musculus*) |

Based on diagnostic and prognostic classification performance, a single best performing 11-gene MTTS/PNS signature was selected for further validation analysis. Based on the information provided in Table 2 above, one of ordinary skill in the art would recognize that further information about these genes is available from numerous sources, such as the National Center for Biotechnology (e.g., by selecting "Gene" from the search window drop down menu for selection of databases to search and by conducting a search for the gene name (e.g., GBX2)). Exemplary cDNA and protein sequences for the genes shown in Table 2 are included in the Sequence Listing included herewith as indicated in the table. In some embodiments the sequence used in the methods and kits of the invention comprises a sequence that has at least 90%, at 91%, at least 92%, at least 93%, at least 94%, at least 95%, at least 96%, at least 97%, at least 98%, or at least 99% identity to the exemplified sequence included in the Sequence Listing.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

3) Malignant Phenotype Classification Performance Tests

Figure 2:
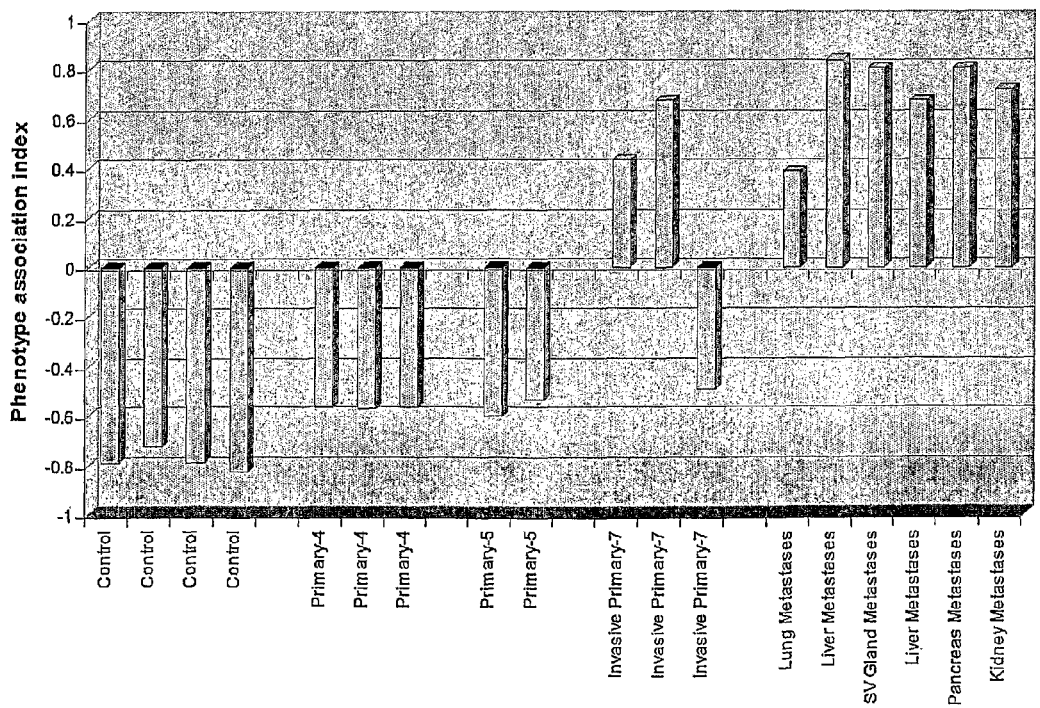
FIG. 2 is a graph showing an expression profile (depicted as a phenotype association index) of the 11-gene MTTS/PNS signature in metastatic lesions at multiple distant target organs and primary prostate carcinomas in the TRAMP transgenic mouse model of prostate cancer.

During the malignant phenotype classification performance tests, we asked whether individual metastatic lesions and primary prostate tumors would exhibit the stem cell-like expression profile of the candidate prognostic signatures. We selected for this analysis three small signatures demonstrating the most significant correlation of expression profiles in stem cells and prostate cancer metastasis. To assess a degree of similarity of the signature expression profiles in individual tumor samples and normal stem cells, we calculated a Pearson correlation coefficient for each sample by comparing signature expression profile in an individual sample to the stem cell-associated expression profile of the corresponding small signatures. Based on expected similarity of the prognostic signatures in stem cells and prostate cancer metastasis, we named the corresponding Pearson correlation coefficients measured for individual samples the stem cell-like phenotype association indices (SPAIs). As shown in FIG. 2, which illustrates the expression profile for one of the signatures, two of three late-stage invasive primary tumors and all distant metastatic lesions in the TRAMP transgenic mouse model of prostate cancer have positive SPAIs, thus, manifesting a stem cell-like expression profile of the small signatures.

Distant Metastatic Lesions and Primary Prostate Tumors from Cancer Patients with Differing Therapy Outcome Display Distinct Expression Profiles of the 11-Gene MTTS/PNS Signature To perform similar analysis for human tumors, we translated the murine small signatures into list of human homologs using the Locuslink database and retrieved the expression data for corresponding Affymetrix probe sets. We calculated the SPAIs for each of 9 metastatic tumors and 23 primary prostate carcinomas and determined that seven of nine samples of distant metastatic lesions from prostate cancer patients exhibit a stem cell-like expression profile of the 11-gene MTTS/PNS signature, as illustrated in FIG. 3. In contrast, a majority of primary prostate tumors seem to display a distinct expression profile of the 11-gene MTTS/PNS signature as manifested in negative values of SPAIs). Interestingly, a sub-set of samples of primary prostate carcinomas manifests expression profiles of the 11-gene MTTS/PNS signature similar to the metastatic tumors as reflected in positive correlation coefficients (positive SPAI values in FIG. 3), suggesting that primary prostate tumors with distinct expression profiles of the PNS neurosphere-derived 11-gene MTTS/PNS signature (e.g., positive and negative values of SPAIs) may have different biological features and distinct clinical course of disease progression. Validation analysis using the CNS neurosphere-derived MITS/CNS 11-gene signature and MTTS/PNS/CNS 14-gene signature indicates that application of these signatures is less informative in distinguishing metastatic and primary human prostate tumors in comparison to the MTTS/PNS 11-gene signature. Thus, we proceeded in our analyses with the MTTS/PNS 11-gene signature.

1) Evaluation of the Clinical Utility of the 11-Gene MTTS/PNS Signature

To evaluate the potential biological significance and clinical utility of the 11-gene MTTS/PNS signature expression in human prostate cancer, we set out to examine whether the detection of a stem cell-like expression profile in primary prostate tumors of individual cancer patients would help in patient's stratification at the time of diagnosis into sub-groups with distinct course of disease progression based on differing therapy outcome after radical prostatectomy. We assessed the prognostic power of the 11-gene MTTS/PNS signature based on ability to segregate the patients with recurrent and non-recurrent course of disease progression after radical prostatectomy into distinct sub-groups. We calculated a Pearson correlation coefficient for each of 21 tumor samples of outcome set 1 by comparing the 11-gene MTTS/PNS signature expression profiles of individual samples to the stem cell-like expression profile of the 11-gene MTTS/PNS signature in PNS neurospheres. To determine the prognostic power of the 11-gene MTTS/PNS signature, we performed Kaplan-Meier survival analysis using as a clinical end-point disease-free interval (DFI) after therapy in prostate cancer patients with positive and negative SPAIs.

The Kaplan-Meier survival curves showed a highly significant difference in the probability that prostate cancer patients would remain disease-free after therapy between the groups with positive and negative SPAIs defined by the 11-gene MTTS/PNS signature, suggesting that patients with positive SPAIs exhibit a poor outcome signature whereas patients with negative SPAIs manifest a good outcome signature. As illustrated in FIG. 4, the estimated hazard ratio for disease recurrence after therapy in the group of patients with positive SPAIs as compared with the group of patients with negative SPAIs defined by the 11-gene MTTS/PNS signature was 9.259 (95% confidence interval of ratio, 1.545 to 26.07; P=0.0104). 58% of patients with the positive SPAIs had a disease recurrence within 3 years after therapy, whereas 90% of patients with the negative SPAIs remained relapse-free. Five-year after therapy, 69% of patients with the positive SPAIs had a disease recurrence, whereas 90% of patients with the negative SPAIs remained relapse-free. Based on this analysis, we proposed to identify the group of prostate cancer patients with positive values of the PNS neurosphere-derived 11-gene MTTS/PNS signature as a poor prognosis group and the group of prostate cancer patients with negative values of the 11-gene MTTS/PNS signature as a good prognosis group.

2) Further Analysis of the 11-Gene MTTS/PNS Signature

The identified signature genes were defined based on a strong correlative behavior in multiple independent sets of experimental and clinical samples obtained from two species (mice and human). To test by independent methods the suspected association of the expression of BMI-1-pathway target genes with the expression of the BMI-1 gene product in the context of human cancer cells, we subjected human prostate carcinoma cells to the siRNA-mediated silencing of expression of the endogenous BMI-1 gene. The PC-3-32 human prostate carcinoma cells were transfected with BMI-1 or control siRNAs and continuously monitored for mRNA expression levels of BMI-1 and selected set of genes using RT-PCR and Q-RT-PCR methods (data not shown). RT-PCR and Q-RT-PCR analyses showed that the employed siRNA-mediated BMI-1-silencing protocol allowed for ~90% inhibition of the endogenous BMI-1 mRNA expression. We validated the effect of siRNA-mediated BMI-1 silencing at the BMI-1 protein expression level using immunofluorescent analysis. The BMI-1 silencing was specific since the expression levels of nine un-related transcripts (such as GAPDH, EZH2, and several other genes) were not altered (data not shown). Consistent with the hypothesis that expression of genes comprising the 11-gene MTTS/PNS signature is associated with the expression of the BMI-1 gene product, mRNA abundance levels of 8 of 11 interrogated BMI-1-pathway target genes were altered in the human prostate carcinoma cells with ~90% silenced BMI-1 gene.

Reduction of the BMI-1 mRNA and protein expression in human prostate carcinoma metastasis precursor cells did not alter significantly the viability of adherent cultures grown at the optimal growth condition and in serum starvation experiments (data not shown) and had only modest inhibitory effect on proliferation (~25-30% reduction in the number of cells during the 3-day silencing protocol). However, the ability of human prostate carcinoma cells to survive in non-adherent state was severely affected after siRNA-mediated reduction of the BMI-1 expression. Fluorescence activated cell sorting (FACS) analysis revealed ~3-fold increase of apoptosis in the BMI-1 siRNA-treated human prostate carcinoma cells cultured in non-adherent conditions. These data suggest that human prostate carcinoma cells expressing high level of the BMI-1 protein are more resistant to apoptosis induced in cells of epithelial origin in response to attachment deprivation (anoikis) and, perhaps, would survive better in blood during metastatic dissemination thus forming a pool of circulatory stress-surviving metastasis precursor cells. Further detail regarding identification of molecular signatures, usage of Pearson coefficients, the Kaplan-Meier survival analysis, and other methods described above is provided in pending U.S. patent application Ser. No. 10/861,003, filed Jun. 3, 2004, and pending U.S. patent application Ser. No. 10/660,434, filed Sep. 10, 2003, both of which are hereby incorporated by reference in their entireties.

Expression of the 11-Gene MTTS/PNS Signature in Primary Prostate Tumors is a Predictor of a Therapy Failure in Prostate Cancer Patients To validate a survival prediction model based on the 11-gene MTTS/PNS signature, we tested the prognostic performance of the model in the multiple independent therapy outcome data sets representing five epithelial and five non-epithelial cancers. We divided patients within individual cohorts into a training set, which was used for the cutoff threshold selection and to test the model, and a test set, which was used to evaluate the reproducibility of the classification performance. Using the training set of samples, we selected the prognosis discrimination cut-off value for a signature based on highest level of statistical significance in patient's stratification into poor and good prognosis groups as determined by the log-rank test (lowest P value and highest hazard ratio in the training set). Clinical samples having the Pearson correlation coefficient at or higher than the cut-off value were identified as having the poor prognosis signature. Clinical samples with the Pearson correlation coefficient lower than the cut-off value were identified as having the good prognosis signature. The same discrimination cut off value was then applied to evaluate the reproducibility of the prognostic performance in the test set of patients. Lastly, we applied the model to the entire outcome set using the same cut off threshold to confirm the classification performance. The training and test sets were balanced with respect to the total number of patients, negative and positive therapy outcomes, and the length of survival. We would like to point out that at this stage of the analysis, we did not carry out additional model training, development or optimization steps, except for selecting the prognostic cut off threshold using the training set. We consistently used throughout the study the same MTTS/PNS expression profile as a reference standard to quantify the Pearson correlation coefficients of the individual samples.

In addition to this analysis, we confirmed the model performance using various sample stratification approaches such as terrain (TRN) clustering, support vector machine (SVM) classification, and weighted survival score algorithm. Finally, we evaluated the therapy outcome predictive power of the 11-gene model in prostate cancer setting using a prognostic test based on an independent method of gene expression analysis, namely quantitative reverse-transcription polymerase chain reaction (Q-RT-PCR) method.

Figure 5:
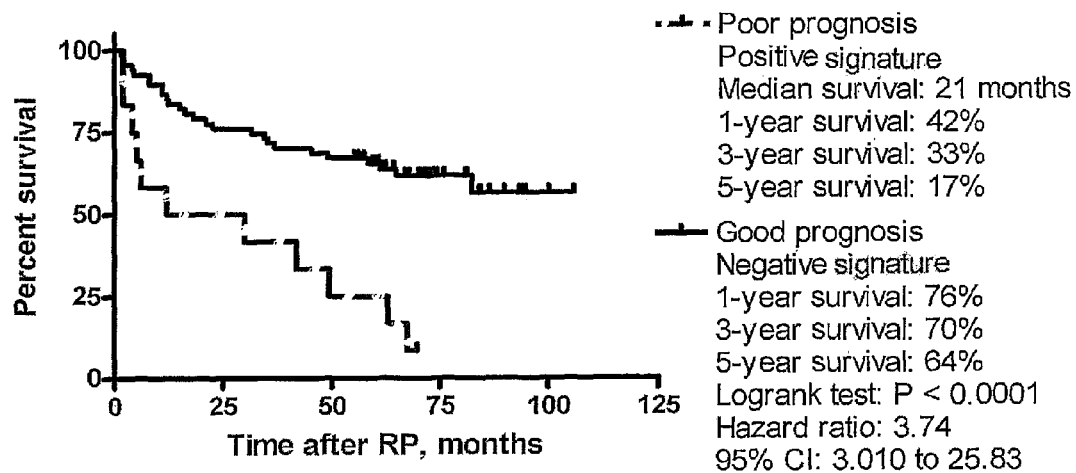
FIG. 5 is a graph showing Kaplan-Meier relapse-free survival curves of prostate cancer patients with distinct expression profile of the 11-gene MTTS/PNS signature. RP, radical prostatectomy.

To further validate the potential clinical utility of the 11-gene MTTS/PNS signature, we evaluated the prognostic power of the 11-gene MTTS/PNS signature applied to an independent set of 79 clinical samples (prostate cancer outcome set 2) obtained from 37 prostate cancer patients who developed recurrence after the therapy and 42 patients who remained disease-free. In this cohort of patients, the Kaplan-Meier survival analysis demonstrated a highly significant difference in the probability that prostate cancer patients would remain disease-free after therapy between the groups with positive and negative SPAIs defined by the 11-gene MTTS/PNS signature. As illustrated in FIG. 5, the estimated hazard ratio for disease recurrence after therapy in the group of patients with positive SPAIs as compared with the group of patients with negative SPAIs defined by the 11-gene MTTS/PNS signature was 3.74 (95% confidence interval of ratio, 3.010 to 25.83; P<0.0001). 67% of patients with the positive SPAIs had a disease recurrence within 3 years after therapy, whereas 70% of patients with the negative SPAIs remained relapse-free. Five-years after therapy, 83% of patients with the positive SPAIs had a disease recurrence, whereas 64% of patients with the negative SPAIs remained relapse-free.

The standard Kaplan-Meier log-rank statistic assesses the difference in the survival curves, however, it does not account for multiple hypothesis testing and random co-occurrence representing inherent problems of gene expression profiling experiments. In part, we attempted to mitigate this problem by using an alternative biological end-point to the patients' survival during the signature selection process and by applying the survival analysis to a single signature, thus eliminating the multiple comparisons from the survival model building protocol. The MTTS signature is likely to carry many gene expression patterns displaying metastatic phenotype discriminative power that has no relation to the transcriptional program of normal stem cells. One of our main goals was to identify the stem cell signature that is associated with the pluripotency self-renewal phenotype and is embedded into MTTS signature. This approach implies that a candidate marker signature would have a defined stem cell-like expression profile that can be used in the subsequent follow-up validation analyses as a reference standard to look for expression of a stem cell-like signature in clinical samples.

To further assess the statistical validity of the 11-gene stem cell-like profile, we performed 1000 random permutations of the 11-gene stem cell profiles randomly selected from the 1973-gene PNS signature. For each random 11-gene stem cell profile we assessed its metastatic phenotype discriminative performance in the TRAMP transgenic mouse model at the discriminative confidence levels of the 11-gene BMI-1-pathway MTTS/PNS signature. Only one random 11-gene stem cell profile of the 1000 permutations demonstrated classification power matching the metastatic phenotype discriminative performance of the 11-gene MTTS/PNS signature. We performed 10,000 permutations test to check how likely small 11-gene signatures derived from the large MTTS signature would display high discrimination power to assess the significance at the 0.1% level. We carried out 10,000 permutations of small 11-gene signatures derived from the large 1345-gene MTTS signature and compared their sample stratification power to the 11-gene MTTS/PNS signature. The classification performance cut-off p-values were established by applying two-tailed T-test to the 11-gene MTTS/PNS signature (p=0.0005 for metastasis versus primary prostate cancer data set and p=0.026 for recurrent versus non-recurrent prostate cancer data set). We found that 10,000 permutations generated 7 random 11-gene signatures performing at sample classification level of the 11-gene MTTS/PNS signature.

Cox Proportional Hazards Survival Regression Analysis

To ascertain the incremental statistical power of the individual covariates as predictors of therapy outcome and unfavorable prognosis, we performed both univariate and multivariate Cox proportional hazard survival analyses. Several individual gene members of the 11-gene MTTS/PNS signature, such as MKI67 and CCNB1, have been described previously as significant predictors of prognosis and may reflect correlation between proliferative fraction and poor therapy outcome as it has been shown recently for the lymphoma survival predictor signature. However, our analysis appears to indicate that the 11-gene MTTS/PNS signature is a more uniform therapy outcome predictor across the multiple data sets compared to the individual genes (see below) and, perhaps, is a better "integrator" and "sensor" of the biological diversity across the spectrum of human cancers. We performed both univariate and multivariate Cox proportional hazard survival analyses to compare the prognostic performance of the entire stemness signature and individual genes. The results of these analyses are shown in Tables 3 and 4, below.

TABLE 3

Cox Proportional Hazard Survival Regression Analysis

| Covariates | Statistics | Remarks |
|---|---|---|
| Prostate Cancer | | |
| GBX2 | Chi Square = 1.5817; df = 1; p = 0.2085 | |
| MKI67 | Chi Square = 9.9016; df = 1; p = 0.0017 | |
| CCNB1 | Chi Square = 0.1370; df = 1; p = 0.7113 | |
| BUB1 | Chi Square = 0.9193; df = 1; p = 0.3377 | |
| KNTC2 | Chi Square = 2.3450; df = 1; p = 0.1257 | |
| USP22 | Chi Square = 0.1376; df = 1; p = 0.7106 | |
| HCFC1 | Chi Square = 2.2379; df = 1; p = 0.1347 | |
| RNF2 | Chi Square = 1.6235; df = 1; p = 0.2026 | |
| ANK3 | Chi Square = 8.9237; df = 1; p = 0.0028 | |
| FGFR2 | Chi Square = 7.7985; df = 1; p = 0.0052 | |
| CES1 | Chi Square = 9.3565; df = 1; p = 0.0022 | |
| Signature | Chi Square = 3.9990; df = 1; p = 0.0455 | |
| 5 Covariates | Chi Square = 26.6628; df = 5; p = 0.0001 | Signature + 4 genes |
| 6 Covariates | Chi Square = 26.9003; df = 6; p = 0.0002 | Signature + 5 genes |
| 11 Covariates | Chi Square = 26.9684; df = 11; p = 0.0046 | 11 genes |
| 12 Covariates | Chi Square = 29.2850; df = 12; p = 0.0036 | Signature + 11 genes |
| 11 Covariates | Chi Square = 50.7039; df = 11; p = 0.0000 | Signature + 4 genes + 6 clinical |
| Breast Cancer | | |
| GBX2 | Chi Square = 0.0021; df = 1; p = 0.9631 | |
| MKI67 | Chi Square = 3.7357; df = 1; p = 0.0533 | |
| CCNB1 | Chi Square = 4.6430; df = 1; p = 0.0312 | |
| BUB1 | Chi Square = 10.4330; df = 1; p = 0.0012 | |
| KNTC2 | Chi Square = 15.6837; df = 1; p = 0.0001 | |
| USP22 | Chi Square = 0.5386; df = 1; p = 0.4630 | |
| HCFC1 | Chi Square = 0.7418; df = 1; p = 0.3891 | |
| RNF2 | Chi Square = 0.0360; df = 1; p = 0.8495 | |
| ANK3 | Chi Square = 2.5573; df = 1; p = 0.1098 | |
| FGFR2 | Chi Square = 0.2834; df = 1; p = 0.5945 | |
| CES1 | Chi Square = 0.0477; df = 1; p = 0.8272 | |
| Signature | Chi Square = 7.1372; df = 1; p = 0.0076 | |
| 4 Covariates | Chi Square = 16.4355; df = 4; p = 0.0025 | Signature + 3 genes |
| 5 Covariates | Chi Square = 16.7995; df = 5; p = 0.0049 | Signature + 4 genes |
| 11 Covariates | Chi Square = 28.7740; df = 11; p = 0.0025 | 11 genes |
| 12 Covariates | Chi Square = 29.3656; df = 12; p = 0.0035 | Signature + 11 genes |

TABLE 4

11 covariates prostate cancer recurrence predictor model

| Covariates | Coefficients | Std Errors | Significance, p | Confidence Intervals, Lo95% | Confidence Intervals, Hi95% |
|---|---|---|---|---|---|
| Signature | −2.3537 | 0.9858 | 0.0170 | −4.2858 | −0.4215 |
| MKI67 | 2.2832 | 0.7823 | 0.0035 | 0.7499 | 3.8166 |
| ANK3 | −0.1563 | 0.7197 | 0.8280 | −1.5670 | 1.2543 |
| FGFR2 | −0.8295 | 0.4955 | 0.0941 | −1.8007 | 0.1418 |
| CES1 | −1.6403 | 0.8113 | 0.0432 | −3.2303 | −0.0502 |
| PRE RP PSA | 0.0493 | 0.0251 | 0.0495 | 0.0001 | 0.0985 |
| RP GLSN SUM | 0.2850 | 0.2385 | 0.2322 | −0.1825 | 0.7525 |
| SM | 1.0609 | 0.4648 | 0.0225 | 0.1499 | 1.9720 |
| Sem Ves Inv | 0.6016 | 0.5064 | 0.2348 | −0.3909 | 1.5941 |

TABLE 4-continued 11 covariates prostate cancer recurrence predictor model

| Covariates | Coefficients | Std Errors | Significance, p | Confidence Intervals, Lo95% | Confidence Intervals, Hi95% |
|---|---|---|---|---|---|
| AGE | 0.0311 | 0.0351 | 0.3755 | −0.0377 | 0.0999 |
| ECE | 0.9296 | 0.4360 | 0.0330 | 0.0751 | 1.7842 |

RP, radical prostatectomy;
PSA, prostate specific antigen;
SM, surgical margins;
GLSN SUM, Gleason sum;
Sem Ves Inv, seminal vesicle invasion;
ECE, extracapsular extension.

In the univariate analysis prognostic performance of MKI67 expression as a predictor of therapy outcome varied in different outcome data sets. It was highly significant in the prostate cancer therapy outcome set 2 (MSKCC data set); however, it showed only a trend toward statistical significance in the prostate cancer outcome set 1 (P=0.1; MIT data set) and breast cancer outcome data set (P=0.0533). In prostate cancer, the significant prognosis predictors in univariate Cox regression analysis were MKI67, ANK3, FGFR2, CES1, and the 11-gene MTTS/PNS signature. In breast cancer, the significant prognosis predictors in univariate analysis were CCNB1, BUB1, KNTC2, and the 11-gene MTTS/PNS signature. Thus, our analysis seems to indicate that individual genes demonstrate a variable performance across multiple outcome data sets and we were unable to identify a single gene uniformly predictive of the poor therapy outcome.

In the multivariate analysis, the most significant prostate cancer recurrence predictor was the model that included 11 covariates [11-gene signature, four individual genes (MKI67; ANK3; FGFR2; CES1); and six clinico-pathological features (pre RP Gleason sum; surgical margins; seminal vesicle invasion; age; and extra-capsular extension)]. Interestingly, several covariates such as the 11-gene MTTS/PNS signature, MKI67, CES1, pre RP PSA level, surgical margins, and extra capsular extension remained statistically significant prognostic markers in the multivariate analysis. Thus, while prognostic performance of individual gene members of the 11-gene MTTS/PNS signature varied greatly in different outcome data sets, the identified 11-gene MTTS/PNS signature seems to perform as the most consistent predictor of poor therapy outcome across multiple independent outcome data sets comprising over 1,000 clinical samples and representing ten distinct types of human cancer (see below). Yet statistically the best-performing multivariate cancer type-specific model seems to require a combination of calls based on expression levels of individual genes, a gene expression signature, and clinico-pathological covariates.

Figure 6:
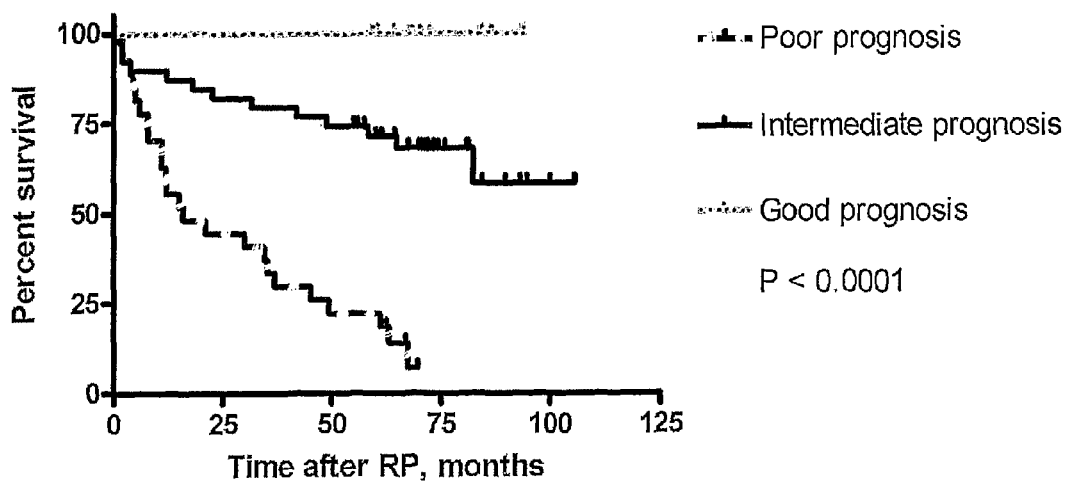
FIG. 6 is a graph showing the Kaplan-Meier survival curves for 79 prostate cancer patients stratified into distinct sub-groups using a weighted survival predictor score algorithm.

We sought to use an alternative statistical metric to further evaluate the prognostic power of the genes comprising the 11-gene MTTS/PNS signature. We implemented the weighted survival score analysis to reflect the incremental statistical power of the individual covariates as predictors of therapy outcome based on a multi-component prognostic model, as illustrated in FIG. 6. Final survival predictor score comprises a sum of scores for individual genes and reflects the relative contribution of each of the eleven genes in the multivariate analysis. The negative weighting values imply that higher expression correlates with longer survival and favorable prognosis, whereas the positive score values indicate that higher expression correlates with poor outcome and shorter survival. Application of the weighted survival predictor model based on a cumulative score of the weighted expression values of eleven genes confirmed the prognostic power of identified 11-gene MTTS/PNS signature in stratification of prostate cancer patients into sub-groups with statistically distinct probability of relapse-free survival after radical prostatectomy.

Figure 7:
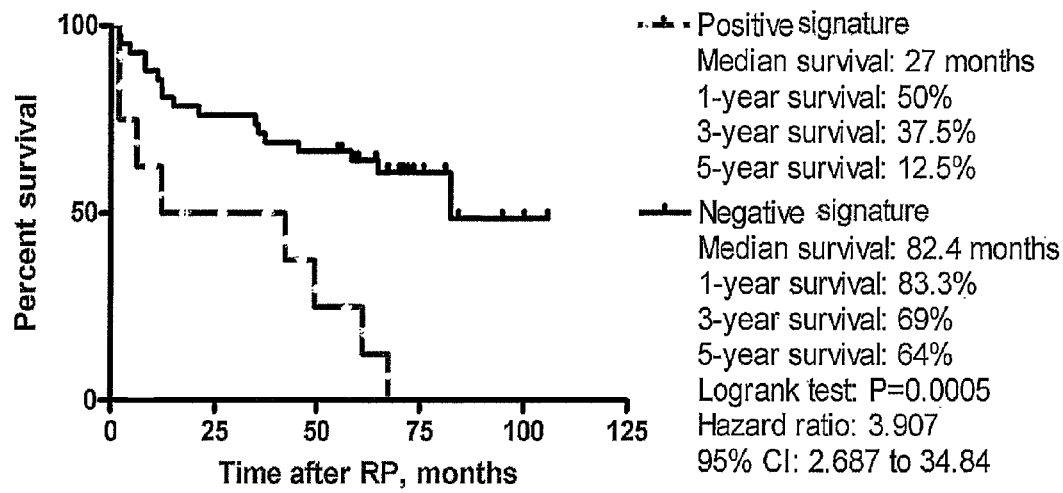
FIG. 7 is a graph showing the Kaplan-Meier survival curves for distinct sub-groups of prostate cancer patients diagnosed with early stage disease (stages 1C and 2A).

Expression of the 11-Gene MTTS/PNS Signature is a Predictor of a Short Relapse-Free Survival after Therapy in Prostate Cancer Patients with an Early Stage Disease Identification of patients with high likelihood of poor outcome after therapy would be particularly desirable in a cohort of patients diagnosed with a seemingly localized early stage prostate cancer. Next we determined whether the 11-gene MTTS/PNS signature would be useful in defining sub-groups of patients diagnosed with an early stage prostate cancer and having a statistically significant difference in the likelihood of disease relapse after therapy. In the group of patients diagnosed with the stage 1C or 2A prostate cancer, as shown in FIG. 7, the median relapse-free survival after therapy in the poor prognosis sub-group defined by the 11-gene MTTS/PNS signature was 27 months. In contrast, the median relapse-free survival after therapy in the good prognosis group was 82.4 months. 88% of patients in the poor prognosis sub-group had a disease recurrence within 5 years after therapy. Conversely, 64% of patients in the good prognosis sub-group remained relapse-free (FIG. 7). The estimated hazard ratio for disease recurrence after therapy in the poor prognosis sub-group as compared with the good prognosis sub-group of patients defined by the 11-gene MTTS/PNS signature was 3.907 (95% confidence interval of ratio, 2.687 to 34.84; P=0.0005).

Figure 8:
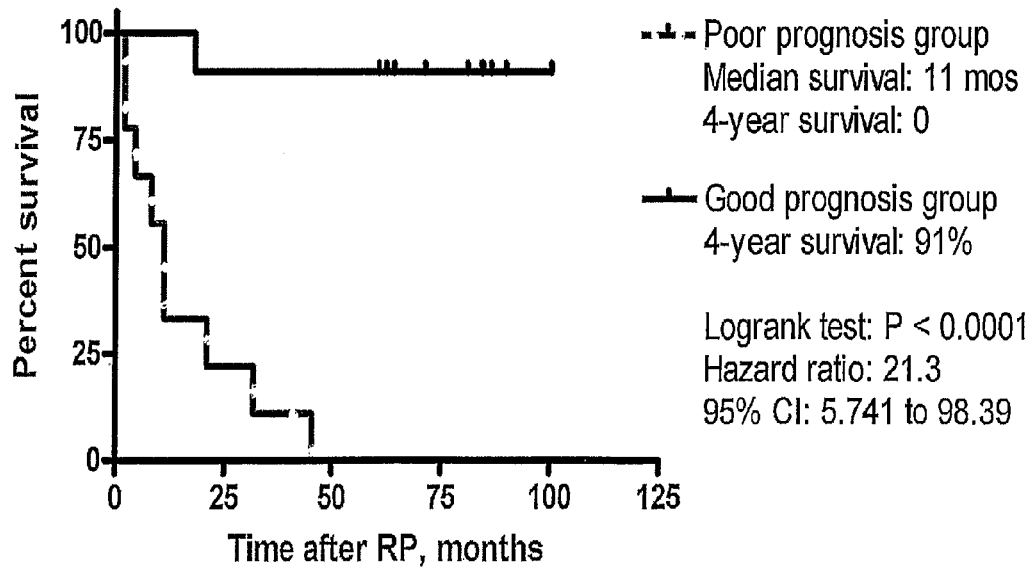
FIG. 8 is a graph showing Kaplan-Meier survival curves for 20 prostate cancer patients stratified into distinct sub-groups using Q-RT-PCR assay of the 11-gene signature

Validation of the Prognostic Performance of the 11-Gene MTTS/PNS Signature Using a Quantitative RT-PCR-Based Assay Routine clinical use of prognostic tests based on microarray-derived gene expression signatures would require the prospective validation study of the utility of identified markers in an experimental setting highly compatible with the state of the art clinical laboratory practice. Since microarray-based assay format is not readily available for application in clinical laboratory, we considered the Q-RT-PCR-based test as an alternative clinically compatible analytical platform suitable for measurements of mRNA expression level of marker genes. Expression of messenger RNA (mRNA) for eleven genes using a set of primers identified in Tables 5 and 6 below and an endogenous control gene (GAPDH) was measured in twenty specimens of primary prostate cancer obtained from patients with documented PSA recurrence within five years after RP and patients who remained disease-free for at least five years after RP (ten patients in each group) by real-time PCR method. As shown in FIG. 8, a prostate cancer therapy outcome test based on measurements of mRNA expression levels of eleven genes using Q-RT-PCR method discriminates prostate cancer patients into subgroups with statistically distinct probability of relapse-free survival after radical prostatectomy.

TABLE 5

Primer sequences for Q-RT-PCR analysis of the mRNA expression levels of genes comprising the 11-gene MTTS/PNS signature

| Gene name | UniGene ID | Sequence (5' - 3') | Amplicon, bp | SEQ ID NO. |
|---|---|---|---|---|
| GBX2-F | Hs.184945 | AAGGCTTCCTGGCCAAAGAG | 104 | 3 |
| GBX2-R | | TGACTCGTCTTTCCCTTGCC | | 4 |
| MKI67-F | Hs.80976 | CGCAAACTCTCCTTGTACCATAAT | 201 | 5 |
| MKI67-R | | ATAGCGATGTGACATGTGCTTG | | 6 |
| CCNB1-F | Hs.23960 | TGCAGCAGGAGCTTTTTGCT | 119 | 7 |
| CCNB1-R | | CCAGGTGCTGCATAACTGGAA | | 8 |
| BUB1-F | Hs.469649 | ACACCATTCCACAAGCTTCCA | 123 | 9 |
| BUB1-R | | TGAAGGCACCACCATGTTTTC | | 10 |
| KNTC2-F | Hs.414407 | TGCCAGTGAGCTTGAGTCCTT | 136 | 11 |
| KNTC2-R | | TTCAGTCGTGGTTTGCACAAC | | 12 |
| USP22-F | Hs.462492 | TCAAGTGTGACGATGCCATCA | 124 | 13 |
| USP22-R | | CTGACCAGCTGCAGATAAGGCT | | 14 |
| HCFC1-F | Hs.83634 | CCAATGGCATCGAGTCCCT | 109 | 15 |
| HCFC1-R | | GTGCCCTTAATGACTCCCACATC | | 16 |
| RNF2-F | Hs.124186 | AGTATTAGCCAGGATCAACAAGCA | 104 | 17 |
| RNF2-R | | TCTTGCCTCGCTGCAGTCT | | 18 |
| ANK3-F | Hs.499725 | CCAAGGCTTAGCCTCCATGAA | 135 | 19 |
| ANK3-R | | ACTGACCGTTCGCTGTTACGAG | | 20 |
| FGFR2(1)-F | Hs.533683 | CTCCGGCCTCTATGCTTGTACT | 114 | 21 |
| FGFR2(1)-R | | CCATCGGTG TCATCCTCATCA | | 22 |
| FGFR2(2)-F | Hs.533683 | ATAGCAGACTTTGGACTCGCCA | 146 | 23 |
| FGFR2(2)-R | | CCGAAGGACCAGACATCACTCT | | 24 |
| CES1(1)-F | Hs.558865 | GGAATTTCCACACTGTCCCCTA | 137 | 25 |
| CES1(1)-R | | GGACTTCCACAGGAGTGACATG | | 26 |
| CES1(2)-F | Hs.558865 | TGTTCCTGGACTTGATAGCAGATG | 117 | 27 |
| CES1(2)-R | | AGCTTGGACGGTACTGAAACTCA | | 28 |

TABLE 6

Primer sequences for human BMI-1 gene used for Q-RT-PCR analysis[1]

| Gene | Orientation | Primer Sequence, 5' - 3' | Product | SEQ ID NO. |
|---|---|---|---|---|
| Human Bmi-1 outer primers | Sense | ctctgtatttcaatggaagtggaccattcc | | 29 |
| | Anti-sense | gtatggttcgttacctggagaccagca | | 30 |
| Human Bmi-1 inner primers | Sense | tcttaagtgcatcacagtcattgctgctg | 359 bp | 31 |
| | Anti-sense | gatgtccaagttcacaagaccagaccactact | | 32 |

[1]Reference: Park, I.-K., Qian, D., Kiel, M., Becker, M. W., Pihalja, M., Weissman While the Tables above provide examples of primer sequences for Q-RT-PCR analysis of the mRNA expression levels of genes comprising the 11-gene MTTS/PNS signature, one of ordinary skill in the art would recognize that other primer sequences for this PCR analysis of the mRNA expression levels of genes of the 11-gene MTTS/PNS signature are available at a number of sources, such as the National Center for Biotechnology (e.g., by selecting "UniSTS" from the search window drop down menu for selection of databases to search and by conducting a search for the gene name (e.g., GBX2)) and at Primer3 for the Whitehead Institute for Biomedical. Research.

The Kaplan-Meier survival analysis demonstrated that application of the 11 gene Q-RT-PCR-based prostate cancer therapy outcome test segregates prostate cancer patients into sub-groups with statistically significant difference in the probability to remain relapse-free after the therapy (FIG. 8). The estimated hazard ratio for disease recurrence after therapy in the poor prognosis group of patients as compared with the good prognosis group defined by the test was 21.3 (95% confidence interval of ratio, 5.741 to 98.39; P<0.0001). 100% of patients in the poor prognosis group had a disease recurrence within four years after RP, whereas 91% of patients in the good prognosis group remained relapse-free (FIG. 8).

Expression of the 11-Gene MTTS/PNS Signature Predicts Metastatic Recurrence and Poor Survival after Therapy in Breast Cancer and Lung Adenocarcinoma Patients Diagnosed with an Early Stage Disease Breast Cancer We also sought to investigate whether measurements of expression of the 11-gene MTTS/PNS signature would be informative in the prediction of the patient's prognosis in the group of 97 young women diagnosed with sporadic lymph-node-negative early stage breast cancer (this group comprises of 46 patients who developed distant metastases within 5 years and 51 patients who continued to be disease-free at least 5 years after therapy; they constitute clinically defined poor prognosis and good prognosis groups, correspondingly). Kaplan-Meier analysis indicates that breast cancer patients with tumors displaying a stem cell-like expression profile of the 11-gene MTTS/PNS signature have significantly higher probability to develop distant metastases within 5 years after therapy and therefore can be identified as a poor prognosis sub-group. Median metastasis-free survival after therapy in the poor prognosis sub-group of breast cancer patients defined by the 11-gene MTTS/PNS signature was 26 months. 84% of patients in the poor prognosis sub-group were diagnosed with distant metastasis within 5 years after therapy. In contrast, 62% of patients in the good prognosis sub-group remained metastasis-free. As shown in FIG. 9, the estimated hazard ratio for metastasis-free survival after therapy in the poor prognosis sub-group as compared with the good prognosis sub-group of patients defined by the 11-gene MTTS/PNS signature was 3.762 (95% confidence interval of ratio, 3.421 to 20.27; P<0.0001). Thus, expression pattern of the 11-gene MTTS/PNS signature is strongly predictive of a short post-diagnosis and post-treatment interval to distant metastases in early stage breast cancer patients.

Lung Adenocarcinoma

Next we asked whether expression analysis of the 11-gene MTTS/PNS signature would be informative in patient's stratification into sub-groups with distinct survival probability after therapy in the group of 125 patients diagnosed with lung adenocarcinoma (34). Similarly to the prostate and breast cancer patients, the Kaplan-Meier analysis shows that patients with tumors displaying a stem cell-like expression profile of the 11-gene MTTS/PNS signature have significantly higher risk of death after therapy and therefore can be defined as a poor prognosis sub-group. Median survival after therapy in the poor prognosis sub-group of lung adenocarcinoma patients defined by the 11-gene MTTS/PNS signature was 15.2 months. In contrast, the median survival after therapy in the good prognosis sub-group was 48.8 months. 100% of patients in the poor prognosis sub-group died within 3 years after therapy. Conversely, 58% of patients in the good prognosis sub-group remained alive. As shown in FIG. 10, the estimated hazard ratio for death after therapy in the poor prognosis sub-group as compared with the good prognosis sub-group of patients defined by the 11-gene MTTS/PNS signature was 3.589 (95% confidence interval of ratio, 2.910 to 46.67; P=0.0005).

Next we examined whether the 11-gene MTTS/PNS signature would be useful in defining sub-groups of patients diagnosed with an early stage lung adenocarcinoma and having a statistically significant difference in the survival probability after therapy. In the group of patients diagnosed with the stage 1A lung adenocarcinoma, the median survival after therapy in the poor prognosis sub-group defined by the 11-gene MTTS/PNS signature was 49.6 months. 53% of patients in the poor prognosis sub-group died within 5 years after therapy. In contrast, 92% of patients remained alive in the good prognosis sub-group. The estimated hazard ratio for death after therapy in the poor prognosis sub-group as compared with the good prognosis sub-group of patients defined by the 11-gene MTTS/PNS signature was 8.909 (95% confidence interval of ratio, 1.418 to 13.12; P=0.01).

Figure 11:
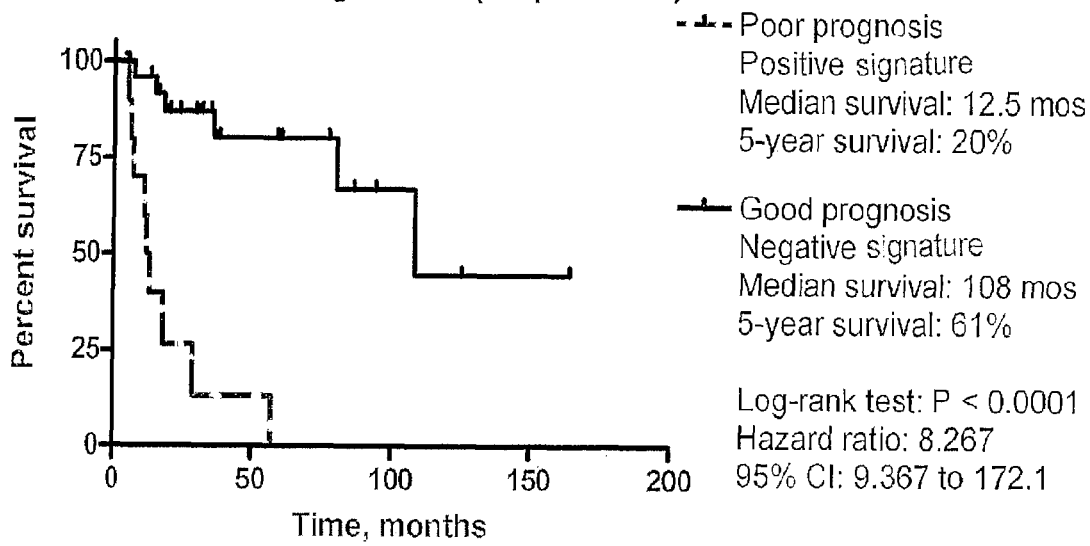
FIG. 11 is a graph showing the Kaplan-Meier analysis of the probability that patients would remain metastasis-free or survive after therapy among 37 ovarian cancer patients of all stages according to whether they had a good-prognosis or poor-prognosis signatures defined by the expression profiles of the 11-gene MTTS/PNS signature.
Figure 12:
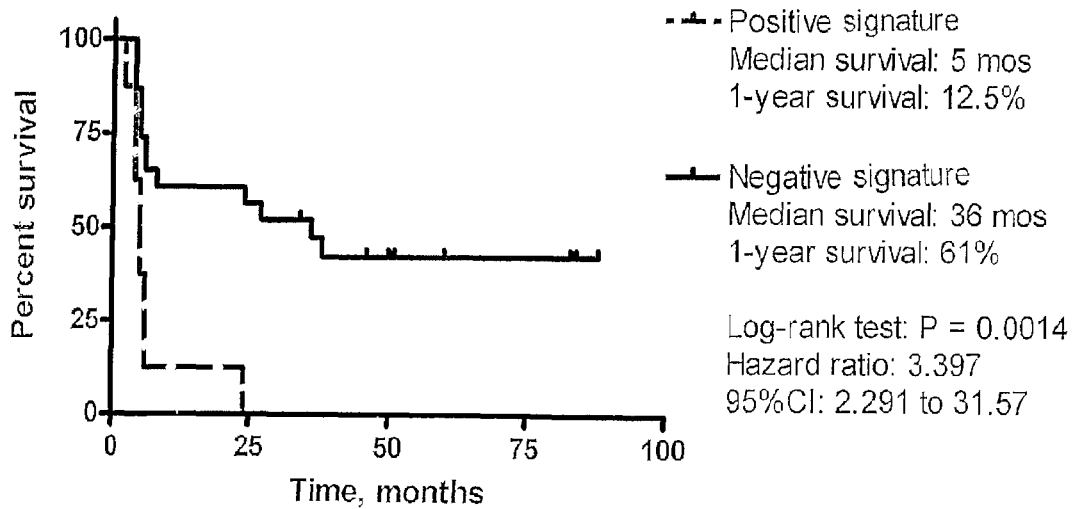
FIG. 12 is a graph showing the Kaplan-Meier analysis of the probability that patients would remain metastasis-free or survive after therapy among 31 bladder cancer patients according to whether they had a good-prognosis or poor-prognosis signatures defined by the expression profiles of the 11-gene MTTS/PNS signature.

Based on this analysis we concluded that detection of a stem cell-like expression profile of the 11-gene MTTS/PNS signature in primary tumors from patients diagnosed with the early stage prostate, breast, and lung carcinomas is associated with a high propensity toward metastatic dissemination and significantly higher risk of poor therapy outcome. Interestingly, therapy outcome in cancer patients diagnosed with other types of epithelial cancers such as ovarian and bladder cancers seems to manifest similar association with distinct patterns of expression of the 11-gene MTTS/PNS signature, as shown in FIGS. 11 and 12.

Figure 13:
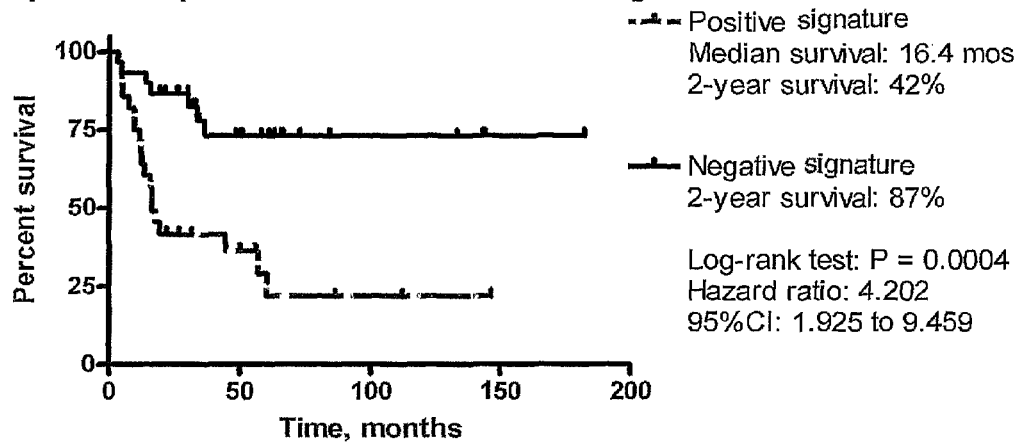
FIG. 13 is a graph showing Kaplan-Meier survival analysis of the probability of a therapy failure in cancer patients diagnosed with a non-epithelial cancer, lymphoma, and having distinct expression profiles of the 11-gene MTTS/PNS signature
Figure 14:
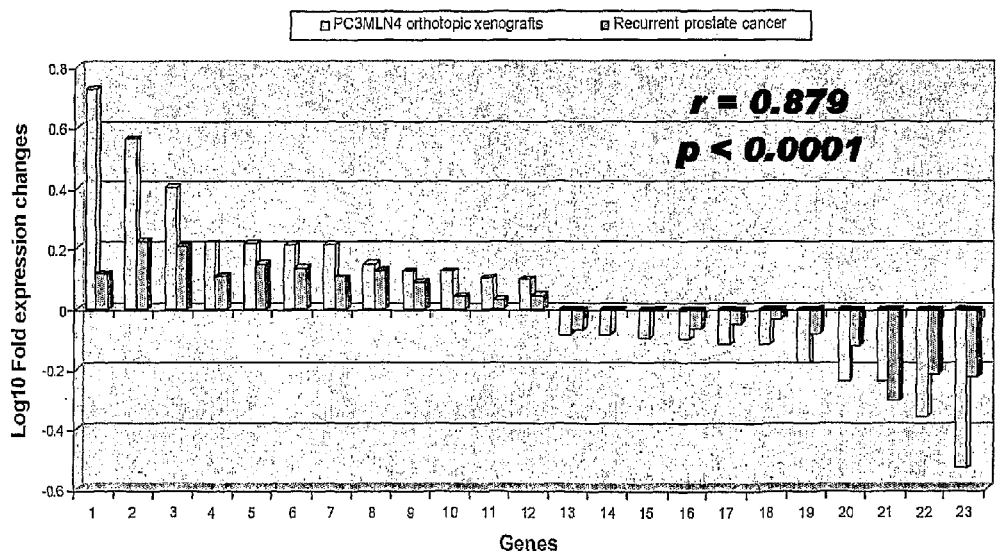
FIG. 14 is a graph showing the expression profile of the 23-gene "stemness" signature in primary prostate tumors from patients with recurrent disease resembling "stemness" transcript abundance patterns in highly metastatic PC3MLN4 orthotopic xenografts in nude mice.
Figure 15:
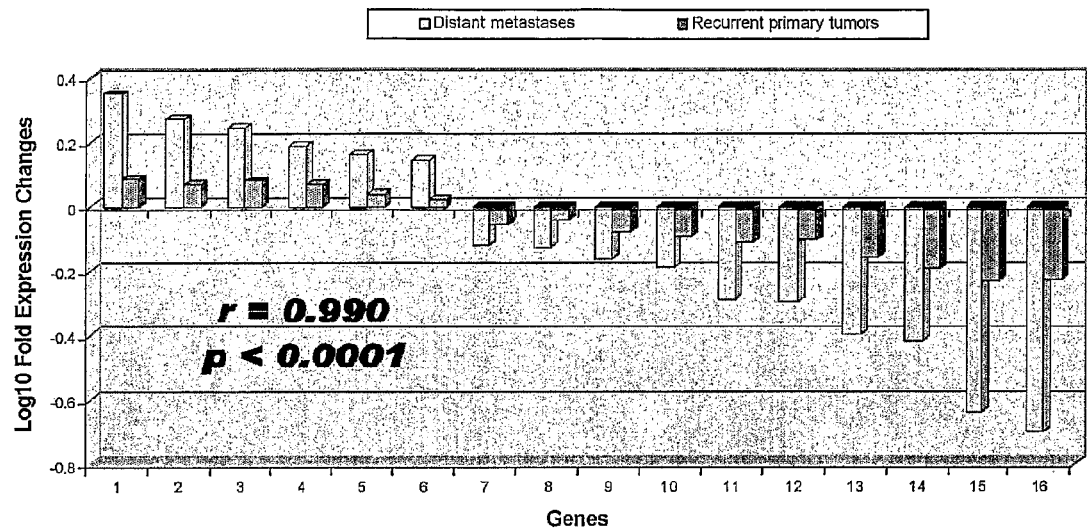
FIG. 15 is a graph showing the expression profile of the 16-gene "stemness" signature in primary prostate tumors from patients with recurrent disease resembling "stemness" transcript abundance patterns in distant prostate cancer metastases.
Figure 16:
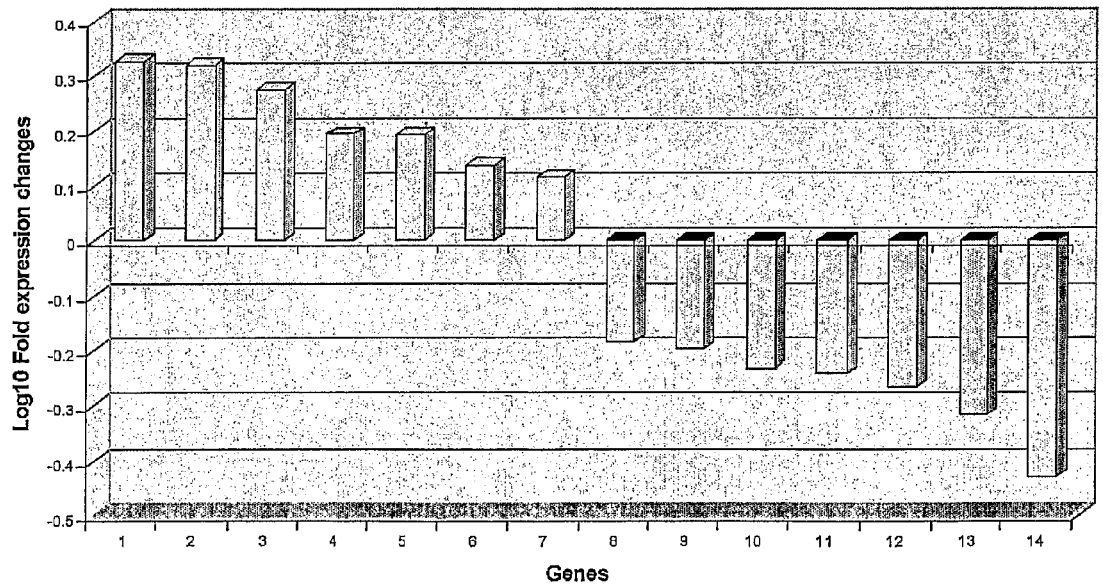
FIG. 16 is a graph showing the expression profile of the 14-gene "stemness" signature in 8 recurrent versus 13 non-recurrent human prostate carcinomas.
Figure 17:
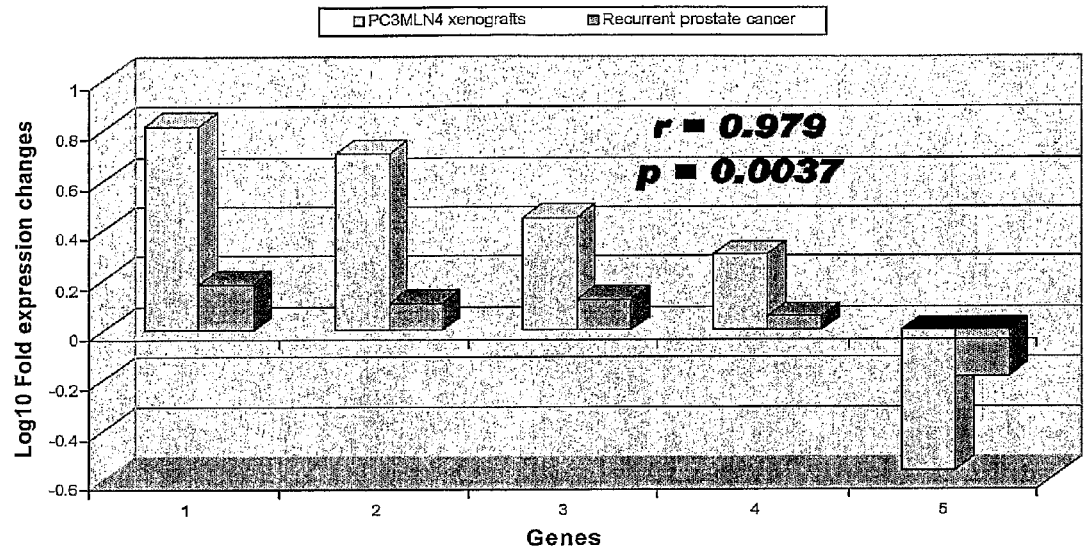
FIG. 17 is a graph showing the expression profile of the 5-gene "stemness" signature in primary prostate tumors from patients with recurrent disease resembling "stemness" transcript abundance patterns in highly metastatic PC3MLN4 orthotopic xenografts in nude mice.

Expression of the 11-Gene MTTS/PNS Signature Predicts Therapy Outcome in Patients Diagnosed with Non-Epithelial Malignancies We further sought to analyze whether the 11-gene MTTS/PNS signature would be useful in defining sub-groups of patients diagnosed with non-epithelial cancers and having a statistically significant difference in the survival probability after therapy. Using Kaplan-Meier method, we analyzed the prognostic power of the 11-gene signature in patients diagnosed with diffuse large B-cell lymphoma; mantle cell lymphoma; acute myeloid leukemia; mesothelioma; medulloblastoma; and glioma (see FIG. 13 as one example showing survival of lymphoma patients). Kaplan-Meier analysis demonstrates that a stem cell-like expression profile of the 11-gene MTTS/PNS signature in primary tumors is a consistent powerful predictor of a therapy failure and short survival in cancer patients diagnosed with five distinct types of non-epithelial cancers. Consistent with our findings, an increased BMI-1 expression in human medulloblastomas was demonstrated in a recent study (van de Vijver, M. J., et al., A gene expression signature as a predictor of survival in breast cancer. N. Engl. J. Med. 2002, 347:1999-2009). Taken together, these data seem to imply the presence of a conserved BMI-1-associated pathway(s) similarly engaged in both neural stem cells and a highly malignant subset of human cancers diagnosed in a wide range of organs and uniformly exhibiting a marked propensity toward metastatic dissemination as well as a high probability of unfavorable therapy outcome.

Example 2

Stemness Expression Signatures for Predicting Clinical Outcome in Patients

Expression Profiles of Invasive Primary Tumors and Distant Metastatic Lesions in a Transgenic Mouse Model of Prostate Cancer Exhibit Marked Similarity to Normal Stem Cells As described above, the emerging concept of cancer stem cells suggests that an engagement of "stemness" genetic pathways in transformed cells may contribute to tumor progression and metastasis of epithelial malignancies. Thus, inappropriate activation of "stemness" genes in cancer cells may be associated with aggressive clinical behavior and increased likelihood of therapy failure. We measured expression levels of ~12,000 genes in primary prostate tumors and distant metastatic lesions at various anatomic sites of six-month old TRAMP mice and defined differentially regulated transcripts by comparison to the gene expression profiles of age-matched wild-type control mice with no evidence of malignant process in the prostate. This analysis identified 276 and 868 genes with increased transcript abundance levels in invasive primary prostate tumors and distant metastatic lesions, respectively.

To test whether expression profiles of primary and metastatic prostate tumors resemble transcriptional program of stem cells, we compared the genes up-regulated in primary tumors and metastases to the lists of genes enriched in three distinct stem cell types namely neural stem cells, hematopoietic stem cells, and embryonic stem cells (Ivanova, N. B., et al., A stem cell molecular signature. Science 2002, 298:601-604, incorporated herein by reference). Remarkably, the search for union/intersection of lists identified a large number of common genes in each binary comparison, shown in Table 7, below. Most significant similarity was observed for expression profiles of both advanced stage primary prostate tumors and distant metastases and transcripts enriched in neural stem cells. These data are consistent with the hypothesis that tumor progression toward metastatic disease in a transgenic mouse model of prostate cancer occurs to a significant degree within transcriptional space defined by the "stemness" gene expression program.

TABLE 7

"Stemness" expression profile of transcripts up-regulated in primary and metastatic tumors of the TRAMP transgenic mouse model of prostate cancer.

| Stem cell type | Number (%) of common genes |
|---|---|
| 276 transcripts up-regulated in primary prostate tumors | |
| Neural stem cells (NSC) | 87 (31.5%) |
| Embryonal stem cells (ESC) | 15 (5.4%) |
| Hematopoietic stem cells (HSC) | 13 (4.7%) |
| NSC/ESC | 88 (31.9%) |
| NSC/HSC | 2 (0.7%) |
| ESC/HSC | 5 (1.8%) |
| NSC/ESC/HSC | 3 (1.1%) |
| Overall | 213 of 276 (77%) |
| 868 transcripts up-regulated in distant metastatic lesions | |
| Neural stem cells (NSC) | 178 (20.5%) |
| Embryonal stem cells (ESC) | 57 (6.6%) |
| Hematopoietic stem cells (HSC) | 80 (9.2%) |

TABLE 7-continued

"Stemness" expression profile of transcripts up-regulated in primary and metastatic tumors of the TRAMP transgenic mouse model of prostate cancer.

| Stem cell type | Number (%) of common genes |
|---|---|
| NSC/ESC | 192 (22.1%) |
| NSC/HSC | 13 (1.5%) |
| ESC/HSC | 21 (2.4%) |
| NSC/ESC/HSC | 17 (2.0%) |
| Overall | 558 of 868 (64%) |

The Table shows that 276 and 868 transcripts up-regulated in primary prostate tumors and distant metastatic lesions, respectively, of six-month old TRAMP mice were compared to genes enriched in neural, embryonic, and hematopoietic stem cells in search for union/intersection of lists.

Altered Expression of "Sternness" Genes in Human Prostate Cancer

Next we set out to determine whether the phenomenon of resemblance of "stemness" expression profile is relevant to human prostate cancer. We make use of the list of human homologs for murine HSC-related genes defined through the mouse-human homologous pairs search by direct sequence comparison of expressed sequence tags assemblies to identify "stemness" gene sub-sets in multiple clinical and experimental settings pertinent to human prostate cancer. Results of this analysis seem to indicate that the expression of a substantial fraction of genes enriched in stem cells appears altered in various clinical and experimental settings pathophysiologically relevant to human prostate cancer. Overall, 334 of the interrogated 460 human "stemness" genes (73%) were differentially regulated in at least one of the surveyed clinical or experimental settings listed in the Table 8.

TABLE 8

Number of "stemness" genes differentially regulated in various clinical and experimental settings relevant to human prostate cancer

| Type (number) of clinical samples | Number of "stemness" genes |
|---|---|
| Distant prostate cancer metastases (9) | 30 |
| Primary prostate tumors (23) | 57 |
| Primary prostate tumors (47) | 89 |
| Adjacent normal prostate (47) | 80 |
| Experimental setting | |
| Orthotopic xenografts, PC3MLN4 | 31 |
| Orthotopic xenografts, PC3 & PC3M | 46 |
| Prostate cancer cell lines | 99 |
| NPEC | 77 |

To identify "stemness" gene sub-sets in multiple clinical and experimental settings pertinent to human prostate cancer, the human "stemness" gene set was compared to genes enriched in metastatic versus primary human prostate tumors, primary prostate tumors versus adjacent normal prostate tissues, and multiple experimental models of human prostate cancer in search for union/intersection of lists for each setting. The human "stemness" gene set was defined from a list of human homologs for murine HSC-related genes defined through the mouse-human homologous pairs search by direct sequence comparison of expressed sequence tags assemblies. In this example, gene expression profiling data derived from the microarray analyses using the Affymetrix U95A GeneChip were utilized in this analysis (460 of the 822 mouse-human homologous pairs).

Our data appear to indicate that components of a "stemness" transcriptome are frequently altered at the transcript abundance levels in established human prostate cancer cell lines, xenografts, clinical samples of primary prostate tumors as well as distant metastases, suggesting that differences in expression of "stemness" genes may be associated with distinct features of malignant phenotype of human prostate carcinoma cells. To assess the potential clinical relevance of the altered expression of "stemness" genes in prostate tumors, we thought to analyze whether primary prostate tumors with distinct clinical outcome after therapy would exhibit distinct expression profiles of "stemness" genes. We identified four molecular signatures comprising 23, 14, 5, and 16 "stemness" genes (Gene Sets A, B, C, and D, respectively), shown in Tables 9a, 9b, 9c and 9d, that appear to exhibit distinct expression profiles in prostate tumors from patients with recurrent and non-recurrent disease (See FIGS. 14, 15, 16, and 17), suggesting that prostate carcinomas with aggressive clinical behavior and adverse outcome after therapy may activate and suppress an opposite spectrum of "stemness" genes compared to the prostate tumors with indolent clinical course of disease and positive therapy outcome.

TABLE 9a

23-Gene "Stemness" gene expression signature associated with recurrent prostate cancer (Gene Set A).

| Signature 1 Gene | 23 genes Gene Name | GenBank ID | UniGene ID |
| --- | --- | --- | --- |
| ENG | Endoglin | X72012 | Hs.76753 |
| NRGN | Neurogranin | X99076 | Hs.232004 |
| CLECSF2 | C-type lectin (activation-induced) | X96719 | Hs.85201 |
| EPB41L2 | Erythrocyte membrane protein band 4.1-like 2 | AF027299 | Hs.440387 |
| GART | Phosphoribosylglycinamide synthetase | X54199 | Hs.82285 |
| MXD4 | MAX dimerization protein 4 | AF040963 | Hs.511752 |
| PLEKHB2 | Pleckstrin homology domain containing | AL120687 | Hs.307033 & Hs.512380 |
| RPGR | Retinitis pigmentosa GTPase regulator | U57629 | Hs.378949 |
| EST | *Homo sapiens* cDNA | W28612 | Hs.184724 |
| ARHQ | Ras homolog gene family, member Q | AL043108 | Hs.442989 |
| MCM5 | Minichromosome maintenance deficient 5 | X74795 | Hs.77171 |
| GORASP2 | Golgi reassembly stacking protein 2 | AA447263 | Hs.6880 |
| SF3A2 | Spliceosomal protein SAP-62 | L21990 | Hs.115232 |
| KIAA0323 | KIAA0323 | AI494623 | Hs.7911 |
| NME2 | Non-metastatic cells 2 | X58965 | Hs.433416 |
| RPL18 | Ribosomal protein L18) | L11566 | Hs.409634 |
| ACADVL | Very long chain acyl-CoA dehydrogenase | L46590 | Hs.437178 |
| IGBP1 | Immunoglobulin-binding protein 1 | Y08915 | Hs.3631 |
| SOX4 | SRY-box 4 | X70683 | Hs.357901 |
| GATA3 | GATA-binding protein 3 | X58072 | Hs.169946 |
| FADS2 | Fatty acid desaturase | AL050118 | Hs.388164 |
| ITPR1 | Type 1 inositol 1,4,5-trisphosphate receptor | D26070 | Hs.149900 |
| KLF4 | Kruppel-like factor 4 | U70663 | Hs.376206 |

TABLE 9b

14-Gene "Stemness" gene expression signature associated with recurrent prostate cancer (Gene Set B).

| Signature 2 Gene | 14 genes Gene Name | GenBank ID | UniGene ID |
| --- | --- | --- | --- |
| ITGA6 | Integrin alpha 6B | S66213 | Hs.212296 |
| CRHR2 | Corticotropin-releasing hormone receptor 2 | U34587 | Hs.66578 |
| HOXB2 | Homeo box B2 | X16665 | Hs.290432 |
| HOXA10 | Homeo box A10 | AC004080 | Hs.110637 |
| SMARCD2 | SWI/SNF complex 60 KDa subunit B (BAF60B) | U66618 | Hs.250581 |
| H2AV | Histone H2A.F/Z variant (H2AV) | AW007731 | Hs.301005 |
| DKFZP564I052 | DKFZP564I052 protein | AL080063 | Hs.5364 |
| ITRR1 | Inositol 1,4,5-triphosphate receptor, type 1 | D26070 | Hs.149900 |
| GCS1 | Glucosidase I | X87237 | Hs.83919 |
| TGOLN2 | Trans-golgi network protein 2 | AF027516 | Hs.14894 |
| APS | Adaptor protein with pleckstrin homology and src homology 2 | AB000520 | Hs.371366 |
| GLA | Galactosidase, alpha | U78027 | Hs.69089 |
| EST | Protein with strong similarity to A48043 | H10776 | Hs.107374 |
| MAFF | V-maff musculoaponeurotic fibrosarcoma oncogene homolog F | AL021977 | Hs.460889 |

TABLE 9c

5-Gene "Stemness" gene expression signature associated with recurrent prostate cancer (Gene Set C).

| Signature 3 Gene | 5 genes Gene Name | GenBank ID | UniGene ID |
|---|---|---|---|
| NRGN | Neurogranin | X99076 | Hs.232004 |
| RGS3 | Regulator of G-protein signaling 3 | U27655 | Hs.82294 |
| EDIL3 | EGF-like repeats and discoidin I-like domains | U70312 | Hs.441044 |
| GPR56 | G protein-coupled receptor 56 | AJ011001 | Hs.6527 |
| ITRR1 | Inositol 1,4,5-triphosphate receptor, type 1 | D26070 | Hs.149900 |

TABLE 9d

16-Gene "Stemness" gene expression signature associated with recurrent prostate cancer (Gene Set D).

| Signature 4 Gene | 16 genes Gene Name | GenBank ID | UniGene ID |
|---|---|---|---|
| LYRIC | LYRIC/3D3 | AA398463 | Hs.377155 |
| TMSB10 | Thymosin, beta 10 | M92383 | Hs.446574 |
| ZNF183 | Zinc finger protein 183 | X98253 | Hs.64794 |
| PRKCBP1 | Protein kinase C-binding protein 1 | W22296 | Hs.37372 & Hs.191990 |
| ALG3 | Asparagine-linked glycosylation 3 homolog | Y09022 | Hs.153591 |
| B4GALT4 | Beta-1,4-galactosyltransferase | AF038662 | Hs.13225 |
| ERCC1 | Excision repair cross-complementing 1 | M13194 | Hs.435981 |
| PTPRK | Protein tyrosine phosphatase, receptor type | L77886 | Hs.354262 |
| POU2F2 | POD domain, class 2, transcriprion factor 2 | M36542 | Hs.1101 |
| NFKBIA | NFKB gene enhancer in B-cells inhibitor, alpha | M69043 | Hs.81328 |
| Unknown | Homo sapiens cDNA | N48190 | Hs.22243 |
| GEM | GTP-binding protein | U10550 | Hs.79022 |
| PDE4B | Phosphodiesterase 4B | L20971 | Hs.188 |
| RBPMS | RNA-binding protein with multiple splicing | D84110 | Hs.195825 |
| GSRP1 | Cysteine and glycine-rich protein 1 | M33146 | Hs.108080 |
| MEIS1 | Myeloid ecotropic viral integration site 1 homolog | U85707 | Hs.170177 |

Affymetrix probe ID numbers for the probes corresponding to each of the genes shown in Tables 9a, 9b, 9c, and 9d, and from the Affymetrix probe set U95Av2 can be found at the Affymetrix web site on the GENECHIP® Human Genome U95 set using the "Array Finder" and either the GenBank ID or Unigene ID as an identifier with which to conduct the search.

Prognostic Value of "Stemness" Gene Expression Signatures

To further examine the potential clinical utility of the altered expression of "stemness" genes in human prostate cancer, we examined whether the assessment of expression profiles of "stemness" signatures in individual prostate tumors would assist in stratification of prostate cancer patients at the time of diagnosis into sub-groups with statistically distinct likelihood of disease recurrence after radical prostatectomy. We evaluated the prognostic power of each identified "stemness" signature based on ability to segregate the patients with recurrent and non-recurrent prostate tumors into distinct sub-groups. To assess a potential prognostic relevance of individual "stemness" signatures, we calculated a Pearson correlation coefficient for each of 21 tumor samples of the outcome set 1 by comparing the expression profiles of individual samples to the "average" expression profile of recurrent versus non-recurrent tumors (14-gene signature or gene set B) or "stemness" expression profiles of relevant experimental or clinical samples (FIGS. 14, 15, 16, 17 and Table 9b). Based on expected correlation of expression profiles of identified "stemness" signatures with recurrent clinical behavior of prostate cancer, we named the corresponding correlation coefficients calculated for individual samples the "stemness" phenotype association indices (SPAIs).

Figure 18:
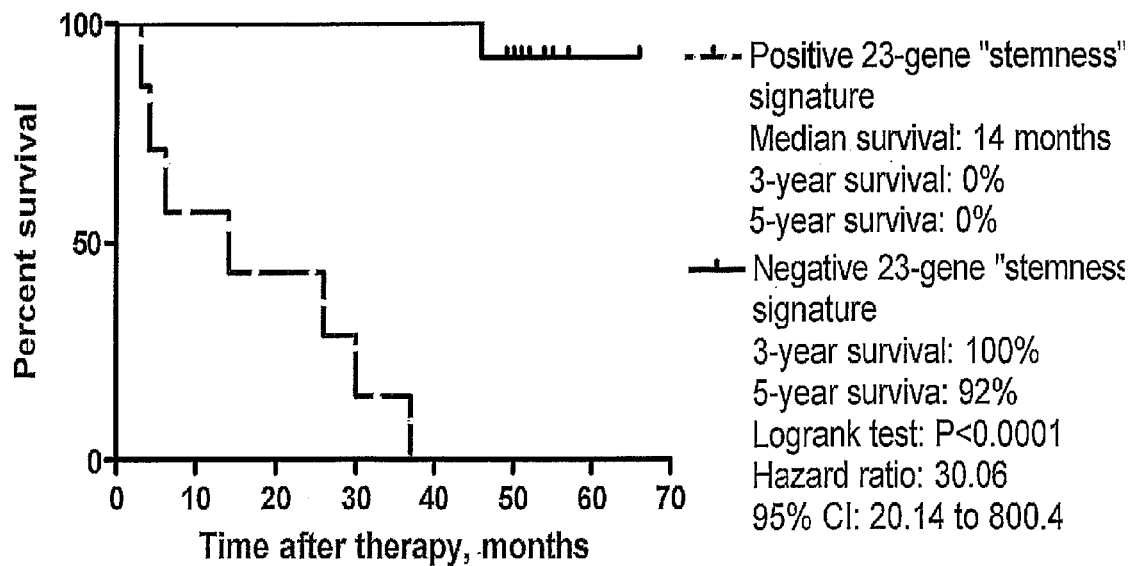
FIG. 18 is a graph showing the Kaplan-Meier analysis of the probability that patients would remain disease-free among 21 prostate cancer patients comprising a clinical outcome group 1 according to whether they had a good-prognosis or poor-prognosis signatures defined by the expression profiles of the 23-gene "stemness" signature.
Figure 19:
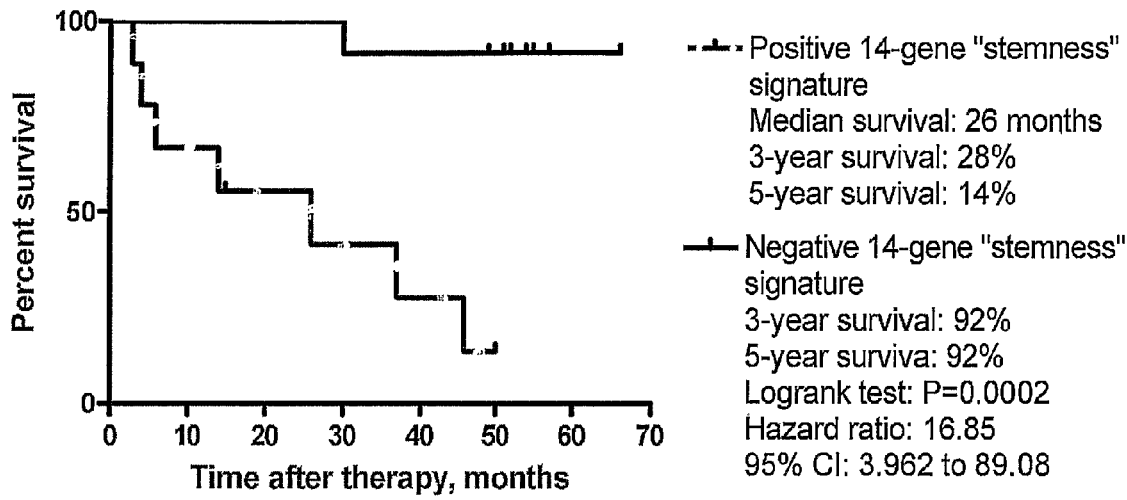
FIG. 19 is a graph showing the Kaplan-Meier analysis of the probability that patients would remain disease-free among 21 prostate cancer patients comprising a clinical outcome group 1 according to whether they had a good-prognosis or poor-prognosis signatures defined by the expression profiles of the 14-gene "stemness" signature.
Figure 20:
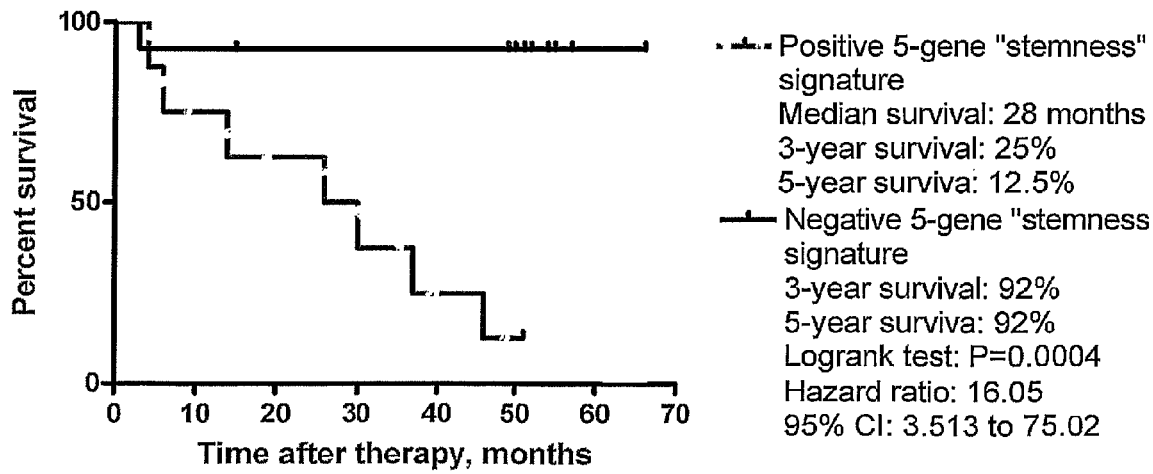
FIG. 20 is a graph showing the Kaplan-Meier analysis of the probability that patients would remain disease-free among 21 prostate cancer patients comprising a clinical outcome group 1 according to whether they had a good-prognosis or poor-prognosis signatures defined by the expression profiles of the 5-gene "stemness" signature.
Figure 21:
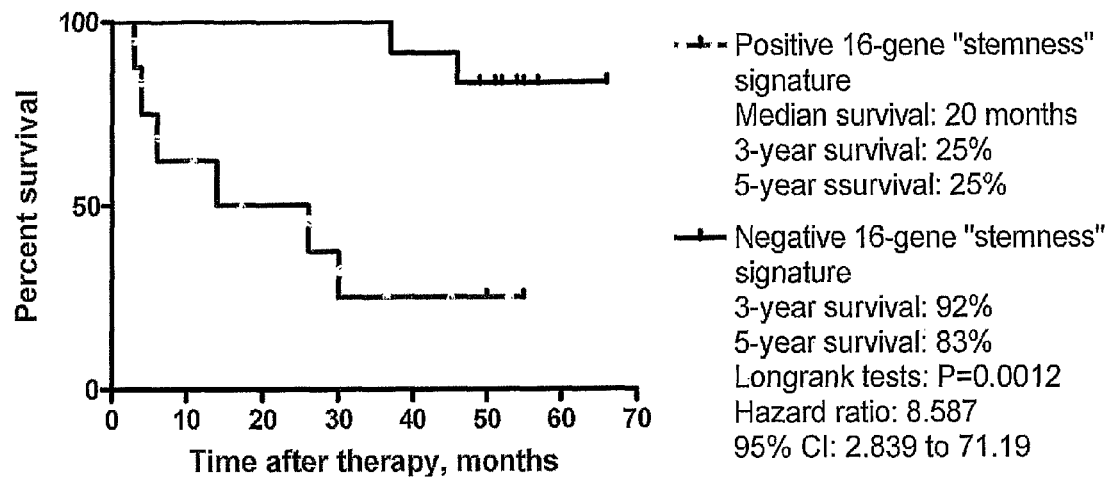
FIG. 21 is a graph showing the Kaplan-Meier analysis of the probability that patients would remain disease-free among 21 prostate cancer patients comprising a clinical outcome group 1 according to whether they had a good-prognosis or poor-prognosis signatures defined by the expression profiles of the 16-gene "stemness" signature.

To evaluate the prognostic power of identified "stemness" gene expression signatures, we performed the Kaplan-Meier survival analysis using as a clinical end-point disease-free interval (DFI) after therapy in prostate cancer patients with positive and negative SPAIs. The Kaplan-Meier survival curves showed a highly significant difference in the probability that prostate cancer patients would remain disease-free after therapy between the groups with positive and negative SPAIs defined by the "stemness" signatures (FIGS. 18, 19, 20, and 21), suggesting that patients with positive SPAIs exhibit a poor outcome signature whereas patients with negative SPAIs manifest a good outcome signature. The estimated hazard ratio for disease recurrence after therapy in the group of patients with positive SPAIs as compared with the group of patients with negative SPAIs defined by the 23-gene "stemness" signature or gene set A (Table 9a, and FIG. 18) was 30.06 (95% confidence interval of ratio, 20.14 to 800.4; $P<0.0001$). 100% of patients with the positive SPAIs had a disease recurrence within 3 years after therapy, whereas 100% of patients with the negative SPAIs remained relapse-free at least 3 years (FIG. 18). Five-year after therapy, 100% of patients with the positive SPAIs had a disease recurrence, whereas 92% of patients with the negative SPAIs remained relapse-free (FIG. 18). Based on this analysis, we propose to identify the group of prostate cancer patients with positive "stemness" signatures as a poor prognosis group and the group of prostate cancer patients with negative "stemness" signatures as a good prognosis group.

Figure 22:
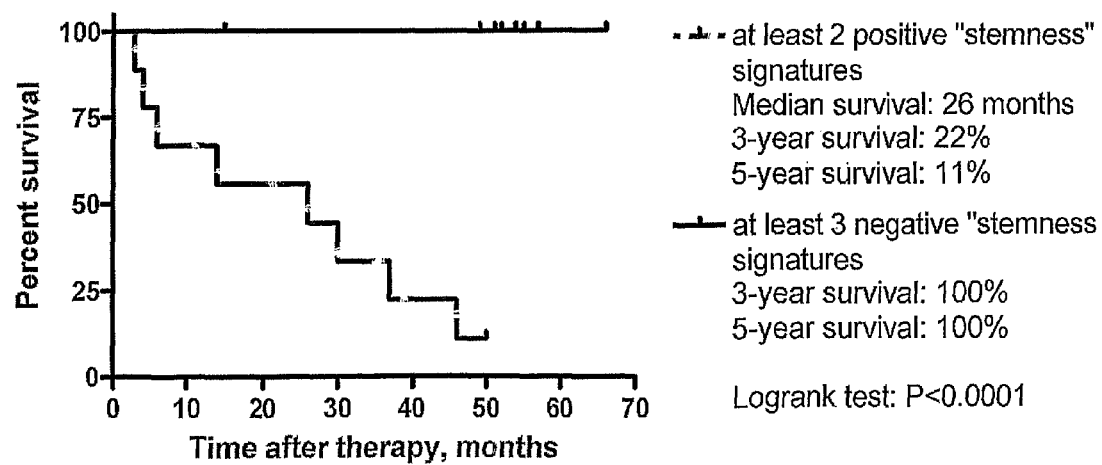
FIG. 22 is a graph showing the Kaplan-Meier analysis of the probability that patients would remain disease-free where patients had at least 2 positive signatures or at least 3 negative signatures.

Theoretically, the recurrence predictor algorithm based on a combination of signatures should be more robust than a single predictor signature, particularly during the validation analysis using an independent test cohort of patients. We therefore analyzed whether a combination of the four "stemness" signatures would perform in the patient's classification test with similar accuracy as the individual signatures. The Kaplan-Meier survival analysis (FIG. 22) showed that the median relapse-free survival after therapy of patients in the poor prognosis group (defined as having two or more positive "stemness" signatures) was 26 months. 89% of patients in the poor prognosis group had a disease recurrence within 5 years after therapy, whereas 100% of patients in the good prognosis group (defined as having 3 or 4 negative "stemness" signatures) remained relapse-free (FIG. 22; P<0.0001). Using "stemness" signature algorithm, all eight patients who developed disease recurrence after therapy were correctly classified into poor prognosis group.

To further validate the potential clinical utility of identified "stemness" signatures, we evaluated the prognostic power of signatures applied to an independent set of 79 clinical samples (outcome set 2) obtained from 37 prostate cancer patients who developed recurrence after the therapy and 42 patients who remained disease-free. The Kaplan-Meier survival analysis demonstrated that all four individual "stemness" signatures segregate prostate cancer patients into poor and good prognosis sub-groups with statistically significant difference in the probability to remain relapse-free after the therapy.

Figure 23:
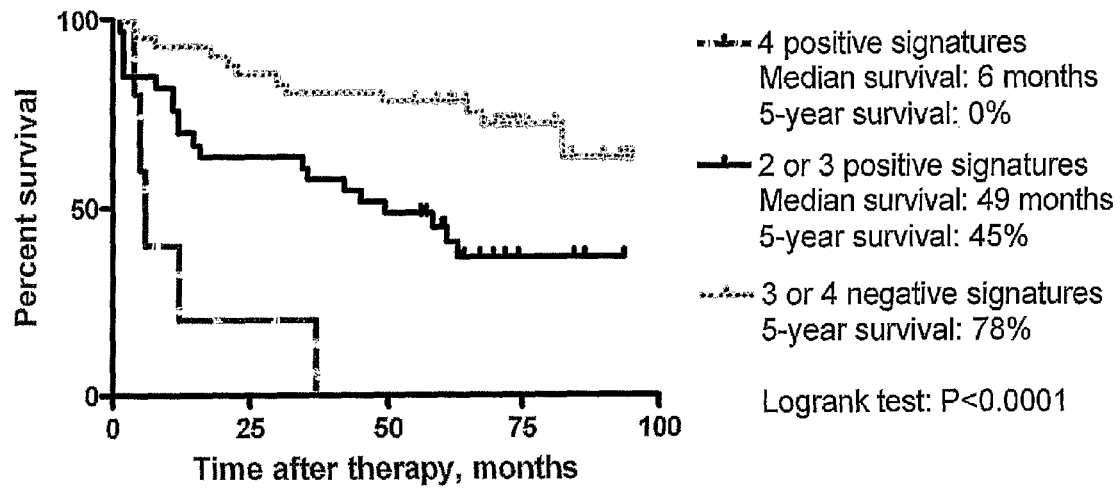
FIG. 23 is a graph showing the Kaplan-Meier analysis of the probability that patients would remain disease-free where patients had 4 positive signatures or 2 or 3 positive signatures, or 3 or 4 negative signatures.
Figure 24:
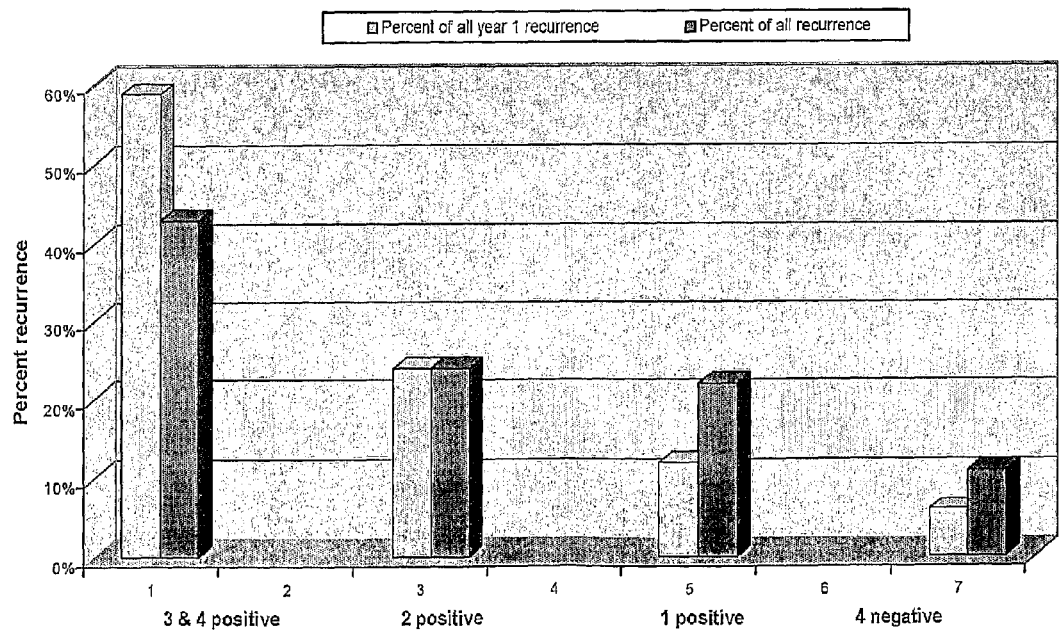
FIG. 24 is a graph showing the actual frequency of disease recurrence after radical prostatectomy in prostate cancer patients with distinct "stemness" gene expression profiles defined by the four "stemness" signature algorithm.

Next we determined whether a combination of the four "stemness" signatures would perform in the patient's classification test with similar accuracy as the individual signatures. The Kaplan-Meier survival analysis showed that the median relapse-free survival after therapy of patients in the poor prognosis group (defined as having four positive "stemness" signature) was 6 months (see FIGS. 23 and 24). 80% of patients in the poor prognosis group had a disease recurrence within one year after therapy, whereas 92% of patients in the good prognosis group (defined as having 3 or 4 negative "stemness" signatures) remained relapse-free. All patients in the poor prognosis group had a disease recurrence within 3 years after therapy, whereas 80% of patients in the good prognosis group remained relapse-free at least 3 years. The estimated hazard ration for disease recurrence after therapy in the poor prognosis group of patients as compared with the good prognosis group of patients defined by the recurrence predictor algorithm was 9.172 (95% confidence interval of ratio, 47.79 to 5484; P<0.0001).

The Kaplan-Meier survival analysis identified in this cohort of patients a group with an intermediate prognosis. The median relapse-free survival after therapy of patients in the intermediate prognosis group defined by the "stemness" algorithm as having 2 or 3 positive signatures was 49.4 months (see FIGS. 23 and 24). 58% of patients in the intermediate prognosis group had a disease recurrence within 3 years after therapy, whereas 80% of patients in the good prognosis group remained relapse-free. 45% of patients in the intermediate prognosis group had a disease recurrence within 5 years after therapy, whereas 78% of patients in the good prognosis group remained relapse-free. The estimated hazard ration for disease recurrence after therapy in the poor prognosis group as compared with the good prognosis group of patients defined by the recurrence predictor algorithm was 2.832 (95% confidence interval of ratio, 1.475 to 6.281; P=0.0026). Overall, the application of the "stemness" recurrence predictor algorithm allowed accurate stratification into poor and intermediate prognosis groups 82% of patients who failed the therapy within one year after prostatectomy.

To further ascertain the potential significance of an aberrant expression of "stemness" genes in human prostate cancer, we analyzed the frequency of actual disease recurrence in prostate cancer patients with distinct "stemness" gene expression profiles. This analysis clearly showed that the sub-group of patients with four and three positive "stemness" signatures had highly aggressive malignant disease even at the early stage of progression: 100% of stage 1C patients in this sub-group were diagnosed with disease recurrence after radical prostatectomy. Overall, 76% of patients in this sub-group had recurrent disease and 48% of patients were diagnosed with recurrence within one year after prostatectomy. In contrast, 79% of patients with four negative "stemness" signatures remained disease-free and only 5% had recurrence within one year after surgery.

In summary, our analysis seems to indicate that expression of genes identified as components of "stemness" transcriptome is frequently altered in prostate cancer, suggesting that prostate cancer progression occurs at least in part within transcriptional space activated in normal stem cells. One of the hallmark biological features of normal stem cells is the ability to fuse spontaneously in vitro and in vivo with other cell types leading to formation of reprogrammed viable somatic cell hybrids (Vassilopoulos, G., Wang, P.-R., Russell, D. W. Transplanted bone marrow regenerates liver by cell fusion. Nature 2003, 422.901-904; Alvarez-Dolado, M., et al., Fusion of bone-marrow-derived cells with Purkinje neurons, cardiomyocytes and hepatocytes. Nature 2003, 425: 968-973; Weimann, J. M., et al., Stable reprogrammed heterokaryons form spontaneously in Purkinje neurons after bone marrow transplant. Nature Cell biology 2003, 5:959-966; LaTulippe, E., et al., Comprehensive gene expression analysis of prostate cancer reveals distinct transcriptional programs associated with metastasis. Cancer Res. 2002, 62:4499-4506, incorporated herein by reference). It would be of interest to study how cancer cells co-opt "stemness" transcriptome into progression pathways and whether some human carcinomas could attract stem cells by mimicking a stem cell "niche" microenvironment thus directly engaging normal stem cells into malignant process.

While the invention has been particularly shown and described with reference to a preferred embodiment and various alternate embodiments, it will be understood by persons skilled in the relevant art that various changes in form and details can be made therein without departing from the spirit and scope of the invention. All references, issued patents and patent applications cited within the body of the instant specification are hereby incorporated by reference in their entirety, for all purposes.

REFERENCES CITED

1 Al-Hajj, M., Wicha, M. S., Benito-Hernandez, A., Morrison, S. J., Clarke, M. F. 2003. Prospective identification of tumorigenic breast cancer cells. Proc. Natl. Acad. Sci. USA 100:3983-3988.
2 Alkema, M. J., Jacobs, H., van Lohuizen, M., Berns, A. 1997. Perturbation of B and T cell development and predisposition to lymphomagenesis in Eμ-Bmi-1 transgenic mice require the Bmi-1 RING finger. Oncogene 15:899-910.
3 Alvarez-Dolado, M., Pardal, R., Garcia-Verdugo, J. M., Fike, J. R., Lee, H. O., Pfeffer, K., Lois, C., Morrison, S. J., Alvarez-Buylla, A. 2003. Fusion of bone-marrow-derived cells with Purkinje neurons, cardiomyocytes and hepatocytes. Nature 425:968-973.

4 Ausubel, F. M. et al., Current Protocols in Molecular Biology, Volume 2, 1997, pp. 11.12.1-11.12.9.

5 Ausubel, F. M. et al., Current Protocols in Molecular Biology, Volume 2, 1997, pp. 11.4.1-11.11.5.

6 Baron, V., De Gregorio, G., Krones-Herzig, A., Virolle, T., Calogero, A., Urcis, R., Mercola, D. 2003. Inhibition of Egr-1 expression reverses transformation of prostate cancer cells in vitro and in vivo. Oncogene 22:4194-4204.

7 Chang, H. Y., Sneddon, J. B., Alizadeh, A. A., Sood, R., West, R. B., et al. (2004). Gene expression signature of fibroblast serum response predicts human cancer progression: Similarities between tumors and wounds. PLOS Biology 2: 1-9.

8 Dick, J. E. 2003. Self-renewal writ in blood. Nature 423: 231-233.

9 Dimri, G. P., Martinez, J.-L., Jacobs, J. J. L., Keblusek, P., Itahana, K., van Lohuizen, M., Campisi, J., Wazer, D. E., Band, V. 2002. The Bmi-1 oncogene induces telomerase activity and immortalizes human mammary epithelial cells. Cancer Res. 62:4736-4745.

10 Gingrich, J. R., Barrios, R. J., Morton, R. A., Boyce, B. F., DeMayo, F. J., Finegold, M. J., Agelopoulou, R., Rosen, J. M., Greenberg, N. M. 1996. Metastatic prostate cancer in a transgenic mouse. Cancer Res. 56:4096-4102.

11 Glinsky, G. V., Krones-Herzig, A., Glinskii, A. B., Gebauer, G. 2003. Microarray analysis of xenograft-derived cancer cell lines representing multiple experimental models of human prostate cancer. Molecular Carcinogenesis 37:209-221.

12 Glinsky, Gennadi V. et al, Microarray analysis identifies a death-from-cancer signature predicting therapy failure in patients with multiple types of cancer, J. Clin. Invest. 2005, 1:115(6):1503-1521

13 Haupt, Y., Bath, M. I., Harris, A. W., Adams, J. M. 1993. BMI-1 transgene induces lymphomas and collaborates with Myc in tumorigenesis. Oncogene 8:3161-3164.

14 Ivanova, N. B., Dimos, J. T., Schaniel, C., Hackney, J. A., Moore, K. A., Lemischka, I. R. 2002. A stem cell molecular signature. Science 298:601-604.

15 Lamb, J., Ramaswamy, S., Ford, H. L., Contreras, B., Martinez, R. V., et al. 2003. A mechanism of cyclin D1 action encoded in the patterns of gene expression in human cancer. Cell 114:323-334.

16 LaTulippe, E., Satagopan, J., Smith, A., Scher, H., Scardino, P., Reuter, V., Gerald, W. L. 2002. Comprehensive gene expression analysis of prostate cancer reveals distinct transcriptional programs associated with metastasis. Cancer Res. 62:4499-4506.

17 Lessard, J. and Sauvageau, G. 2003. BMI-1 determines the proliferative capacity of normal and leukaemic stem cells. Nature 423:255-260.

18 Lessard, J., Baban, S., Sauvageau, G. 1998. Stage-specific expression of polycomb group genes in human bone marrow cells. Blood 91:1216-1224.

19 Magee, J. A., Araki, T., Patil, S., Ehrig, T., True, L., Humphrey, P. A., Catalona, W. J., Watson, M. A., Milbrandt, J. 2001. Expression profiling reveals hepsin overexpression in prostate cancer. Cancer Res. 61:5692-5696.

20 Molofsky, A. V., Pardal, R., Iwashita, T., Park, I.-K., Clarke, M. F., Morrison, S. J. 2003. Bmi-1 dependence distinguishes neural stem cell self-renewal from progenitor proliferation. Nature 425:962-967.

21 Pardal, R., Clarke, M. F., Morrison, S. J. 2003. Applying the principle of stem-cell biology to cancer. Nature Review Cancer 3:895-902.

22 Park, I.-K., Qian, D., Kiel, M., Becker, M. W., Pihalja, M., Weissman, I. L., Morrison, S. J., Clarke, M. F. Bmi-1 is required for maintenance of adult self-renewing haematopoietic stem cells. 2003. Nature 423:302-305.

23 Raaphorst, F. M. Vermeer, M., Fieret, E., Blokzijl, T., Mommers, E., Buerger, H., Packeisen, J., Sewalt, R. A., Otte, A. P., van Diset, P. J. 2003. Poorly differentiated breast carcinoma is associated with increased expression of the human polycomb group EZH2 gene. Neoplasia 5:481-488.

24 Smalley, M. and Ashworth, A. Stem cells and breast cancer: a field in transit. 2003. Nature Review Cancer 3:832-844.

25 van de Vijver, M. J., He, Y. D., van 't Veer, L. J., et al. 2002. A gene expression signature as a predictor of survival in breast cancer. N. Engl. J. Med. 347:19992009.

26 Vassilopoulos, G., Wang, P.-R., Russell, D. W. 2003. Transplanted bone marrow regenerates liver by cell fusion. Nature 422:901-904.

27 Vonlanthen, S., et al. 2001. The Bmi-1 oncoprotein is differentially expressed in non-small-cell lung cancer and correlates with INK4A-ARF locus expression. Br. J. Cancer 84:1372-1376.

28 Weimann, J. M., Johansson, C. B., Trejo, A., Blau, H. M. 2003. Stable reprogrammed heterokaryons form spontaneously in Purkinje neurons after bone marrow transplant. Nature Cell Biology 5:959-966.

What is claimed is:

1. A method for predicting a clinical outcome for a human subject having prostate cancer, comprising:
   determining the mRNA expression of a set of genes in a sample from the human subject having prostate cancer, wherein the set of genes consists of the following 11 genes GBX2, MK167, CCNB1, BUB1, KNTC2, USP22, HCFC1, RNF2, ANK3, FGFR2, and CES1, and
   determining the stem cell-resembling phenotype association index ("SPAI") for the set of genes in the sample by comparison of the mRNA expression of each of the 11 genes from the human subject having prostate cancer to each of the 11 genes in a reference sample from a stem cell, wherein said stem cell is a peripheral nervous system neurosphere;
   wherein a subject whose sample has a positive SPAI is predicted to have a poor clinical outcome and a subject whose sample has a negative SPAI is predicted to have a good clinical outcome.

2. The method of claim 1, wherein said poor clinical outcome is selected from the group consisting of recurrence, failure, likelihood of metastasis, likelihood of distant metastasis, and invasiveness, and said good clinical outcome is selected from disease free survival and likelihood of survival at a predetermined time period.

3. The method of claim 1, further comprising analyzing a clinico-pathological feature selected from the group consisting of a pre-radical prostatectomy Gleason sum, a surgical margin evaluation, a seminal vesicle invasion, an age, and an extra-capsular extension.

* * * * *

SEQUENCE LISTING

```
<160> NUMBER OF SEQ ID NOS: 76

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctcaacga ccactttgtc a                                                   21

<210> SEQ ID NO 2
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcctcttgt gctcttgctg g                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaggcttcct ggccaaagag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgactcgtct ttcccttgcc                                                20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcaaactct ccttgtacca taat                                           24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atagcgatgt gacatgtgct tg                                             22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcagcagga gcttttttgct                                               20

<210> SEQ ID NO 8
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 8
ccaggtgctg cataactgga a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acaccattcc acaagcttcc a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaaggcacc accatgtttt c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgccagtgag cttgagtcct t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcagtcgtg gtttgcacaa c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcaagtgtga cgatgccatc a                                              21

<210> SEQ ID NO 14
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 14
ctgaccagct gcagataagg ct                                              22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccaatggcat cgagtccct                                                  19

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgcccttaa tgactcccac atc                                             23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtattagcc aggatcaaca agca                                            24

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcttgcctcg ctgcagtct                                                  19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccaaggctta gcctccatga a                                               21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 20
actgaccgtt cgctgttacg ag                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctccggcctc tatgcttgta ct                                              22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatcggtgt catcctcatc a                                               21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atagcagact ttggactcgc ca                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccgaaggacc agacatcact ct                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggaatttcca cactgtcccc ta                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggacttccac aggagtgaca tg                                              22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgttcctgga cttgatagca gatg                                            24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcttggacg gtactgaaac tca                                             23

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctctgtattt caatggaagt ggaccattcc                                      30

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtatggttcg ttacctggag accagca                                         27

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcttaagtgc atcacagtca ttgctgctg                                       29

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatgtccaag ttcacaagac cagaccacta ct                                   32

<210> SEQ ID NO 33
<211> LENGTH: 1047
<212> TYPE: DNA
<213> ORGANISM: Homo sapiens

<400> SEQUENCE: 33

```
atgagcgcag cgttcccgcc gtcgctgatg atgatgcagc gcccgctggg gagtagcacc      60
gccttcagca tagactcgct gatcggcagc ccgccgcagc ccagccccgg ccatttcgtc     120
tacaccggct accccatgtt catgccctac cggccggtag tgctgccgcc gccgccgccg     180
ccgccgcccg cgctgcccca ggccgcgctg cagcagcgc tgccgcccgc acaccctcac     240
caccagatcc ccagcctgcc acaggcttc tgctccagcc tggcgcaggg catggcgctc     300
acctctacgc tcatggccac gctccccggc ggcttctccg cgtcgcccca gcaccaggag     360
gcggcagcgg cccgcaagtt cgcgccgcag ccgctgcccg gcggcggtaa cttcgacaag     420
gcggaggcgc tgcaggctga cgcggaggac ggcaaaggct tcctggccaa agagggctcg     480
ctgctcgcct tctccgcggc cgagacggtg caggcttcgc tcgtcgggc tgtccgaggg     540
caagggaaag acgagtcaaa ggtggaagac gacccgaagg gcaaggagga gagcttctcg     600
ctggagagcg atgtggacta cagctcggat gacaatctga ctggccaggc agctcacaag     660
gaggaagacc cggccacgc gctggaggag accccgccga gcagcggcgc cgcgggcagc     720
accacgtcta cgggcaagaa ccggcggcgg cggactgcct tcaccagcga gcagctgctg     780
gagctagaga aggagttcca ctgcaaaaag tacctctcct tgaccgagcg ctcgcagatc     840
gcccacgccc tcaaactcag cgaggtgcag gtgaaaatct ggttccagaa ccgacgggcc     900
aagtggaaac gggtgaaggc aggcaatgcc aattccaaga caggggagcc ctcccggaac     960
cctaagatcg tcgtccccat ccctgtccac gtcagcaggt tcgctatcag aagtcagcat    1020
cagcagctag aacaggcccg gccctga                                        1047
```

<210> SEQ ID NO 34
<211> LENGTH: 348
<212> TYPE: PRT
<213> ORGANISM: Homo sapiens

<400> SEQUENCE: 34

Met Ser Ala Ala Phe Pro Pro Ser Leu Met Met Met Gln Arg Pro Leu
1               5                   10                  15

Gly Ser Ser Thr Ala Phe Ser Ile Asp Ser Leu Ile Gly Ser Pro Pro
            20                  25                  30

Gln Pro Ser Pro Gly His Phe Val Tyr Thr Gly Tyr Pro Met Phe Met
        35                  40                  45

Pro Tyr Arg Pro Val Val Leu Pro Pro Pro Pro Pro Pro Pro Pro Ala
    50                  55                  60

Leu Pro Gln Ala Ala Leu Gln Pro Ala Leu Pro Pro Ala His Pro His
65                  70                  75                  80

His Gln Ile Pro Ser Leu Pro Thr Gly Phe Cys Ser Ser Leu Ala Gln
                85                  90                  95

Gly Met Ala Leu Thr Ser Thr Leu Met Ala Thr Leu Pro Gly Gly Phe
            100                 105                 110

Ser Ala Ser Pro Gln His Gln Glu Ala Ala Ala Arg Lys Phe Ala
        115                 120                 125

Pro Gln Pro Leu Pro Gly Gly Gly Asn Phe Asp Lys Ala Glu Ala Leu
    130                 135                 140

```
Gln Ala Asp Ala Glu Asp Gly Lys Gly Phe Leu Ala Lys Glu Gly Ser
145                 150                 155                 160

Leu Leu Ala Phe Ser Ala Ala Glu Thr Val Gln Ala Ser Leu Val Gly
                165                 170                 175

Ala Val Arg Gly Gln Gly Lys Asp Glu Ser Lys Val Glu Asp Asp Pro
            180                 185                 190

Lys Gly Lys Glu Glu Ser Phe Ser Leu Glu Ser Asp Val Asp Tyr Ser
        195                 200                 205

Ser Asp Asp Asn Leu Thr Gly Gln Ala Ala His Lys Glu Glu Asp Pro
210                 215                 220

Gly His Ala Leu Glu Glu Thr Pro Pro Ser Ser Gly Ala Ala Gly Ser
225                 230                 235                 240

Thr Thr Ser Thr Gly Lys Asn Arg Arg Arg Thr Ala Phe Thr Ser
                245                 250                 255

Glu Gln Leu Leu Glu Leu Glu Lys Glu Phe His Cys Lys Lys Tyr Leu
                260                 265                 270

Ser Leu Thr Glu Arg Ser Gln Ile Ala His Ala Leu Lys Leu Ser Glu
                275                 280                 285

Val Gln Val Lys Ile Trp Phe Gln Asn Arg Arg Ala Lys Trp Lys Arg
290                 295                 300

Val Lys Ala Gly Asn Ala Asn Ser Lys Thr Gly Glu Pro Ser Arg Asn
305                 310                 315                 320

Pro Lys Ile Val Val Pro Ile Pro Val His Val Ser Arg Phe Ala Ile
                325                 330                 335

Arg Ser Gln His Gln Gln Leu Glu Gln Ala Arg Pro
            340                 345

<210> SEQ ID NO 35
<211> LENGTH: 1047
<212> TYPE: DNA
<213> ORGANISM: Mus musculus

<400> SEQUENCE: 35
atgagcgcag cgttcccgcc gtcgctgatg atgatgcagc gccgctgggg gagtagtacc      60
gccttcagca tagactcgct gatcggcagc ccgccgcagc ccagtcccgg ccatttcgtc     120
tacaccggct accccatgtt catgccctac cggccggtgg tgctgccgcc accgccgcca     180
ccgcctcccg cgctgcccca ggcagcgctg cagcccgctc tgccgcccgc gcaccctcac     240
caccagatcc ccagcctgcc caccggcttc tgctccagcc tggcgcaggg catggcgctc     300
acctccacgc tcatggccac tctgcccggc ggcttctctg cgtcgcccca gcaccaagag     360
gcggcggctg cccgcaagtt cgctccacag ccactgcccg gaggcggcaa cttcgacaaa     420
gccgaggcgc tccaagcgga tgcggaagac ggcaaagcct tcttggccaa ggagggctcg     480
ctgctcgctt tctctgcggc cgaagcggtg caggcgtcgc tcgtcgggc tgtccgaggg     540 caagggaaag acgagtcaaa ggtggaagat gacccgaagg gcaaggagga gagcttctct     600
ctggagagcg atgtggatta cagctcagat gacaatttgc ctggtcagac tgctcataag     660
gaagaagacc ccgccacgc actggaggag accccgcaga gcggcggtgc agcaggcagc     720
accacgtcca caggcaagaa ccggcggcgg cggactgcct tcaccagcga acagctgctg     780
gagctggaga agaattccac ctgcaaaaag tacctctccc tgaccgagcg ctcacagatc     840
gcccacgccc tcaaactcag cgaggtgcaa gtaaaaatct ggttccagaa ccgccgggcc     900
aagtggaaac gtgtcaaggc aggcaacgcc aattccaaga cggggagcc ctctcggaac     960 cccaagattg tcgtccccat ccctgttcac gttagcaggt tcgctattcg aagtcaacac    1020
```

-continued cagcagctgg agcaggcccg accctga                                             1047

<210> SEQ ID NO 36
<211> LENGTH: 348
<212> TYPE: PRT
<213> ORGANISM: Mus musculus

<400> SEQUENCE: 36

Met Ser Ala Ala Phe Pro Pro Ser Leu Met Met Gln Arg Pro Leu
1               5                   10                  15

Gly Ser Ser Thr Ala Phe Ser Ile Asp Ser Leu Ile Gly Ser Pro Pro
            20                  25                  30

Gln Pro Ser Pro Gly His Phe Val Tyr Thr Gly Tyr Pro Met Phe Met
        35                  40                  45

Pro Tyr Arg Pro Val Val Leu Pro Pro Pro Pro Pro Pro Pro Ala
    50                  55                  60

Leu Pro Gln Ala Ala Leu Gln Pro Ala Leu Pro Pro Ala His Pro His
65                  70                  75                  80

His Gln Ile Pro Ser Leu Pro Thr Gly Phe Cys Ser Ser Leu Ala Gln
                85                  90                  95

Gly Met Ala Leu Thr Ser Thr Leu Met Ala Thr Leu Pro Gly Gly Phe
            100                 105                 110

Ser Ala Ser Pro Gln His Gln Glu Ala Ala Ala Arg Lys Phe Ala
        115                 120                 125

Pro Gln Pro Leu Pro Gly Gly Gly Asn Phe Asp Lys Ala Glu Ala Leu
    130                 135                 140

Gln Ala Asp Ala Glu Asp Gly Lys Ala Phe Leu Ala Lys Glu Gly Ser
145                 150                 155                 160

Leu Leu Ala Phe Ser Ala Ala Glu Ala Val Gln Ala Ser Leu Val Gly
                165                 170                 175

Ala Val Arg Gly Gln Gly Lys Asp Glu Ser Lys Val Glu Asp Asp Pro
            180                 185                 190

Lys Gly Lys Glu Glu Ser Phe Ser Leu Glu Ser Asp Val Asp Tyr Ser
        195                 200                 205

Ser Asp Asp Asn Leu Pro Gly Gln Thr Ala His Lys Glu Glu Asp Pro
    210                 215                 220

Gly His Ala Leu Glu Glu Thr Pro Gln Ser Gly Gly Ala Ala Gly Ser
225                 230                 235                 240

Thr Thr Ser Thr Gly Lys Asn Arg Arg Arg Thr Ala Phe Thr Ser
                245                 250                 255

Glu Gln Leu Leu Glu Leu Glu Lys Glu Phe His Cys Lys Lys Tyr Leu
            260                 265                 270

Ser Leu Thr Glu Arg Ser Gln Ile Ala His Ala Leu Lys Leu Ser Glu
        275                 280                 285

Val Gln Val Lys Ile Trp Phe Gln Asn Arg Arg Ala Lys Trp Lys Arg
    290                 295                 300

Val Lys Ala Gly Asn Ala Asn Ser Lys Thr Gly Glu Pro Ser Arg Asn
305                 310                 315                 320

Pro Lys Ile Val Val Pro Ile Pro Val His Val Ser Arg Phe Ala Ile
                325                 330                 335

Arg Ser Gln His Gln Leu Glu Gln Ala Arg Pro
            340                 345

<210> SEQ ID NO 37
<211> LENGTH: 9771

<212> TYPE: DNA
<213> ORGANISM: Homo sapiens

<400> SEQUENCE: 37

```
atgtggccca cgagacgcct ggttactatc aaaaggagcg ggtcgacgg tccccacttt      60
cccctgagcc tcagcacctg cttgtttgga agggtattg aatgtgacat ccgtatccag     120
cttcctgttg tgtcaaaaca acattgcaaa attgaaatcc atgagcagga ggcaatatta    180
cataatttca gttccacaaa tccaacacaa gtaaatgggt ctgttattga tgagcctgta    240
cggctaaaac atggagatgt aataactatt attgatcgtt ccttcaggta tgaaaatgaa    300
agtcttcaga atggaaggaa gtcaactgaa tttccaagaa aaatacgtga acaggagcca    360
gcacgtcgtg tctcaagatc tagcttctct tctgaccctg atgagaaagc tcaagattcc    420
aaggcctatt caaaaatcac tgaaggaaaa gtttcaggaa atcctcaggt acatatcaag    480
aatgtcaaag aagacagtac cgcagatgac tcaaaagaca gtgttgctca gggaacaact    540
aatgttcatt cctcagaaca tgctggacgt aatggcagaa atgcagctga tcccatttct    600
ggggatttta agaaatttc cagcgttaaa ttagtgagcc gttatggaga attgaagtct    660
gttcccacta cacaatgtct tgacaatagc aaaaaaatg aatctccctt ttggaagctt    720
tatgagtcag tgaagaaaga gttggatgta aaatcacaaa agaaaatgt cctacagtat    780
tgtagaaaat ctggattaca aactgattac gcaacagaga agaaagtgc tgatggttta    840
cagggggaga cccaactgtt ggtctcgcgt aagtcaagac caaatctgg tgggagcggc    900
cacgctgtgg cagagcctgc ttcacctgaa caagagcttg accagaacaa ggggaaggga    960
agagacgtgg agtctgttca gactcccagc aaggctgtgg gcgccagctt tcctctctat   1020
gagccggcta aatgaagac ccctgtacaa tattcacagc aacaaaattc tccacaaaaa   1080
cataagaaca agacctgta tactactggt agaagagaat ctgtgaatct gggtaaaagt   1140
gaaggcttca aggctggtga taaaactctt actcccagga agctttcaac tagaaatcga   1200
acaccagcta agttgaaga tgcagctgac tctgccacta agccagaaaa tctctcttcc   1260
aaaaccagag gaagtattcc tacagatgtg gaagttctgc ctacgaaac tgaaattcac   1320
aatgagccat ttttaactct gtggctcact caagttgaga ggaagatcca aaaggattcc   1380
ctcagcaagc tgagaaatt gggcactaca gctggacaga tgtgctctgg gttacctggt   1440
cttagttcag ttgatatcaa caactttggt gattccatta atgagagtga gggaatacct   1500
ttgaaaagaa ggcgtgtgtc ctttggtggg cacctaagac ctgaactatt tgatgaaaac   1560
ttgcctccta atacgcctct caaaagggga gaagcccca ccaaaagaaa gtctctggta   1620
atgcacactc cacctgtcct gaagaaaatc atcaaggaac agcctcaacc atcaggaaaa   1680
caagagtcag gttcagaaat ccatgtggaa gtgaaggcac aaagcttggt tataagccct   1740
ccagctccta gtcctaggaa aactccagtt gccagtgatc aacgccgtag gtcctgcaaa   1800
acagcccctg cttccagcag caaatctcag acagaggttc ctaagagagg aggagaaaga   1860
gtggcaacct gccttcaaaa gagagtgtct atcagccgaa gtcaacatga tattttacag   1920
atgatatgtt ccaaaagaag aagtggtgct tcggaagcaa atctgattgt tgcaaaatca   1980
tgggcagatg tagtaaaact tggtgcaaaa caaacacaaa ctaaagtcat aaaacatggt   2040
cctcaaaggt caatgaacaa aaggcaaaga agacctgcta ctccaaagaa gcctgtgggc   2100
gaagttcaca gtcaatttag tacaggccac gcaaactctc cttgtaccat aataatggg    2160
aaagctcata ctgaaaaagt acatgtgcct gctcgaccct acagagtgct caacaacttc   2220
atttccaacc aaaaaatgga ctttaaggaa gatctttcag gaatagctga aatgttcaag   2280
```

```
accccagtga aggagcaacc gcagttgaca agcacatgtc acatcgctat ttcaaattca    2340
gagaatttgc ttggaaaaca gtttcaagga actgattcag gagaagaacc tctgctcccc    2400
acctcagaga gttttggagg aaatgtgttc ttcagtgcac agaatgcagc aaaacagcca    2460
tctgataaat gctctgcaag ccctcccttt agacggcagt gtattagaga aaatggaaac    2520
gtagcaaaaa cgcccaggaa cacctacaaa atgacttctc tggagacaaa aacttcagat    2580
actgagacag agccttcaaa aacagtatcc actgtaaaca ggtcaggaag gtctacagag    2640
ttcaggaata tacagaagct acctgtggaa agtaagagtg aagaaacaaa tacagaaatt    2700
gttgagtgca tcctaaaaag aggtcagaag gcaacactac tacaacaaag gagagaagga    2760
gagatgaagg aaatagaaag acctttttgag acatataagg aaaatattga attaaaagaa    2820
aacgatgaaa agatgaaagc aatgaagaga tcaagaactt gggggcagaa atgtgcacca    2880
atgtctgacc tgacagacct caagagcttg cctgatacag aactcatgaa agacacggca    2940
cgtggccaga atctcctcca aacccaagat catgccaagg caccaaagag tgagaaaggc    3000
aaaatcacta aaatgccctg ccagtcatta caaccagaac caataaacac cccaacacac    3060
acaaaacaac agttgaaggc atccctgggg aaagtaggtg tgaaagaaga gctcctagca    3120
gtcggcaagt tcacacggac gtcaggggag accacgcaca cgcacagaga gccagcagga    3180
gatggcaaga gcatcagaac gtttaaggag tctccaaagc agatcctgga cccagcagcc    3240
cgtgtaactg gaatgaagaa gtggccaaga acgcctaagg aagaggccca gtcactagaa    3300
gacctggctg gcttcaaaga gctcttccag acaccaggtc cctctgagga atcaatgact    3360
gatgagaaaa ctaccaaaat agcctgcaaa tctccaccac cagaatcagt ggacactcca    3420
acaagcacaa agcaatggcc taagagaagt ctcaggaaag cagatgtaga ggaagaattc    3480
ttagcactca ggaaactaac accatcagca gggaaagcca tgcttacgcc caaaccagca    3540
ggaggtgatg agaaagacat taagcatttt atgggaactc cagtgcagaa actggacctg    3600
gcaggaactt tacctggcag caaaagacag ctacagactc ctaaggaaaa ggcccaggct    3660
ctagaagacc tggctggctt taagagctc ttccagactc ctggtcacac cgaggaatta    3720
gtggctgctg gtaaaaccac taaaatacc tgcgactctc cacagtcaga cccagtggac    3780
accccaacaa gcacaaagca acgacccaag agaagtatca ggaaagcaga tgtagaggga    3840
gaactcttag cgtgcaggaa tctaatgcca tcagcaggca aagccatgca cacgcctaaa    3900
ccatcagtag gtgaagagaa agacatcatc atatttgtgg gaactccagt gcagaaactg    3960
gacctgacag agaacttaac cggcagcaag agacggccac aaactcctaa ggaagaggcc    4020
caggctctgg aagacctgac tggctttaaa gagctcttcc agaccctgg tcatactgaa    4080 gaagcagtgg ctgctggcaa aactactaaa atgccctgcg aatcttctcc accagaatca    4140
gcagacaccc caacaagcac aagaaggcag cccaagacac ctttggagaa aagggacgta    4200
cagaaggagc tctcagccct gaagaagctc acacagacat caggggaaac cacacacaca    4260
gataaagtac caggaggtga ggataaaagc atcaacgcgt ttaggaaac tgcaaaacag    4320 aaactggacc cagcagcaag tgtaactggt agcaagaggc acccaaaaac taaggaaaag    4380
gcccaacccc tagaagacct ggctggctgg aaagagctct tccagacacc agtatgcact    4440
gacaagccca cgactcacga gaaaactacc aaaatagcct gcagatcaca accagaccca    4500
gtggacacac caacaagctc caagccacag tccaagagaa gtctcaggaa agtggacgta    4560
gaagaagaat tcttcgcact caggaaacga acaccatcag caggcaaagc catgcacaca    4620
cccaaaccag cagtaagtgg tgagaaaaac atctacgcat ttatgggaac tccagtgcag    4680
```

```
aaactggacc tgacagagaa cttaactggc agcaagagac ggctacaaac tcctaaggaa    4740
aaggcccagg ctctagaaga cctggctggc tttaaagagc tcttccagac acgaggtcac    4800
actgaggaat caatgactaa cgataaaact gccaaagtag cctgcaaatc ttcacaacca    4860
gacctagaca aaacccagc aagctccaag cgacggctca agacatccct ggggaaagtg     4920
ggcgtgaaag aagagctcct agcagttggc aagctcacac agacatcagg agagactaca    4980
cacacacaca cagagccaac aggagatggt aagagcatga aagcatttat ggagtctcca    5040
aagcagatct tagactcagc agcaagtcta actggcagca agaggcagct gagaactcct    5100
aagggaaagt ctgaagtccc tgaagacctg gccggcttca tcgagctctt ccagacacca    5160
agtcacacta aggaatcaat gactaatgaa aaaactacca agtatcccta cagagcttca    5220
cagccagacc tagtggacac cccaacaagc tccaagccac agcccaagag aagtctcagg    5280
aaagcagaca ctgaagaaga atttttagca tttaggaaac aaacgccatc agcaggcaaa    5340
gccatgcaca cacccaaacc agcagtaggt gaagagaaag acatcaacac gttttgggga    5400
actccagtgc agaaactgga ccagccagga aatttacctg gcagcaatag acggctacaa    5460
actcgtaagg aaaaggccca ggctctagaa gaactgactg gcttcagaga gcttttccag    5520
acaccatgca ctgataaccc cacagctgat gagaaaacta ccaaaaaaat actctgcaaa    5580
tctccgcaat cagacccagc ggacacccca acaaacacaa agcaacggcc caagagaagc    5640
ctcaagaaag cagacgtaga ggaagaattt ttagcattca ggaaactaac accatcagca    5700
ggcaaagcca tgcacacgcc taagcagca gtaggtgaag agaaagacat caacacattt     5760
gtggggactc cagtggagaa actggacctg ctaggaaatt tacctggcag caagagacgg    5820
ccacaaactc ctaagaaaaa ggccaaggct ctagaagatc tggctggctt caaagagctc    5880
ttccagacac caggtcacac tgaggaatca atgaccgatg acaaaatcac agaagtatcc    5940
tgcaaatctc cacaaccaga cccagtcaaa accccaacaa gctccaagca acgactcaag    6000
atatccttgg ggaaagtagg tgtgaaagaa gaggtcctac cagtcggcaa gctcacacag    6060
acgtcaggga agaccacaca gacacacaga gagacagcag gagatggaaa gagcatcaaa    6120
gcgtttaagg aatctgcaaa gcagatgctg gacccagcaa actatggaac tgggatggag    6180
aggtggccaa gaacacctaa ggaagaggcc caatcactag aagacctggc cggcttcaaa    6240
gagctcttcc agacaccaga ccacactgag gaatcaacaa ctgatgacaa aactaccaaa    6300
atagcctgca aatctccacc accagaatca atggacactc aacaagcac aaggaggcgg    6360 cccaaaacac ctttggggaa aagggatata gtggaagagc tctcagccct gaagcagctc    6420
acacagacca cacacacaga caaagtacca ggagatgagg ataaaggcat caacgtgttc    6480
agggaaactg caaaacagaa actggaccca gcagcaagtg taactggtag caagaggcag    6540
ccaagaactc ctaagggaaa agcccaaccc ctagaagact tggctggctt gaaagagctc    6600
ttccagacac cagtatgcac tgacaagccc acgactcacg agaaaactac caaaatagcc    6660
tgcagatctc cacaaccaga cccagtgggt accccaacaa tcttcaagcc acagtccaag    6720
agaagtctca ggaaagcaga cgtagaggaa gaatccttag cactcaggaa acgaacacca    6780
tcagtaggga aagctatgga cacacccaaa ccagcaggag gtgatgagaa agacatgaaa    6840
gcatttatgg gaactccagt gcagaaattg gacctgccag gaaatttacc tggcagcaaa    6900
agatggccac aaactcctaa ggaaaaggcc caggctctag aagacctggc tggcttcaaa    6960
gagctcttcc agacaccagg cactgacaag cccacgactg atgagaaaac taccaaaata    7020
gcctgcaaat ctccacaacc agacccagtg gacaccccag caagcacaaa gcaacggccc    7080
```

```
aagagaaacc tcaggaaagc agacgtagag gaagaattt tagcactcag gaaacgaaca   7140
ccatcagcag gcaaagccat ggacacccca aaaccagcag taagtgatga gaaaaatatc   7200
aacacatttg tggaaactcc agtgcagaaa ctggacctgc taggaaattt acctggcagc   7260
aagagacagc cacagactcc taaggaaaag gctgaggctc tagaggacct ggttggcttc   7320
aaagaactct tccagacacc aggtcacact gaggaatcaa tgactgatga caaaatcaca   7380
gaagtatcct gtaaatctcc acagccagag tcattcaaaa cctcaagaag ctccaagcaa   7440
aggctcaaga tacccctggt gaaagtggac atgaaagaag agcccctagc agtcagcaag   7500
ctcacacgga catcagggga gactacgcaa acacacacag agccaacagg agatagtaag   7560
agcatcaaag cgtttaagga gtctccaaag cagatcctgg acccagcagc aagtgtaact   7620
ggtagcagga ggcagctgag aactcgtaag gaaaaggccc gtgctctaga agacctggtt   7680
gacttcaaag agctcttctc agcaccaggt cacactgaag agtcaatgac tattgacaaa   7740
aacacaaaaa ttccctgcaa atctccccca ccagaactaa cagacactgc cacgagcaca   7800
aagagatgcc ccaagacacg tcccaggaaa gaagtaaaag aggagctctc agcagttgag   7860
aggctcacgc aaacatcagg gcaaagcaca cacacacaca aagaaccagc aagcggtgat   7920
gagggcatca agtattgaa gcaacgtgca aagaagaaac caaacccagt agaagaggaa   7980
cccagcagga gaaggccaag agcacctaag gaaaaggccc aaccccctgga agacctggcc   8040 ggcttcacag agctctctga acatcaggt cacactcagg aatcactgac tgctggcaaa   8100
gccactaaaa taccctgcga atctccccca ctagaagtgg tagacaccac agcaagcaca   8160
aagaggcatc tcaggacacg tgtgcagaag gtacaagtaa agaagagcc ttcagcagtc   8220 aagttcacac aaacatcagg ggaaaccacg gatgcagaca aagaaccagc aggtgaagat   8280
aaaggcatca aagcattgaa ggaatctgca aaacagacac cggctccagc agcaagtgta   8340
actggcagca ggagacggcc aagagcaccc agggaaagtg cccaagccat agaagaccta   8400
gctggcttca agacccagc agcaggtcac actgaagaat caatgactga tgacaaaacc   8460
actaaaatac cctgcaaatc atcaccgaaa ctagaagaca ccgcaacaag ctcaaagaga   8520
cggcccagga cacgtgccca gaaagtagaa gtgaaggagg agctgttagc agttggcaag   8580
ctcacacaaa cctcagggga gaccacgcac accgacaaag agccggtagg tgagggcaaa   8640
ggcacgaaag catttaagca acctgcaaag cggaacgtgg acgcagaaga tgtaattggc   8700
agcaggagac agccaagagc acctaaggaa aaggcccaac ccctggaaga cctggccagc   8760
ttccaagagc tctctcaaac accaggccac actgaggaac tggcaaatgg tgctgctgat   8820
agctttacaa gcgctccaaa gcaaacacct gacagtggaa aacctctaaa aatatccaga   8880
agagttcttc gggcccctaa agtagaaccc gtgggagacg tggtaagcac cagagaccct   8940
gtaaaatcac aaagcaaaag caacacttcc ctgcccccac tgcccttcaa gaggggaggt   9000
ggcaaagatg gaagcgtcac gggaaccaag aggctgcgct gcatgccagc accagaggaa   9060
attgtggagg agctgccagc cagcaagaag cagagggttg ctcccagggc aagaggcaaa   9120
tcatccgaac ccgtggtcat catgaagaga gtttgagga cttctgcaaa aagaattgaa   9180
cctgcggaag agctgaacag caacgacatg aaaaccaaca agaggaaca caaattacaa   9240 gactcggtcc ctgaaaataa gggaatatcc ctgcgctcca gacgcaagaa taagactgag   9300
gcagaacagc aaataactga ggtctttgta ttagcagaaa gaatagaaat aaacagaaat   9360
gaaaagaagc ccatgaagac ctccccagag atggacattc agaatccaga tgatggagcc   9420
cggaaaccca tacctagaga caaagtcact gagaacaaaa ggtgcttgag gtctgctaga   9480
```

```
cagaatgaga gctcccagcc taaggtggca gaggagagcg gagggcagaa gagtgcgaag    9540
gttctcatgc agaatcagaa agggaaagga gaagcaggaa attcagactc catgtgcctg    9600
agatcaagaa agacaaaaag ccagcctgca gcaagcactt tggagagcaa atctgtgcag    9660
agagtaacgc ggagtgtcaa gaggtgtgca gaaaatccaa agaaggctga ggacaatgtg    9720
tgtgtcaaga aaataacaac cagaagtcat agggacagtg aagatatttg a             9771
```

<210> SEQ ID NO 38
<211> LENGTH: 3256
<212> TYPE: PRT
<213> ORGANISM: Homo sapiens

<400> SEQUENCE: 38

```
Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
```

-continued

```
                325                 330                 335
Phe Pro Leu Tyr Glu Pro Ala Lys Met Lys Thr Pro Val Gln Tyr Ser
            340                 345                 350
Gln Gln Gln Asn Ser Pro Gln Lys His Lys Asn Lys Asp Leu Tyr Thr
            355                 360                 365
Thr Gly Arg Arg Glu Ser Val Asn Leu Gly Lys Ser Glu Gly Phe Lys
            370                 375             380
Ala Gly Asp Lys Thr Leu Thr Pro Arg Lys Leu Ser Thr Arg Asn Arg
385                 390                 395                 400
Thr Pro Ala Lys Val Glu Asp Ala Ala Asp Ser Ala Thr Lys Pro Glu
                405                 410                 415
Asn Leu Ser Ser Lys Thr Arg Gly Ser Ile Pro Thr Asp Val Glu Val
            420                 425                 430
Leu Pro Thr Glu Thr Glu Ile His Asn Glu Pro Phe Leu Thr Leu Trp
            435                 440                 445
Leu Thr Gln Val Glu Arg Lys Ile Gln Lys Asp Ser Leu Ser Lys Pro
            450                 455                 460
Glu Lys Leu Gly Thr Thr Ala Gly Gln Met Cys Ser Gly Leu Pro Gly
465                 470                 475                 480
Leu Ser Ser Val Asp Ile Asn Asn Phe Gly Asp Ser Ile Asn Glu Ser
                485                 490                 495
Glu Gly Ile Pro Leu Lys Arg Arg Val Ser Phe Gly Gly His Leu
            500                 505                 510
Arg Pro Glu Leu Phe Asp Glu Asn Leu Pro Pro Asn Thr Pro Leu Lys
            515                 520                 525
Arg Gly Glu Ala Pro Thr Lys Arg Lys Ser Leu Val Met His Thr Pro
            530                 535                 540
Pro Val Leu Lys Lys Ile Ile Lys Glu Gln Pro Gln Pro Ser Gly Lys
545                 550                 555                 560
Gln Glu Ser Gly Ser Glu Ile His Val Glu Val Lys Ala Gln Ser Leu
                565                 570                 575
Val Ile Ser Pro Pro Ala Pro Ser Pro Arg Lys Thr Pro Val Ala Ser
            580                 585                 590
Asp Gln Arg Arg Arg Ser Cys Lys Thr Ala Pro Ala Ser Ser Ser Lys
            595                 600                 605
Ser Gln Thr Glu Val Pro Lys Arg Gly Gly Glu Arg Val Ala Thr Cys
            610                 615                 620
Leu Gln Lys Arg Val Ser Ile Ser Arg Ser Gln His Asp Ile Leu Gln
625                 630                 635                 640
Met Ile Cys Ser Lys Arg Arg Ser Gly Ala Ser Glu Ala Asn Leu Ile
                645                 650                 655
Val Ala Lys Ser Trp Ala Asp Val Val Lys Leu Gly Ala Lys Gln Thr
            660                 665                 670
Gln Thr Lys Val Ile Lys His Gly Pro Gln Arg Ser Met Asn Lys Arg
            675                 680                 685
Gln Arg Arg Pro Ala Thr Pro Lys Lys Pro Val Gly Glu Val His Ser
            690                 695                 700
Gln Phe Ser Thr Gly His Ala Asn Ser Pro Cys Thr Ile Ile Ile Gly
705                 710                 715                 720
Lys Ala His Thr Glu Lys Val His Val Pro Ala Arg Pro Tyr Arg Val
                725                 730                 735
Leu Asn Asn Phe Ile Ser Asn Gln Lys Met Asp Phe Lys Glu Asp Leu
            740                 745                 750
```

-continued

```
Ser Gly Ile Ala Glu Met Phe Lys Thr Pro Val Lys Glu Gln Pro Gln
        755                 760                 765

Leu Thr Ser Thr Cys His Ile Ala Ile Ser Asn Ser Glu Asn Leu Leu
        770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
            820                 825                 830

Gln Cys Ile Arg Glu Asn Gly Asn Val Ala Lys Thr Pro Arg Asn Thr
                835                 840                 845

Tyr Lys Met Thr Ser Leu Glu Thr Lys Thr Ser Asp Thr Glu Thr Glu
        850                 855                 860

Pro Ser Lys Thr Val Ser Thr Val Asn Arg Ser Gly Arg Ser Thr Glu
865                 870                 875                 880

Phe Arg Asn Ile Gln Lys Leu Pro Val Glu Ser Lys Ser Glu Glu Thr
                885                 890                 895

Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
        915                 920                 925

Phe Glu Thr Tyr Lys Glu Asn Ile Glu Leu Lys Glu Asn Asp Glu Lys
        930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
            980                 985                 990

Lys Ala Pro Lys Ser Glu Lys Gly Lys Ile Thr Lys Met Pro Cys Gln
        995                 1000                1005

Ser Leu Gln Pro Glu Pro Ile Asn Thr Pro Thr His  Thr Lys Gln
        1010                1015                1020

Gln Leu Lys Ala Ser Leu Gly Lys Val Gly Val Lys  Glu Glu Leu
        1025                1030                1035

Leu Ala Val Gly Lys Phe Thr Arg Thr Ser Gly Glu  Thr Thr His
        1040                1045                1050

Thr His Arg Glu Pro Ala Gly Asp Gly Lys Ser Ile  Arg Thr Phe
        1055                1060                1065

Lys Glu Ser Pro Lys Gln Ile Leu Asp Pro Ala Ala  Arg Val Thr
        1070                1075                1080

Gly Met Lys Lys Trp Pro Arg Thr Pro Lys Glu Glu  Ala Gln Ser
        1085                1090                1095

Leu Glu Asp Leu Ala Gly Phe Lys Glu Leu Phe Gln  Thr Pro Gly
        1100                1105                1110

Pro Ser Glu Glu Ser Met Thr Asp Glu Lys Thr Thr  Lys Ile Ala
        1115                1120                1125

Cys Lys Ser Pro Pro Pro Glu Ser Val Asp Thr Pro  Thr Ser Thr
        1130                1135                1140

Lys Gln Trp Pro Lys Arg Ser Leu Arg Lys Ala Asp  Val Glu Glu
        1145                1150                1155

Glu Phe Leu Ala Leu Arg Lys Leu Thr Pro Ser Ala  Gly Lys Ala
        1160                1165                1170
```

```
Met Leu Thr Pro Lys Pro Ala Gly Gly Asp Glu Lys Asp Ile Lys
1175                1180                    1185

Ala Phe Met Gly Thr Pro Val Gln Lys Leu Asp Leu Ala Gly Thr
1190                1195                    1200

Leu Pro Gly Ser Lys Arg Gln Leu Gln Thr Pro Lys Glu Lys Ala
1205                1210                    1215

Gln Ala Leu Glu Asp Leu Ala Gly Phe Lys Glu Leu Phe Gln Thr
1220                1225                    1230

Pro Gly His Thr Glu Glu Leu Val Ala Ala Gly Lys Thr Thr Lys
1235                1240                    1245

Ile Pro Cys Asp Ser Pro Gln Ser Asp Pro Val Asp Thr Pro Thr
1250                1255                    1260

Ser Thr Lys Gln Arg Pro Lys Arg Ser Ile Arg Lys Ala Asp Val
1265                1270                    1275

Glu Gly Glu Leu Leu Ala Cys Arg Asn Leu Met Pro Ser Ala Gly
1280                1285                    1290

Lys Ala Met His Thr Pro Lys Pro Ser Val Gly Glu Glu Lys Asp
1295                1300                    1305

Ile Ile Ile Phe Val Gly Thr Pro Val Gln Lys Leu Asp Leu Thr
1310                1315                    1320

Glu Asn Leu Thr Gly Ser Lys Arg Arg Pro Gln Thr Pro Lys Glu
1325                1330                    1335

Glu Ala Gln Ala Leu Glu Asp Leu Thr Gly Phe Lys Glu Leu Phe
1340                1345                    1350

Gln Thr Pro Gly His Thr Glu Glu Ala Val Ala Ala Gly Lys Thr
1355                1360                    1365

Thr Lys Met Pro Cys Glu Ser Ser Pro Pro Glu Ser Ala Asp Thr
1370                1375                    1380

Pro Thr Ser Thr Arg Arg Gln Pro Lys Thr Pro Leu Glu Lys Arg
1385                1390                    1395

Asp Val Gln Lys Glu Leu Ser Ala Leu Lys Lys Leu Thr Gln Thr
1400                1405                    1410

Ser Gly Glu Thr Thr His Thr Asp Lys Val Pro Gly Gly Glu Asp
1415                1420                    1425

Lys Ser Ile Asn Ala Phe Arg Glu Thr Ala Lys Gln Lys Leu Asp
1430                1435                    1440

Pro Ala Ala Ser Val Thr Gly Ser Lys Arg His Pro Lys Thr Lys
1445                1450                    1455

Glu Lys Ala Gln Pro Leu Glu Asp Leu Ala Gly Trp Lys Glu Leu
1460                1465                    1470

Phe Gln Thr Pro Val Cys Thr Asp Lys Pro Thr Thr His Glu Lys
1475                1480                    1485

Thr Thr Lys Ile Ala Cys Arg Ser Gln Pro Asp Pro Val Asp Thr
1490                1495                    1500

Pro Thr Ser Ser Lys Pro Gln Ser Lys Arg Ser Leu Arg Lys Val
1505                1510                    1515

Asp Val Glu Glu Glu Phe Phe Ala Leu Arg Lys Arg Thr Pro Ser
1520                1525                    1530

Ala Gly Lys Ala Met His Thr Pro Lys Pro Ala Val Ser Gly Glu
1535                1540                    1545

Lys Asn Ile Tyr Ala Phe Met Gly Thr Pro Val Gln Lys Leu Asp
1550                1555                    1560

Leu Thr Glu Asn Leu Thr Gly Ser Lys Arg Arg Leu Gln Thr Pro
```

-continued

```
            1565                1570                1575

Lys Glu Lys Ala Gln Ala Leu Glu Asp Leu Ala Gly Phe Lys Glu
    1580                1585                1590

Leu Phe Gln Thr Arg Gly His Thr Glu Glu Ser Met Thr Asn Asp
    1595                1600                1605

Lys Thr Ala Lys Val Ala Cys Lys Ser Ser Gln Pro Asp Leu Asp
    1610                1615                1620

Lys Asn Pro Ala Ser Ser Lys Arg Arg Leu Lys Thr Ser Leu Gly
    1625                1630                1635

Lys Val Gly Val Lys Glu Glu Leu Leu Ala Val Gly Lys Leu Thr
    1640                1645                1650

Gln Thr Ser Gly Glu Thr Thr His Thr His Thr Glu Pro Thr Gly
    1655                1660                1665

Asp Gly Lys Ser Met Lys Ala Phe Met Glu Ser Pro Lys Gln Ile
    1670                1675                1680

Leu Asp Ser Ala Ala Ser Leu Thr Gly Ser Lys Arg Gln Leu Arg
    1685                1690                1695

Thr Pro Lys Gly Lys Ser Glu Val Pro Glu Asp Leu Ala Gly Phe
    1700                1705                1710

Ile Glu Leu Phe Gln Thr Pro Ser His Thr Lys Glu Ser Met Thr
    1715                1720                1725

Asn Glu Lys Thr Thr Lys Val Ser Tyr Arg Ala Ser Gln Pro Asp
    1730                1735                1740

Leu Val Asp Thr Pro Thr Ser Ser Lys Pro Gln Pro Lys Arg Ser
    1745                1750                1755

Leu Arg Lys Ala Asp Thr Glu Glu Phe Leu Ala Phe Arg Lys
    1760                1765                1770

Gln Thr Pro Ser Ala Gly Lys Ala Met His Thr Pro Lys Pro Ala
    1775                1780                1785

Val Gly Glu Glu Lys Asp Ile Asn Thr Phe Leu Gly Thr Pro Val
    1790                1795                1800

Gln Lys Leu Asp Gln Pro Gly Asn Leu Pro Gly Ser Asn Arg Arg
    1805                1810                1815

Leu Gln Thr Arg Lys Glu Lys Ala Gln Ala Leu Glu Glu Leu Thr
    1820                1825                1830

Gly Phe Arg Glu Leu Phe Gln Thr Pro Cys Thr Asp Asn Pro Thr
    1835                1840                1845

Ala Asp Glu Lys Thr Thr Lys Lys Ile Leu Cys Lys Ser Pro Gln
    1850                1855                1860

Ser Asp Pro Ala Asp Thr Pro Thr Asn Thr Lys Gln Arg Pro Lys
    1865                1870                1875

Arg Ser Leu Lys Lys Ala Asp Val Glu Glu Phe Leu Ala Phe
    1880                1885                1890

Arg Lys Leu Thr Pro Ser Ala Gly Lys Ala Met His Thr Pro Lys
    1895                1900                1905

Ala Ala Val Gly Glu Glu Lys Asp Ile Asn Thr Phe Val Gly Thr
    1910                1915                1920

Pro Val Glu Lys Leu Asp Leu Leu Gly Asn Leu Pro Gly Ser Lys
    1925                1930                1935

Arg Arg Pro Gln Thr Pro Lys Glu Lys Ala Lys Ala Leu Glu Asp
    1940                1945                1950

Leu Ala Gly Phe Lys Glu Leu Phe Gln Thr Pro Gly His Thr Glu
    1955                1960                1965
```

-continued

Glu Ser Met Thr Asp Asp Lys Ile Thr Glu Val Ser Cys Lys Ser
1970                1975                1980

Pro Gln Pro Asp Pro Val Lys Thr Pro Thr Ser Ser Lys Gln Arg
1985                1990                1995

Leu Lys Ile Ser Leu Gly Lys Val Gly Val Lys Glu Glu Val Leu
2000                2005                2010

Pro Val Gly Lys Leu Thr Gln Thr Ser Gly Lys Thr Thr Gln Thr
2015                2020                2025

His Arg Glu Thr Ala Gly Asp Gly Lys Ser Ile Lys Ala Phe Lys
2030                2035                2040

Glu Ser Ala Lys Gln Met Leu Asp Pro Ala Asn Tyr Gly Thr Gly
2045                2050                2055

Met Glu Arg Trp Pro Arg Thr Pro Lys Glu Glu Ala Gln Ser Leu
2060                2065                2070

Glu Asp Leu Ala Gly Phe Lys Glu Leu Phe Gln Thr Pro Asp His
2075                2080                2085

Thr Glu Glu Ser Thr Thr Asp Asp Lys Thr Thr Lys Ile Ala Cys
2090                2095                2100

Lys Ser Pro Pro Pro Glu Ser Met Asp Thr Pro Thr Ser Thr Arg
2105                2110                2115

Arg Arg Pro Lys Thr Pro Leu Gly Lys Arg Asp Ile Val Glu Glu
2120                2125                2130

Leu Ser Ala Leu Lys Gln Leu Thr Gln Thr Thr His Thr Asp Lys
2135                2140                2145

Val Pro Gly Asp Glu Asp Lys Gly Ile Asn Val Phe Arg Glu Thr
2150                2155                2160

Ala Lys Gln Lys Leu Asp Pro Ala Ala Ser Val Thr Gly Ser Lys
2165                2170                2175

Arg Gln Pro Arg Thr Pro Lys Gly Lys Ala Gln Pro Leu Glu Asp
2180                2185                2190

Leu Ala Gly Leu Lys Glu Leu Phe Gln Thr Pro Val Cys Thr Asp
2195                2200                2205

Lys Pro Thr Thr His Glu Lys Thr Thr Lys Ile Ala Cys Arg Ser
2210                2215                2220

Pro Gln Pro Asp Pro Val Gly Thr Pro Thr Ile Phe Lys Pro Gln
2225                2230                2235

Ser Lys Arg Ser Leu Arg Lys Ala Asp Val Glu Glu Glu Ser Leu
2240                2245                2250

Ala Leu Arg Lys Arg Thr Pro Ser Val Gly Lys Ala Met Asp Thr
2255                2260                2265

Pro Lys Pro Ala Gly Gly Asp Glu Lys Asp Met Lys Ala Phe Met
2270                2275                2280

Gly Thr Pro Val Gln Lys Leu Asp Leu Pro Gly Asn Leu Pro Gly
2285                2290                2295

Ser Lys Arg Trp Pro Gln Thr Pro Lys Glu Lys Ala Gln Ala Leu
2300                2305                2310

Glu Asp Leu Ala Gly Phe Lys Glu Leu Phe Gln Thr Pro Gly Thr
2315                2320                2325

Asp Lys Pro Thr Thr Asp Glu Lys Thr Thr Lys Ile Ala Cys Lys
2330                2335                2340

Ser Pro Gln Pro Asp Pro Val Asp Thr Pro Ala Ser Thr Lys Gln
2345                2350                2355

Arg Pro Lys Arg Asn Leu Arg Lys Ala Asp Val Glu Glu Glu Phe
2360                2365                2370

-continued

```
Leu Ala Leu Arg Lys Arg Thr Pro Ser Ala Gly Lys Ala Met Asp
        2375                2380                2385

Thr Pro Lys Pro Ala Val Ser Asp Glu Lys Asn Ile Asn Thr Phe
        2390                2395                2400

Val Glu Thr Pro Val Gln Lys Leu Asp Leu Leu Gly Asn Leu Pro
        2405                2410                2415

Gly Ser Lys Arg Gln Pro Gln Thr Pro Lys Glu Lys Ala Glu Ala
        2420                2425                2430

Leu Glu Asp Leu Val Gly Phe Lys Glu Leu Phe Gln Thr Pro Gly
        2435                2440                2445

His Thr Glu Glu Ser Met Thr Asp Asp Lys Ile Thr Glu Val Ser
        2450                2455                2460

Cys Lys Ser Pro Gln Pro Glu Ser Phe Lys Thr Ser Arg Ser Ser
        2465                2470                2475

Lys Gln Arg Leu Lys Ile Pro Leu Val Lys Val Asp Met Lys Glu
        2480                2485                2490

Glu Pro Leu Ala Val Ser Lys Leu Thr Arg Thr Ser Gly Glu Thr
        2495                2500                2505

Thr Gln Thr His Thr Glu Pro Thr Gly Asp Ser Lys Ser Ile Lys
        2510                2515                2520

Ala Phe Lys Glu Ser Pro Lys Gln Ile Leu Asp Pro Ala Ala Ser
        2525                2530                2535

Val Thr Gly Ser Arg Arg Gln Leu Arg Thr Arg Lys Glu Lys Ala
        2540                2545                2550

Arg Ala Leu Glu Asp Leu Val Asp Phe Lys Glu Leu Phe Ser Ala
        2555                2560                2565

Pro Gly His Thr Glu Glu Ser Met Thr Ile Asp Lys Asn Thr Lys
        2570                2575                2580

Ile Pro Cys Lys Ser Pro Pro Glu Leu Thr Asp Thr Ala Thr
        2585                2590                2595

Ser Thr Lys Arg Cys Pro Lys Thr Arg Pro Arg Lys Glu Val Lys
        2600                2605                2610

Glu Glu Leu Ser Ala Val Glu Arg Leu Thr Gln Thr Ser Gly Gln
        2615                2620                2625

Ser Thr His Thr His Lys Glu Pro Ala Ser Gly Asp Glu Gly Ile
        2630                2635                2640

Lys Val Leu Lys Gln Arg Ala Lys Lys Lys Pro Asn Pro Val Glu
        2645                2650                2655

Glu Glu Pro Ser Arg Arg Arg Pro Arg Ala Pro Lys Glu Lys Ala
        2660                2665                2670

Gln Pro Leu Glu Asp Leu Ala Gly Phe Thr Glu Leu Ser Glu Thr
        2675                2680                2685

Ser Gly His Thr Gln Glu Ser Leu Thr Ala Gly Lys Ala Thr Lys
        2690                2695                2700

Ile Pro Cys Glu Ser Pro Pro Leu Glu Val Val Asp Thr Thr Ala
        2705                2710                2715

Ser Thr Lys Arg His Leu Arg Thr Arg Val Gln Lys Val Gln Val
        2720                2725                2730

Lys Glu Glu Pro Ser Ala Val Lys Phe Thr Gln Thr Ser Gly Glu
        2735                2740                2745

Thr Thr Asp Ala Asp Lys Glu Pro Ala Gly Glu Asp Lys Gly Ile
        2750                2755                2760

Lys Ala Leu Lys Glu Ser Ala Lys Gln Thr Pro Ala Pro Ala Ala
```

```
                    2765                2770                2775
          Ser Val Thr Gly Ser Arg Arg Pro Arg Ala Pro Arg Glu Ser
                2780                2785                2790
          Ala Gln Ala Ile Glu Asp Leu Ala Gly Phe Lys Asp Pro Ala Ala
                2795                2800                2805
          Gly His Thr Glu Glu Ser Met Thr Asp Asp Lys Thr Thr Lys Ile
                2810                2815                2820
          Pro Cys Lys Ser Ser Pro Glu Leu Glu Asp Thr Ala Thr Ser Ser
                2825                2830                2835
          Lys Arg Arg Pro Arg Thr Arg Ala Gln Lys Val Glu Val Lys Glu
                2840                2845                2850
          Glu Leu Leu Ala Val Gly Lys Leu Thr Gln Thr Ser Gly Glu Thr
                2855                2860                2865
          Thr His Thr Asp Lys Glu Pro Val Gly Glu Gly Lys Gly Thr Lys
                2870                2875                2880
          Ala Phe Lys Gln Pro Ala Lys Arg Asn Val Asp Ala Glu Asp Val
                2885                2890                2895
          Ile Gly Ser Arg Arg Gln Pro Arg Ala Pro Lys Glu Lys Ala Gln
                2900                2905                2910
          Pro Leu Glu Asp Leu Ala Ser Phe Gln Glu Leu Ser Gln Thr Pro
                2915                2920                2925
          Gly His Thr Glu Glu Leu Ala Asn Gly Ala Ala Asp Ser Phe Thr
                2930                2935                2940
          Ser Ala Pro Lys Gln Thr Pro Asp Ser Gly Lys Pro Leu Lys Ile
                2945                2950                2955
          Ser Arg Arg Val Leu Arg Ala Pro Lys Val Glu Pro Val Gly Asp
                2960                2965                2970
          Val Val Ser Thr Arg Asp Pro Val Lys Ser Gln Ser Lys Ser Asn
                2975                2980                2985
          Thr Ser Leu Pro Pro Leu Pro Phe Lys Arg Gly Gly Lys Asp
                2990                2995                3000
          Gly Ser Val Thr Gly Thr Lys Arg Leu Arg Cys Met Pro Ala Pro
                3005                3010                3015
          Glu Glu Ile Val Glu Glu Leu Pro Ala Ser Lys Lys Gln Arg Val
                3020                3025                3030
          Ala Pro Arg Ala Arg Gly Lys Ser Ser Glu Pro Val Val Ile Met
                3035                3040                3045
          Lys Arg Ser Leu Arg Thr Ser Ala Lys Arg Ile Glu Pro Ala Glu
                3050                3055                3060
          Glu Leu Asn Ser Asn Asp Met Lys Thr Asn Lys Glu Glu His Lys
                3065                3070                3075
          Leu Gln Asp Ser Val Pro Glu Asn Lys Gly Ile Ser Leu Arg Ser
                3080                3085                3090
          Arg Arg Gln Asp Lys Thr Glu Ala Glu Gln Gln Ile Thr Glu Val
                3095                3100                3105
          Phe Val Leu Ala Glu Arg Ile Glu Ile Asn Arg Asn Glu Lys Lys
                3110                3115                3120
          Pro Met Lys Thr Ser Pro Glu Met Asp Ile Gln Asn Pro Asp Asp
                3125                3130                3135
          Gly Ala Arg Lys Pro Ile Pro Arg Asp Lys Val Thr Glu Asn Lys
                3140                3145                3150
          Arg Cys Leu Arg Ser Ala Arg Gln Asn Glu Ser Ser Gln Pro Lys
                3155                3160                3165
```

```
Val Ala Glu Glu Ser Gly Gly Gln Lys Ser Ala Lys Val Leu Met
3170          3175              3180

Gln Asn Gln Lys Gly Lys Gly Glu Ala Gly Asn Ser Asp Ser Met
3185          3190              3195

Cys Leu Arg Ser Arg Lys Thr Lys Ser Gln Pro Ala Ala Ser Thr
3200          3205              3210

Leu Glu Ser Lys Ser Val Gln Arg Val Thr Arg Ser Val Lys Arg
3215          3220              3225

Cys Ala Glu Asn Pro Lys Lys Ala Glu Asp Asn Val Cys Val Lys
3230          3235              3240

Lys Ile Thr Thr Arg Ser His Arg Asp Ser Glu Asp Ile
3245          3250              3255

<210> SEQ ID NO 39
<211> LENGTH: 8817
<212> TYPE: DNA
<213> ORGANISM: Mus musculus

<400> SEQUENCE: 39
atggcgtcct cggctcacct ggtcaccatc aagcggagcg gcgatgacgg cgcacacttc      60
ccgctgagcc tcagctcctg cctgtttgga aggagtattg aatgtgacat tcgtatccag     120
ctgcctgtag tgtctcaaag acattgccca attgtagtcc aagagcaaga ggcgatatta     180
tataatttca gttctaccaa tccaactcaa gtaaacgggg ttactataga tgagcctgtg     240
aggctgagac atggagacat aataaccatc attgaccgct cctttaggta tgaagatgga     300
aatcatgagg atggaagcaa accaacagaa tttccaggaa agtcccttgg aaaggaacca     360
tcaaggcgag cctcaagaga tagcttctgt gctgaccctg atggggaagg tcaagatacc     420
aaagcttcaa aaatgactgc ttcaagaaga tcttttgtgt atgccaaggg cctttctgca     480
gatagccctg cctcagatgg ctcaaagaac agtgttagcc aagactcatc agggcatgta     540
gaacagcaca ctggcagaaa catagtagag cccacttctg ggggatctct tttaagaagt     600
ccaggtctac agggagcagt tacagggaac cgaagtcttc ttcctacaca gagccttagc     660
aatagcaacg aaaaggaatc tccctttgag aaactttatc aatcaatgaa ggaagagttg     720
gatgtaaaat cccagaaatc ttgtaggaaa tcagaacccc aacctgaccg tgcagcagag     780
gaatcgcggg agacacagct attggtgtca ggcagggcaa agcaaagtc tagtggaagc     840 acccctgtta ctgcagcctc ttcacccaaa gtaggaaaga tctggactga gatggcgc      900 ggtggaatgg tgcctgtcca gacttccaca gagacagcta aatgaagac cctgtgcgg     960 cattcacagc aacttaagga tgaagactct cgtgttactg gcagacgaca ttctgtgaat    1020
ctggatgaag tgaagtgc ccaggcagtc cataaaacag tcactcctgg aaactggcg     1080 actagaaacc aaactccggt ggaggctggg gatgttggca gccccgctga tacaccagaa    1140
cattcctctt cccccagag aagtattcct gcaaaggtag aggctccatc tgcagagaca    1200
caaaatcggc tctctttaac tcagcgcctt gttccaggtg aaaagaaaac tcccaagggt    1260
tccttcagca agcctgagaa actggccaca gccgccgaac agacttgctc tggcctacct    1320
ggtcttagtt ccgttgatat cagcaacttt ggtgattcca ttaacaagag tgagggaatg    1380
cctatgaaga aagacgtgt atcctttggt ggacatctaa gacctgaatt attttgatgaa    1440 aacttgcctc ctaatacacc actgaaaaga ggagaaacgc caaccaagag gaagtctctt    1500
ggcactcaca gcccagctgt cctcaagaca atcatcaagg aacggcccca gtctccaggg    1560
aaacaagagt ctcctgggat aacgccaccg aggacaaatg atcaaagacg cagatcaggc    1620
```

```
aggacttcca gtggaagcaa tttcttatgt gagacagaca ttcccaagaa agcaggcagg    1680
aagagcggta acctgcctgc gaagagagca tccatcagcc ggagtcagca tggcattcta    1740
cagatgattt gctccaaaag gcgaagtgga gcttctgaag ccaacttgat tgttgcaaaa    1800
tcatgggctg atgttgtaaa acttggcgtg aaacaaacac aaacgaaagt tgcgaaacat    1860
gtccctccaa agcagacgag caagagacaa agaagaccca gcactccaaa gaaacccaca    1920
agcaatcttc acaatcaatt tactacaggc catgcaaact ctccctgtac cattgtagta    1980
ggtagagcgc agattgaaaa agtaagtgtg cctgcccgac cctacaaaat gctgaataac    2040
ttgatgctaa accgaaaagt ggacttcagt gaagatctgt caggactaac tgaaatgttc    2100
aagactccag tgaaggagaa gcagcagcag atgagtgata caggctccgt actttccaat    2160
tcagcgaatt tgtctgaaag acaattgcaa gtaactaatt caggagacat acctgagccc    2220
atcaccacag agattttggg agaaaaagtg ctatccagta ctcggaatgc agcaaagcag    2280
cagtctgata gatattctgc aagtcctacc ttaagacggc ggagcatcaa acatgaaaac    2340
acagtgcaaa ctcctaagaa tgtccataac attactgacc ttgagaagaa gactccggtc    2400
tctgagacag agcccctgaa gactgcatcg agtgtgagca gttaagaag atctagagag    2460 ctcagacata cccttgtgga aactatgaat gaaaaaacag aagcagtcct tgctgagaac    2520
accacagcaa gacatttaag ggggacattt cgagaacaaa aagtagatca acaggtgcag    2580
gacaatgaaa acgctcctca agatgcaag gaaagtggtg aattaagtga aggttcagaa    2640
aagacatcag ctaggagatc aagtgccagg aagcagaagc cgacaaaaga cttactagga    2700
agtcagatgg tcacccaaac agcagactat gctgaggaac tacttagtca aggacaagga    2760
accatacaaa acctagagga atccatgcac atgcaaaaca catcaataag tgaggatcaa    2820
ggaattacag aaaagaaagt gaacataata gtatatgcaa ccaaagagaa gcactcgcca    2880 aagaccctg gcaaaaggc acaacctcta aagggccag ctggtctcaa ggaacacttt    2940
gaaacaccaa accccaaaga taaacctata acggaagaca gaactagagt cctttgcaaa    3000
tcaccacaag tcacaacaga gaatatcaca acaaacacaa agccacagac tagcacatct    3060
gggaagaaag tagacatgaa ggaagaaagc tctgccttga caaaacgtat acatatgcca    3120
ggggaatcca ggcataatcc caaaatttta aaacttgagt gtgaggatat caaagctttg    3180
aagcaatctg aaaatgaaat gctgacctca acagtaaatg gaagcaagag gactttagga    3240
aaatctaaaa aaaaggctca gcccctggaa gacctgactt gtttccagga actctttata    3300
tcaccagttc ctactaacat aatcaaaaaa attcccagca atctccaca cacacaacca    3360 gtcagaaccc cagcgagcac aaagagactc tccaagacag gtctcagtaa agtggatgtg    3420
agacaagaac cttcaacact tgggaaaaga acgaagtcac caggcagagc cccaggcaca    3480
ccagcaccag tgcaggaaga aaatgactgc acagcctaca tggaaactcc aaagcagaaa    3540
ctggagtcta tagaaaattt aacagggctt aggaaacagt ccagaacacc taaagacatc    3600
actggtttcc aggatagttt ccaaatacca gatcatgcta atggcccatt agtggttgtc    3660
aaaaccaaaa aaatgttctt taattctcca caaccagaaa gtgccataac ccgaaagagc    3720
agagagagac agtctagggc aagtataagt aaaatagatg ttaaagaaga acttttagaa    3780
tcagaggaac acctacaatt aggagaaggt gtagacacat ttcaggtatc caccaacaaa    3840
gtcattagat catctaggaa acctgcaaag cgtaaactgg attcaacagc tggtatgcct    3900
aacagcaaga ggatgcgctg ttcttcaaag gataacacac catgcctaga agacctgaat    3960
ggcttccaag agctcttcca aatgccaggc tatgctaatg actctttgac cactggaatc    4020
```

```
tcaacaatgc ttgctagatc accacaatta ggaccagtta gaacccaaat caacaaaaag    4080
agtctgccca agatcatctt gagaaaaatg gatgtgacag aagaaatttc aggtctctgg    4140
aagcagtcac tgggcagagt ccacaccaca caagagcagg aggataatgc aatcaaagca    4200
attatggaga ttccaaagga aacactgcag actgcagcag atggaactag gcttaccaga    4260
cagccacaaa cacctaagga aaaagttcaa ccgctggaag atcacagtgt cttccaagaa    4320
ctcttccaaa catcacgcta ctgttctgat ccattaattg gtaacaaaca aacaagaatg    4380
tccttgagat ctccacaacc aggatttgtt agaactccac gaacctcaaa gagactggct    4440
aagacaagtg ttgggaatat tgctgtgaga gaaaagatct ctccagtgag tctgccacag    4500
tgtgctacag gggaggttgt acacataccc atagggccag aagatgacac agagaacaaa    4560
ggtgtgaagg aatccacacc tcagacactg gactcatcag caagtcgaac tgtcagcaag    4620
aggcagcaag gggcacatga ggaaaggcct cagttctcag gagacttatt tcatccccaa    4680
gagctctttc aaacaccagc cagtggcaaa gacccagtaa ctgttgatga aactacaaaa    4740
atagctctgc agtctccaca accaggacat atcataaacc cagcaagcat gaagagacag    4800
tccaacatga gtctcaggaa agacatgaga gaattttcca tacttgaaaa acaaacacag    4860
tcacgaggca gagacgcagg cacaccagca ccaatgcagg aagaaaatgg caccacagcc    4920
attatggaaa caccaaagca gaaactggat ttcataggaa attcaacagg acataagagg    4980
aggcctcgga caccaaaaaa cagggctcag cccctagaag acctggatgg cttccaagaa    5040
ctctttcaaa caccagctgg tgccagtgac cctgtgagtg ttgaagaaag tgcaaagata    5100
tctttggcat cttcacaagc agaaccagtc agaaccccag caagtacaaa gagacgctcc    5160
aagacaggtc tcagtaaagt ggatgtgaga caagaacctt caacacttgg gaaaagaatg    5220
aagtcactag gcagagcccc aggcacacca gcaccagtgc aggaagaaaa tgacagcaca    5280
gccttcatgg aaactccaaa gcagaaactg gatttcacag gaaattcatc aggacataag    5340
aggaggccac agacacctaa gatcagggct cagcccctag aagacctgga tggcttccaa    5400
gaactcttcc aaacaccagc tggtgccaat gactcagtga ctgttgagga aagtgtaaag    5460
atgtctttgg aatcttcaca agcagaacca gtcaaaaccc cggcaagcac aaagagactc    5520
tccaagacag gtctcagtaa ggtggatgtg agagaagacc cttcaatact tgagaaaaaa    5580
acaaagtcac caggcacacc agcaccagtg caggaagaaa atgactgcac agccttcatg    5640
gaaactccaa agcagaaact ggatttcaca ggaaattcat caggacataa gaggaggcca    5700
cggcacccta agatcagagc tcagccccta aagacctgg atggcttcca agaactcttc    5760
caaacaccag ctggtgctag tgactcagtg actgttgagg aaagtgcaaa gatgtctttg    5820
gaatcttcac aagcaaaacc agtcaaaacc ccggcaagca caagagact ctccaagaca    5880 ggtctcagta aggtggatgt gagagaagac ccttcaacac ttgggaaaaa aacaaagtca    5940
ccaggcagag cccaggcac accagcacca gtgcaggaag aaaatgacag cacagccttc    6000
atggaaactc caaagcagaa actggatttt gcagagaatt catcagggag taagagaagg    6060
tcacgaacat ctaagaacag gtctcagccc ctagaagacc tggatggctt ccaagaactc    6120
ttccaaacac cagctggtgc cagtaaccct gtgagtgttg aagaaagtgc aaagatatct    6180
ttggaatctt cacaagcaga accagtcaga acccgggcaa gcacaaagag actttccaag    6240
acaggtctca ataagatgga tgtgagagaa gggcactctc cgctcagtaa gtcaagctgt    6300
gcatcacaga aagtcatgca aaccctcaca cttggagaag atcatggcag agagaccaaa    6360
gatgggaagg tattgttagc tcagaaattg gaaccagcaa tatatgttac tcgtggcaag    6420
```

```
aggcagcaaa ggtcatgtaa gaaaaggtcc cagtccccag aagacctctc tggtgttcag    6480
gaggtcttcc aaacatcagg ccataacaag gattcagtga cagtggacaa tcttgcaaaa    6540
ctgcccagct cgtctccacc actagagcca acagacactt cagtaacctc acggagacag    6600
gccagaactg gtctgaggaa agttcacgtg aaaaatgaac tttcaggagg cataatgcat    6660
ccacaaatat caggggaaat tgtggactta cctagagaac cagaaggtga aggcaaagtc    6720
attaaaacaa ggaagcaatc tgtaaaacgg aaattggaca cagaagtcaa tgtgcctcgc    6780
agtaagaggc aaagaattac aagagcagaa aagaccctag aggatctgcc tggcttccaa    6840
gagctctgcc aagctccaag cttggtaatg gactcagtta ttgttgagaa accccaaag    6900 atgcccgaca aatctccaga acctgtggat acaacttcag agacacaggc aagaagaaga    6960
ctcaggagac tggttgttac tgaagagccc ataccacaaa gaaagactac aagagttgta    7020
aggcaaacca gaaacacaca gaaagagccc ataagtgaca atcaaggtat ggaagagttt    7080
aaggaatctt cagtacagaa acaagaccca agtgtaagtt taactggcag gaggaaccaa    7140
ccaaggacag ttaaggagaa acccaacccc ttagaagaac tcaccagttt ccaagaggaa    7200
actgccaaaa gaatatcttc caaatctcca caaccggaag agaaggaaac cttagcaggt    7260
ttaaagaggc agctcagaat acaactaatc aacgatggtg taaaagaaga gcccacagca    7320 cagaaaagc aaccatccag ggaaaccagg aacacactca aagagcctgt aggtgacagt    7380
ataaatgttg aagaggttaa gaagtctaca aagcagaaaa ttgatccagt agcaagtgtg    7440
cctgtcagca agaggccacg gagggtaccc aaggaaaagg cacaggccct agaattggct    7500
ggtctcaaag gaccaatcca aaccctaggc cacactgatg aatcagcaag tgataaagga    7560
cccacacaga tgccctgtaa ttctctacaa ccagagcaag ttgacagctt ccaaagctca    7620
ccaaggcgac ccaggacaag acgtgggaaa gtagaggcag atgaagagcc ttcagcagta    7680
agaaagacag tatcaacatc aaggcaaact atgcgatccc gcaaggtccc tgaaattggt    7740
aacaatggta cccaagtttc aaaggcctcc ataaagcaga cattagatac agtagccaaa    7800
gtaactggca gcaggaggca gctaaggaca cataaaggat ggggttcaac cctcttgaag    7860
ttgttaggtg actccaaaga aataacccaa atatcagatc actctgagaa actagcacat    7920
gacaccagta tccttaagag cactcaacag caaaagccag actcagtaaa acctctgaga    7980
acatgcagaa gagtgctgag ggcctctaaa gaggtcccca aggaagtgtt ggtggacacc    8040
agagaccatg caacattaca aagcaaaagc aacccttgc tgtccccgaa gaggaagtct    8100
gcaagagatg gaagcattgt gagaaccagg gctttgcgct ctttagcacc aaagcaggaa    8160
gcaacagatg agaagcctgt acctgagaaa aaagggctg cttccagcaa gaggtatgta    8220
tcacctgagc ctgtgaagat gaaacacctg aaaatcgtgt caaacaaact tgaatctgtg    8280
gaagagcagg ttagcactgt tatgaaaaca gaagaaatgg aagccaaaag agaaaatcct    8340
gtcactccag atcagaactc taggtaccga agaaaaccaa atgtaaaaca gccaaggccc    8400
aagtttgatg catctgcaga gaatgtcggg ataaagaaaa acgagaagac tatgaagact    8460 gcctccagg agacagagct gcagaatcca gatgatggag ccaagaaatc tacatctcgg    8520
ggccaagtca gtgggaaaag aacatgcttg aggtctagag aacgactga gatgccccag    8580 ccttgtgaag cagaagagaa acaagcaaa ccagctgcag aaatcttgat aaagcctcag    8640
gaagagaaag gagtctctgg agagtctgat gttaggtgtt tgaggtccag aaaaactaga    8700
gtcgctttgg acagtgaacc taagccaagg gtaactcgtg gaaccaagaa agatgcaaaa    8760
actctgaagg aggatgaaga cattgtatgc accaagaagt taagaacaag aagttaa      8817
```

-continued

```
<210> SEQ ID NO 40
<211> LENGTH: 2938
<212> TYPE: PRT
<213> ORGANISM: Mus musculus

<400> SEQUENCE: 40
```

| | | | | | | | | | | | | | | | |
|---|---|---|---|---|---|---|---|---|---|---|---|---|---|---|---|
| Met | Ala | Ser | Ser | Ala | His | Leu | Val | Thr | Ile | Lys | Arg | Ser | Gly | Asp | Asp |
| 1 | | | | 5 | | | | | 10 | | | | | 15 | |
| Gly | Ala | His | Phe | Pro | Leu | Ser | Leu | Ser | Ser | Cys | Leu | Phe | Gly | Arg | Ser |
| | | | | 20 | | | | | 25 | | | | | 30 | |
| Ile | Glu | Cys | Asp | Ile | Arg | Ile | Gln | Leu | Pro | Val | Val | Ser | Gln | Arg | His |
| | | | 35 | | | | | 40 | | | | | 45 | | |
| Cys | Pro | Ile | Val | Val | Gln | Glu | Gln | Ala | Ile | Leu | Tyr | Asn | Phe | Ser | Ser |
| | 50 | | | | | 55 | | | | | 60 | | | | |
| Ser | Thr | Asn | Pro | Thr | Gln | Val | Asn | Gly | Val | Thr | Ile | Asp | Glu | Pro | Val |
| 65 | | | | | 70 | | | | | 75 | | | | | 80 |
| Arg | Leu | Arg | His | Gly | Asp | Ile | Ile | Thr | Ile | Ile | Asp | Arg | Ser | Phe | Arg |
| | | | | 85 | | | | | 90 | | | | | 95 | |
| Tyr | Glu | Asp | Gly | Asn | His | Glu | Asp | Gly | Ser | Lys | Pro | Thr | Glu | Phe | Pro |
| | | | | 100 | | | | | 105 | | | | | 110 | |
| Gly | Lys | Ser | Leu | Gly | Lys | Glu | Pro | Ser | Arg | Arg | Ala | Ser | Arg | Asp | Ser |
| | | | 115 | | | | | 120 | | | | | 125 | | |
| Phe | Cys | Ala | Asp | Pro | Asp | Gly | Glu | Gly | Gln | Asp | Thr | Lys | Ala | Ser | Lys |
| | 130 | | | | | 135 | | | | | 140 | | | | |
| Met | Thr | Ala | Ser | Arg | Arg | Ser | Phe | Val | Tyr | Ala | Lys | Gly | Leu | Ser | Ala |
| 145 | | | | | 150 | | | | | 155 | | | | | 160 |
| Asp | Ser | Pro | Ala | Ser | Asp | Gly | Ser | Lys | Asn | Ser | Val | Ser | Gln | Asp | Ser |
| | | | | 165 | | | | | 170 | | | | | 175 | |
| Ser | Gly | His | Val | Glu | Gln | His | Thr | Gly | Arg | Asn | Ile | Val | Glu | Pro | Thr |
| | | | 180 | | | | | 185 | | | | | 190 | | |
| Ser | Gly | Gly | Ser | Leu | Leu | Arg | Ser | Pro | Gly | Leu | Gln | Gly | Ala | Val | Thr |
| | | 195 | | | | | 200 | | | | | 205 | | | |
| Gly | Asn | Arg | Ser | Leu | Leu | Pro | Thr | Gln | Ser | Leu | Ser | Asn | Ser | Asn | Glu |
| | 210 | | | | | 215 | | | | | 220 | | | | |
| Lys | Glu | Ser | Pro | Phe | Glu | Lys | Leu | Tyr | Gln | Ser | Met | Lys | Glu | Glu | Leu |
| 225 | | | | | 230 | | | | | 235 | | | | | 240 |
| Asp | Val | Lys | Ser | Gln | Lys | Ser | Cys | Arg | Lys | Ser | Glu | Pro | Gln | Pro | Asp |
| | | | | 245 | | | | | 250 | | | | | 255 | |
| Arg | Ala | Ala | Glu | Glu | Ser | Arg | Glu | Thr | Gln | Leu | Leu | Val | Ser | Gly | Arg |
| | | | 260 | | | | | 265 | | | | | 270 | | |
| Ala | Arg | Ala | Lys | Ser | Ser | Gly | Ser | Thr | Pro | Val | Thr | Ala | Ala | Ser | Ser |
| | | 275 | | | | | 280 | | | | | 285 | | | |
| Pro | Lys | Val | Gly | Lys | Ile | Trp | Thr | Glu | Arg | Trp | Arg | Gly | Gly | Met | Val |
| | 290 | | | | | 295 | | | | | 300 | | | | |
| Pro | Val | Gln | Thr | Ser | Thr | Glu | Thr | Ala | Lys | Met | Lys | Thr | Pro | Val | Arg |
| 305 | | | | | 310 | | | | | 315 | | | | | 320 |
| His | Ser | Gln | Gln | Leu | Lys | Asp | Glu | Asp | Ser | Arg | Val | Thr | Gly | Arg | Arg |
| | | | | 325 | | | | | 330 | | | | | 335 | |
| His | Ser | Val | Asn | Leu | Asp | Glu | Gly | Gly | Ser | Ala | Gln | Ala | Val | His | Lys |
| | | | 340 | | | | | 345 | | | | | 350 | | |
| Thr | Val | Thr | Pro | Gly | Lys | Leu | Ala | Thr | Arg | Asn | Gln | Thr | Pro | Val | Glu |
| | | 355 | | | | | 360 | | | | | 365 | | | |
| Ala | Gly | Asp | Val | Gly | Ser | Pro | Ala | Asp | Thr | Pro | Glu | His | Ser | Ser | Ser |
| | 370 | | | | | 375 | | | | | 380 | | | | |

```
Pro Gln Arg Ser Ile Pro Ala Lys Val Glu Ala Pro Ser Ala Glu Thr
385                 390                 395                 400

Gln Asn Arg Leu Ser Leu Thr Gln Arg Leu Val Pro Gly Glu Lys Lys
                405                 410                 415

Thr Pro Lys Gly Ser Phe Ser Lys Pro Glu Lys Leu Ala Thr Ala Ala
            420                 425                 430

Glu Gln Thr Cys Ser Gly Leu Pro Gly Leu Ser Ser Val Asp Ile Ser
        435                 440                 445

Asn Phe Gly Asp Ser Ile Asn Lys Ser Glu Gly Met Pro Met Lys Arg
    450                 455                 460

Arg Arg Val Ser Phe Gly Gly His Leu Arg Pro Glu Leu Phe Asp Glu
465                 470                 475                 480

Asn Leu Pro Pro Asn Thr Pro Leu Lys Arg Gly Glu Thr Pro Thr Lys
                485                 490                 495

Arg Lys Ser Leu Gly Thr His Ser Pro Ala Val Leu Lys Thr Ile Ile
            500                 505                 510

Lys Glu Arg Pro Gln Ser Pro Gly Lys Gln Glu Ser Pro Gly Ile Thr
        515                 520                 525

Pro Pro Arg Thr Asn Asp Gln Arg Arg Ser Gly Arg Thr Ser Ser
    530                 535                 540

Gly Ser Asn Phe Leu Cys Glu Thr Asp Ile Pro Lys Lys Ala Gly Arg
545                 550                 555                 560

Lys Ser Gly Asn Leu Pro Ala Lys Arg Ala Ser Ile Ser Arg Ser Gln
                565                 570                 575

His Gly Ile Leu Gln Met Ile Cys Ser Lys Arg Arg Ser Gly Ala Ser
            580                 585                 590

Glu Ala Asn Leu Ile Val Ala Lys Ser Trp Ala Asp Val Val Lys Leu
        595                 600                 605

Gly Val Lys Gln Thr Gln Thr Lys Val Ala Lys His Val Pro Pro Lys
    610                 615                 620

Gln Thr Ser Lys Arg Gln Arg Arg Pro Ser Thr Pro Lys Lys Pro Thr
625                 630                 635                 640

Ser Asn Leu His Asn Gln Phe Thr Thr Gly His Ala Asn Ser Pro Cys
                645                 650                 655

Thr Ile Val Val Gly Arg Ala Gln Ile Glu Lys Val Ser Val Pro Ala
            660                 665                 670

Arg Pro Tyr Lys Met Leu Asn Asn Leu Met Leu Asn Arg Lys Val Asp
        675                 680                 685

Phe Ser Glu Asp Leu Ser Gly Leu Thr Glu Met Phe Lys Thr Pro Val
    690                 695                 700

Lys Glu Lys Gln Gln Met Ser Asp Thr Gly Ser Val Leu Ser Asn
705                 710                 715                 720

Ser Ala Asn Leu Ser Glu Arg Gln Leu Gln Val Thr Asn Ser Gly Asp
                725                 730                 735

Ile Pro Glu Pro Ile Thr Thr Glu Ile Leu Gly Glu Lys Val Leu Ser
            740                 745                 750

Ser Thr Arg Asn Ala Ala Lys Gln Gln Ser Asp Arg Tyr Ser Ala Ser
        755                 760                 765

Pro Thr Leu Arg Arg Arg Ser Ile Lys His Glu Asn Thr Val Gln Thr
    770                 775                 780

Pro Lys Asn Val His Asn Ile Thr Asp Leu Glu Lys Lys Thr Pro Val
785                 790                 795                 800

Ser Glu Thr Glu Pro Leu Lys Thr Ala Ser Ser Val Ser Lys Leu Arg
                805                 810                 815
```

```
Arg Ser Arg Glu Leu Arg His Thr Leu Val Glu Thr Met Asn Glu Lys
            820                 825                 830

Thr Glu Ala Val Leu Ala Glu Asn Thr Thr Ala Arg His Leu Arg Gly
            835                 840                 845

Thr Phe Arg Glu Gln Lys Val Asp Gln Gln Val Gln Asp Asn Glu Asn
            850                 855                 860

Ala Pro Gln Arg Cys Lys Glu Ser Gly Glu Leu Ser Glu Gly Ser Glu
865                 870                 875                 880

Lys Thr Ser Ala Arg Arg Ser Ser Ala Arg Lys Gln Lys Pro Thr Lys
                885                 890                 895

Asp Leu Leu Gly Ser Gln Met Val Thr Gln Thr Ala Asp Tyr Ala Glu
            900                 905                 910

Glu Leu Leu Ser Gln Gly Gln Gly Thr Ile Gln Asn Leu Glu Glu Ser
            915                 920                 925

Met His Met Gln Asn Thr Ser Ile Ser Glu Asp Gln Gly Ile Thr Glu
            930                 935                 940

Lys Lys Val Asn Ile Ile Val Tyr Ala Thr Lys Glu Lys His Ser Pro
945                 950                 955                 960

Lys Thr Pro Gly Lys Lys Ala Gln Pro Leu Glu Gly Pro Ala Gly Leu
                965                 970                 975

Lys Glu His Phe Glu Thr Pro Asn Pro Lys Asp Lys Pro Ile Thr Glu
            980                 985                 990

Asp Arg Thr Arg Val Leu Cys Lys  Ser Pro Gln Val Thr  Thr Glu Asn
            995                 1000                1005

Ile Thr  Thr Asn Thr Lys Pro  Gln Thr Ser Thr Ser  Gly Lys Lys
    1010                1015                1020

Val Asp  Met Lys Glu Glu Ser  Ser Ala Leu Thr Lys  Arg Ile His
    1025                1030                1035

Met Pro  Gly Glu Ser Arg His  Asn Pro Lys Ile Leu  Lys Leu Glu
    1040                1045                1050

Cys Glu  Asp Ile Lys Ala Leu  Lys Gln Ser Glu Asn  Glu Met Leu
    1055                1060                1065

Thr Ser  Thr Val Asn Gly Ser  Lys Arg Thr Leu Gly  Lys Ser Lys
    1070                1075                1080

Lys Lys  Ala Gln Pro Leu Glu  Asp Leu Thr Cys Phe  Gln Glu Leu
    1085                1090                1095

Phe Ile  Ser Pro Val Pro Thr  Asn Ile Ile Lys Lys  Ile Pro Ser
    1100                1105                1110

Lys Ser  Pro His Thr Gln Pro  Val Arg Thr Pro Ala  Ser Thr Lys
    1115                1120                1125

Arg Leu  Ser Lys Thr Gly Leu  Ser Lys Val Asp Val  Arg Gln Glu
    1130                1135                1140

Pro Ser  Thr Leu Gly Lys Arg  Thr Lys Ser Pro Gly  Arg Ala Pro
    1145                1150                1155

Gly Thr  Pro Ala Pro Val Gln  Glu Glu Asn Asp Cys  Thr Ala Tyr
    1160                1165                1170

Met Glu  Thr Pro Lys Gln Lys  Leu Glu Ser Ile Glu  Asn Leu Thr
    1175                1180                1185

Gly Leu  Arg Lys Gln Ser Arg  Thr Pro Lys Asp Ile  Thr Gly Phe
    1190                1195                1200

Gln Asp  Ser Phe Gln Ile Pro  Asp His Ala Asn Gly  Pro Leu Val
    1205                1210                1215

Val Val  Lys Thr Lys Lys Met  Phe Phe Asn Ser Pro  Gln Pro Glu
```

-continued

```
            1220                1225                1230

Ser Ala Ile Thr Arg Lys Ser Arg Glu Arg Gln Ser Arg Ala Ser
    1235                1240                1245

Ile Ser Lys Ile Asp Val Lys Glu Glu Leu Leu Glu Ser Glu Glu
    1250                1255                1260

His Leu Gln Leu Gly Glu Gly Val Asp Thr Phe Gln Val Ser Thr
    1265                1270                1275

Asn Lys Val Ile Arg Ser Ser Arg Lys Pro Ala Lys Arg Lys Leu
    1280                1285                1290

Asp Ser Thr Ala Gly Met Pro Asn Ser Lys Arg Met Arg Cys Ser
    1295                1300                1305

Ser Lys Asp Asn Thr Pro Cys Leu Glu Asp Leu Asn Gly Phe Gln
    1310                1315                1320

Glu Leu Phe Gln Met Pro Gly Tyr Ala Asn Asp Ser Leu Thr Thr
    1325                1330                1335

Gly Ile Ser Thr Met Leu Ala Arg Ser Pro Gln Leu Gly Pro Val
    1340                1345                1350

Arg Thr Gln Ile Asn Lys Lys Ser Leu Pro Lys Ile Ile Leu Arg
    1355                1360                1365

Lys Met Asp Val Thr Glu Glu Ile Ser Gly Leu Trp Lys Gln Ser
    1370                1375                1380

Leu Gly Arg Val His Thr Thr Gln Glu Gln Glu Asp Asn Ala Ile
    1385                1390                1395

Lys Ala Ile Met Glu Ile Pro Lys Glu Thr Leu Gln Thr Ala Ala
    1400                1405                1410

Asp Gly Thr Arg Leu Thr Arg Gln Pro Gln Thr Pro Lys Glu Lys
    1415                1420                1425

Val Gln Pro Leu Glu Asp His Ser Val Phe Gln Glu Leu Phe Gln
    1430                1435                1440

Thr Ser Arg Tyr Cys Ser Asp Pro Leu Ile Gly Asn Lys Gln Thr
    1445                1450                1455

Arg Met Ser Leu Arg Ser Pro Gln Pro Gly Phe Val Arg Thr Pro
    1460                1465                1470

Arg Thr Ser Lys Arg Leu Ala Lys Thr Ser Val Gly Asn Ile Ala
    1475                1480                1485

Val Arg Glu Lys Ile Ser Pro Val Ser Leu Pro Gln Cys Ala Thr
    1490                1495                1500

Gly Glu Val Val His Ile Pro Ile Gly Pro Glu Asp Asp Thr Glu
    1505                1510                1515

Asn Lys Gly Val Lys Glu Ser Thr Pro Gln Thr Leu Asp Ser Ser
    1520                1525                1530

Ala Ser Arg Thr Val Ser Lys Arg Gln Gln Gly Ala His Glu Glu
    1535                1540                1545

Arg Pro Gln Phe Ser Gly Asp Leu Phe His Pro Gln Glu Leu Phe
    1550                1555                1560

Gln Thr Pro Ala Ser Gly Lys Asp Pro Val Thr Val Asp Glu Thr
    1565                1570                1575

Thr Lys Ile Ala Leu Gln Ser Pro Gln Pro Gly His Ile Ile Asn
    1580                1585                1590

Pro Ala Ser Met Lys Arg Gln Ser Asn Met Ser Leu Arg Lys Asp
    1595                1600                1605

Met Arg Glu Phe Ser Ile Leu Glu Lys Gln Thr Gln Ser Arg Gly
    1610                1615                1620
```

```
Arg Asp Ala Gly Thr Pro Ala Pro Met Gln Glu Glu Asn Gly Thr
1625                1630                1635

Thr Ala Ile Met Glu Thr Pro Lys Gln Lys Leu Asp Phe Ile Gly
1640                1645                1650

Asn Ser Thr Gly His Lys Arg Arg Pro Arg Thr Pro Lys Asn Arg
1655                1660                1665

Ala Gln Pro Leu Glu Asp Leu Asp Gly Phe Gln Glu Leu Phe Gln
1670                1675                1680

Thr Pro Ala Gly Ala Ser Asp Pro Val Ser Val Glu Glu Ser Ala
1685                1690                1695

Lys Ile Ser Leu Ala Ser Ser Gln Ala Glu Pro Val Arg Thr Pro
1700                1705                1710

Ala Ser Thr Lys Arg Arg Ser Lys Thr Gly Leu Ser Lys Val Asp
1715                1720                1725

Val Arg Gln Glu Pro Ser Thr Leu Gly Lys Arg Met Lys Ser Leu
1730                1735                1740

Gly Arg Ala Pro Gly Thr Pro Ala Pro Val Gln Glu Glu Asn Asp
1745                1750                1755

Ser Thr Ala Phe Met Glu Thr Pro Lys Gln Lys Leu Asp Phe Thr
1760                1765                1770

Gly Asn Ser Ser Gly His Lys Arg Arg Pro Gln Thr Pro Lys Ile
1775                1780                1785

Arg Ala Gln Pro Leu Glu Asp Leu Asp Gly Phe Gln Glu Leu Phe
1790                1795                1800

Gln Thr Pro Ala Gly Ala Asn Asp Ser Val Thr Val Glu Glu Ser
1805                1810                1815

Val Lys Met Ser Leu Glu Ser Ser Gln Ala Glu Pro Val Lys Thr
1820                1825                1830

Pro Ala Ser Thr Lys Arg Leu Ser Lys Thr Gly Leu Ser Lys Val
1835                1840                1845

Asp Val Arg Glu Asp Pro Ser Ile Leu Glu Lys Lys Thr Lys Ser
1850                1855                1860

Pro Gly Thr Pro Ala Pro Val Gln Glu Glu Asn Asp Cys Thr Ala
1865                1870                1875

Phe Met Glu Thr Pro Lys Gln Lys Leu Asp Phe Thr Gly Asn Ser
1880                1885                1890

Ser Gly His Lys Arg Arg Pro Arg Thr Pro Lys Ile Arg Ala Gln
1895                1900                1905

Pro Leu Glu Asp Leu Asp Gly Phe Gln Glu Leu Phe Gln Thr Pro
1910                1915                1920

Ala Gly Ala Ser Asp Ser Val Thr Val Glu Glu Ser Ala Lys Met
1925                1930                1935

Ser Leu Glu Ser Ser Gln Ala Lys Pro Val Lys Thr Pro Ala Ser
1940                1945                1950

Thr Lys Arg Leu Ser Lys Thr Gly Leu Ser Lys Val Asp Val Arg
1955                1960                1965

Glu Asp Pro Ser Thr Leu Gly Lys Lys Thr Lys Ser Pro Gly Arg
1970                1975                1980

Ala Pro Gly Thr Pro Ala Pro Val Gln Glu Glu Asn Asp Ser Thr
1985                1990                1995

Ala Phe Met Glu Thr Pro Lys Gln Lys Leu Asp Phe Ala Glu Asn
2000                2005                2010

Ser Ser Gly Ser Lys Arg Arg Ser Arg Thr Ser Lys Asn Arg Ser
2015                2020                2025
```

```
Gln Pro Leu Glu Asp Leu Asp Gly Phe Gln Leu Phe Gln Thr
    2030            2035                2040
Pro Ala Gly Ala Ser Asn Pro Val Ser Val Glu Glu Ser Ala Lys
    2045            2050                2055
Ile Ser Leu Glu Ser Ser Gln Ala Glu Pro Val Arg Thr Arg Ala
    2060            2065                2070
Ser Thr Lys Arg Leu Ser Lys Thr Gly Leu Asn Lys Met Asp Val
    2075            2080                2085
Arg Glu Gly His Ser Pro Leu Ser Lys Ser Ser Cys Ala Ser Gln
    2090            2095                2100
Lys Val Met Gln Thr Leu Thr Leu Gly Glu Asp His Gly Arg Glu
    2105            2110                2115
Thr Lys Asp Gly Lys Val Leu Leu Ala Gln Lys Leu Glu Pro Ala
    2120            2125                2130
Ile Tyr Val Thr Arg Gly Lys Arg Gln Gln Arg Ser Cys Lys Lys
    2135            2140                2145
Arg Ser Gln Ser Pro Glu Asp Leu Ser Gly Val Gln Glu Val Phe
    2150            2155                2160
Gln Thr Ser Gly His Asn Lys Asp Ser Val Thr Val Asp Asn Leu
    2165            2170                2175
Ala Lys Leu Pro Ser Ser Ser Pro Pro Leu Glu Pro Thr Asp Thr
    2180            2185                2190
Ser Val Thr Ser Arg Arg Gln Ala Arg Thr Gly Leu Arg Lys Val
    2195            2200                2205
His Val Lys Asn Glu Leu Ser Gly Gly Ile Met His Pro Gln Ile
    2210            2215                2220
Ser Gly Glu Ile Val Asp Leu Pro Arg Glu Pro Glu Gly Glu Gly
    2225            2230                2235
Lys Val Ile Lys Thr Arg Lys Gln Ser Val Lys Arg Lys Leu Asp
    2240            2245                2250
Thr Glu Val Asn Val Pro Arg Ser Lys Arg Gln Arg Ile Thr Arg
    2255            2260                2265
Ala Glu Lys Thr Leu Glu Asp Leu Pro Gly Phe Gln Glu Leu Cys
    2270            2275                2280
Gln Ala Pro Ser Leu Val Met Asp Ser Val Ile Val Glu Lys Thr
    2285            2290                2295
Pro Lys Met Pro Asp Lys Ser Pro Glu Pro Val Asp Thr Thr Ser
    2300            2305                2310
Glu Thr Gln Ala Arg Arg Arg Leu Arg Arg Leu Val Val Thr Glu
    2315            2320                2325
Glu Pro Ile Pro Gln Arg Lys Thr Thr Arg Val Val Arg Gln Thr
    2330            2335                2340
Arg Asn Thr Gln Lys Glu Pro Ile Ser Asp Asn Gln Gly Met Glu
    2345            2350                2355
Glu Phe Lys Glu Ser Ser Val Gln Lys Gln Asp Pro Ser Val Ser
    2360            2365                2370
Leu Thr Gly Arg Arg Asn Gln Pro Arg Thr Val Lys Glu Lys Thr
    2375            2380                2385
Gln Pro Leu Glu Glu Leu Thr Ser Phe Gln Glu Thr Ala Lys
    2390            2395                2400
Arg Ile Ser Ser Lys Ser Pro Gln Pro Glu Glu Lys Glu Thr Leu
    2405            2410                2415
Ala Gly Leu Lys Arg Gln Leu Arg Ile Gln Leu Ile Asn Asp Gly
```

2420                    2425                    2430

Val Lys Glu Glu Pro Thr Ala Gln Arg Lys Gln Pro Ser Arg Glu
    2435                    2440                    2445

Thr Arg Asn Thr Leu Lys Glu Pro Val Gly Asp Ser Ile Asn Val
    2450                    2455                    2460

Glu Glu Val Lys Lys Ser Thr Lys Gln Lys Ile Asp Pro Val Ala
    2465                    2470                    2475

Ser Val Pro Val Ser Lys Arg Pro Arg Arg Val Pro Lys Glu Lys
    2480                    2485                    2490

Ala Gln Ala Leu Glu Leu Ala Gly Leu Lys Gly Pro Ile Gln Thr
    2495                    2500                    2505

Leu Gly His Thr Asp Glu Ser Ala Ser Asp Lys Gly Pro Thr Gln
    2510                    2515                    2520

Met Pro Cys Asn Ser Leu Gln Pro Glu Gln Val Asp Ser Phe Gln
    2525                    2530                    2535

Ser Ser Pro Arg Arg Pro Arg Thr Arg Arg Gly Lys Val Glu Ala
    2540                    2545                    2550

Asp Glu Glu Pro Ser Ala Val Arg Lys Thr Val Ser Thr Ser Arg
    2555                    2560                    2565

Gln Thr Met Arg Ser Arg Lys Val Pro Glu Ile Gly Asn Asn Gly
    2570                    2575                    2580

Thr Gln Val Ser Lys Ala Ser Ile Lys Gln Thr Leu Asp Thr Val
    2585                    2590                    2595

Ala Lys Val Thr Gly Ser Arg Arg Gln Leu Arg Thr His Lys Gly
    2600                    2605                    2610

Trp Gly Ser Thr Leu Leu Lys Leu Leu Gly Asp Ser Lys Glu Ile
    2615                    2620                    2625

Thr Gln Ile Ser Asp His Ser Glu Lys Leu Ala His Asp Thr Ser
    2630                    2635                    2640

Ile Leu Lys Ser Thr Gln Gln Gln Lys Pro Asp Ser Val Lys Pro
    2645                    2650                    2655

Leu Arg Thr Cys Arg Arg Val Leu Arg Ala Ser Lys Glu Val Pro
    2660                    2665                    2670

Lys Glu Val Leu Val Asp Thr Arg Asp His Ala Thr Leu Gln Ser
    2675                    2680                    2685

Lys Ser Asn Pro Leu Leu Ser Pro Lys Arg Lys Ser Ala Arg Asp
    2690                    2695                    2700

Gly Ser Ile Val Arg Thr Arg Ala Leu Arg Ser Leu Ala Pro Lys
    2705                    2710                    2715

Gln Glu Ala Thr Asp Glu Lys Pro Val Pro Glu Lys Lys Arg Ala
    2720                    2725                    2730

Ala Ser Ser Lys Arg Tyr Val Ser Pro Glu Pro Val Lys Met Lys
    2735                    2740                    2745

His Leu Lys Ile Val Ser Asn Lys Leu Glu Ser Val Glu Glu Gln
    2750                    2755                    2760

Val Ser Thr Val Met Lys Thr Glu Glu Met Glu Ala Lys Arg Glu
    2765                    2770                    2775

Asn Pro Val Thr Pro Asp Gln Asn Ser Arg Tyr Arg Lys Lys Thr
    2780                    2785                    2790

Asn Val Lys Gln Pro Arg Pro Lys Phe Asp Ala Ser Ala Glu Asn
    2795                    2800                    2805

Val Gly Ile Lys Lys Asn Glu Lys Thr Met Lys Thr Ala Ser Gln
    2810                    2815                    2820

| | | | | | | | | | | | |
|---|---|---|---|---|---|---|---|---|---|---|---|
|Glu|Thr|Glu|Leu|Gln|Asn|Pro|Asp|Asp|Gly|Ala|Lys|Lys|Ser|Thr|
| |2825| | | |2830| | | |2835| | | | | |

| Ser | Arg | Gly | Gln | Val | Ser | Gly | Lys | Arg | Thr | Cys | Leu | Arg | Ser | Arg |
|---|---|---|---|---|---|---|---|---|---|---|---|---|---|---|
| 2840 | | | | | 2845 | | | | | 2850 | | | | |

| Gly | Thr | Thr | Glu | Met | Pro | Gln | Pro | Cys | Glu | Ala | Glu | Glu | Lys | Thr |
|---|---|---|---|---|---|---|---|---|---|---|---|---|---|---|
| 2855 | | | | | 2860 | | | | | 2865 | | | | |

| Ser | Lys | Pro | Ala | Ala | Glu | Ile | Leu | Ile | Lys | Pro | Gln | Glu | Glu | Lys |
|---|---|---|---|---|---|---|---|---|---|---|---|---|---|---|
| 2870 | | | | | 2875 | | | | | 2880 | | | | |

| Gly | Val | Ser | Gly | Glu | Ser | Asp | Val | Arg | Cys | Leu | Arg | Ser | Arg | Lys |
|---|---|---|---|---|---|---|---|---|---|---|---|---|---|---|
| 2885 | | | | | 2890 | | | | | 2895 | | | | |

| Thr | Arg | Val | Ala | Leu | Asp | Ser | Glu | Pro | Lys | Pro | Arg | Val | Thr | Arg |
|---|---|---|---|---|---|---|---|---|---|---|---|---|---|---|
| 2900 | | | | | 2905 | | | | | 2910 | | | | |

| Gly | Thr | Lys | Lys | Asp | Ala | Lys | Thr | Leu | Lys | Glu | Asp | Glu | Asp | Ile |
|---|---|---|---|---|---|---|---|---|---|---|---|---|---|---|
| 2915 | | | | | 2920 | | | | | 2925 | | | | |

| Val | Cys | Thr | Lys | Lys | Leu | Arg | Thr | Arg | Ser |
|---|---|---|---|---|---|---|---|---|---|
| 2930 | | | | | 2935 | | | | |

<210> SEQ ID NO 41
<211> LENGTH: 1302
<212> TYPE: DNA
<213> ORGANISM: Homo sapiens

<400> SEQUENCE: 41

```
atggcgctcc gagtcaccag gaactcgaaa attaatgctg aaaataaggc gaagatcaac      60
atggcaggcg caaagcgcgt tcctacggcc cctgctgcaa cctccaagcc cggactgagg     120
ccaagaacag ctcttgggga cattggtaac aaagtcagtg aacaactgca ggccaaaatg     180
cctatgaaga aggaagcaaa accttcagct actggaaaag tcattgataa aaaactacca     240
aaacctcttg aaaaggtacc tatgctggtg ccagtgccag tgtctgagcc agtgccagag     300
ccagaacctg agccagaacc tgagcctgtt aagaagaaa aactttcgcc tgagcctatt     360
ttggttgata ctgcctctcc aagcccaatg gaaacatctg atgtgcccc tgcagaagaa      420
gacctgtgtc aggctttctc tgatgtaatt cttgcagtaa atgatgtgga tgcagaagat     480
ggagctgatc aaaccttttg tagtgaatat gtgaaagata tttatgctta tctgagacaa     540
cttgaggaag agcaagcagt cagaccaaaa tacctactgg gtcgggaagt cactggaaac     600
atgagagcca tcctaattga ctggctagta caggttcaaa tgaaattcag gttgttgcag     660
gagaccatgt acatgactgt ctccattatt gatcggttca tgcagaataa ttgtgtgccc     720
aagaagatgc tgcagctggt tggtgtcact gccatgttta tgcaagcaa atatgaagaa      780
atgtaccctc agaaaattgg tgactttgct tttgtgactg acaacactta tactaagcac     840
caaatcagac agatggaaat gaagattcta agagctttaa actttggtct gggtcggcct     900
ctacctttgc acttccttcg gagagcatct aagattggag aggttgatgt cgagcaacat     960
actttggcca ataccctgat ggaactaact atgttggact atgacatggt gcactttcct    1020
ccttctcaaa ttgcagcagg agcttttttgc ttagcactga aaattctgga taatggtgaa    1080
tggacaccaa ctctacaaca ttacctgtca tatactgaag aatctcttct tccagttatg    1140
cagcacctgg ctaagaatgt agtcatggta aatcaaggac ttacaaagca catgactgtc    1200
aagaacaagt atgccacatc gaagcatgct aagatcagca ctctaccaca gctgaattct    1260
gcactagttc aagatttagc caaggctgtg gcaaaggtgt aa                       1302
```

<210> SEQ ID NO 42
<211> LENGTH: 433
<212> TYPE: PRT

<213> ORGANISM: Homo sapiens

<400> SEQUENCE: 42

```
Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45

Gly Asn Lys Val Ser Glu Gln Leu Gln Ala Lys Met Pro Met Lys Lys
50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
            115                 120                 125

Pro Met Glu Thr Ser Gly Cys Ala Pro Ala Glu Glu Asp Leu Cys Gln
            130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
            260                 265                 270

Thr Asp Asn Thr Tyr Thr Lys His Gln Ile Arg Gln Met Glu Met Lys
            275                 280                 285

Ile Leu Arg Ala Leu Asn Phe Gly Leu Gly Arg Pro Leu Pro Leu His
290                 295                 300

Phe Leu Arg Arg Ala Ser Lys Ile Gly Glu Val Asp Val Glu Gln His
305                 310                 315                 320

Thr Leu Ala Lys Tyr Leu Met Glu Leu Thr Met Leu Asp Tyr Asp Met
                325                 330                 335

Val His Phe Pro Pro Ser Gln Ile Ala Ala Gly Ala Phe Cys Leu Ala
            340                 345                 350

Leu Lys Ile Leu Asp Asn Gly Glu Trp Thr Pro Thr Leu Gln His Tyr
        355                 360                 365

Leu Ser Tyr Thr Glu Glu Ser Leu Leu Pro Val Met Gln His Leu Ala
    370                 375                 380

Lys Asn Val Val Met Val Asn Gln Gly Leu Thr Lys His Met Thr Val
385                 390                 395                 400

Lys Asn Lys Tyr Ala Thr Ser Lys His Ala Lys Ile Ser Thr Leu Pro
```

Gln Leu Asn Ser Ala Leu Val Gln Asp Leu Ala Lys Ala Val Ala Lys
        405                 410                 415
Val
        420                 425                 430

<210> SEQ ID NO 43
<211> LENGTH: 1293
<212> TYPE: DNA
<213> ORGANISM: Mus musculus

<400> SEQUENCE: 43

```
atggccctca gggtcactag gaacacgaaa attaacgcag aaaataaggc caaggtcagt      60
atggcaggcg caatgcgtgt gcctgtgaca gttactgctg cttccaagcc cgggctgaga     120
ccgagaactg ctcttggaga cattggtaat aaagtcagcg aagagctaca ggcaagagtg     180
cctctgaaaa gggaagcaaa aacgctaggt actggaaaag gtactgttaa agccctacca     240
aaacctgtag agaaggtgcc tgtgtgtgaa ccagaggtgg aacttgctga gcctgagcct     300
gaacctgaac ttgaacatgt tagagaagag aagctttctc ctgaacctat tttggttgat     360
aatccctctc aagcccgat ggaaacatct ggatgtgcgc ctgcagaaga gtatctgtgt     420
caggctttct ctgatgtaat ccttgcagtg agtgacgtag acgcagatga tggggctgac     480
ccaaacctct gtagtgaata tgtgaaagat atctatgctt atctccgaca actggaggaa     540
gagcagtcag ttagaccaaa atacctacag ggtcgtgaag tgactggaaa catgagagct     600
atcctcattg actggctaat acaggttcag atgaaattta ggctgcttca ggagaccatg     660
tacatgactg tgtccattat tgatcggttc atgcagaaca gttgtgtgcc aagaagatg      720
ctacagctgg tcggtgtaac ggccatgttt attgcaagca atatgaggga gatgtaccct     780
ccagaaatag gtgacttcgc ctttgtgact aacaacacgt acactaagca ccagatcaga     840
cagatggaga tgaagattct cagagttctg aacttcagcc tgggtcgccc tctgcctctg     900
cacttcctcc gtagagcatc taaagtcgga gaggttgacg tcgagcagca cactttggcc     960
aaatacctca tggagctctc catgctggac tgcgacatgg tgcattttgc tccttctcaa    1020
attgcagctg ggctttctg cttagcgctg aaaattcttg acaacggtga atggacacca    1080
actctgcagc actacctatc ctacagtgaa gactccctgc ttcctgttat gcagcacctg    1140
gctaagaatg tagtcatggt gaactgtggc ctcacaaagc acatgactgt caagaacaag    1200
tatgcagcat ctaagcatgc taagatcagc acgctggcac agctgaactg tacactagtt    1260
cagaatttgt ctaaggccgt gacaaaggca taa                                 1293
```

<210> SEQ ID NO 44
<211> LENGTH: 430
<212> TYPE: PRT
<213> ORGANISM: Mus musculus

<400> SEQUENCE: 44

Met Ala Leu Arg Val Thr Arg Asn Thr Lys Ile Asn Ala Glu Asn Lys
1               5                   10                  15

Ala Lys Val Ser Met Ala Gly Ala Met Arg Val Pro Val Thr Val Thr
            20                  25                  30

Ala Ala Ser Lys Pro Gly Leu Arg Pro Arg Thr Ala Leu Gly Asp Ile
        35                  40                  45

Gly Asn Lys Val Ser Glu Glu Leu Gln Ala Arg Val Pro Leu Lys Arg
    50                  55                  60

Glu Ala Lys Thr Leu Gly Thr Gly Lys Gly Thr Val Lys Ala Leu Pro

```
            65                   70                   75                   80
Lys Pro Val Glu Lys Val Pro Val Cys Glu Pro Glu Val Glu Leu Ala
                 85                   90                   95
Glu Pro Glu Pro Glu Pro Glu Leu Glu His Val Arg Glu Glu Lys Leu
            100                  105                  110
Ser Pro Glu Pro Ile Leu Val Asp Asn Pro Ser Pro Ser Pro Met Glu
            115                  120                  125
Thr Ser Gly Cys Ala Pro Ala Glu Glu Tyr Leu Cys Gln Ala Phe Ser
            130                  135                  140
Asp Val Ile Leu Ala Val Ser Asp Val Asp Ala Asp Gly Ala Asp
145                  150                  155                  160
Pro Asn Leu Cys Ser Glu Tyr Val Lys Asp Ile Tyr Ala Tyr Leu Arg
                 165                  170                  175
Gln Leu Glu Glu Glu Gln Ser Val Arg Pro Lys Tyr Leu Gln Gly Arg
            180                  185                  190
Glu Val Thr Gly Asn Met Arg Ala Ile Leu Ile Asp Trp Leu Ile Gln
            195                  200                  205
Val Gln Met Lys Phe Arg Leu Leu Gln Glu Thr Met Tyr Met Thr Val
            210                  215                  220
Ser Ile Ile Asp Arg Phe Met Gln Asn Ser Cys Val Pro Lys Lys Met
225                  230                  235                  240
Leu Gln Leu Val Gly Val Thr Ala Met Phe Ile Ala Ser Lys Tyr Glu
                 245                  250                  255
Glu Met Tyr Pro Pro Glu Ile Gly Asp Phe Ala Phe Val Thr Asn Asn
            260                  265                  270
Thr Tyr Thr Lys His Gln Ile Arg Gln Met Glu Met Lys Ile Leu Arg
            275                  280                  285
Val Leu Asn Phe Ser Leu Gly Arg Pro Leu Pro Leu His Phe Leu Arg
            290                  295                  300
Arg Ala Ser Lys Val Gly Glu Val Asp Val Glu Gln His Thr Leu Ala
305                  310                  315                  320
Lys Tyr Leu Met Glu Leu Ser Met Leu Asp Cys Asp Met Val His Phe
                 325                  330                  335
Ala Pro Ser Gln Ile Ala Ala Gly Ala Phe Cys Leu Ala Leu Lys Ile
            340                  345                  350
Leu Asp Asn Gly Glu Trp Thr Pro Thr Leu Gln His Tyr Leu Ser Tyr
            355                  360                  365
Ser Glu Asp Ser Leu Leu Pro Val Met Gln His Leu Ala Lys Asn Val
370                  375                  380
Val Met Val Asn Cys Gly Leu Thr Lys His Met Thr Val Lys Asn Lys
385                  390                  395                  400
Tyr Ala Ala Ser Lys His Ala Lys Ile Ser Thr Leu Ala Gln Leu Asn
                 405                  410                  415
Cys Thr Leu Val Gln Asn Leu Ser Lys Ala Val Thr Lys Ala
            420                  425                  430

<210> SEQ ID NO 45
<211> LENGTH: 3258
<212> TYPE: DNA
<213> ORGANISM: Homo sapiens

<400> SEQUENCE: 45
atggacaccc cggaaaatgt ccttcagatg cttgaagccc acatgcagag ctacaagggc       60
aatgaccctc ttggtgaatg ggaaagatac atacagtggg tagaagagaa ttttcctgag      120
```

```
aataaagaat acttgataac tttactagaa catttaatga aggaattttt agataagaag      180
aaataccaca atgacccaag attcatcagt tattgtttaa aatttgctga gtacaacagt      240
gacctccatc aattttttga gtttctgtac aaccatggga ttggaaccct gtcatcccct      300
ctgtacattg cctgggcggg gcatctggaa gcccaaggag agctgcagca tgccagtgct      360
gtccttcaga gaggaattca aaaccaggct gaacccagag agttcctgca caacaatac       420 aggttatttc agacacgcct cactgaaacc catttgccag ctcaagctag aacctcagaa      480
cctctgcata atgttcaggt tttaaatcaa atgataacat caaaatcaaa tccaggaaat      540
aacatggcct gcatttctaa gaatcagggt tcagagcttt ctggagtgat atcttcagct      600
tgtgataaag agtcaaatat ggaacgaaga gtgatcacga tttctaaatc agaatattct      660
gtgcactcat cttttggcatc caaagttgat gttgagcagg ttgttatgta ttgcaaggag      720
aagcttattc gtggggaatc agaattttcc tttgaagaat tgagagccca gaaatacaat      780
caacggagaa agcatgagca atgggtaaat gaagacagac attatatgaa aaggaaagaa      840
gcaaatgctt ttgaagaaca gctattaaaa cagaaaatgg atgaacttca taagaagttg      900
catcaggtgg tggagacatc ccatgaggat ctgcccgctt cccaggaaag gtccgaggtt      960
aatccagcac gtatggggcc aagtgtaggc tcccagcagg aactgagagc gccatgtctt     1020
ccagtaacct atcagcagac accagtgaac atggaaaaga acccaagaga ggcacctcct     1080
gttgttcctc ctttggcaaa tgctatttct gcagctttgg tgtccccagc caccagccag     1140
agcattgctc ctcctgttcc tttgaaagcc cagacagtaa cagactccat gtttgcagtg     1200
gccagcaaag atgctggatg tgtgaataag agtactcatg aattcaagcc acagagtgga     1260
gcagagatca agaagggtg tgaaacacat aaggttgcca acacaagttc ttttcacaca      1320
actccaaaca catcactggg aatggttcag gcaacgccat ccaaagtgca gccatcaccc     1380
accgtgcaca caaaagaagc attaggtttc atcatgaata tgtttcaggc tcctacactt     1440
cctgatattt ctgatgacaa agatgaatgg caatctctag atcaaaatga agatgcattt     1500
gaagcccagt ttcaaaaaaa tgtaaggtca tctgggggctt ggggagtcaa taagatcatc     1560
tcttctttgt catctgcttt tcatgtgttt gaagatggaa acaaagaaaa ttatggatta     1620
ccacagccta aaaataaacc cacaggagcc aggacctttg gagaacgctc tgtcagcaga     1680
cttccttcaa aaccaaagga ggaagtgcct catgctgaag agttttttgga tgactcaact     1740 gtatggggta ttcgctgcaa caaaaccctg gcacccagtc ctaagagccc aggagacttc     1800
acatctgctg cacaacttgc gtctacacca ttccacaagc ttccagtgga gtcagtgcac     1860
attttagaag ataaagaaaa tgtggtagca aaacagtgta cccaggcgac tttggattct     1920
tgtgaggaaa acatggtggt gccttcaagg gatggaaaat tcagtccaat tcaagagaaa     1980
agcccaaaac aggccttgtc gtctcacatg tattcagcat ccttacttcg tctgagccag     2040
cctgctgcag gtggggtact tacctgtgag gcagagttgg gcgttgaggc ttgcagactc     2100
acagacactg acgctgccat tgcagaagat ccaccagatg ctattgctgg gctccaagca     2160
gaatggatgc agatgagttc acttgggact gttgatgctc caaacttcat tgttgggaac     2220
ccatgggatg ataagctgat tttcaaactt ttatctgggc tttctaaacc agtgagttcc     2280
tatccaaata cttttgaatg gcaatgtaaa cttccagcca tcaagcccaa gactgaattt     2340
caattgggtt ctaagctggt ctatgtccat caccttcttg gagaaggagc ctttgcccag     2400
gtgtacgaag ctacccaggg agatctgaat gatgctaaaa ataaacagaa atttgtttta     2460
aaggtccaaa agcctgccaa cccctgggaa ttctacattg ggacccagtt gatggaaaga     2520
```

-continued

```
ctaaagccat ctatgcagca catgtttatg aagttctatt ctgcccactt attccagaat    2580
ggcagtgtat tagtaggaga gctctacagc tatggaacat tattaaatgc cattaacctc    2640
tataaaaata cccctgaaaa agtgatgcct caaggtcttg tcatctcttt tgctatgaga    2700
atgctttaca tgattgagca agtgcatgac tgtgaaatca ttcatggaga cattaaacca    2760
gacaatttca tacttggaaa cggattttg gaacaggatg atgaagatga tttatctgct     2820
ggcttggcac tgattgacct gggtcagagt atagatatga aacttttcc aaaaggaact     2880 atattcacag caaagtgtga aacatctggt tttcagtgtg ttgagatgct cagcaacaaa    2940
ccatggaact accagatcga ttactttggg gttgctgcaa cagtatattg catgctcttt    3000
ggcacttaca tgaaagtgaa aaatgaagga ggagagtgta agcctgaagg tcttttttaga   3060 aggcttcctc atttggatat gtggaatgaa tttttttcatg ttatgttgaa tattccagat   3120
tgtcatcatc ttccatcttt ggatttgtta aggcaaaagc tgaagaaagt atttcaacaa    3180
cactatacta acaagattag ggccctacgt aataggctaa ttgtactgct cttagaatgt    3240
aagcgttcac gaaaataa                                                  3258
```

<210> SEQ ID NO 46
<211> LENGTH: 1085
<212> TYPE: PRT
<213> ORGANISM: Homo sapiens

<400> SEQUENCE: 46

```
Met Asp Thr Pro Glu Asn Val Leu Gln Met Leu Glu Ala His Met Gln
1               5                  10                  15

Ser Tyr Lys Gly Asn Asp Pro Leu Gly Glu Trp Glu Arg Tyr Ile Gln
            20                  25                  30

Trp Val Glu Glu Asn Phe Pro Glu Asn Lys Glu Tyr Leu Ile Thr Leu
        35                  40                  45

Leu Glu His Leu Met Lys Glu Phe Leu Asp Lys Lys Lys Tyr His Asn
    50                  55                  60

Asp Pro Arg Phe Ile Ser Tyr Cys Leu Lys Phe Ala Glu Tyr Asn Ser
65                  70                  75                  80

Asp Leu His Gln Phe Phe Glu Phe Leu Tyr Asn His Gly Ile Gly Thr
                85                  90                  95

Leu Ser Ser Pro Leu Tyr Ile Ala Trp Ala Gly His Leu Glu Ala Gln
            100                 105                 110

Gly Glu Leu Gln His Ala Ser Ala Val Leu Gln Arg Gly Ile Gln Asn
        115                 120                 125

Gln Ala Glu Pro Arg Glu Phe Leu Gln Gln Gln Tyr Arg Leu Phe Gln
    130                 135                 140

Thr Arg Leu Thr Glu Thr His Leu Pro Ala Gln Ala Arg Thr Ser Glu
145                 150                 155                 160

Pro Leu His Asn Val Gln Val Leu Asn Gln Met Ile Thr Ser Lys Ser
                165                 170                 175

Asn Pro Gly Asn Asn Met Ala Cys Ile Ser Lys Asn Gln Gly Ser Glu
            180                 185                 190

Leu Ser Gly Val Ile Ser Ser Ala Cys Asp Lys Glu Ser Asn Met Glu
        195                 200                 205

Arg Arg Val Ile Thr Ile Ser Lys Ser Glu Tyr Ser Val His Ser Ser
    210                 215                 220

Leu Ala Ser Lys Val Asp Val Glu Gln Val Val Met Tyr Cys Lys Glu
225                 230                 235                 240

Lys Leu Ile Arg Gly Glu Ser Glu Phe Ser Phe Glu Glu Leu Arg Ala
```

```
                245                 250                 255
Gln Lys Tyr Asn Gln Arg Arg Lys His Glu Gln Trp Val Asn Glu Asp
            260                 265                 270
Arg His Tyr Met Lys Arg Lys Glu Ala Asn Ala Phe Glu Glu Gln Leu
            275                 280                 285
Leu Lys Gln Lys Met Asp Glu Leu His Lys Lys Leu His Gln Val Val
            290                 295                 300
Glu Thr Ser His Glu Asp Leu Pro Ala Ser Gln Glu Arg Ser Glu Val
305                 310                 315                 320
Asn Pro Ala Arg Met Gly Pro Ser Val Gly Ser Gln Gln Glu Leu Arg
                325                 330                 335
Ala Pro Cys Leu Pro Val Thr Tyr Gln Gln Thr Pro Val Asn Met Glu
            340                 345                 350
Lys Asn Pro Arg Glu Ala Pro Val Val Pro Pro Leu Ala Asn Ala
            355                 360                 365
Ile Ser Ala Ala Leu Val Ser Pro Ala Thr Ser Gln Ser Ile Ala Pro
370                 375                 380
Pro Val Pro Leu Lys Ala Gln Thr Val Thr Asp Ser Met Phe Ala Val
385                 390                 395                 400
Ala Ser Lys Asp Ala Gly Cys Val Asn Lys Ser Thr His Glu Phe Lys
                405                 410                 415
Pro Gln Ser Gly Ala Glu Ile Lys Glu Gly Cys Glu Thr His Lys Val
            420                 425                 430
Ala Asn Thr Ser Ser Phe His Thr Thr Pro Asn Thr Ser Leu Gly Met
            435                 440                 445
Val Gln Ala Thr Pro Ser Lys Val Gln Pro Ser Pro Thr Val His Thr
            450                 455                 460
Lys Glu Ala Leu Gly Phe Ile Met Asn Met Phe Gln Ala Pro Thr Leu
465                 470                 475                 480
Pro Asp Ile Ser Asp Lys Asp Glu Trp Gln Ser Leu Asp Gln Asn
                485                 490                 495
Glu Asp Ala Phe Glu Ala Gln Phe Gln Lys Asn Val Arg Ser Ser Gly
            500                 505                 510
Ala Trp Gly Val Asn Lys Ile Ile Ser Ser Leu Ser Ser Ala Phe His
            515                 520                 525
Val Phe Glu Asp Gly Asn Lys Glu Asn Tyr Gly Leu Pro Gln Pro Lys
            530                 535                 540
Asn Lys Pro Thr Gly Ala Arg Thr Phe Gly Glu Arg Ser Val Ser Arg
545                 550                 555                 560
Leu Pro Ser Lys Pro Lys Glu Glu Val Pro His Ala Glu Glu Phe Leu
                565                 570                 575
Asp Asp Ser Thr Val Trp Gly Ile Arg Cys Asn Lys Thr Leu Ala Pro
            580                 585                 590
Ser Pro Lys Ser Pro Gly Asp Phe Thr Ser Ala Ala Gln Leu Ala Ser
            595                 600                 605
Thr Pro Phe His Lys Leu Pro Val Glu Ser Val His Ile Leu Glu Asp
            610                 615                 620
Lys Glu Asn Val Val Ala Lys Gln Cys Thr Gln Ala Thr Leu Asp Ser
625                 630                 635                 640
Cys Glu Glu Asn Met Val Val Pro Ser Arg Asp Gly Lys Phe Ser Pro
                645                 650                 655
Ile Gln Glu Lys Ser Pro Lys Gln Ala Leu Ser Ser His Met Tyr Ser
            660                 665                 670
```

-continued

Ala Ser Leu Leu Arg Leu Ser Gln Pro Ala Ala Gly Gly Val Leu Thr
                675                 680                 685

Cys Glu Ala Glu Leu Gly Val Glu Ala Cys Arg Leu Thr Asp Thr Asp
    690                 695                 700

Ala Ala Ile Ala Glu Asp Pro Pro Asp Ala Ile Ala Gly Leu Gln Ala
705                 710                 715                 720

Glu Trp Met Gln Met Ser Ser Leu Gly Thr Val Asp Ala Pro Asn Phe
                725                 730                 735

Ile Val Gly Asn Pro Trp Asp Asp Lys Leu Ile Phe Lys Leu Leu Ser
                740                 745                 750

Gly Leu Ser Lys Pro Val Ser Ser Tyr Pro Asn Thr Phe Glu Trp Gln
                755                 760                 765

Cys Lys Leu Pro Ala Ile Lys Pro Lys Thr Glu Phe Gln Leu Gly Ser
    770                 775                 780

Lys Leu Val Tyr Val His His Leu Leu Gly Glu Gly Ala Phe Ala Gln
785                 790                 795                 800

Val Tyr Glu Ala Thr Gln Gly Asp Leu Asn Asp Ala Lys Asn Lys Gln
                805                 810                 815

Lys Phe Val Leu Lys Val Gln Lys Pro Ala Asn Pro Trp Glu Phe Tyr
                820                 825                 830

Ile Gly Thr Gln Leu Met Glu Arg Leu Lys Pro Ser Met Gln His Met
                835                 840                 845

Phe Met Lys Phe Tyr Ser Ala His Leu Phe Gln Asn Gly Ser Val Leu
    850                 855                 860

Val Gly Glu Leu Tyr Ser Tyr Gly Thr Leu Leu Asn Ala Ile Asn Leu
865                 870                 875                 880

Tyr Lys Asn Thr Pro Glu Lys Val Met Pro Gln Gly Leu Val Ile Ser
                885                 890                 895

Phe Ala Met Arg Met Leu Tyr Met Ile Glu Gln Val His Asp Cys Glu
                900                 905                 910

Ile Ile His Gly Asp Ile Lys Pro Asp Asn Phe Ile Leu Gly Asn Gly
    915                 920                 925

Phe Leu Glu Gln Asp Asp Glu Asp Asp Leu Ser Ala Gly Leu Ala Leu
    930                 935                 940

Ile Asp Leu Gly Gln Ser Ile Asp Met Lys Leu Phe Pro Lys Gly Thr
945                 950                 955                 960

Ile Phe Thr Ala Lys Cys Glu Thr Ser Gly Phe Gln Cys Val Glu Met
                965                 970                 975

Leu Ser Asn Lys Pro Trp Asn Tyr Gln Ile Asp Tyr Phe Gly Val Ala
                980                 985                 990

Ala Thr Val Tyr Cys Met Leu Phe Gly Thr Tyr Met Lys Val Lys Asn
                995                 1000                1005

Glu Gly Gly Glu Cys Lys Pro Glu Gly Leu Phe Arg Arg Leu Pro
    1010                1015                1020

His Leu Asp Met Trp Asn Glu Phe Phe His Val Met Leu Asn Ile
    1025                1030                1035

Pro Asp Cys His His Leu Pro Ser Leu Asp Leu Leu Arg Gln Lys
    1040                1045                1050

Leu Lys Lys Val Phe Gln Gln His Tyr Thr Asn Lys Ile Arg Ala
    1055                1060                1065

Leu Arg Asn Arg Leu Ile Val Leu Leu Leu Glu Cys Lys Arg Ser
    1070                1075                1080

Arg Lys
    1085

<210> SEQ ID NO 47
<211> LENGTH: 3177
<212> TYPE: DNA
<213> ORGANISM: Mus musculus

<400> SEQUENCE: 47

| | | | | | | |
|---|---|---|---|---|---|---|
| atggacaacc | tagaaaatgt | ctttcgcatg | tttgaagccc | atatgcaaag | ctacacgggt | 60 |
| aatgacccac | ttggagaatg | ggaaagcttt | ataaagtggg | tagaagagaa | ttttcctgac | 120 |
| aataaagaat | acttgatgac | attattagaa | catttaatga | aggaattttt | acataagaag | 180 |
| aactaccaca | atgattcaag | attcatcaat | tattgcttaa | aatttgctga | gtacaacagc | 240 |
| gaccgtcatc | agtttttttga | gtttctgtac | aaccagggaa | ttggaaccaa | gtcatcatat | 300 |
| atatacatgt | cctgggcagg | gcatctggaa | gcccaggag | agctgcagca | tgccagtgct | 360 |
| atttttcaga | caggaattca | caatgaggct | gaacctaaag | aactactaca | gcaacaatac | 420 |
| aggctattcc | aagcacgcct | tactggaatc | catttgccag | ctcaagctac | aacctcagaa | 480 |
| cctttgcata | gtgcacagat | tttaaaccaa | gttatgatga | caaactcaag | tccagaaaaa | 540 |
| aactcagcct | gtgttcctaa | gagtcaggt | tcagaatgtt | ctggtgtggc | atcttccact | 600 |
| tgtgatgaaa | agtctaatat | ggaacaaagg | gtgatcatga | tttccaagtc | agaatgctct | 660 |
| gtcagctcat | ctgtggcacc | caagcctgag | gctcagcaag | ttatgtactg | caaggaaaag | 720 |
| cttattcgtg | gagattcaga | atttctttt | gaagaactga | gagcccagaa | atataatcaa | 780 |
| aggaagaagc | atgagcagtg | ggttagtgaa | gacagaaatt | atatgaaaag | gaagaagca | 840 |
| aatgcttttg | aagagcaatt | attaaaacag | aaaatggatg | aacttcacaa | gaaattgcat | 900 |
| caagtggtgg | aattgtcaca | caaggacctt | cctgcttctg | agaacaggcc | tgatgttagt | 960 |
| ctagtatgtg | ttggacaaaa | tacttgctcc | cagcaggaat | tgaggggtcc | aagtctttca | 1020 |
| tccatcagtc | atcagacctc | agagagttca | ggagagaaac | cacaggaaga | accttctgtt | 1080 |
| cctcttatgg | taaatgctgt | taacagcact | ttgctgttcc | cagctgccaa | cctgccagct | 1140 |
| cttcctgttc | ctgtaagtgg | ccagtcattg | acagactcca | gatgtgtgaa | tcaaagtgtt | 1200 |
| catgaattca | tgccacagtg | tggaccagaa | acaaagaag | tgtgtgaaac | aaataaagtt | 1260 |
| gccagcatta | atgattttca | tacaactcca | aacacatcat | tgggaatggt | tcaaggaaca | 1320 |
| ccatgcaaag | tgcagccatc | accaactgtc | cacaccaagg | aagcattagg | tttcatcatg | 1380 |
| gacatgtttc | aggctccaac | acttcctgac | atttctgatg | ataaagatga | atggccatct | 1440 |
| ctggaccaaa | atgaagatgc | atttgaagcc | cagtttcaaa | aaatgcagt | atcttcggga | 1500 |
| gattggggag | ttaaaaaaat | tatgactttg | tcatctgctt | ttcctatttt | tgaagatgga | 1560 |
| aacaaagaaa | attatggctt | accacagcct | aaaaataagc | ccttaggagc | taggaccttt | 1620 |
| ggagaacgat | ctctcagtaa | atattcctcg | agatcaaatg | aaatgcctca | cactgatgag | 1680 |
| tttatggatg | attcaacagt | atgtggtatt | cgctgcaaca | aaactctagc | tcccagtcct | 1740 |
| aaagtatag | agactttac | atctgctgcc | caactttcgt | ctacaccatt | ccacaaattt | 1800 |
| ccagcagatt | tagtacagat | tccagaagat | aaagaaaatg | tggtagccac | acagtataca | 1860 |
| catatggctt | tggattcttg | taaagaaaac | atagtggacc | tctcaaaagg | cagaaagctt | 1920 |
| gggccaattc | aagagaaaat | ttcagcatct | ttaccctgtc | ctagtcagcc | tgccacaggt | 1980 |
| ggtttgttca | cccaggaagc | agtgttcggc | cttgaggctt | ttaaatgcac | aggcattgac | 2040 |
| catgcgacag | tggaagacct | atccgatgcc | aatgctgggc | tccaagttga | atgcgtgcag | 2100 |
| acacttggaa | atgtcaatgc | tccaagcttt | actgttgaga | acccatggga | tgatgaattg | 2160 |

```
attcttaaac ttctctctgg actttctaag ccagttactt cctattcaaa tactttgag    2220 tggcagagta aacttccagc catcaagacc aagacagaat atcaattggg ttctttgctg    2280
gtctatgtga atcaccttct tggagaagga gcctttgctc aagtctttga agctattcat    2340
ggagatgtga gaaatgccaa aagtgaacag aaatgcattt tgaaggtgca gagacctgcc    2400
aactcctggg aattctacat tgggatgcag ctgatggaaa gactaaagcc agaagtacat    2460
cacatgttca tcaagtttta ttctgctcat ttattcaaga acggcagcat attagtaggg    2520
gaactctaca gctatgggac gttactaaat gtcattaacc tctataaaaa tacctctgaa    2580
aaagtgatgc cccaggctct tgtcctcact ttcgctatca gaatgcttta catggttgaa    2640
caagtccaca gctgcgaaat cattcatgga gacattaagc cagataactt catactagga    2700
cacagatttt tggaacaggc tgatgaagac ttagctaccg gcttggcatt gattgacctg    2760
ggtcagagta tagatatgaa acttttccct aaaggaactg tatttacagg aaaatgtgaa    2820
acatctggtt ttcagtgtcc tgagatgctc agtaacaagc catggaacta ccagattgat    2880
tactttggag ttgctgcaac aatatactgt atgctctttg gctcttacat gaaagtaaaa    2940
aatgaaggag gagtctggaa acctgaaggt cttttagaa ggcttcctca tttggatatg    3000
tgggaggaat tttttcacat catgttgaat ataccggatt gtcataatct tccatctttg    3060
gattttctga gacagaatat gaagaaatta cttgaacaac agtattccaa caagattaag    3120
accttgcgta ataggctaat tgtgatgctt tcagaatata agcgttcaag aaaataa      3177

<210> SEQ ID NO 48
<211> LENGTH: 1058
<212> TYPE: PRT
<213> ORGANISM: Mus musculus

<400> SEQUENCE: 48

Met Asp Asn Leu Glu Asn Val Phe Arg Met Phe Glu Ala His Met Gln
1               5                  10                  15

Ser Tyr Thr Gly Asn Asp Pro Leu Gly Glu Trp Glu Ser Phe Ile Lys
            20                  25                  30

Trp Val Glu Glu Asn Phe Pro Asp Asn Lys Glu Tyr Leu Met Thr Leu
        35                  40                  45

Leu Glu His Leu Met Lys Glu Phe Leu His Lys Lys Asn Tyr His Asn
    50                  55                  60

Asp Ser Arg Phe Ile Asn Tyr Cys Leu Lys Phe Ala Glu Tyr Asn Ser
65                  70                  75                  80

Asp Arg His Gln Phe Phe Glu Phe Leu Tyr Asn Gln Gly Ile Gly Thr
                85                  90                  95

Lys Ser Ser Tyr Ile Tyr Met Ser Trp Ala Gly His Leu Glu Ala Gln
            100                 105                 110

Gly Glu Leu Gln His Ala Ser Ala Ile Phe Gln Thr Gly Ile His Asn
        115                 120                 125

Glu Ala Glu Pro Lys Glu Leu Leu Gln Gln Gln Tyr Arg Leu Phe Gln
    130                 135                 140

Ala Arg Leu Thr Gly Ile His Leu Pro Ala Gln Ala Thr Thr Ser Glu
145                 150                 155                 160

Pro Leu His Ser Ala Gln Ile Leu Asn Gln Val Met Thr Asn Ser
                165                 170                 175

Ser Pro Glu Lys Asn Ser Ala Cys Val Pro Lys Ser Gln Gly Ser Glu
            180                 185                 190

Cys Ser Gly Val Ala Ser Ser Thr Cys Asp Glu Lys Ser Asn Met Glu
```

```
                195                 200                 205
Gln Arg Val Ile Met Ile Ser Lys Ser Glu Cys Ser Val Ser Ser
210                 215                 220

Val Ala Pro Lys Pro Glu Ala Gln Gln Val Met Tyr Cys Lys Glu Lys
225                 230                 235                 240

Leu Ile Arg Gly Asp Ser Glu Phe Ser Phe Glu Leu Arg Ala Gln
                245                 250                 255

Lys Tyr Asn Gln Arg Lys Lys His Glu Gln Trp Val Ser Glu Asp Arg
                260                 265                 270

Asn Tyr Met Lys Arg Lys Glu Ala Asn Ala Phe Glu Glu Gln Leu Leu
                275                 280                 285

Lys Gln Lys Met Asp Glu Leu His Lys Lys Leu His Gln Val Val Glu
290                 295                 300

Leu Ser His Lys Asp Leu Pro Ala Ser Glu Asn Arg Pro Asp Val Ser
305                 310                 315                 320

Leu Val Cys Val Gly Gln Asn Thr Cys Ser Gln Gln Glu Leu Arg Gly
                325                 330                 335

Pro Ser Leu Ser Ser Ile Ser His Gln Thr Ser Glu Ser Ser Gly Glu
                340                 345                 350

Lys Pro Gln Glu Glu Pro Ser Val Pro Leu Met Val Asn Ala Val Asn
                355                 360                 365

Ser Thr Leu Leu Phe Pro Ala Ala Asn Leu Pro Ala Leu Pro Val Pro
                370                 375                 380

Val Ser Gly Gln Ser Leu Thr Asp Ser Arg Cys Val Asn Gln Ser Val
385                 390                 395                 400

His Glu Phe Met Pro Gln Cys Gly Pro Glu Thr Lys Glu Val Cys Glu
                405                 410                 415

Thr Asn Lys Val Ala Ser Ile Asn Asp Phe His Thr Thr Pro Asn Thr
                420                 425                 430

Ser Leu Gly Met Val Gln Gly Thr Pro Cys Lys Val Gln Pro Ser Pro
                435                 440                 445

Thr Val His Thr Lys Glu Ala Leu Gly Phe Ile Met Asp Met Phe Gln
450                 455                 460

Ala Pro Thr Leu Pro Asp Ile Ser Asp Asp Lys Asp Glu Trp Pro Ser
465                 470                 475                 480

Leu Asp Gln Asn Glu Asp Ala Phe Glu Ala Gln Phe Gln Lys Asn Ala
                485                 490                 495

Val Ser Ser Gly Asp Trp Gly Val Lys Lys Ile Met Thr Leu Ser Ser
                500                 505                 510

Ala Phe Pro Ile Phe Glu Asp Gly Asn Lys Glu Asn Tyr Gly Leu Pro
                515                 520                 525

Gln Pro Lys Asn Lys Pro Leu Gly Ala Arg Thr Phe Gly Glu Arg Ser
                530                 535                 540

Leu Ser Lys Tyr Ser Ser Arg Ser Asn Glu Met Pro His Thr Asp Glu
545                 550                 555                 560

Phe Met Asp Asp Ser Thr Val Cys Gly Ile Arg Cys Asn Lys Thr Leu
                565                 570                 575

Ala Pro Ser Pro Lys Ser Ile Gly Asp Phe Thr Ser Ala Ala Gln Leu
                580                 585                 590

Ser Ser Thr Pro Phe His Lys Phe Pro Ala Asp Leu Val Gln Ile Pro
                595                 600                 605

Glu Asp Lys Glu Asn Val Val Ala Thr Gln Tyr Thr His Met Ala Leu
610                 615                 620
```

-continued

Asp Ser Cys Lys Glu Asn Ile Val Asp Leu Ser Lys Gly Arg Lys Leu
625                 630                 635                 640

Gly Pro Ile Gln Glu Lys Ile Ser Ala Ser Leu Pro Cys Pro Ser Gln
            645                 650                 655

Pro Ala Thr Gly Gly Leu Phe Thr Gln Glu Ala Val Phe Gly Leu Glu
        660                 665                 670

Ala Phe Lys Cys Thr Gly Ile Asp His Ala Thr Val Glu Asp Leu Ser
    675                 680                 685

Asp Ala Asn Ala Gly Leu Gln Val Glu Cys Val Gln Thr Leu Gly Asn
690                 695                 700

Val Asn Ala Pro Ser Phe Thr Val Glu Asn Pro Trp Asp Asp Glu Leu
705                 710                 715                 720

Ile Leu Lys Leu Leu Ser Gly Leu Ser Lys Pro Val Thr Ser Tyr Ser
                725                 730                 735

Asn Thr Phe Glu Trp Gln Ser Lys Leu Pro Ala Ile Lys Thr Lys Thr
            740                 745                 750

Glu Tyr Gln Leu Gly Ser Leu Leu Val Tyr Val Asn His Leu Leu Gly
        755                 760                 765

Glu Gly Ala Phe Ala Gln Val Phe Glu Ala Ile His Gly Asp Val Arg
    770                 775                 780

Asn Ala Lys Ser Glu Gln Lys Cys Ile Leu Lys Val Gln Arg Pro Ala
785                 790                 795                 800

Asn Ser Trp Glu Phe Tyr Ile Gly Met Gln Leu Met Glu Arg Leu Lys
                805                 810                 815

Pro Glu Val His His Met Phe Ile Lys Phe Tyr Ser Ala His Leu Phe
            820                 825                 830

Lys Asn Gly Ser Ile Leu Val Gly Glu Leu Tyr Ser Tyr Gly Thr Leu
        835                 840                 845

Leu Asn Val Ile Asn Leu Tyr Lys Asn Thr Ser Glu Lys Val Met Pro
    850                 855                 860

Gln Ala Leu Val Leu Thr Phe Ala Ile Arg Met Leu Tyr Met Val Glu
865                 870                 875                 880

Gln Val His Ser Cys Glu Ile Ile His Gly Asp Ile Lys Pro Asp Asn
                885                 890                 895

Phe Ile Leu Gly His Arg Phe Leu Glu Gln Ala Asp Glu Asp Leu Ala
            900                 905                 910

Thr Gly Leu Ala Leu Ile Asp Leu Gly Gln Ser Ile Asp Met Lys Leu
        915                 920                 925

Phe Pro Lys Gly Thr Val Phe Thr Gly Lys Cys Glu Thr Ser Gly Phe
    930                 935                 940

Gln Cys Pro Glu Met Leu Ser Asn Lys Pro Trp Asn Tyr Gln Ile Asp
945                 950                 955                 960

Tyr Phe Gly Val Ala Ala Thr Ile Tyr Cys Met Leu Phe Gly Ser Tyr
                965                 970                 975

Met Lys Val Lys Asn Glu Gly Val Trp Lys Pro Glu Gly Leu Phe
            980                 985                 990

Arg Arg Leu Pro His Leu Asp Met Trp Glu Glu Phe Phe His Ile Met
        995                 1000                1005

Leu Asn Ile Pro Asp Cys His Asn Leu Pro Ser Leu Asp Phe Leu
    1010                1015                1020

Arg Gln Asn Met Lys Lys Leu Leu Glu Gln Gln Tyr Ser Asn Lys
    1025                1030                1035

Ile Lys Thr Leu Arg Asn Arg Leu Ile Val Met Leu Ser Glu Tyr
    1040                1045                1050

Lys Arg  Ser Arg Lys
     1055

<210> SEQ ID NO 49
<211> LENGTH: 1929
<212> TYPE: DNA
<213> ORGANISM: Homo sapiens

<400> SEQUENCE: 49

```
atgaagcgca gttcagtttc cagcggtggt gctggccgcc tctccatgca ggagttaaga     60
tcccaggatg taaataaaca aggcctctat acccctcaaa ccaaagagaa accaaccttt    120
ggaaagttga gtataaacaa accgacatct gaaagaaaag tctcgctatt tggcaaaaga    180
actagtggac atggatcccg aatagtcaa cttggtatat tttccagttc tgagaaaatc     240
aaggacccga gaccacttaa tgacaaagca ttcattcagc agtgtattcg acaactctgt    300
gagtttctta cagaaaatgg ttatgcacat aatgtgtcca tgaatctct acaagctccc     360
tctgttaaag acttcctgaa gatcttcaca tttctttatg gcttcctgtg cccctcatac    420
gaacttcctg cacaaagtt tgaagaagag gttccaagaa tctttaaaga ccttgggtat    480
cctttttgcac tatccaaaag ctccatgtac acagtggggg ctcctcatac atggcctcac    540
attgtggcag cctagtttg gctaatagac tgcatcaaga tacatactgc catgaaagaa    600
agctcacctt tatttgatga tgggcagcct tggggagaag aaactgaaga tggaattatg    660
cataataagt tgttttttgga ctacaccata aatgtctatg agagttttat gagtggtgcc    720
gacagctttg atgagatgaa tgcagagctg cagtcaaaac tgaaggattt atttaatgtg    780
gatgctttta gctggaatc attagaagca aaaacagag cattgaatga acagattgca      840
agattggaac aagaaagaga aaagaaccg aatcgtctag agtcgttgag aaaactgaag     900
gcttccttac aaggagatgt tcaaaagtat caggcataca tgagcaattt ggagtctcat    960
tcagccattc ttgaccagaa attaaatggt ctcaatgagg aaattgctag agtagaacta   1020
gaatgtgaaa caataaaaca ggagaacact cgactacaga atatcattga caaccagaag   1080
tactcagttg cagacattga gcgaataaat catgaaagaa atgaattgca gcagactatt   1140
ataaaattaa ccaaggacct ggaagctgaa caacagaagt tgtggaatga ggagttaaaa   1200
tatgccagag caagaagc gattgaaaca caattagcag agtatcacaa attggctaga    1260
aaattaaaac ttattcctaa aggtgctgag aattccaaag ttatgacttt gaaattaag    1320
tttaatcccg aggctggtgc caactgcctt gtcaaataca gggctcaagt ttatgtacct   1380
cttaaggaac tcctgaatga aactgaagaa gaaattaata agccctaaa taaaaaaatg    1440
ggtttggagg atactttaga acaattgaat gcaatgataa cagaaagcaa gagagtgtg   1500
agaactctga agaagaagt tcaaaagctg gatgatcttt accaacaaaa aattaaggaa   1560
gcagaggaag aggatgaaaa atgtgccagt gagcttgagt ccttggagaa acacaagcac   1620
ctgctagaaa gtactgttaa ccaggggctc agtgaagcta tgaatgaatt agatgctgtt   1680
cagcgggaat accaactagt tgtgcaaacc acgactgaag aaagacgaaa agtgggaaat   1740
aacttgcaac gtctgttaga gatggttgct acacatgttg ggtctgtaga gaaacatctt   1800
gaggagcaga ttgctaaagt tgatagagaa tatgaagaat gcatgtcaga agatctctcg   1860
gaaaatatta aagagattag agataagtat gagaagaaag ctactctaat taagtcttct   1920
gaagaatga                                                            1929
```

<210> SEQ ID NO 50

<211> LENGTH: 642
<212> TYPE: PRT
<213> ORGANISM: Homo sapiens

<400> SEQUENCE: 50

Met Lys Arg Ser Ser Val Ser Gly Gly Ala Gly Arg Leu Ser Met
1               5                   10                  15

Gln Glu Leu Arg Ser Gln Asp Val Asn Lys Gln Gly Leu Tyr Thr Pro
            20                  25                  30

Gln Thr Lys Glu Lys Pro Thr Phe Gly Lys Leu Ser Ile Asn Lys Pro
        35                  40                  45

Thr Ser Glu Arg Lys Val Ser Leu Phe Gly Lys Arg Thr Ser Gly His
    50                  55                  60

Gly Ser Arg Asn Ser Gln Leu Gly Ile Phe Ser Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
    130                 135                 140

Thr Lys Phe Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
            180                 185                 190

Lys Ile His Thr Ala Met Lys Glu Ser Ser Pro Leu Phe Asp Asp Gly
        195                 200                 205

Gln Pro Trp Gly Glu Glu Thr Glu Asp Gly Ile Met His Asn Lys Leu
    210                 215                 220

Phe Leu Asp Tyr Thr Ile Lys Cys Tyr Glu Ser Phe Met Ser Gly Ala
225                 230                 235                 240

Asp Ser Phe Asp Glu Met Asn Ala Glu Leu Gln Ser Lys Leu Lys Asp
                245                 250                 255

Leu Phe Asn Val Asp Ala Phe Lys Leu Glu Ser Leu Glu Ala Lys Asn
            260                 265                 270

Arg Ala Leu Asn Glu Gln Ile Ala Arg Leu Glu Gln Arg Glu Lys
        275                 280                 285

Glu Pro Asn Arg Leu Glu Ser Leu Arg Lys Leu Lys Ala Ser Leu Gln
    290                 295                 300

Gly Asp Val Gln Lys Tyr Gln Ala Tyr Met Ser Asn Leu Glu Ser His
305                 310                 315                 320

Ser Ala Ile Leu Asp Gln Lys Leu Asn Gly Leu Asn Glu Glu Ile Ala
                325                 330                 335

Arg Val Glu Leu Glu Cys Glu Thr Ile Lys Gln Glu Asn Thr Arg Leu
            340                 345                 350

Gln Asn Ile Ile Asp Asn Gln Lys Tyr Ser Val Ala Asp Ile Glu Arg
        355                 360                 365

Ile Asn His Glu Arg Asn Glu Leu Gln Gln Thr Ile Asn Lys Leu Thr
    370                 375                 380

Lys Asp Leu Glu Ala Glu Gln Gln Lys Leu Trp Asn Glu Glu Leu Lys
385                 390                 395                 400

Tyr Ala Arg Gly Lys Glu Ala Ile Glu Thr Gln Leu Ala Tyr His
            405                 410                 415
Lys Leu Ala Arg Lys Leu Lys Leu Ile Pro Lys Gly Ala Glu Asn Ser
        420                 425                 430
Lys Gly Tyr Asp Phe Glu Ile Lys Phe Asn Pro Glu Ala Gly Ala Asn
            435                 440                 445
Cys Leu Val Lys Tyr Arg Ala Gln Val Tyr Val Pro Leu Lys Glu Leu
    450                 455                 460
Leu Asn Glu Thr Glu Glu Ile Asn Lys Ala Leu Asn Lys Lys Met
465                 470                 475                 480
Gly Leu Glu Asp Thr Leu Glu Gln Leu Asn Ala Met Ile Thr Glu Ser
            485                 490                 495
Lys Arg Ser Val Arg Thr Leu Lys Glu Glu Val Gln Lys Leu Asp Asp
        500                 505                 510
Leu Tyr Gln Gln Lys Ile Lys Glu Ala Glu Glu Asp Glu Lys Cys
            515                 520                 525
Ala Ser Glu Leu Glu Ser Leu Glu Lys His Lys His Leu Leu Glu Ser
    530                 535                 540
Thr Val Asn Gln Gly Leu Ser Glu Ala Met Asn Glu Leu Asp Ala Val
545                 550                 555                 560
Gln Arg Glu Tyr Gln Leu Val Val Gln Thr Thr Glu Glu Arg Arg
            565                 570                 575
Lys Val Gly Asn Asn Leu Gln Arg Leu Leu Glu Met Val Ala Thr His
        580                 585                 590
Val Gly Ser Val Glu Lys His Leu Glu Glu Gln Ile Ala Lys Val Asp
    595                 600                 605
Arg Glu Tyr Glu Glu Cys Met Ser Glu Asp Leu Ser Gly Asn Ile Lys
            610                 615                 620
Glu Ile Arg Asp Lys Tyr Glu Lys Lys Ala Thr Leu Ile Lys Ser Ser
625                 630                 635                 640
Glu Glu

<210> SEQ ID NO 51
<211> LENGTH: 1929
<212> TYPE: DNA
<213> ORGANISM: Mus musculus

<400> SEQUENCE: 51
atgaagcgca gttcagtttc cacctgtggt gctggccgcc tctctatgca ggagttaagg      60
accctggacc tcaataagcc aggcctttat acccctcaaa ccaagaaaag atcaaccttt     120
ggaaagctga gtacacacaa accgacatcg gaaagaaaag tctcaatatt tgggaaaagg     180
actagcggac atggatccag gaatagtcaa cttggtatat tttccagttc tgaaaaaatc     240
aaggacccaa gaccacttaa tgacaaagca ttcattcagc agtgtattcg acaactctat     300
gagtttctta cagaaaacgg ttatgtgtat agtgtatcca tgaagtctct gcaagctcca     360
tccactaaag agttcctaaa gatcttcgcc tttctttatg gctttctgtg cccgtcgtat     420
gaacttcctg gtacaaaatg tgaagaagag gtcccaagaa ttttttaaagc acttgggtat     480 cccttcacac tgtccaagag ctccatgtat acagtgggag cccctcacac gtggcctcac     540
atcgtggctg ccttggtgtg gctcatagac tgcatcaaga ttgatactgc catgaaagaa     600
agctcacctt tatttgatga tgggcagctc tggggagaag agactgaaga tggaattaaa     660
cacaataagt tgtttttgga gtacaccaaa aagtgctatg agaagttcat gaccggggcc     720

```
gacagctttg aagaagagga tgctgagctg caggcgaagc tgaaggactt gtacaaggta    780
gatgcatcta agctggagtc actcgaagca gaaaacaaag aactaaatga acagattgca    840
agactggagg aggaaagaga aagagaaccg aaccgtctga tgtcattgaa gaaactgaaa    900
gcgtccttac aagcagatgt tcaaaactat aaagcataca tgagcaactt ggagtctcat    960
ttagccgttc tgaaacagaa atcgaatagt cttgatgaag aaattggtag agtagaacaa    1020
gaatgtgaaa ctgttaaaca ggaaaacact cgactacaga gtatcgttga taaccagaag   1080
tattcagtcg ctgacattga gaataaat catgagaaaa atgaattgca gcagactatt      1140
aataaattaa ccaaagacct ggaagccgaa cagcaacaga tgtggaatga agaattaaaa    1200
tacgcaagag gcaaagaggc gattgaagcg cagctagcgg agtaccacaa gttggctaga    1260
aaattaaagc ttatccccaa aggtgctgag aattccaaag gttacgactt tgaaattaag    1320
tttaatcctg aggcgggtgc caactgcctt gtcaaataca ggactcaagt gtatgcaccg    1380
ctcaaagagc tcttgaatga aagcgaagaa gaaattaaca aagctctgaa taaaaagagg    1440
catctggagg atactttaga caactgaac accatgaaaa cggaaagcaa gaacactgtg     1500
aggatgctga aggaggagat tcagaaactg gatgaccttc accagcaggc agtgaaggaa    1560
gctgaggaaa aagacaagaa gagtgccagt gagcttgagt ccctggagaa acacaagcac    1620
ctgctggaga gcgggtgaa cgatggcctc agcgaggcca tggatgagtt ggacgctgtc     1680
cagcgggaat accagctaac tgtgaagacc acaactgaag aaagaagaaa ggtggaaaac    1740
aacttacaac gtcttttgga gatggtcgcc acacacgtag ggtctttgga gaaacatctt    1800
gaagaggaga atgctaaagc cgacagagag tacgaagaat tcatgtctga agatctcctg    1860
gaaaacatca gggagatggc agagaagtat aagagaaatg ctgcccaact taaggctccc    1920
gacaaatga                                                            1929

<210> SEQ ID NO 52
<211> LENGTH: 642
<212> TYPE: PRT
<213> ORGANISM: Mus musculus

<400> SEQUENCE: 52

Met Lys Arg Ser Ser Val Ser Thr Cys Gly Ala Gly Arg Leu Ser Met
1               5                   10                  15

Gln Glu Leu Arg Thr Leu Asp Leu Asn Lys Pro Gly Leu Tyr Thr Pro
            20                  25                  30

Gln Thr Lys Glu Arg Ser Thr Phe Gly Lys Leu Ser Thr His Lys Pro
        35                  40                  45

Thr Ser Glu Arg Lys Val Ser Ile Phe Gly Lys Arg Thr Ser Gly His
    50                  55                  60

Gly Ser Arg Asn Ser Gln Leu Gly Ile Phe Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Tyr Glu Phe Leu Thr Glu Asn Gly Tyr Val Tyr Ser Val
            100                 105                 110

Ser Met Lys Ser Leu Gln Ala Pro Ser Thr Lys Glu Phe Leu Lys Ile
        115                 120                 125

Phe Ala Phe Leu Tyr Gly Phe Leu Cys Pro Ser Tyr Glu Leu Pro Gly
    130                 135                 140

Thr Lys Cys Glu Glu Val Pro Arg Ile Phe Lys Ala Leu Gly Tyr
145                 150                 155                 160
```

-continued

```
Pro Phe Thr Leu Ser Lys Ser Ser Met Tyr Thr Val Gly Ala Pro His
            165                 170                 175
Thr Trp Pro His Ile Val Ala Ala Leu Val Trp Leu Ile Asp Cys Ile
        180                 185                 190
Lys Ile Asp Thr Ala Met Lys Glu Ser Ser Pro Leu Phe Asp Asp Gly
    195                 200                 205
Gln Leu Trp Gly Glu Thr Glu Asp Gly Ile Lys His Asn Lys Leu
210                 215                 220
Phe Leu Glu Tyr Thr Lys Lys Cys Tyr Glu Lys Phe Met Thr Gly Ala
225                 230                 235                 240
Asp Ser Phe Glu Glu Asp Ala Glu Leu Gln Ala Lys Leu Lys Asp
            245                 250                 255
Leu Tyr Lys Val Asp Ala Ser Lys Leu Glu Ser Leu Glu Ala Glu Asn
        260                 265                 270
Lys Glu Leu Asn Glu Gln Ile Ala Arg Leu Glu Glu Arg Glu Arg
    275                 280                 285
Glu Pro Asn Arg Leu Met Ser Leu Lys Lys Leu Lys Ala Ser Leu Gln
    290                 295                 300
Ala Asp Val Gln Asn Tyr Lys Ala Tyr Met Ser Asn Leu Glu Ser His
305                 310                 315                 320
Leu Ala Val Leu Lys Gln Lys Ser Asn Ser Leu Asp Glu Glu Ile Gly
            325                 330                 335
Arg Val Glu Gln Glu Cys Glu Thr Val Lys Gln Glu Asn Thr Arg Leu
        340                 345                 350
Gln Ser Ile Val Asp Asn Gln Lys Tyr Ser Val Ala Asp Ile Glu Arg
    355                 360                 365
Ile Asn His Glu Lys Asn Glu Leu Gln Gln Thr Ile Asn Lys Leu Thr
370                 375                 380
Lys Asp Leu Glu Ala Glu Gln Gln Met Trp Asn Glu Glu Leu Lys
            385                 390                 395                 400
Tyr Ala Arg Gly Lys Glu Ala Ile Glu Ala Gln Leu Ala Glu Tyr His
        405                 410                 415
Lys Leu Ala Arg Lys Leu Lys Leu Ile Pro Lys Gly Ala Glu Asn Ser
    420                 425                 430
Lys Gly Tyr Asp Phe Glu Ile Lys Phe Asn Pro Glu Ala Gly Ala Asn
    435                 440                 445
Cys Leu Val Lys Tyr Arg Thr Gln Val Tyr Ala Pro Leu Lys Glu Leu
450                 455                 460
Leu Asn Glu Ser Glu Glu Ile Asn Lys Ala Leu Asn Lys Lys Arg
465                 470                 475                 480
His Leu Glu Asp Thr Leu Glu Gln Leu Asn Thr Met Lys Thr Glu Ser
            485                 490                 495
Lys Asn Thr Val Arg Met Leu Lys Glu Ile Gln Lys Leu Asp Asp
        500                 505                 510
Leu His Gln Gln Ala Val Lys Glu Ala Glu Lys Asp Lys Lys Ser
    515                 520                 525
Ala Ser Glu Leu Glu Ser Leu Lys His Lys His Leu Leu Glu Ser
    530                 535                 540
Gly Val Asn Asp Gly Leu Ser Glu Ala Met Asp Glu Leu Asp Ala Val
545                 550                 555                 560
Gln Arg Glu Tyr Gln Leu Thr Val Lys Thr Thr Glu Glu Arg Arg
            565                 570                 575
Lys Val Glu Asn Asn Leu Gln Arg Leu Leu Glu Met Val Ala Thr His
        580                 585                 590
```

```
Val Gly Ser Leu Glu Lys His Leu Glu Glu Glu Asn Ala Lys Ala Asp
        595                 600                 605

Arg Glu Tyr Glu Glu Phe Met Ser Glu Asp Leu Leu Glu Asn Ile Arg
    610                 615                 620

Glu Met Ala Glu Lys Tyr Lys Arg Asn Ala Ala Gln Leu Lys Ala Pro
625                 630                 635                 640

Asp Lys

<210> SEQ ID NO 53
<211> LENGTH: 2244
<212> TYPE: DNA
<213> ORGANISM: Homo sapiens

<400> SEQUENCE: 53
```

| | |
|---|---|
| atggcgccgg gttggccctc actatcagcg ggctcccgac aggaggcgcc ccagcttgcg | 60 |
| gccggggca gcgcctacca ggcagttggc aggcagttcc agccccgggc cacggcactg | 120 |
| cagggcccga gccaggttac ggcaaccggg ggccctgcaa acagctcccg attagggggt | 180 |
| gcttttgggt gggaaagcgc aggccctgga tggaggcccg acctgcggcg ctccagctca | 240 |
| tcgccccgcc tctttgcggc agagctcagg ccggcgcaaa ccggttcagt gctaggactg | 300 |
| acgtctcgcg ccgcccaacc gcagcacgcc ccgcctccc cagtcctctg aagagacag | 360 |
| ggaacgtcta gccgccaggg tcccggagg cggctctgta ccagacggac tatactgaga | 420 |
| gcctatgaca atagccgaag agcgcagcgc aggcggtccg cagcagccgc agctcggggg | 480 |
| cggtgcctgc cttgcagcct cccctcggcg atcgcgcagc ccatctttg tccggcctcc | 540 |
| gcgctttgtt ctcggcgccc gggccttggc agcctggcc agccgccgag cagccccac | 600 |
| gccgcgctgg cgtcgtcctc gcctcccctcg ccgccgcccc ccgcgcgcgg ccgggccttg | 660 |
| ccccccatgg tgtcccggcc agagcccgag ggcgaggcca tggacgccga gctggcggta | 720 |
| gcgccgccgg gctgctcgca cctgggcagc ttcaaggtgg acaactggaa gcagaacctg | 780 |
| cgggccatct accagtgctt cgtgtggagc ggcacggctg aggcccgcaa gcgcaaggcc | 840 |
| aagtcctgta tctgccatgt ctgtggcgtc cacctcaaca ggctgcattc ctgcctctac | 900 |
| tgtgtcttct tcggctgttt cacaaagaag catattcacg agcatgcgaa ggcgaagcgg | 960 |
| cacaacctgg ccattgatct gatgtacgga ggcatctact gttttctgtg ccaggactac | 1020 |
| atctatgaca agacatgga ataatcgcc aaggaggagc agcgaaaagc ttggaaaatg | 1080 |
| caaggcgttg gagagaagtt ttcaacttgg gaaccaacca acggagct gaactgctg | 1140 |
| aagcacaacc cgaaaaggag aaagatcacc tcgaactgca ccataggtct gcgtgggctg | 1200 |
| atcaaccttg gaacacatg cttcatgaac tgcatcgtgc aggccctgac ccacacgcca | 1260 |
| cttctgcggg acttcttcct gtctgacagg caccgctgtg agatgcagag ccccagctcc | 1320 |
| tgtctggtct gtgagatgtc ctcactgttt caggagtttt actctggaca ccggtccct | 1380 |
| cacatcccgt ataagttgct gcacctggtg tggacccacg cgaggcacct agcaggctac | 1440 |
| gagcagcagg acgccacga gttcctcatc gcggccctgg acgtgctcca ccgacactgc | 1500 |
| aaaggtgatg acaatgggaa gaaggccaac aaccccaacc actgcaactg catcatagac | 1560 |
| cagatcttca caggcgggtt gcagtcgac gtcacctgcc aagtctgcca tggagtctcc | 1620 |
| accaccatcg acccccttctg ggacatcagc ttggatctcc ccgctcttc caccccattc | 1680 |
| tggcccctga gccagggag cgagggcaac gtggtaaacg ggaaagcca cgtgtcggga | 1740 |
| accaccacgc tcacggactg cctgcgacga ttcaccagac cagagcactt gggcagcagc | 1800 |

-continued

```
gccaagatca agtgcagcgg ttgccatagc taccaggagt ccacaaagca gctcactatg    1860
aagaaactgc ccatcgtagc ctgttttcat ctcaaacgat ttgaacactc agccaagctg    1920
cggcggaaga tcaccacgta tgtgtccttc ccctggagc tggacatgac ccctttcatg     1980
gcctccagca agagagcag gatgaatgga cagtaccagc agcccacgga cagtctcaac     2040
aatgacaaca gtattccct gtttgctgtt gttaaccatc aagggacctt ggagagtggc     2100
cactacacca gctttatccg gcagcacaaa gaccagtggt tcaagtgtga cgatgccatc    2160
atcaccaagg ccagcatcaa ggacgtcctg gacagcgaag ggtacttgct gttctatcac    2220
aaacagttcc tggaatacga gtag                                           2244
```

<210> SEQ ID NO 54
<211> LENGTH: 747
<212> TYPE: PRT
<213> ORGANISM: Homo sapiens

<400> SEQUENCE: 54

```
Met Ala Pro Gly Trp Pro Ser Leu Ser Ala Gly Ser Arg Gln Glu Ala
1               5                   10                  15

Pro Gln Leu Ala Ala Gly Gly Ser Ala Tyr Gln Ala Val Gly Arg Gln
            20                  25                  30

Phe Gln Pro Arg Ala Thr Ala Leu Gln Gly Pro Ser Gln Val Thr Ala
        35                  40                  45

Thr Gly Gly Pro Ala Asn Ser Ser Arg Leu Gly Gly Ala Phe Gly Trp
    50                  55                  60

Glu Ser Ala Gly Pro Gly Trp Arg Pro Asp Leu Arg Ser Ser Ser
65                  70                  75                  80

Ser Pro Arg Leu Phe Ala Ala Glu Leu Arg Pro Ala Gln Thr Gly Ser
                85                  90                  95

Val Leu Gly Leu Thr Ser Arg Ala Ala Gln Pro Gln His Ala Pro Ala
            100                 105                 110

Ser Pro Val Leu Trp Lys Arg Gln Gly Thr Ser Ser Arg Gln Gly Pro
        115                 120                 125

Gly Arg Arg Leu Cys Thr Arg Thr Ile Leu Arg Ala Tyr Asp Asn
    130                 135                 140

Ser Arg Arg Ala Gln Arg Arg Ser Ala Ala Ala Ala Arg Gly
145                 150                 155                 160

Arg Cys Leu Pro Cys Ser Leu Pro Ser Ala Ile Ala Gln Pro His Leu
                165                 170                 175

Cys Pro Ala Ser Ala Leu Cys Ser Arg Arg Pro Gly Leu Gly Gln Pro
            180                 185                 190

Gly Gln Pro Pro Ser Ser Pro His Ala Ala Leu Ala Ser Ser Ser Pro
        195                 200                 205

Pro Ser Pro Pro Pro Pro Ala Arg Gly Arg Ala Leu Pro Pro Met Val
    210                 215                 220

Ser Arg Pro Glu Pro Glu Gly Glu Ala Met Asp Ala Glu Leu Ala Val
225                 230                 235                 240

Ala Pro Pro Gly Cys Ser His Leu Gly Ser Phe Lys Val Asp Asn Trp
                245                 250                 255

Lys Gln Asn Leu Arg Ala Ile Tyr Gln Cys Phe Val Trp Ser Gly Thr
            260                 265                 270

Ala Glu Ala Arg Lys Arg Lys Ala Lys Ser Cys Ile Cys His Val Cys
        275                 280                 285

Gly Val His Leu Asn Arg Leu Ser Cys Leu Tyr Cys Val Phe Phe
    290                 295                 300
```

-continued

```
Gly Cys Phe Thr Lys Lys His Ile His Glu His Ala Lys Ala Lys Arg
305                 310                 315                 320

His Asn Leu Ala Ile Asp Leu Met Tyr Gly Gly Ile Tyr Cys Phe Leu
            325                 330                 335

Cys Gln Asp Tyr Ile Tyr Asp Lys Asp Met Glu Ile Ile Ala Lys Glu
            340                 345                 350

Glu Gln Arg Lys Ala Trp Lys Met Gln Gly Val Gly Glu Lys Phe Ser
            355                 360                 365

Thr Trp Glu Pro Thr Lys Arg Glu Leu Glu Leu Leu Lys His Asn Pro
370                 375                 380

Lys Arg Arg Lys Ile Thr Ser Asn Cys Thr Ile Gly Leu Arg Gly Leu
385                 390                 395                 400

Ile Asn Leu Gly Asn Thr Cys Phe Met Asn Cys Ile Val Gln Ala Leu
            405                 410                 415

Thr His Thr Pro Leu Leu Arg Asp Phe Phe Leu Ser Asp Arg His Arg
            420                 425                 430

Cys Glu Met Gln Ser Pro Ser Ser Cys Leu Val Cys Glu Met Ser Ser
            435                 440                 445

Leu Phe Gln Glu Phe Tyr Ser Gly His Arg Ser Pro His Ile Pro Tyr
450                 455                 460

Lys Leu Leu His Leu Val Trp Thr His Ala Arg His Leu Ala Gly Tyr
465                 470                 475                 480

Glu Gln Gln Asp Ala His Glu Phe Leu Ile Ala Ala Leu Asp Val Leu
            485                 490                 495

His Arg His Cys Lys Gly Asp Asp Asn Gly Lys Lys Ala Asn Asn Pro
            500                 505                 510

Asn His Cys Asn Cys Ile Ile Asp Gln Ile Phe Thr Gly Gly Leu Gln
            515                 520                 525

Ser Asp Val Thr Cys Gln Val Cys His Gly Val Ser Thr Thr Ile Asp
530                 535                 540

Pro Phe Trp Asp Ile Ser Leu Asp Leu Pro Gly Ser Ser Thr Pro Phe
545                 550                 555                 560

Trp Pro Leu Ser Pro Gly Ser Glu Gly Asn Val Val Asn Gly Glu Ser
            565                 570                 575

His Val Ser Gly Thr Thr Thr Leu Thr Asp Cys Leu Arg Arg Phe Thr
            580                 585                 590

Arg Pro Glu His Leu Gly Ser Ser Ala Lys Ile Lys Cys Ser Gly Cys
            595                 600                 605

His Ser Tyr Gln Glu Ser Thr Lys Gln Leu Thr Met Lys Lys Leu Pro
            610                 615                 620

Ile Val Ala Cys Phe His Leu Lys Arg Phe Glu His Ser Ala Lys Leu
625                 630                 635                 640

Arg Arg Lys Ile Thr Thr Tyr Val Ser Phe Pro Leu Glu Leu Asp Met
            645                 650                 655

Thr Pro Phe Met Ala Ser Ser Lys Glu Ser Arg Met Asn Gly Gln Tyr
            660                 665                 670

Gln Gln Pro Thr Asp Ser Leu Asn Asn Asp Asn Lys Tyr Ser Leu Phe
            675                 680                 685

Ala Val Val Asn His Gln Gly Thr Leu Glu Ser Gly His Tyr Thr Ser
            690                 695                 700

Phe Ile Arg Gln His Lys Asp Gln Trp Phe Lys Cys Asp Asp Ala Ile
705                 710                 715                 720

Ile Thr Lys Ala Ser Ile Lys Asp Val Leu Asp Ser Glu Gly Tyr Leu
```

Leu Phe Tyr His Lys Gln Phe Leu Glu Tyr Glu
        740                 745

<210> SEQ ID NO 55
<211> LENGTH: 1578
<212> TYPE: DNA
<213> ORGANISM: Mus musculus

<400> SEQUENCE: 55

| | | | | | |
|---|---|---|---|---|---|
| atggtggcca | ggccggagcc | tgaggtcgag | gccatggacg | ctgagctggc | ggtaccgccg | 60 |
| cctggctgct | cgcacctggg | cagcttcaag | gtggacaact | ggaagcaaaa | cctgcgggcc | 120 |
| atctaccagt | gcttcgtgtg | gagcggaact | gccgaggctc | gcaagcgcaa | ggcaaagtcc | 180 |
| tgtgtctgcc | atgtctgcgg | catccacctg | aaccggctgc | actcttgcct | ctactgtgtc | 240 |
| ttctttggct | gtttcacgaa | gaagcacatc | catgaccatg | ccaagtcaaa | gcgacacaac | 300 |
| ctggccatcg | acctgatgta | cggaggtatt | tactgcttct | gtgtcagga | ctacatctat | 360 |
| gacaaagaca | tagaaatcat | tgccaaagag | gagcagcgca | aggcttggaa | gatgcaaggt | 420 |
| gttggagaga | agttttcaac | ttgggaacca | actaaacggg | agctggaact | gctgaagcat | 480 |
| aacccaaaga | ggcggaagat | cacctccaat | tgtaccatag | gtctgcgtgg | actgatcaac | 540 |
| ctggggaaca | cgtgtttcat | ggactgcatc | gtgcaggcgc | tgacccacac | tccgctcctg | 600 |
| agagacttct | ttctgtcgga | taggcaccgc | tgtgagatgc | agagcccag | ctcctgcttg | 660 |
| gtctgtgaga | tgtcctctct | cttccaggag | ttttactcag | ggcaccgctc | ccacacatt | 720 |
| ccatacaagc | tgctgcacct | ggtgtggacg | cacgcccggc | acctggcggg | ttatgagcag | 780 |
| caggacgcac | atgagttcct | cattgcagcc | ctggacgtcc | tccaccggca | ctgcaaaggt | 840 |
| gatgacaatg | ggaagaaagc | caacaatcct | aaccactgca | attgcatcat | tgaccagatc | 900 |
| tttacgggtg | ggctccagtc | tgatgttaca | tgccaagtct | gccacggggt | ctccaccacc | 960 |
| atagacccct | tctgggacat | cagtttagac | cttcccggtt | cttctacccc | attctggccc | 1020 |
| ttgagcccag | ggagcgaggg | cagtgtggtt | aatggggaga | gccatgcatc | cgggaccacc | 1080 |
| actctcacag | actgcctgcg | aagatttacc | agaccagagc | acttaggaag | cagtgccaag | 1140 |
| atcaagtgta | gcggttgcca | tagctaccaa | gagtccacaa | agcagctcac | catgaagaag | 1200 |
| ctgcccattg | tggcctgttt | ccatctcaaa | cgatttgaac | actcagccaa | acttcggcgg | 1260 |
| aagatcacca | catatgtgtc | ttttcccctg | gaactggaca | tgacgccctt | catggcctcc | 1320 |
| agcaaagaga | gcaggatgaa | tgggcaatac | cagcagcccc | tggacagtct | caacaatgac | 1380 |
| aacaaatact | ccctgtttgc | tgtcgttaac | catcaaggga | ccttggagag | tggccactac | 1440 |
| accagcttca | tccggcagca | caagaccag | tggttcaagt | gtgatgacgc | cattatcacc | 1500 |
| aaggccagca | tcaaagatgt | actggacagt | gaagggtacc | tactcttcta | tcacaaacag | 1560 |
| ttcctggaat | acgagtag | | | | | 1578 |

<210> SEQ ID NO 56
<211> LENGTH: 525
<212> TYPE: PRT
<213> ORGANISM: Mus musculus

<400> SEQUENCE: 56

Met Val Ala Arg Pro Glu Pro Glu Val Glu Ala Met Asp Ala Glu Leu
1               5                   10                  15

Ala Val Pro Pro Pro Gly Cys Ser His Leu Gly Ser Phe Lys Val Asp
            20                  25                  30

-continued

```
Asn Trp Lys Gln Asn Leu Arg Ala Ile Tyr Gln Cys Phe Val Trp Ser
     35                  40                  45

Gly Thr Ala Glu Ala Arg Lys Arg Lys Ala Lys Ser Cys Val Cys His
 50                  55                  60

Val Cys Gly Ile His Leu Asn Arg Leu His Ser Cys Leu Tyr Cys Val
 65              70                  75                  80

Phe Phe Gly Cys Phe Thr Lys Lys His Ile His Asp His Ala Lys Ser
             85                  90                  95

Lys Arg His Asn Leu Ala Ile Asp Leu Met Tyr Gly Ile Tyr Cys
             100                 105             110

Phe Leu Cys Gln Asp Tyr Ile Tyr Asp Lys Asp Ile Glu Ile Ile Ala
         115                 120             125

Lys Glu Glu Gln Arg Lys Ala Trp Lys Met Gln Gly Val Gly Glu Lys
     130                 135             140

Phe Ser Thr Trp Glu Pro Thr Lys Arg Glu Leu Glu Leu Leu Lys His
145             150                 155                 160

Asn Pro Lys Arg Arg Lys Ile Thr Ser Asn Cys Thr Ile Gly Leu Arg
             165                 170                 175

Gly Leu Ile Asn Leu Gly Asn Thr Cys Phe Met Asp Cys Ile Val Gln
         180                 185             190

Ala Leu Thr His Thr Pro Leu Leu Arg Asp Phe Phe Leu Ser Asp Arg
     195                 200                 205

His Arg Cys Glu Met Gln Ser Pro Ser Ser Cys Leu Val Cys Glu Met
 210             215                 220

Ser Ser Leu Phe Gln Glu Phe Tyr Ser Gly His Arg Ser Pro His Ile
225             230                 235                 240

Pro Tyr Lys Leu Leu His Leu Val Trp Thr His Ala Arg His Leu Ala
             245                 250                 255

Gly Tyr Glu Gln Gln Asp Ala His Glu Phe Leu Ile Ala Ala Leu Asp
         260                 265             270

Val Leu His Arg His Cys Lys Gly Asp Asp Asn Gly Lys Lys Ala Asn
     275                 280             285

Asn Pro Asn His Cys Asn Cys Ile Ile Asp Gln Ile Phe Thr Gly Gly
     290             295                 300

Leu Gln Ser Asp Val Thr Cys Gln Val Cys His Gly Val Ser Thr Thr
305             310                 315             320

Ile Asp Pro Phe Trp Asp Ile Ser Leu Asp Leu Pro Gly Ser Ser Thr
             325                 330             335

Pro Phe Trp Pro Leu Ser Pro Gly Ser Glu Gly Ser Val Val Asn Gly
         340                 345             350

Glu Ser His Ala Ser Gly Thr Thr Thr Leu Thr Asp Cys Leu Arg Arg
         355                 360             365

Phe Thr Arg Pro Glu His Leu Gly Ser Ser Ala Lys Ile Lys Cys Ser
     370                 375             380

Gly Cys His Ser Tyr Gln Glu Ser Thr Lys Gln Leu Thr Met Lys Lys
385             390                 395             400

Leu Pro Ile Val Ala Cys Phe His Leu Lys Arg Phe Glu His Ser Ala
             405                 410             415

Lys Leu Arg Arg Lys Ile Thr Thr Tyr Val Ser Phe Pro Leu Glu Leu
             420             425             430

Asp Met Thr Pro Phe Met Ala Ser Ser Lys Glu Ser Arg Met Asn Gly
         435             440             445

Gln Tyr Gln Gln Pro Leu Asp Ser Leu Asn Asn Asp Asn Lys Tyr Ser
```

```
                450            455            460
Leu Phe Ala Val Val Asn His Gln Gly Thr Leu Glu Ser Gly His Tyr
465                 470                 475                 480

Thr Ser Phe Ile Arg Gln His Lys Asp Gln Trp Phe Lys Cys Asp Asp
                485                 490                 495

Ala Ile Ile Thr Lys Ala Ser Ile Lys Asp Val Leu Asp Ser Glu Gly
                500                 505                 510

Tyr Leu Leu Phe Tyr His Lys Gln Phe Leu Glu Tyr Glu
                515                 520                 525

<210> SEQ ID NO 57
<211> LENGTH: 5817
<212> TYPE: DNA
<213> ORGANISM: Homo sapiens

<400> SEQUENCE: 57
```

| | | | | | |
|---|---|---|---|---|---|
| atggtggagt | atgggaaata | cagcaatgac | ctctacgaac | tccaggcgag | ccggtgggag | 60 |
| tggaagagac | tcaaagcaaa | gacgcccaaa | aacgggcccc | ctccgtgtcc | tcgactcggg | 120 |
| cacagcttct | cccttgtggg | caacaaatgc | tacctgtttg | ggggtctggc | caatgatagc | 180 |
| gaggacccaa | agaacaacat | tccaaggtac | ctgaatgact | tatatatcct | ggaattacgg | 240 |
| ccaggctctg | gagtggtagc | ctgggacatt | cccatcactt | acggggtcct | accaccaccc | 300 |
| cgggagtcac | atactgccgt | ggtctacacc | gaaaaagaca | taagaagtc | caagctggtg | 360 |
| atctacggcg | ggatgagtgg | ctgcaggctg | ggggacctgt | ggaccctaga | tattgacacc | 420 |
| ctgacgtgga | ataagcccag | tctcagcggg | gtggcgcctc | ttcctcgcag | tctccactcg | 480 |
| gcaaccacca | tcggaaataa | aatgtacgtg | tttggtggct | gggtgcctct | cgtcatggat | 540 |
| gacgtcaaag | tggccacaca | cgagaaggag | tggaagtgta | ccaacacgct | ggcttgtctc | 600 |
| aacctggata | ccatggcctg | ggagaccatc | ctgatggata | cactggagga | caacatcccc | 660 |
| cgtgctcggg | ctggccactg | cgcagtcgcc | atcaacaccc | gcctgtacat | ttggagtggg | 720 |
| cgtgacggct | accgcaaggc | ctggaacaac | caggtctgct | gcaaggacct | ctggtaccta | 780 |
| gagacagaaa | agccaccacc | cccagcccga | gtacaactgg | tacgcgccaa | caccaactcc | 840 |
| ctggaggtga | gctgggggc | agtggcaaca | gccgacagct | accttctcca | gctccagaaa | 900 |
| tatgacattc | ctgccacggc | tgctactgcc | acctccccta | cacccaatcc | ggtcccatct | 960 |
| gtgcctgcca | accctcccaa | gagccctgcc | ccagcagcag | ccgcacctgc | tgtgcagccg | 1020 |
| ctgacccaag | taggcatcac | gctcctgccc | caggctgccc | ccgcaccccc | gaccaccacc | 1080 |
| accatccagg | tcttgccaac | ggtgcctggc | agctccattt | ctgtgcccac | cgcagccagg | 1140 |
| actcaaggtg | tccctgctgt | tctcaaagtg | accggtcctc | aggctacaac | aggaactcca | 1200 |
| ttggtcacca | tgcgacctgc | cagccaggct | gggaaagccc | ctgtcaccgt | gacctccctt | 1260 |
| cccgccggag | tgcggatggt | tgtgccaaca | cagagtgccc | agggaacggt | gattggcagt | 1320 |
| agcccacaga | tgagtgggat | ggccgcactg | gccgctgcgg | ccgctgccac | ccagaagatc | 1380 |
| cccccttcct | cgcgacccac | ggtgctgagt | gtcccagcgg | gtaccaccat | cgtgaagacc | 1440 |
| atggctgtga | cacctggcac | taccaccctc | ccagccactg | tgaaggtggc | ctcctcgcca | 1500 |
| gtcatggtga | gcgtgagcaa | ccctgccact | cgcatgctga | agactgcagc | cgcccaggtg | 1560 |
| gggacatcgg | tttcctccgc | caccaacacg | tctacccgcc | ctatcatcac | agtgcacaag | 1620 |
| tcaggcactg | tgcagtggcc | cagcaagcc | aggtggtga | ccacagttgt | gggcggggtc | 1680 |
| accaagacca | tcaccctggt | gaagagcccc | atctctgtcc | caggaggcag | tgctctgatt | 1740 |

-continued

```
tccaatctgg gcaaagtgat gtcggtggtc cagaccaaac cagttcagac ttcagcagtc    1800
acaggccagg cgtccacggg tcctgtgact cagatcatcc agaccaaagg cccctgcca     1860
gcgggaacaa tcctgaagct ggtgacctca gcagatggca agcccaccac catcatcact    1920
accacgcagg ccagtggggc ggggaccaag cccaccatcc tgggcatcag cagcgtctcc    1980
cccagtacca ccaagcccgg cacgaccacc atcatcaaaa ccatccccat gtcggccatc    2040
atcacccagg cgggcgccac gggtgtgacc agcagtcctg gcatcaagtc acccatcacc    2100
atcatcacca ccaaggtgat gacttcagga actggagcac ctgcgaaaat catcactgct    2160
gtccccaaaa ttgccactgg ccacgggcag caggagtga cccaggtggt gcttaagggg     2220
gccccgggac agccaggcac catcctccgc actgtgccca tgggggggtgt tcgcctggtc    2280
acacccgtca ccgtctccgc cgtcaagcca gccgtcacca cgttggttgt gaaaggcacc    2340
acaggtgtca cgaccctagg cacagtgaca ggcaccgtct ccaccagcct tgccggggcg    2400
gggggccaca gcactagtgc ttccctggcc acgcccatca ccaccttggg caccattgcc    2460
accctctcaa gccaggtgat caaccccact gccatcactg tgtcggccgc acagaccacg    2520
ctgacagcgg caggcgggct cacaacccg accatcacca tgcagcccgt gtcccagccc    2580
acccaggtaa ctctgatcac ggcacctagt ggggtggagg cccagcctgt gcatgacctc    2640
cctgtgtcca ttctggcctc cccgactaca gaacagccca ccgccacagt taccatcgcc    2700
gactcaggcc agggtgatgt gcagcctggc actgtcacct tggtgtgctc caacccaccc    2760
tgtgagaccc acgagactgg caccaccaac acggccacca ctactgttgt ggctaacctt    2820
ggggacacc cccagcccac ccaagtgcag ttcgtctgtg acagacagga ggcagctgct     2880
tctcttgtga cctcgactgt gggccagcag aatggtagcg tggtccgagt ctgttcgaac    2940
ccgccctgcg agacccacga cacgggcacc accaacaccg ccaccaccgc cacctccaac    3000
atggccgggc agcatggctg ctcaaaccca ccctgcgaga cccacgagac gggcaccacc    3060
aacactgcca ctacagccat gtcgagcgtc ggcgccaacc accagcgaga tgcccgtcgg    3120
gcctgtgcag ctggcacccc tgccgtgatc cggatcagtg tggccactgg ggcgctggag    3180
gcagcccagg gctctaagcc ccagtgccaa acccgccaga ccagcgcgac cagcaccacc    3240
atgactgtga tggccaccgg ggccccgtgc tcggccggcc cactccttgg gccgagcatg    3300
gcacgggagc ccgggggccg cagccctgct tttgtgcagt tggcccctct gagcagcaaa    3360
gtcaggctga gcagcccaag cattaaggac cttcctgcgg ggcgccacag ccatgcggtc    3420
agcaccgctg ccatgacccg ttccagcgtg ggtgctgggg agcccgcat ggcacctgtg      3480
tgcgagagcc tccagggtgg ctcgcccagc accacagtga ctgtgacagc cctggaggca    3540
ctgctgtgcc cctcggccac cgtgacccaa gtctgctcca cccaccatg tgagacccac     3600
gagacaggca ccaccaacac cgccactacc tcgaatgcag gcagcgccca gagggtgtgc    3660
tccaacccgc catgcgagac ccacgagacg gcaccaccc acacgccac caccgctact     3720
tcaaacgggg gcacgggcca gcccgagggt gggcagcagc cccctgctgg tcgcccctgt    3780
gagacacacc agaccacttc cactggcacc accatgtcgg tcagcgtggg tgccctgctt    3840
cccgacgcca cttcttccca caggaccgtg gagtctggcc tagaggtggc ggcggcaccc    3900
agcgtcaccc ccaggctgg caccgcgctg ctggctcctt tcccaacaca gagggtgtgc    3960
tccaacccccc cctgtgagac ccacgagacg ggcaccactc acacggccac cactgtcact    4020
tccaacatga gttcaaacca agaccccca cctgctgcca gcgatcaggg agaggtggag      4080
agcacccagg gcgacagcgt gaacatcacc agctccagtg ccatcacgac aaccgtgtcc    4140
```

```
tccacactga cgcgggctgt gaccaccgtg acgcagtcca caccggtccc gggcccctct    4200
gtgccgcccc cagaggaact ccaggtgtcg ccaggtcctc gccagcagct gccaccacgg    4260
cagcttctgc agtcggcttc cacagccctg atggggagt ccgccgaggt cctgtcagcc     4320
tcccagaccc ctgagctccc ggccgccgtg atctgagca gcacagggga gccatcttcg     4380
ggccaggagt ctgccggctc tgcggtggtg gccactgtgg tggtccagcc acccccaccc    4440
acacagtccg aagtagacca gttatcactt ccccaagagc taatggccga ggcccaagct    4500
ggcaccacca ccctcatggt aacggggctc acccccgagg agctggcagt gacggctgct    4560
gcagaagcag ctgcccaggc cgcagccacg gaggaagccc aggccctggc catccaggcg    4620
gtgctccagg ccgcgcagca ggccgtcatg gcaccggcg agcccatgga cacctccgag     4680
gcagcagcaa ccgtgactca gcggagctg gggcacctgt cggccgaggg tcaggagggc     4740
caggccacca ccatacccat tgtgctgaca gcaggagc tggctgccct ggtgcagcag      4800
cagcagctgc aggaggccca ggcccagcag cagcatcacc acctccccac tgaggccctg    4860
gcccctgccg acagtctcaa cgacccagcc attgagagca attgcctcaa tgagctggcc    4920
ggcacggtcc ccagcactgt ggcgctgctg ccctcaacgg ccactgagag cctggctcca    4980
tccaacacat ttgtggcccc ccagccggtt gtggtggcca gccagccaa gctgcaggct    5040
gcagctaccc tgaccgaagt ggccaatggc atcgagtccc tgggtgtgaa gccagacctg    5100
ccgcccccac ccagcaaagc ccccatgaag aaggaaaacc agtggtttga tgtgggagtc    5160
attaagggca ccaatgtaat ggtgacacac tatttcctgc caccagatga tgctgtccca    5220
tcagacgatg atttgggcac cgtccctgac tataaccagc tgaagaagca ggagctgcag    5280
ccaggcacag cctataagtt tcgtgttgcc ggaatcaatg cctgtgcgcg ggggcccttc    5340
agcgaaatct cagcctttaa gacgtgcctg cctggtttcc caggggcccc ttgtgccatt    5400
aaaatcagca aaagtccgga tggtgctcac ctcacctggg agccaccctc tgtgacctcc    5460
ggcaagatta tcgagtactc cgtgtacctg gccatccaga gctcacaggc tggggcgag    5520
ctcaagagct ccaccccggc ccagctggcc ttcatgcggg tgtactgcgg gcccagcccc    5580
tcctgcctgg tgcagtcctc cagcctttcc aacgcccaca tcgactacac caccaagccc    5640
gccatcatct tccgcatcgc cgcccgcaat gagaagggct atggcccggc cacacaagtg    5700
aggtggctgc aggaaaccag taaagacagc tctggcacca agccagccaa caagcggccc    5760
atgtcctctc cagaaatgaa atctgctcca aagaaatcta aggccgatgg tcagtga       5817
```

<210> SEQ ID NO 58
<211> LENGTH: 1938
<212> TYPE: PRT
<213> ORGANISM: Homo sapiens

<400> SEQUENCE: 58

```
Met Val Glu Tyr Gly Lys Tyr Ser Asn Asp Leu Tyr Glu Leu Gln Ala
1               5                  10                  15

Ser Arg Trp Glu Trp Lys Arg Leu Lys Ala Lys Thr Pro Lys Asn Gly
            20                  25                  30

Pro Pro Pro Cys Pro Arg Leu Gly His Ser Phe Ser Leu Val Gly Asn
        35                  40                  45

Lys Cys Tyr Leu Phe Gly Gly Leu Ala Asn Asp Ser Glu Asp Pro Lys
    50                  55                  60

Asn Asn Ile Pro Arg Tyr Leu Asn Asp Leu Tyr Ile Leu Glu Leu Arg
65                  70                  75                  80

Pro Gly Ser Gly Val Val Ala Trp Asp Ile Pro Ile Thr Tyr Gly Val
```

```
                85                  90                  95
Leu Pro Pro Pro Arg Glu Ser His Thr Ala Val Val Tyr Thr Glu Lys
            100                 105                 110

Asp Asn Lys Lys Ser Lys Leu Val Ile Tyr Gly Gly Met Ser Gly Cys
            115                 120                 125

Arg Leu Gly Asp Leu Trp Thr Leu Asp Ile Asp Thr Leu Thr Trp Asn
            130                 135                 140

Lys Pro Ser Leu Ser Gly Val Ala Pro Leu Pro Arg Ser Leu His Ser
145                 150                 155                 160

Ala Thr Thr Ile Gly Asn Lys Met Tyr Val Phe Gly Gly Trp Val Pro
                165                 170                 175

Leu Val Met Asp Asp Val Lys Val Ala Thr His Glu Lys Glu Trp Lys
                180                 185                 190

Cys Thr Asn Thr Leu Ala Cys Leu Asn Leu Asp Thr Met Ala Trp Glu
                195                 200                 205

Thr Ile Leu Met Asp Thr Leu Glu Asp Asn Ile Pro Arg Ala Arg Ala
                210                 215                 220

Gly His Cys Ala Val Ala Ile Asn Thr Arg Leu Tyr Ile Trp Ser Gly
225                 230                 235                 240

Arg Asp Gly Tyr Arg Lys Ala Trp Asn Asn Gln Val Cys Cys Lys Asp
                245                 250                 255

Leu Trp Tyr Leu Glu Thr Glu Lys Pro Pro Pro Ala Arg Val Gln
                260                 265                 270

Leu Val Arg Ala Asn Thr Asn Ser Leu Glu Val Ser Trp Gly Ala Val
                275                 280                 285

Ala Thr Ala Asp Ser Tyr Leu Leu Gln Leu Gln Lys Tyr Asp Ile Pro
                290                 295                 300

Ala Thr Ala Ala Thr Ala Thr Ser Pro Thr Pro Asn Pro Val Pro Ser
305                 310                 315                 320

Val Pro Ala Asn Pro Pro Lys Ser Pro Ala Pro Ala Ala Ala Ala Pro
                325                 330                 335

Ala Val Gln Pro Leu Thr Gln Val Gly Ile Thr Leu Leu Pro Gln Ala
                340                 345                 350

Ala Pro Ala Pro Pro Thr Thr Thr Thr Ile Gln Val Leu Pro Thr Val
                355                 360                 365

Pro Gly Ser Ser Ile Ser Val Pro Thr Ala Ala Arg Thr Gln Gly Val
                370                 375                 380

Pro Ala Val Leu Lys Val Thr Gly Pro Gln Ala Thr Thr Gly Thr Pro
385                 390                 395                 400

Leu Val Thr Met Arg Pro Ala Ser Gln Ala Gly Lys Ala Pro Val Thr
                405                 410                 415

Val Thr Ser Leu Pro Ala Gly Val Arg Met Val Val Pro Thr Gln Ser
                420                 425                 430

Ala Gln Gly Thr Val Ile Gly Ser Ser Pro Gln Met Ser Gly Met Ala
                435                 440                 445

Ala Leu Ala Ala Ala Ala Ala Thr Gln Lys Ile Pro Pro Ser Ser
                450                 455                 460

Arg Pro Thr Val Leu Ser Val Pro Ala Gly Thr Thr Ile Val Lys Thr
465                 470                 475                 480

Met Ala Val Thr Pro Gly Thr Thr Thr Leu Pro Ala Thr Val Lys Val
                485                 490                 495

Ala Ser Ser Pro Val Met Val Ser Val Ser Asn Pro Ala Thr Arg Met
                500                 505                 510
```

-continued

```
Leu Lys Thr Ala Ala Ala Gln Val Gly Thr Ser Val Ser Ser Ala Thr
    515                 520                 525
Asn Thr Ser Thr Arg Pro Ile Ile Thr Val His Lys Ser Gly Thr Val
530                 535                 540
Thr Val Ala Gln Gln Ala Gln Val Val Thr Thr Val Val Gly Gly Val
545                 550                 555                 560
Thr Lys Thr Ile Thr Leu Val Lys Ser Pro Ile Ser Val Pro Gly Gly
                565                 570                 575
Ser Ala Leu Ile Ser Asn Leu Gly Lys Val Met Ser Val Val Gln Thr
            580                 585                 590
Lys Pro Val Gln Thr Ser Ala Val Thr Gly Gln Ala Ser Thr Gly Pro
        595                 600                 605
Val Thr Gln Ile Ile Gln Thr Lys Gly Pro Leu Pro Ala Gly Thr Ile
    610                 615                 620
Leu Lys Leu Val Thr Ser Ala Asp Gly Lys Pro Thr Thr Ile Ile Thr
625                 630                 635                 640
Thr Thr Gln Ala Ser Gly Ala Gly Thr Lys Pro Thr Ile Leu Gly Ile
                645                 650                 655
Ser Ser Val Ser Pro Ser Thr Thr Lys Pro Gly Thr Thr Thr Ile Ile
            660                 665                 670
Lys Thr Ile Pro Met Ser Ala Ile Ile Thr Gln Ala Gly Ala Thr Gly
        675                 680                 685
Val Thr Ser Ser Pro Gly Ile Lys Ser Pro Ile Thr Ile Ile Thr Thr
    690                 695                 700
Lys Val Met Thr Ser Gly Thr Gly Ala Pro Ala Lys Ile Ile Thr Ala
705                 710                 715                 720
Val Pro Lys Ile Ala Thr Gly His Gly Gln Gln Gly Val Thr Gln Val
                725                 730                 735
Val Leu Lys Gly Ala Pro Gly Gln Pro Gly Thr Ile Leu Arg Thr Val
            740                 745                 750
Pro Met Gly Gly Val Arg Leu Val Thr Pro Val Thr Val Ser Ala Val
        755                 760                 765
Lys Pro Ala Val Thr Thr Leu Val Val Lys Gly Thr Thr Gly Val Thr
    770                 775                 780
Thr Leu Gly Thr Val Thr Gly Thr Val Ser Thr Ser Leu Ala Gly Ala
785                 790                 795                 800
Gly Gly His Ser Thr Ser Ala Ser Leu Ala Thr Pro Ile Thr Thr Leu
                805                 810                 815
Gly Thr Ile Ala Thr Leu Ser Ser Gln Val Ile Asn Pro Thr Ala Ile
            820                 825                 830
Thr Val Ser Ala Ala Gln Thr Thr Leu Thr Ala Ala Gly Gly Leu Thr
        835                 840                 845
Thr Pro Thr Ile Thr Met Gln Pro Val Ser Gln Pro Thr Gln Val Thr
    850                 855                 860
Leu Ile Thr Ala Pro Ser Gly Val Glu Ala Gln Pro Val His Asp Leu
865                 870                 875                 880
Pro Val Ser Ile Leu Ala Ser Pro Thr Thr Glu Gln Pro Thr Ala Thr
                885                 890                 895
Val Thr Ile Ala Asp Ser Gly Gln Gly Asp Val Gln Pro Gly Thr Val
            900                 905                 910
Thr Leu Val Cys Ser Asn Pro Pro Cys Glu Thr His Glu Thr Gly Thr
        915                 920                 925
Thr Asn Thr Ala Thr Thr Thr Val Val Ala Asn Leu Gly Gly His Pro
    930                 935                 940
```

```
Gln Pro Thr Gln Val Gln Phe Val Cys Asp Arg Gln Glu Ala Ala Ala
945                 950                 955                 960

Ser Leu Val Thr Ser Thr Val Gly Gln Gln Asn Gly Ser Val Val Arg
            965                 970                 975

Val Cys Ser Asn Pro Pro Cys Glu Thr His Glu Thr Gly Thr Thr Asn
                980                 985                 990

Thr Ala Thr Thr Ala Thr Ser Asn Met Ala Gly Gln His Gly Cys Ser
        995                 1000                1005

Asn Pro Pro Cys Glu Thr His Glu Thr Gly Thr Thr Asn Thr Ala
1010                1015                1020

Thr Thr Ala Met Ser Ser Val Gly Ala Asn His Gln Arg Asp Ala
1025                1030                1035

Arg Arg Ala Cys Ala Ala Gly Thr Pro Ala Val Ile Arg Ile Ser
1040                1045                1050

Val Ala Thr Gly Ala Leu Glu Ala Ala Gln Gly Ser Lys Pro Gln
1055                1060                1065

Cys Gln Thr Arg Gln Thr Ser Ala Thr Ser Thr Met Thr Val
1070                1075                1080

Met Ala Thr Gly Ala Pro Cys Ser Ala Gly Pro Leu Leu Gly Pro
1085                1090                1095

Ser Met Ala Arg Glu Pro Gly Gly Arg Ser Pro Ala Phe Val Gln
1100                1105                1110

Leu Ala Pro Leu Ser Ser Lys Val Arg Leu Ser Ser Pro Ser Ile
1115                1120                1125

Lys Asp Leu Pro Ala Gly Arg His Ser His Ala Val Ser Thr Ala
1130                1135                1140

Ala Met Thr Arg Ser Ser Val Gly Ala Gly Glu Pro Arg Met Ala
1145                1150                1155

Pro Val Cys Glu Ser Leu Gln Gly Gly Ser Pro Thr Thr Val
1160                1165                1170

Thr Val Thr Ala Leu Glu Ala Leu Leu Cys Pro Ser Ala Thr Val
1175                1180                1185

Thr Gln Val Cys Ser Asn Pro Pro Cys Glu Thr His Glu Thr Gly
1190                1195                1200

Thr Thr Asn Thr Ala Thr Thr Ser Asn Ala Gly Ser Ala Gln Arg
1205                1210                1215

Val Cys Ser Asn Pro Pro Cys Glu Thr His Glu Thr Gly Thr Thr
1220                1225                1230

His Thr Ala Thr Thr Ala Thr Ser Asn Gly Gly Thr Gly Gln Pro
1235                1240                1245

Glu Gly Gly Gln Gln Pro Pro Ala Gly Arg Pro Cys Glu Thr His
1250                1255                1260

Gln Thr Thr Ser Thr Gly Thr Met Ser Val Ser Val Gly Ala
1265                1270                1275

Leu Leu Pro Asp Ala Thr Ser Ser His Arg Thr Val Glu Ser Gly
1280                1285                1290

Leu Glu Val Ala Ala Ala Pro Ser Val Thr Pro Gln Ala Gly Thr
1295                1300                1305

Ala Leu Leu Ala Pro Phe Pro Thr Gln Arg Val Cys Ser Asn Pro
1310                1315                1320

Pro Cys Glu Thr His Glu Thr Gly Thr Thr His Thr Ala Thr Thr
1325                1330                1335

Val Thr Ser Asn Met Ser Ser Asn Gln Asp Pro Pro Pro Ala Ala
```

1340              1345               1350

Ser Asp Gln Gly Glu Val Glu Ser Thr Gln Gly Asp Ser Val Asn
    1355             1360              1365

Ile Thr Ser Ser Ser Ala Ile Thr Thr Thr Val Ser Ser Thr Leu
    1370             1375              1380

Thr Arg Ala Val Thr Thr Val Thr Gln Ser Thr Pro Val Pro Gly
    1385             1390              1395

Pro Ser Val Pro Pro Pro Glu Leu Gln Val Ser Pro Gly Pro
    1400             1405              1410

Arg Gln Gln Leu Pro Pro Arg Gln Leu Leu Gln Ser Ala Ser Thr
    1415             1420              1425

Ala Leu Met Gly Glu Ser Ala Glu Val Leu Ser Ala Ser Gln Thr
    1430             1435              1440

Pro Glu Leu Pro Ala Ala Val Asp Leu Ser Ser Thr Gly Glu Pro
    1445             1450              1455

Ser Ser Gly Gln Glu Ser Ala Gly Ser Ala Val Val Ala Thr Val
    1460             1465              1470

Val Val Gln Pro Pro Pro Thr Gln Ser Glu Val Asp Gln Leu
    1475             1480              1485

Ser Leu Pro Gln Glu Leu Met Ala Glu Ala Gln Ala Gly Thr Thr
    1490             1495              1500

Thr Leu Met Val Thr Gly Leu Thr Pro Glu Glu Leu Ala Val Thr
    1505             1510              1515

Ala Ala Ala Glu Ala Ala Ala Gln Ala Ala Ala Thr Glu Glu Ala
    1520             1525              1530

Gln Ala Leu Ala Ile Gln Ala Val Leu Gln Ala Ala Gln Gln Ala
    1535             1540              1545

Val Met Gly Thr Gly Glu Pro Met Asp Thr Ser Glu Ala Ala Ala
    1550             1555              1560

Thr Val Thr Gln Ala Glu Leu Gly His Leu Ser Ala Glu Gly Gln
    1565             1570              1575

Glu Gly Gln Ala Thr Thr Ile Pro Ile Val Leu Thr Gln Gln Glu
    1580             1585              1590

Leu Ala Ala Leu Val Gln Gln Gln Gln Leu Gln Glu Ala Gln Ala
    1595             1600              1605

Gln Gln Gln His His His Leu Pro Thr Glu Ala Leu Ala Pro Ala
    1610             1615              1620

Asp Ser Leu Asn Asp Pro Ala Ile Glu Ser Asn Cys Leu Asn Glu
    1625             1630              1635

Leu Ala Gly Thr Val Pro Ser Thr Val Ala Leu Leu Pro Ser Thr
    1640             1645              1650

Ala Thr Glu Ser Leu Ala Pro Ser Asn Thr Phe Val Ala Pro Gln
    1655             1660              1665

Pro Val Val Val Ala Ser Pro Ala Lys Leu Gln Ala Ala Ala Thr
    1670             1675              1680

Leu Thr Glu Val Ala Asn Gly Ile Glu Ser Leu Gly Val Lys Pro
    1685             1690              1695

Asp Leu Pro Pro Pro Pro Ser Lys Ala Pro Met Lys Lys Glu Asn
    1700             1705              1710

Gln Trp Phe Asp Val Gly Val Ile Lys Gly Thr Asn Val Met Val
    1715             1720              1725

Thr His Tyr Phe Leu Pro Pro Asp Asp Ala Val Pro Ser Asp Asp
    1730             1735              1740

-continued

| | | | | | | | | | | |
|---|---|---|---|---|---|---|---|---|---|---|
| Asp | Leu | Gly | Thr | Val | Pro | Asp | Tyr | Asn | Gln | Leu | Lys | Lys | Gln | Glu |
| | 1745 | | | | 1750 | | | | | 1755 | | | | |
| Leu | Gln | Pro | Gly | Thr | Ala | Tyr | Lys | Phe | Arg | Val | Ala | Gly | Ile | Asn |
| 1760 | | | | | 1765 | | | | | 1770 | | | | |
| Ala | Cys | Ala | Arg | Gly | Pro | Phe | Ser | Glu | Ile | Ser | Ala | Phe | Lys | Thr |
| 1775 | | | | | 1780 | | | | | 1785 | | | | |
| Cys | Leu | Pro | Gly | Phe | Pro | Gly | Ala | Pro | Cys | Ala | Ile | Lys | Ile | Ser |
| 1790 | | | | | 1795 | | | | | 1800 | | | | |
| Lys | Ser | Pro | Asp | Gly | Ala | His | Leu | Thr | Trp | Glu | Pro | Pro | Ser | Val |
| 1805 | | | | | 1810 | | | | | 1815 | | | | |
| Thr | Ser | Gly | Lys | Ile | Ile | Glu | Tyr | Ser | Val | Tyr | Leu | Ala | Ile | Gln |
| 1820 | | | | | 1825 | | | | | 1830 | | | | |
| Ser | Ser | Gln | Ala | Gly | Gly | Glu | Leu | Lys | Ser | Ser | Thr | Pro | Ala | Gln |
| 1835 | | | | | 1840 | | | | | 1845 | | | | |
| Leu | Ala | Phe | Met | Arg | Val | Tyr | Cys | Gly | Pro | Ser | Pro | Ser | Cys | Leu |
| 1850 | | | | | 1855 | | | | | 1860 | | | | |
| Val | Gln | Ser | Ser | Ser | Leu | Ser | Asn | Ala | His | Ile | Asp | Tyr | Thr | Thr |
| 1865 | | | | | 1870 | | | | | 1875 | | | | |
| Lys | Pro | Ala | Ile | Ile | Phe | Arg | Ile | Ala | Ala | Arg | Asn | Glu | Lys | Gly |
| 1880 | | | | | 1885 | | | | | 1890 | | | | |
| Tyr | Gly | Pro | Ala | Thr | Gln | Val | Arg | Trp | Leu | Gln | Glu | Thr | Ser | Lys |
| 1895 | | | | | 1900 | | | | | 1905 | | | | |
| Asp | Ser | Ser | Gly | Thr | Lys | Pro | Ala | Asn | Lys | Arg | Pro | Met | Ser | Ser |
| 1910 | | | | | 1915 | | | | | 1920 | | | | |
| Pro | Glu | Met | Lys | Ser | Ala | Pro | Lys | Lys | Ser | Lys | Ala | Asp | Gly | Gln |
| 1925 | | | | | 1930 | | | | | 1935 | | | | |

<210> SEQ ID NO 59
<211> LENGTH: 6138
<212> TYPE: DNA
<213> ORGANISM: Mus musculus

<400> SEQUENCE: 59

| | | |
|---|---|---|
| atggcttcgg ctgtgtctcc cgcaaacttg ccagcggtgc ttctgcagcc ccgctggaaa | 60 |
| cgggtggtgg gctggtcggg tcccgtgccc cgaccccgcc acggccaccg tgcagtggct | 120 |
| atcaaggagc ttatagtggt gtttggcggc ggcaacgagg ggatagtgga cgaactacac | 180 |
| gtgtacaaca ctgcaaccaa ccagtggttc atcccagctg tgagagggga tatccctcca | 240 |
| gggtgtgcag cctatggctt tgtgtgtgat ggtactcgcc tattggtgtt tggtggaatg | 300 |
| gtagagtatg gaaaatacag caacgacctc tatgaactcc aggcaagtcg ttgggaatgg | 360 |
| aagagactga aggcaaagac acccaaaaat gggcctcctc catgtcctcg gcttggacat | 420 |
| agcttctccc ttgtgggcaa caaatgttac ctgtttgggg gtctggccaa tgatagtgag | 480 |
| gaccccaaga caacattcc gaggtacctg aatgacttat atattctcga actacggcca | 540 |
| ggctctggag tggtagcttg ggacatcccc atcacttacg gtgtcctgcc tccaccccgg | 600 |
| gagtcacata ctgctgtggt ctacactgaa aaagataaca gaaatccaa gctggtgatc | 660 |
| tatggaggga tgagtggctg caggctaggg gacctttgga ccctggacat tgagacactg | 720 |
| acatggaata agcccagcct tagtggggtg gcaccccttc ctcgcagcct ccactctgca | 780 |
| accaccatag gaaacaaaat gtatgtattt ggtggctggg tgccccttgt catggacgat | 840 |
| gtcaaagtgg ccacacacga gaaggagtgg aagtgtacca acacactggc ttgtctcaac | 900 |
| ctggatacca tggcctggga aaccatcctg atggatacat tggaggacaa cattcctcga | 960 |
| gctcgagcag gccactgtgc tgttgccatc aatactcgtc tgtatatttg gagtggccgt | 1020 |

```
gatggctacc gcaaggcctg gaacaaccag gtctgctgca aggacttgtg gtatttggag   1080
acagaaaagc caccaccccc agcccgagta caactagtac gagccaacac caactcactg   1140
gaggttagct ggggtgcagt ggcaacagct gacagttacc ttctacaact ccagaaatat   1200
gacattcctg ccacagctgc tacggctacc tcccccactc ccaatccagt cccgtctgtg   1260
cctgccaacc ctcccaagag ccctgcgcca gcagcagctg cacctgctgt acagccactg   1320
acccaagtag gcatcacact tgtgcccag gctgccactg cacccccaag cacaaccacc    1380
atccaggtct tgccgacagt gccaggcagc tccatttctg tgcccactgc agccaggact   1440
caaggtgtcc ctgctgttct caaagtgact ggtcctcaag ctacaacagg aacaccactg   1500
gttaccatga gacctgcaag ccaggctgga aaagctcctg tcactgtgac ttccctgcct   1560
gccagtgttc gaatggttgt acccacacag agtgcccagg ggacggtgat cggcagcaac   1620
ccacagatga gtgggatggc cgcattggct gctgctgctg ctgccacaca gaaaatccct   1680
ccatcctcag cacccacggt gctgagtgtc ccagcaggga ccaccatcgt caagacagtg   1740
gctgtgacac ctggcacgac cactcttcca gccactgtga aggtggcctc ctcccctgtc   1800
atggtgagca cccagccac tcgaatgcta aagactgcag ctgcccaagt ggggacatct    1860
gtgtcctctg ctgccaacac atctactcgc cctatcatca cagtacacaa atcaggaact   1920
gtaacagtgg cccagcaagc caggtggtg accacggtgg taggtggagt caccaagacc    1980
atcaccctag tgaagagccc catctctgtc ccaggaggca gtgctctgat tccaatctg    2040 ggaaaagtga tgtcggtggt ccagaccaaa ccagttcaga catcagcagt gacaggccaa   2100
gcatctacag gtcctgtgac tcagatcatc agaccaaag gaccctgcc agcggggact    2160 atcctgaagc tggtgacatc agcagatggc aagcccacaa ccatcattac caccacacag   2220
gctagtgggg cagggaccaa gcccactatc ctgggcatca gtagtgtttc tcccagcacc   2280
accaaacctg gcacaactac cattattaag accattccta tgtcggccat tatcacccag   2340
gcaggtgcca caggtgttac cagcagtcct ggcattaagt ccccaattac aattatcacc   2400
accaaagtga tgacttcagg aacaggagcg cctgctaaaa tcatcactgc tgtccccaag   2460
attgctactg gccatgggca acaaggagtg acccaggtgg tgctaaaggg ggcccctgga   2520
caaccaggca ccatcctccg tactgtgcct atgggcggcg ttcgcctggt cacccctgtc   2580
accgtctctg ctgtcaagcc agctgtcacc acattggttg tgaagggtac cacaggtgtt   2640
acaacgctag gcacagtgac aggcactgtc tccaccagcc tggccggagc tggggcacat   2700
agcaccagtg cttccctggc tacacctatc actaccttgg gcactattgc tacgctctca   2760
agccaggtga tcaaccctac tgctatcaca gtgtcagctg cacagactac actaacagct   2820
gctggtgggc ttaccacacc cacaatcaca atgcagcctg tctcccagcc tacccaggtc   2880
actctgatta cagcacccag tggggttgaa gcacagcctg tacatgacct tcctgtatcc   2940
attttggcct cacctactac agagcagccc acagcaacag tcaccatcgc tgactcaggc   3000
cagggtgatg tgcagcccgg cactgtgaca ctggtgtgtt ccaacccacc ctgtgaaacc   3060
catgaaacag gcaccaccaa cacagctacc accactgttg tggctaacct tggtggacat   3120
cctcaaccta cccaggtgca gtttgtttgt gacagacagg agacagctgc ttcacttgtg   3180
acctcagctg taggacaaca gaatggtaat gtggtccgtg tctgttcaaa ccccccctgt   3240
gagacccatg agacgggcac taccaacact gccacaacag ccacctccaa catggctggg   3300
cagcatggct gctcgaaccc ccctgtgag actcatgaga caggcaccac cagcactgcc     3360
actacagcaa tgtccagcat gggcactggg cagcagcgag acactcgtcg taccactaac   3420
```

```
accccccactg tagtgcggat cactgtggct cctggggcat tggagagagt ccagggtacc    3480
gtgaagcctc agtgccaaac ccagcagacc aacatgacca ccaccaccat gactgtgcag    3540
gccactggag ctccatgctc agctggcccc ctgcttaggc caagtgtggc actggagtct    3600
gggagccaca gccctgcctt tgtgcaacta gcccttccaa gtgtcagagt tgggctaagt    3660
ggccccagca gcaaggacat gcccacaggg cgccaaccag agacatatca tacttacaca    3720
actaataccc caaccacaac ccgctctatc atggttgctg gggagcttgg tgcagctcgg    3780
gtggtcccca catctacata tgagagcctc caggcaagct ctcctagcag caccatgact    3840
atgacagccc tagaggcact gctgtgccct tcggctactg tcacccaagt ctgctccaac    3900
ccgccatgtg agacccatga gacgggtacc accaacaccg ccactacctc caatgcgggc    3960
agtgctcagc gagtatgctc caacccgcct tgtgagactc atgagacggg caccacacac    4020
acagctacca ctgccacatc aaatggaggt gcaggccagc ctgagggtgg acaacagcct    4080
gccagtggcc atccctgcga cacaccagac cacttccaac tggcaccac tatgtcagtc    4140
agtgtgggta ccctgattcc tgatgctact tcctctcatg gaaccctgga gtcgggctta    4200
gaggtggtag cagtgcccac tgtcacctcc caggctggtt ccacattgct ggcctctttc    4260
ccaacacaga gggtatgctc caaccctcct tgcgagaccc acgagacagg taccacgcac    4320
acagccacca ctgtcacctc taacatgagc tcaaaccaag accctccacc agctgccagt    4380
gaccaaggag aggtggcaag cacccaaggt gacagcacaa atatcaccag tgccagtgct    4440
atcactacaa gtgtgtcttc tacattgcca cgagcagtga ccactgtgac acagtctaca    4500
ccagtccctg gtccctctgt gccgccccca gaggaactcc aggtctcacc agggcctcgc    4560
cagcagctgc ctccacggca actcctgcag tctgcctcca cccctgat gggggagtct    4620
actgaggtcc tgtcagcctc ccagaccccc gagctccagg ccgccgtgga tctgagcagc    4680
actgggacc catcttcagg ccaggagcct accacctctg ctgtcgtggc cactgtggtg    4740
gtccaaccac ccccacccac acagtctgaa gtagaccagt tatcacttcc ccaagagctg    4800
atggctgaag cccaggcggg caccacaacc cttatggtaa cagggctcac tccagaggag    4860
ctggcagtga ctgctgctgc tgaagcagct gctcaagctg cagccactga agaagcccaa    4920
gccttggcca tccaggctgt gctccaggcc gcacagcagg ctgtcatggg cactggggag    4980
cccatggata catctgaagc agcagcagca gtgacacaag cagaactggg tcacctttca    5040
gctgaaggcc aagagggtca ggctaccacc atacccattg tgttgacaca gcaggagctt    5100
gcagccctgg tgcagcagca gcagcagctc caggaggctc aagctcaagc ccagcaacag    5160
caccatcttc ccactgaggc tctgccccca gctgacagtc tcaatgaccc atccatcgag    5220
agcaactgcc tcaacgagtt agctagtgct gtcccaagca ccgtggcttt gctaccctca    5280
acagctaccg agagcctggc tccatctaac acatttgtgg ctccccagcc tgttgtagct    5340
agtccagcaa agatgcaggc tgcagctacc cttactgaag tggccaatgg cattgagtcc    5400
ctgggtgtga accggactt gccaccccca cccagcaaag cccctgtgaa aaaggagaac    5460
cagtggtttg atgtgggggt cattaagggt accagtgtaa tggtgacaca ctattttctg    5520
ccaccagatg atgctgttca gtcagatgat gactcaggca cggtcccaga ctataaccag    5580
ctaaagaagc aggagctaca gccaggcacg gcttacaaat tcgagttgc tggaatcaat    5640
gcttgtggcc ggggaccctt cagtgagatc tcagccttta agacttgtct gcctgggttc    5700
ccaggggctc cttgtgctat taaaatcagc aagagcccag atggtgctca cctcacctgg    5760
gagccaccgt ctgtgacctc cggcaagatc atcgagtact ctgtgtacct ggccatccag    5820
```

-continued

```
agctcacagg ccagtggtga gccaaagagc tccaccccag cccagctggc cttcatgcga    5880
gtgtactgtg ggcctagccc ttcctgccta gtgcagtcct ccagcctctc caacgcccac    5940
attgactata ctacaaagcc tgccatcatc ttccgcattg ctgcccgcaa tgaaaagggc    6000
tacggccctg ccacacaagt gaggtggttg caagaaacta gtaaagacag ctctggcacc    6060
aagccggcca gcaagcggcc catgtcgtct ccagaaatga atctgctccc aaagaagtct    6120
aaggctgatg gtcagtga                                                 6138
```

<210> SEQ ID NO 60
<211> LENGTH: 2045
<212> TYPE: PRT
<213> ORGANISM: Mus musculus

<400> SEQUENCE: 60

```
Met Ala Ser Ala Val Ser Pro Ala Asn Leu Pro Ala Val Leu Leu Gln
1               5                   10                  15

Pro Arg Trp Lys Arg Val Val Gly Trp Ser Gly Pro Val Pro Arg Pro
            20                  25                  30

Arg His Gly His Arg Ala Val Ala Ile Lys Glu Leu Ile Val Val Phe
        35                  40                  45

Gly Gly Gly Asn Glu Gly Ile Val Asp Glu Leu His Val Tyr Asn Thr
    50                  55                  60

Ala Thr Asn Gln Trp Phe Ile Pro Ala Val Arg Gly Asp Ile Pro Pro
65                  70                  75                  80

Gly Cys Ala Ala Tyr Gly Phe Val Cys Asp Gly Thr Arg Leu Leu Val
                85                  90                  95

Phe Gly Gly Met Val Glu Tyr Gly Lys Tyr Ser Asn Asp Leu Tyr Glu
            100                 105                 110

Leu Gln Ala Ser Arg Trp Glu Trp Lys Arg Leu Lys Ala Lys Thr Pro
        115                 120                 125

Lys Asn Gly Pro Pro Pro Cys Pro Arg Leu Gly His Ser Phe Ser Leu
    130                 135                 140

Val Gly Asn Lys Cys Tyr Leu Phe Gly Gly Leu Ala Asn Asp Ser Glu
145                 150                 155                 160

Asp Pro Lys Asn Asn Ile Pro Arg Tyr Leu Asn Asp Leu Tyr Ile Leu
                165                 170                 175

Glu Leu Arg Pro Gly Ser Gly Val Val Ala Trp Asp Ile Pro Ile Thr
            180                 185                 190

Tyr Gly Val Leu Pro Pro Pro Arg Glu Ser His Thr Ala Val Val Tyr
        195                 200                 205

Thr Glu Lys Asp Asn Lys Lys Ser Lys Leu Val Ile Tyr Gly Gly Met
    210                 215                 220

Ser Gly Cys Arg Leu Gly Asp Leu Trp Thr Leu Asp Ile Glu Thr Leu
225                 230                 235                 240

Thr Trp Asn Lys Pro Ser Leu Ser Gly Val Ala Pro Leu Pro Arg Ser
                245                 250                 255

Leu His Ser Ala Thr Thr Ile Gly Asn Lys Met Tyr Val Phe Gly Gly
            260                 265                 270

Trp Val Pro Leu Val Met Asp Asp Val Lys Val Ala Thr His Glu Lys
        275                 280                 285

Glu Trp Lys Cys Thr Asn Thr Leu Ala Cys Leu Asn Leu Asp Thr Met
    290                 295                 300

Ala Trp Glu Thr Ile Leu Met Asp Thr Leu Glu Asp Asn Ile Pro Arg
305                 310                 315                 320
```

-continued

```
Ala Arg Ala Gly His Cys Ala Val Ala Ile Asn Thr Arg Leu Tyr Ile
            325                 330                 335

Trp Ser Gly Arg Asp Gly Tyr Arg Lys Ala Trp Asn Asn Gln Val Cys
            340                 345                 350

Cys Lys Asp Leu Trp Tyr Leu Glu Thr Glu Lys Pro Pro Pro Pro Ala
            355                 360                 365

Arg Val Gln Leu Val Arg Ala Asn Thr Asn Ser Leu Glu Val Ser Trp
        370                 375                 380

Gly Ala Val Ala Thr Ala Asp Ser Tyr Leu Leu Gln Leu Gln Lys Tyr
385                 390                 395                 400

Asp Ile Pro Ala Thr Ala Ala Thr Ala Thr Ser Pro Thr Pro Asn Pro
                    405                 410                 415

Val Pro Ser Val Pro Ala Asn Pro Pro Lys Ser Pro Ala Pro Ala Ala
                420                 425                 430

Ala Ala Pro Ala Val Gln Pro Leu Thr Gln Val Gly Ile Thr Leu Val
            435                 440                 445

Pro Gln Ala Ala Thr Ala Pro Pro Ser Thr Thr Thr Ile Gln Val Leu
        450                 455                 460

Pro Thr Val Pro Gly Ser Ser Ile Ser Val Pro Thr Ala Ala Arg Thr
465                 470                 475                 480

Gln Gly Val Pro Ala Val Leu Lys Val Thr Gly Pro Gln Ala Thr Thr
                    485                 490                 495

Gly Thr Pro Leu Val Thr Met Arg Pro Ala Ser Gln Ala Gly Lys Ala
                500                 505                 510

Pro Val Thr Val Thr Ser Leu Pro Ala Ser Val Arg Met Val Val Pro
            515                 520                 525

Thr Gln Ser Ala Gln Gly Thr Val Ile Gly Ser Asn Pro Gln Met Ser
        530                 535                 540

Gly Met Ala Ala Leu Ala Ala Ala Ala Thr Gln Lys Ile Pro
545                 550                 555                 560

Pro Ser Ser Ala Pro Thr Val Leu Ser Val Pro Ala Gly Thr Thr Ile
                    565                 570                 575

Val Lys Thr Val Ala Val Thr Pro Gly Thr Thr Thr Leu Pro Ala Thr
                580                 585                 590

Val Lys Val Ala Ser Ser Pro Val Met Val Ser Asn Pro Ala Thr Arg
            595                 600                 605

Met Leu Lys Thr Ala Ala Ala Gln Val Gly Thr Ser Val Ser Ser Ala
        610                 615                 620

Ala Asn Thr Ser Thr Arg Pro Ile Ile Thr Val His Lys Ser Gly Thr
625                 630                 635                 640

Val Thr Val Ala Gln Gln Ala Gln Val Val Thr Thr Val Val Gly Gly
                    645                 650                 655

Val Thr Lys Thr Ile Thr Leu Val Lys Ser Pro Ile Ser Val Pro Gly
                660                 665                 670

Gly Ser Ala Leu Ile Ser Asn Leu Gly Lys Val Met Ser Val Val Gln
            675                 680                 685

Thr Lys Pro Val Gln Thr Ser Ala Val Thr Gly Gln Ala Ser Thr Gly
        690                 695                 700

Pro Val Thr Gln Ile Ile Gln Thr Lys Gly Pro Leu Pro Ala Gly Thr
705                 710                 715                 720

Ile Leu Lys Leu Val Thr Ser Ala Asp Gly Lys Pro Thr Thr Ile Ile
                    725                 730                 735

Thr Thr Thr Gln Ala Ser Gly Ala Gly Thr Lys Pro Thr Ile Leu Gly
```

-continued

```
                    740                 745                 750
Ile Ser Ser Val Ser Pro Ser Thr Thr Lys Pro Gly Thr Thr Thr Ile
                755                 760                 765
Ile Lys Thr Ile Pro Met Ser Ala Ile Ile Thr Gln Ala Gly Ala Thr
            770                 775                 780
Gly Val Thr Ser Ser Pro Gly Ile Lys Ser Pro Ile Thr Ile Ile Thr
785                 790                 795                 800
Thr Lys Val Met Thr Ser Gly Thr Gly Ala Pro Ala Lys Ile Ile Thr
                805                 810                 815
Ala Val Pro Lys Ile Ala Thr Gly His Gly Gln Gln Gly Val Thr Gln
                820                 825                 830
Val Val Leu Lys Gly Ala Pro Gly Gln Pro Gly Thr Ile Leu Arg Thr
                835                 840                 845
Val Pro Met Gly Gly Val Arg Leu Val Thr Pro Val Thr Val Ser Ala
            850                 855                 860
Val Lys Pro Ala Val Thr Thr Leu Val Val Lys Gly Thr Thr Gly Val
865                 870                 875                 880
Thr Thr Leu Gly Thr Val Thr Gly Thr Val Ser Thr Ser Leu Ala Gly
                885                 890                 895
Ala Gly Ala His Ser Thr Ser Ala Ser Leu Ala Thr Pro Ile Thr Thr
                900                 905                 910
Leu Gly Thr Ile Ala Thr Leu Ser Ser Gln Val Ile Asn Pro Thr Ala
                915                 920                 925
Ile Thr Val Ser Ala Ala Gln Thr Thr Leu Thr Ala Ala Gly Gly Leu
            930                 935                 940
Thr Thr Pro Thr Ile Thr Met Gln Pro Val Ser Gln Pro Thr Gln Val
945                 950                 955                 960
Thr Leu Ile Thr Ala Pro Ser Gly Val Glu Ala Gln Pro Val His Asp
                965                 970                 975
Leu Pro Val Ser Ile Leu Ala Ser Pro Thr Thr Glu Gln Pro Thr Ala
                980                 985                 990
Thr Val Thr Ile Ala Asp Ser Gly  Gln Gly Asp Val Gln  Pro Gly Thr
                995                 1000                1005
Val Thr  Leu Val Cys Ser Asn  Pro Pro Cys Glu Thr  His Glu Thr
            1010                1015                1020
Gly Thr  Thr Asn Thr Ala Thr  Thr Thr Val Val Ala  Asn Leu Gly
            1025                1030                1035
Gly His  Pro Gln Pro Thr Gln  Val Gln Phe Val Cys  Asp Arg Gln
            1040                1045                1050
Glu Thr  Ala Ala Ser Leu Val  Thr Ser Ala Val Gly  Gln Gln Asn
            1055                1060                1065
Gly Asn  Val Val Arg Val Cys  Ser Asn Pro Pro Cys  Glu Thr His
            1070                1075                1080
Glu Thr  Gly Thr Thr Asn Thr  Ala Thr Thr Ala Thr  Ser Asn Met
            1085                1090                1095
Ala Gly  Gln His Gly Cys Ser  Asn Pro Pro Cys Glu  Thr His Glu
            1100                1105                1110
Thr Gly  Thr Thr Ser Thr Ala  Thr Thr Ala Met Ser  Ser Met Gly
            1115                1120                1125
Thr Gly  Gln Gln Arg Asp Thr  Arg Arg Thr Thr Asn  Thr Pro Thr
            1130                1135                1140
Val Val  Arg Ile Thr Val Ala  Pro Gly Ala Leu Glu  Arg Val Gln
            1145                1150                1155
```

```
Gly Thr Val Lys Pro Gln Cys Gln Thr Gln Thr Asn Met Thr
1160            1165             1170

Thr Thr Thr Met Thr Val Gln Ala Thr Gly Ala Pro Cys Ser Ala
1175             1180             1185

Gly Pro Leu Leu Arg Pro Ser Val Ala Leu Glu Ser Gly Ser His
1190             1195             1200

Ser Pro Ala Phe Val Gln Leu Ala Leu Pro Ser Val Arg Val Gly
1205             1210             1215

Leu Ser Gly Pro Ser Ser Lys Asp Met Pro Thr Gly Arg Gln Pro
1220             1225             1230

Glu Thr Tyr His Thr Tyr Thr Thr Asn Thr Pro Thr Thr Thr Arg
1235             1240             1245

Ser Ile Met Val Ala Gly Glu Leu Gly Ala Ala Arg Val Val Pro
1250             1255             1260

Thr Ser Thr Tyr Glu Ser Leu Gln Ala Ser Ser Pro Ser Ser Thr
1265             1270             1275

Met Thr Met Thr Ala Leu Glu Ala Leu Leu Cys Pro Ser Ala Thr
1280             1285             1290

Val Thr Gln Val Cys Ser Asn Pro Pro Cys Glu Thr His Glu Thr
1295             1300             1305

Gly Thr Thr Asn Thr Ala Thr Thr Ser Asn Ala Gly Ser Ala Gln
1310             1315             1320

Arg Val Cys Ser Asn Pro Pro Cys Glu Thr His Glu Thr Gly Thr
1325             1330             1335

Thr His Thr Ala Thr Thr Ala Thr Ser Asn Gly Gly Ala Gly Gln
1340             1345             1350

Pro Glu Gly Gly Gln Gln Pro Ala Ser Gly His Pro Cys Glu Thr
1355             1360             1365

His Gln Thr Thr Ser Thr Gly Thr Thr Met Ser Val Ser Val Gly
1370             1375             1380

Thr Leu Ile Pro Asp Ala Thr Ser Ser His Gly Thr Leu Glu Ser
1385             1390             1395

Gly Leu Glu Val Val Ala Val Pro Thr Val Thr Ser Gln Ala Gly
1400             1405             1410

Ser Thr Leu Leu Ala Ser Phe Pro Thr Gln Arg Val Cys Ser Asn
1415             1420             1425

Pro Pro Cys Glu Thr His Glu Thr Gly Thr Thr His Thr Ala Thr
1430             1435             1440

Thr Val Thr Ser Asn Met Ser Ser Asn Gln Asp Pro Pro Pro Ala
1445             1450             1455

Ala Ser Asp Gln Gly Glu Val Ala Ser Thr Gln Gly Asp Ser Thr
1460             1465             1470

Asn Ile Thr Ser Ala Ser Ala Ile Thr Thr Ser Val Ser Ser Thr
1475             1480             1485

Leu Pro Arg Ala Val Thr Thr Val Thr Gln Ser Thr Pro Val Pro
1490             1495             1500

Gly Pro Ser Val Pro Pro Glu Glu Leu Gln Val Ser Pro Gly
1505             1510             1515

Pro Arg Gln Gln Leu Pro Pro Arg Gln Leu Leu Gln Ser Ala Ser
1520             1525             1530

Thr Pro Leu Met Gly Glu Ser Thr Glu Val Leu Ser Ala Ser Gln
1535             1540             1545

Thr Pro Glu Leu Gln Ala Ala Val Asp Leu Ser Ser Thr Gly Asp
1550             1555             1560
```

```
Pro Ser Ser Gly Gln Glu Pro Thr Thr Ser Ala Val Val Ala Thr
    1565            1570                1575

Val Val Val Gln Pro Pro Pro Thr Gln Ser Glu Val Asp Gln
    1580            1585                1590

Leu Ser Leu Pro Gln Glu Leu Met Ala Glu Ala Gln Ala Gly Thr
    1595            1600                1605

Thr Thr Leu Met Val Thr Gly Leu Thr Pro Glu Glu Leu Ala Val
    1610            1615                1620

Thr Ala Ala Ala Glu Ala Ala Ala Gln Ala Ala Ala Thr Glu Glu
    1625            1630                1635

Ala Gln Ala Leu Ala Ile Gln Ala Val Leu Gln Ala Ala Gln Gln
    1640            1645                1650

Ala Val Met Gly Thr Gly Glu Pro Met Asp Thr Ser Glu Ala Ala
    1655            1660                1665

Ala Ala Val Thr Gln Ala Glu Leu Gly His Leu Ser Ala Glu Gly
    1670            1675                1680

Gln Glu Gly Gln Ala Thr Thr Ile Pro Ile Val Leu Thr Gln Gln
    1685            1690                1695

Glu Leu Ala Ala Leu Val Gln Gln Gln Gln Leu Gln Glu Ala
    1700            1705                1710

Gln Ala Gln Ala Gln Gln His His Leu Pro Thr Glu Ala Leu
    1715            1720                1725

Ala Pro Ala Asp Ser Leu Asn Asp Pro Ser Ile Glu Ser Asn Cys
    1730            1735                1740

Leu Asn Glu Leu Ala Ser Ala Val Pro Ser Thr Val Ala Leu Leu
    1745            1750                1755

Pro Ser Thr Ala Thr Glu Ser Leu Ala Pro Ser Asn Thr Phe Val
    1760            1765                1770

Ala Pro Gln Pro Val Val Ala Ser Pro Ala Lys Met Gln Ala Ala
    1775            1780                1785

Ala Thr Leu Thr Glu Val Ala Asn Gly Ile Glu Ser Leu Gly Val
    1790            1795                1800

Lys Pro Asp Leu Pro Pro Pro Ser Lys Ala Pro Val Lys Lys
    1805            1810                1815

Glu Asn Gln Trp Phe Asp Val Gly Val Ile Lys Gly Thr Ser Val
    1820            1825                1830

Met Val Thr His Tyr Phe Leu Pro Pro Asp Asp Ala Val Gln Ser
    1835            1840                1845

Asp Asp Asp Ser Gly Thr Val Pro Asp Tyr Asn Gln Leu Lys Lys
    1850            1855                1860

Gln Glu Leu Gln Pro Gly Thr Ala Tyr Lys Phe Arg Val Ala Gly
    1865            1870                1875

Ile Asn Ala Cys Gly Arg Gly Pro Phe Ser Glu Ile Ser Ala Phe
    1880            1885                1890

Lys Thr Cys Leu Pro Gly Phe Pro Gly Ala Pro Cys Ala Ile Lys
    1895            1900                1905

Ile Ser Lys Ser Pro Asp Gly Ala His Leu Thr Trp Glu Pro Pro
    1910            1915                1920

Ser Val Thr Ser Gly Lys Ile Ile Glu Tyr Ser Val Tyr Leu Ala
    1925            1930                1935

Ile Gln Ser Ser Gln Ala Ser Gly Glu Pro Lys Ser Ser Thr Pro
    1940            1945                1950

Ala Gln Leu Ala Phe Met Arg Val Tyr Cys Gly Pro Ser Pro Ser
```

Cys Leu Val Gln Ser Ser Ser Leu Ser Asn Ala His Ile Asp Tyr
         1970                1975                1980

Thr Thr Lys Pro Ala Ile Ile Phe Arg Ile Ala Ala Arg Asn Glu
         1985                1990                1995

Lys Gly Tyr Gly Pro Ala Thr Gln Val Arg Trp Leu Gln Glu Thr
         2000                2005                2010

Ser Lys Asp Ser Ser Gly Thr Lys Pro Ala Ser Lys Arg Pro Met
         2015                2020                2025

Ser Ser Pro Glu Met Lys Ser Ala Pro Lys Lys Ser Lys Ala Asp
         2030                2035                2040

Gly Gln
 2045

<210> SEQ ID NO 61
<211> LENGTH: 1011
<212> TYPE: DNA
<213> ORGANISM: Homo sapiens

<400> SEQUENCE: 61
atgtctcagg ctgtgcagac aaacggaact caaccattaa gcaaacatg ggaactcagt      60 ttatatgagt tacaacgaac acctcaggag gcaataacag atggcttaga aattgtggtt    120
tcacctcgaa gtctacacag tgaattaatg tgcccaattt gtttggatat gttgaagaac    180
accatgacta caaggagtg tttacatcgt ttttgtgcag actgcatcat cacagccctt    240
agaagtggca caaagaatg tcctacctgt cggaaaaaac tagtttccaa aagatcacta    300
aggccagacc caaactttga tgcactcatc agcaaaattt atccaagtcg tgatgagtat    360
gaagctcatc aagagagagt attagccagg atcaacaagc acaataatca gcaagcactc    420
agtcacagca ttgaggaagg actgaagata caggccatga acagactgca gcgaggcaag    480
aaacaacaga ttgaaaatgg tagtggagca gaagataatg gtgacagttc acactgcagt    540
aatgcatcca cacatagcaa tcaggaagca ggccctagta caaacggac caaaacatct    600 gatgattctg ggctagagct tgataataac aatgcagcaa tggcaattga tccagtaatg    660
gatggtgcta gtgaaattga attagtattc aggcctcatc ccacacttat ggaaaaagat    720
gacagtgcac agacgagata cataaagact tctggtaacg ccactgttga tcacttatcc    780
aagtatctgg ctgtgaggtt agctttagaa gaacttcgaa gcaaaggtga atcaaaccag    840
atgaaccttg atacagccag tgagaagcag tataccattt atagcaac agccagtggc    900 cagttcactg tattaaatgg ctcttttct ttggaattgg tcagtgagaa atactggaaa    960
gtgaacaaac ccatggaact ttattacgca cctacaaagg agcacaaatg a            1011

<210> SEQ ID NO 62
<211> LENGTH: 336
<212> TYPE: PRT
<213> ORGANISM: Homo sapiens

<400> SEQUENCE: 62

Met Ser Gln Ala Val Gln Thr Asn Gly Thr Gln Pro Leu Ser Lys Thr
 1               5                  10                  15

Trp Glu Leu Ser Leu Tyr Glu Leu Gln Arg Thr Pro Gln Glu Ala Ile
                 20                  25                  30

Thr Asp Gly Leu Glu Ile Val Val Ser Pro Arg Ser Leu His Ser Glu
             35                  40                  45

Leu Met Cys Pro Ile Cys Leu Asp Met Leu Lys Asn Thr Met Thr Thr

```
                50                  55                  60
Lys Glu Cys Leu His Arg Phe Cys Ala Asp Cys Ile Ile Thr Ala Leu
 65                  70                  75                  80

Arg Ser Gly Asn Lys Glu Cys Pro Thr Cys Arg Lys Lys Leu Val Ser
                 85                  90                  95

Lys Arg Ser Leu Arg Pro Asp Pro Asn Phe Asp Ala Leu Ile Ser Lys
            100                 105                 110

Ile Tyr Pro Ser Arg Asp Glu Tyr Glu Ala His Gln Glu Arg Val Leu
            115                 120                 125

Ala Arg Ile Asn Lys His Asn Asn Gln Gln Ala Leu Ser His Ser Ile
            130                 135                 140

Glu Glu Gly Leu Lys Ile Gln Ala Met Asn Arg Leu Gln Arg Gly Lys
145                 150                 155                 160

Lys Gln Gln Ile Glu Asn Gly Ser Gly Ala Glu Asp Asn Gly Asp Ser
                165                 170                 175

Ser His Cys Ser Asn Ala Ser Thr His Ser Asn Gln Glu Ala Gly Pro
            180                 185                 190

Ser Asn Lys Arg Thr Lys Thr Ser Asp Asp Ser Gly Leu Glu Leu Asp
            195                 200                 205

Asn Asn Asn Ala Ala Met Ala Ile Asp Pro Val Met Asp Gly Ala Ser
210                 215                 220

Glu Ile Glu Leu Val Phe Arg Pro His Pro Thr Leu Met Glu Lys Asp
225                 230                 235                 240

Asp Ser Ala Gln Thr Arg Tyr Ile Lys Thr Ser Gly Asn Ala Thr Val
                245                 250                 255

Asp His Leu Ser Lys Tyr Leu Ala Val Arg Leu Ala Leu Glu Glu Leu
            260                 265                 270

Arg Ser Lys Gly Glu Ser Asn Gln Met Asn Leu Asp Thr Ala Ser Glu
            275                 280                 285

Lys Gln Tyr Thr Ile Tyr Ile Ala Thr Ala Ser Gly Gln Phe Thr Val
            290                 295                 300

Leu Asn Gly Ser Phe Ser Leu Glu Leu Val Ser Glu Lys Tyr Trp Lys
305                 310                 315                 320

Val Asn Lys Pro Met Glu Leu Tyr Tyr Ala Pro Thr Lys Glu His Lys
                325                 330                 335

<210> SEQ ID NO 63
<211> LENGTH: 1011
<212> TYPE: DNA
<213> ORGANISM: Mus musculus

<400> SEQUENCE: 63
atgtctcagg ctgtgcagac aaatggaact caaccattaa gcaaacatgg gaactcagt       60 ttgtatgagt acaacgaac acctcaggag gcaataacag atggcttgga aattgtggtt      120
tcacctagaa gtctacacag tgaattaatg tgcccaattt gtttggatat gttaaagaac      180
accatgacta caaaggagtg tttacatcgg ttttgcgcgg attgtattat cacagccctt      240
agaagtggca acaaagagtg tcctacctgt cggaaaaaac tggttctaa aagatcacta       300 aggccagacc cgaactttga tgcactcatc agcaagattt atcccagtcg tgatgagtat      360
gaagcgcatc aggaaagggt cttagcaagg atcaacaaac acaacaatca gcaggctctc      420
agccacagca tcgaggaggg gctgaagata caggccatga acagattaca gcgaggcaaa      480
aagcagcaga tagaaaatgg tagtggagca gaagataatg gtgacagctc ccactgtagt      540
aacgcatcca cacacagcaa ccaggaagcg ggcccgagta caaacggac caaaacctct       600
```

```
gatgactctg ggcttgaact tgataacaac aatgcagcag tggcgattga tccagtcatg    660
gacggtgcca gtgagattga gttagtcttc aggccccatc caactcttat ggaaaaggac    720
gacagcgcac agacaagata cataaagact tcaggcaatg ccactgttga tcacttatcc    780
aagtatctgg ctgtgaggtt agctttagaa gaacttcgaa gcaaaggaga atcaaaccag    840
atgaacctgg atacagccag tgagaagcag tacaccattt acatagccac agccagtggc    900
cagttcaccg tttttaaatgg ctccttttct ttggaattgg tcagtgagaa atactggaaa    960
gtgaacaaac ccatggaact ttattatgca cccaccaagg agcacaaatg a             1011
```

<210> SEQ ID NO 64
<211> LENGTH: 336
<212> TYPE: PRT
<213> ORGANISM: Mus musculus

<400> SEQUENCE: 64

```
Met Ser Gln Ala Val Gln Thr Asn Gly Thr Gln Pro Leu Ser Lys Thr
 1               5                  10                  15

Trp Glu Leu Ser Leu Tyr Glu Leu Gln Arg Thr Pro Gln Glu Ala Ile
             20                  25                  30

Thr Asp Gly Leu Glu Ile Val Val Ser Pro Arg Ser Leu His Ser Glu
         35                  40                  45

Leu Met Cys Pro Ile Cys Leu Asp Met Leu Lys Asn Thr Met Thr Thr
     50                  55                  60

Lys Glu Cys Leu His Arg Phe Cys Ala Asp Cys Ile Ile Thr Ala Leu
 65                  70                  75                  80

Arg Ser Gly Asn Lys Glu Cys Pro Thr Cys Arg Lys Lys Leu Val Ser
                 85                  90                  95

Lys Arg Ser Leu Arg Pro Asp Pro Asn Phe Asp Ala Leu Ile Ser Lys
            100                 105                 110

Ile Tyr Pro Ser Arg Asp Glu Tyr Glu Ala His Gln Glu Arg Val Leu
        115                 120                 125

Ala Arg Ile Asn Lys His Asn Asn Gln Gln Ala Leu Ser His Ser Ile
    130                 135                 140

Glu Glu Gly Leu Lys Ile Gln Ala Met Asn Arg Leu Gln Arg Gly Lys
145                 150                 155                 160

Lys Gln Gln Ile Glu Asn Gly Ser Gly Ala Glu Asp Asn Gly Asp Ser
                165                 170                 175

Ser His Cys Ser Asn Ala Ser Thr His Ser Asn Gln Glu Ala Gly Pro
            180                 185                 190

Ser Asn Lys Arg Thr Lys Thr Ser Asp Asp Ser Gly Leu Glu Leu Asp
        195                 200                 205

Asn Asn Asn Ala Ala Val Ala Ile Asp Pro Val Met Asp Gly Ala Ser
    210                 215                 220

Glu Ile Glu Leu Val Phe Arg Pro His Pro Thr Leu Met Glu Lys Asp
225                 230                 235                 240

Asp Ser Ala Gln Thr Arg Tyr Ile Lys Thr Ser Gly Asn Ala Thr Val
                245                 250                 255

Asp His Leu Ser Lys Tyr Leu Ala Val Arg Leu Ala Leu Glu Glu Leu
            260                 265                 270

Arg Ser Lys Gly Glu Ser Asn Gln Met Asn Leu Asp Thr Ala Ser Glu
        275                 280                 285

Lys Gln Tyr Thr Ile Tyr Ile Ala Thr Ala Ser Gly Gln Phe Thr Val
    290                 295                 300
```

```
Leu Asn Gly Ser Phe Ser Leu Glu Leu Val Ser Glu Lys Tyr Trp Lys
305                 310                 315                 320

Val Asn Lys Pro Met Glu Leu Tyr Tyr Ala Pro Thr Lys Glu His Lys
            325                 330                 335

<210> SEQ ID NO 65
<211> LENGTH: 13134
<212> TYPE: DNA
<213> ORGANISM: Homo sapiens

<400> SEQUENCE: 65
atggctcatg cagcctcaca attaaagaaa aacagggatt tagaaatcaa tgctgaagaa      60
gagcctgaga aaaaaggaa acaccgcaaa cggtcccggg atcggaagaa aaagtctgat     120
gccaatgcaa gttacttaag agcagctcga gctggacacc ttgaaaaggc cctcgactac     180
ataaaaaatg gagttgacat caacatttgc aatcagaatg gttgaacgc tctccacctt     240 gcttccaaag aaggccatgt agaggttgtt tctgagctgc tgcagagaga gccaatgtg     300 gatgcagcta caaagaaagg aaacacagca ttgcacatcg catctttggc tgggcaagca     360
gaggtggtaa aagtcttggt tacaaatgga gccaatgtca atgcacaatc tcagaatggt     420
ttcacgccat tgtatatggc agcccaggaa aatcacctgg aagttgtcaa gtttcttctt     480
gacaatggtg caagccagag cctagccaca gaggatggct tcacaccatt ggcagtggct     540
ttgcaacaag gtcacgacca gtcgtttcg ctcctgctag agaatgacac caaaggaaaa     600
gtgcgtctcc cagctcttca tatcgcggcc cgaaaagacg cacgaaaagc cgccgccctg     660
ctgctgcaga tgacaacaa tgcagatgtg gaatcaaaga gtggcttcac tccgctccac     720
atagctgctc actatggaaa tatcaatgta gccacgttgc tgttaaaccg agcggctgct     780
gtggatttca ccgcaaggaa tgacatcact cctttacatg ttgcatcaaa aagaggaaat     840
gcaaatatgg taaaactatt gctcgatcga ggagctaaaa tcgatgccaa aaccagggat     900
ggtctgacac cactgcactg tggagcaagg agtggccacg agcaggtggt agaaatgttg     960
cttgatcgag ctgcccccat tcttttcaaa accaagaatg gattatctcc attgcacatg    1020
gccacacaag gggatcattt aaactgcgtc cagcttctcc tccagcataa tgtacccgtg    1080
gatgatgtca ccaatgacta cctgactgcc ctacacgtgg ctgcccactg tggccattac    1140
aaagttgcca aggttctctt ggataagaaa gctaaccca atgccaaagc cctgaatggc    1200 tttaccccctc ttcatattgc ctgcaagaag aatcgaatta agtaatgga actccttctg    1260 aaacacggtg catccatcca agctgtaacc gagtcgggcc ttaccccaat ccatgttgct    1320
gccttcatgg ggcatgtaaa tattgtatca caactaatgc atcatggagc ctcaccaaac    1380
accaccaatg tgagaggaga acagcactg cacatggcag ctcgctccgg ccaagctgaa    1440
gttgtgcggt atctggtaca agacggagct caggtagaag ctaaagctaa ggatgaccaa    1500
acaccactcc acatttcagc ccgactgggg aaagcagaca tagtacaaca gctgttgcag    1560 caagggcat ctccaaatgc agccacaact tctgggtaca ccccacttca cctttccgcc    1620
cgagaggggc atgaggatgt ggccgcgttc cttttggatc atggagcgtc tttatctata    1680
acaacaaaga aaggatttac tcctcttcat gtggcagcaa aatatggaaa gcttgaagtc    1740
gccaatctcc tgctacagaa aagtgcatct ccagatgctg ctgggaagag cgggctaaca    1800
ccactgcatg tagctgcaca ttacgataat cagaaagtgg cccttctgct tttggaccaa    1860
ggagcctcac ctcacgcagc cgcaaagaat ggttatacgc cactgcacat cgctgccaaa    1920
aagaaccaga tggacatagc gacaactctg ctggaatatg gtgctgatgc caacgcagtt    1980
```

```
acccggcaag gaattgcttc cgtccatctc gcagctcagg aagggcacgt ggacatggtg    2040
tcgctgctcc tcggtagaaa tgcgaatgtg aacctgagca ataagagcgg cctgacccca    2100
ctccatttgg ctgctcaaga agatcgagtg aatgtggcag aagtcctcgt aaaccaaggg    2160
gctcatgtga acgcccagac aaagatggga tacacaccac tgcatgtggg ctgccactat    2220
ggaaatatca agattgttaa tttcctgctc cagcattctg caaaagttaa tgccaaaaca    2280
aagaatgggt atacgccatt acatcaagca gcacagcagg ggcatacgca tataataaat    2340
gtcttacttc agaacaacgc ctcccccaat gaactcactg tgaatgggaa tactgccctt    2400
ggcattgccc ggcgcctcgg ctacatctca gtagtggaca ccctgaagat agtgaccgaa    2460
gagaccatga ccacaactac tgtcacagag aagcacaaaa tgaatgttcc agaaacgatg    2520
aatgaagttc ttgatatgtc tgatgatgaa gttcgtaaag ccaatgcccc tgaaatgctc    2580
agtgatggcg aatatatctc agatgttgaa gaaggtgaag atgcaatgac cggggacaca    2640
gacaaatatc ttgggccaca ggaccttaag gaattgggtg atgattccct gcctgcagag    2700
ggttacatgg gctttagtct cggagcgcgt tctgccagcc tccgctcctt cagttcggat    2760
aggtcttaca ccttgaacag aagctcctat gcacgggaca gcatgatgat tgaagaactc    2820
cttgtgccat ccaaagagca gcatctaaca ttcacaaggg aatttgattc agattctctt    2880
agacattaca gctgggctgc agacacctta gacaatgtca atcttgtttc aagccccatt    2940
cattctgggt ttctggttag ctttatggtg gacgcgagag ggggctccat gagaggaagc    3000
cgtcatcacg ggatgagaat catcattcct ccacgcaagt gtacggcccc cactcgaatc    3060
acctgccgtt tggtaaagag acataaactg gccaacccac cccccatggt ggaaggagag    3120
ggattagcca gtaggctggt agaaatgggt cctgcagggg cacaattttt aggccctgtc    3180
atagtggaaa tccctcactt tgggtccatg agaggaaaag agagagaact cattgttctt    3240
cgaagtgaaa atggtgaaac ttggaaggag catcagtttg acagcaaaaa tgaagattta    3300
accgagttac ttaatggcat ggatgaagaa cttgatagcc cagaagagtt agggaaaaag    3360
cgtatctgca ggattatcac gaaagatttc ccccagtatt ttgcagtggt ttcccggatt    3420
aagcaggaaa gcaaccagat tggtcctgaa ggtggaattc tgagcagcac cacagtgccc    3480
cttgttcaag catctttccc agagggtgcc ctaactaaaa gaattcgagt gggcctccag    3540
gcccagcctg ttccagatga aattgtgaaa aagatccttg gaaacaaagc aacttttagc    3600
ccaattgtca ctgtggaacc aagaagacgg aaattccata aaccaatcac aatgaccatt    3660
ccggtgcccc cgcccctcagg agaaggtgta tccaatggat acaaagggga cactacaccc    3720
aatctgcgtc ttctctgtag cattacaggg ggcacttcgc ctgctcagtg gaagacatc    3780 acaggaacaa ctcctttgac gtttataaaa gattgtgtct cctttacaac caatgtttca    3840
gccagatttt ggcttgcaga ctgccatcaa gttttagaaa ctgtggggtt agccacgcaa    3900
ctgtacagag aattgatatg tgttccatat atggccaagt tgttgttttt tgccaaaatg    3960
aatgatcccg tagaatcttc cttgcgatgt ttctgcatga cagatgacaa agtggacaaa    4020
actttagagc aacaagagaa ttttgaggaa gtcgcaagaa gcaaagatat tgaggttctg    4080
gaaggaaaac ctatttatgt tgattgttat ggaaatttgg ccccacttac caaaggagga    4140
cagcaacttg ttttttaactt ttattctttc aaagaaaata gactgccatt ttccatcaag    4200
attagagaca ccagccaaga gccctgtggt cgtctgtctt ttctgaaaga accaaagaca    4260
acaaaaggac tgcctcaaac agcggttttgc aacttaaata tcactctgcc agcacataaa    4320
aaggagacag agtcagatca agatgatgag attgagaaaa cagatagacg acagagcttc    4380
```

```
gcatccttag ctttacgtaa gcgctacagc tacttgactg agcctggaat gattgaacgg    4440
agtacaggag caacaagatc cctcccacc acttactcat acaagccatt cttttctaca     4500
agaccatacc agtcctggac aacagctccg attacagtgc ctgggccagc caagtcaggc    4560
ttcacttcct tatcaagttc ttcctctaat acgccatcag cttctccgtt aaaatcaata    4620
tggtctgttt cgacaccttc tccaatcaaa tccacattag gcgcgtcaac tacatcttca    4680
gttaaatcca ttagtgacgt ggcatctcca attagatcct ttcggacaat gtcttcgccg    4740
ataaaaactg tggtgtcaca atctccatac aatatccaag tttcctctgg taccctggct    4800
agagctccag cagtcacgga agctacgccc ttaaaagggc tggcatccaa ttctacgttt    4860
tcctctcgaa cctctccagt gactacagca gggtctcttt tggagaggtc atcaattact    4920
atgcaccccc ctgcctcccc caaatcaaac attaatatgt attcctcaag tttgccattt    4980
aagtcaatta ttacatcagc agcaccgcta atatcttcac ctttaaagtc agtggtgtct    5040
ccagttaaat cagcagttga tgtcatttca tcagccaaaa ttacaatggc atcttctctc    5100
tcatcacctg tgaagcagat gcctggacat gcagaggtag cattagtcaa tggatctatt    5160 tccctctaa aatatccatc atcctcaact ttaattaatg gatgcaaagc cactgccacg     5220
ttacaggaaa aaatttcttc tgctacaaac tctgtgagct ctgtggtcag tgcagccact    5280
gacacagttg agaaagtgtt ttctaccacg actgcaatgc catttccccc actcaggtca    5340
tatgtttctg cagcaccatc agcttttcag tctctaagaa ctccttccgc aagtgcactc    5400
tatacatccc ttgggtcgtc aatatctgca actacctcat ctgtaacttc atcaattata    5460
acagtgccag tatactctgt agtcaatgtt ttgccagaac cagcattaaa gaaacttcca    5520
gactctaatt catttacaaa atcagcagca gccttgctgt cacccattaa acattgact     5580 acggagacac atcctcagcc tcacttcagt cgaacttcat ctccagttaa gtcatctttg    5640
ttccttgcac cctctgccct taagttgtct acaccatctt ctttatcttc cagtcaggag    5700
atactaaaag atgtagctga aatgaaagag gacctaatgc ggatgaccgc aatactacag    5760
acagatgtgc ctgaggagaa gccattccaa cctgaactcc caaaggaagg gagaatagat    5820
gatgaagaac ctttcaaaat tgtagagaaa gtaaaggaag acttagtgaa agttagtgaa    5880
atccttaaaa aggatgtatg tgtagataat aaaggatcac ccaaatcacc aaagagtgac    5940
aaaggacact ctcctgaaga tgactggata gaatttagtt cggaagaaat ccgggaagcc    6000
agacaacaag ctgctgcgag ccagtctcca tctctgccag agagagtgca agtaaaagca    6060
aaagccgcct ccgaaaagga ttataacttg accaaagtta ttgattacct aacaaatgat    6120
attgggagta gttcactgac aaacttaaaa tacaagtttg aggatgcaaa aaggatggt    6180 gaggagagac agaaaagagt tttaaaacca gcaattgctt tgcaggaaca caaactcaaa    6240
atgcctccag cctccatgag gacttccacc tctgagaaag aattgtgtaa aatggctgat    6300 tcctttttg gaacagatac tattttagag tctcctgatg acttttctca acacgaccaa    6360
gataaaagtc ccttgtctga cagtggcttt gaaacaagaa gtgaaaagac accttcagcc    6420
ccacaaagcg ctgaaagcac tggtcctaaa ccactttttc atgaagttcc catccctcct    6480
gtcattacag aaacaagaac tgaagtggtt catgttatca ggagctatga tccctcagct    6540
ggggatgttc cccagaccca accagaggag cctgtgtcac ctaaaccttc acctactttt    6600
atggaattgg aaccaaagcc caccacctct agtattaaag aaaaggttaa agcatttcaa    6660
atgaaagcca gtagtgaaga agatgaccac aatcgggttt taagcaaagg catgcgtgtt    6720
aaagaagaga ctcacataac cacaaccacc agaatggttt atcattctcc accaggcggt    6780
```

```
gaaggtgcat ctgaaagaat tgaagaaacc atgtcagtcc atgacatcat gaaggccttt    6840
cagtccgggc gggatccttc caaagaactg gcaggtctgt ttgaacataa gtcggcagtg    6900
tctccagatg ttcacaagtc tgctgctgaa acctcagccc agcatgcaga gaaggacaac    6960
caaatgaaac ccaaactgga gcgtataata gaagtccaca tcgaaaaagg taaccaagct    7020
gagcccactg aagtcattat tagagaaacc aaaaagcatc cagaaaaaga aatgtatgta    7080
tatcagaaag acttatcccg gggagatatt aacctaaaag attttctgcc agaaaaacac    7140
gatgcttttc cttgttcaga ggaacagggt cagcaagaag aagaagaact tactgctgaa    7200
gagtcattgc cttcttatct ggagtcttcc agagtaaaca ctcctgtgtc caagaagaa     7260 gatagccgcc ctagttctgc tcaactcata tctgatgact cttataaaac attgaagctt    7320
ttgagtcaac actcaataga ataccatgac gatgagttgt cagaactaag agggagtct    7380 tacaggtttg ctgagaaaat gcttctgtca gaaaagctag atgtgtctca ttctgatact    7440
gaggaatcgg ttacagacca tgcaggaccc cctagctcag agttacaggg gtctgataag    7500
cggtccagag aaaaaatagc cactgccccc aaaaagaaa ttctctccaa aatctataaa     7560
gatgtttctg aaaatggtgt aggtaaagtg tctaaagatg agcattttga taaagtgaca    7620
gtgttgcact attctggcaa tgttagtagt ccaaaacatg ccatgtggat gcgctttact    7680
gaggacagat tagacagagg tagagagaag ttgatatatg aagataggat ggacaggact    7740
gtgaaggagg ctgaagaaaa actgactgaa gtgtcacagt tttttcgtga caaaactgaa    7800
aagctaaatg atgaactgca gtccccagag aaaaaggcac gccctaaaaa tggcaaagaa    7860
tattcttctc aaagccctac cagtagcagc cctgagaaag tgctactgac agaactgctg    7920
gcatccaatg atgagtgggt taaggcaaga cagcatggcc ctgatggaca aggcttcccc    7980
aaggccgagg agaaggcacc cagtctgccc agcagcccag agaagatggt tctctcccaa    8040
cagactgagg acagcaagtc cacagtggaa gccaaaggaa gtatttcaca gagcaaagca    8100
ccagatgggc cccagtctgg attccagctc aaacaatcta aactcagttc cattagatta    8160
aaatttgaac aaggcacaca cgcaaaaagt aaggacatgt ctcaagaaga cagaaagtca    8220
gatggccagt ccagaatccc agttaaaaaa atacaggaga gcaagctacc cgtctaccaa    8280 gttttttgcta gagaaaaaca gcagaaggcc atagacctcc cagatgaaag tgtatctgtg    8340
caaaaagatt ttatggtatt aaaaaccaaa gatgagcatg cccaaagcaa cgaaattgtt    8400
gtaaatgatt ctggctctga taatgtgaaa aaacagagaa ctgaaatgtc aagtaaagca    8460
atgcctgact ctttttctga gcagcaggct aaagacttgg catgtcatat aacctcagat    8520
ttagcaacta ggggaccatg ggacaaaaag gtctttagaa catgggagag ttcgggagcc    8580
actaacaata agtctcagaa agaaaaactt tcgcatgtac ttgttcatga tgtaagagag    8640
aatcacattg gtcaccctga gagtaaaagt gttgatcaaa agaatgaatt tatgtctgtg    8700
actgagagag aacgcaaatt gttaacaaac ggctctctct cagaaattaa agaaatgact    8760
gtaaaatctc cctccaaaaa agtcttatat agggaatatg ttgtgaaaga aggggaccat    8820
ccaggcggat tgcttgatca gccttccagg aggagcgaga gctcagcagt gtcacacatt    8880
cccgtcagag ttgctgatga gaggagaatg ctgtcttcta atattcccga tggttttttgt    8940 gaacagtcgg catttccaaa acatgaacta tcacaaaaat tgtcccagtc aagcatgagt    9000
aaagagacag ttgagacaca gcactttaat tctatagaag atgaaaaagt tacctattca    9060
gaaatcagca agtttccaa acaccagagt tatgtaggtt tatgcccacc tctcgaggaa     9120
accgaaacct cccccaccaa atctcctgat tctttagagt ttagcccagg aaaggaatct    9180
```

```
ccctctagtg atgtattcga ccacagtccc attgatggat tggaaaaact cgcaccacta   9240
gcccagacag agggagggaa agagataaaa actttacccg tttatgtcag ttttgtacaa   9300
gtggggaagc aatatgaaaa ggagatacaa caaggaggtg taaaaaaaat cataagtcag   9360
gaatgtaaga cagtacaaga aaccaggggg acctttata caactagaca gcaaaagcaa    9420
cctccttctc cccaaggtag tccagaagat gatactctag agcaagtatc ctttctagac   9480
agctctggga aaagcccttt aaccccagaa acacccagtt cagaggaagt gagttatgaa   9540
tttacatcta agacacctga ctcgctcata gcttatatac caggcaaacc cagcccaatt   9600
cccgaggttt ctgaggagtc agaggaggag gaacaggcca agtcaacctc ccttaagcag   9660
actacagtgg aggaaacagc agttgagcgt gaaatgccta atgacgtgag caaagactct   9720
aaccaaagac ccaaaaataa cagagttgcc tatattgaat tccccctcc tccaccactg    9780 gatgcggacc agattgagtc agataagaag catcattatc tcccagaaaa agaggttgac   9840
atgattgaag tcaatctgca agatgagcat gacaagtacc agctggctga acctgtcatt   9900
agagtgcagc caccttcacc agttcctccc ggggcagacg tcagtgattc aagcgatgac   9960
gaatctattt atcagccagt cccagttaaa aaatatacct tcaaattaaa ggaagtggac   10020
gatgaacaaa agaaaaaacc caaagcttct gctgaaaagg cttccaacca gaaagaactg   10080
gaaagtaatg gatctggaaa agataatgaa tttggccttg gccttgattc acctcagaat   10140
gaaattgccc agaatgggaa caacgaccag tccatcacag agtgttccat tgccaccaca   10200
gcagagtttt ctcatgacac ggatgccaca gagatcgact ctctggatgg ctatgacctg   10260
caagatgaag atgatggctt gacagagagt gattctaaac tcccaattca agccatggaa   10320
attaagaaag atatctggaa cacagagggc attctgaagc cagctgaccg ctcttttagc   10380
caaagtaaac ttgaagttat cgaggaggag ggaaaggtgg gaccagatga ggacaagcca   10440
ccttctaaaa gttcttcatc tgaaaagact cctgataaga ctgatcagaa gtcaggggcc   10500
cagttcttca cactggaagg cagacatcct gacagatcag tgtttcctga tacttacttc   10560
agttacaaag tagatgaaga attttgccact cctttttaaaa cagtagctac caaaggtcta   10620
gattttgacc cttggtctaa taaccgaggg gatgatgaag ttttgacag taaatcacgg    10680 gaagatgaaa ctaagccatt tgggctggcg gtagaagacc gctctccagc aacaacccct   10740
gatacaacgc cagccagaac gccaactgat gaaagtaccc caactagtga gcctaacccc   10800
ttcccatttc atgaaggaaa aatgtttgag atgactcgca gtggtgcaat tgacatgagc   10860
aagagggatt tgttgaaga gaggctccaa ttttttccaga ttggtgagca tacttctgaa    10920
gggaagtcag gggaccaggg ggaagggat aaaagtatgg tcactgccac accacagcca    10980
cagtcagggg acaccactgt agaaaccaat ctagagagaa atgtagagac acctacagtg   11040
gaacctaacc ccagcatccc gaccagcgga gagtgtcagg aaggcacatc cagtagtggc   11100
tccctggaga atcagcagc agccactaac acctctaaag ttgacccccaa gttgcgcacg   11160 cctataaaaa tgggaatttc tgcatccacc atgaccatga agaaagaagg ccctggagaa   11220
ataacagata agatagaagc ggtgatgacc agttgtcagg gattagaaaa tgaaactata   11280
acaatgattt caaatacagc caatagccag atgggcgtta ggccccatga aaaacatgat   11340
tttcaaaaag ataactttaa taacaacaac aatttggatt cttccactat acagacagat   11400
aacattatga gtaatatagt tctgacagaa cattctgcac ccacttgtac cacagagaaa   11460
gataacccag tgaagtctc atcaggaaaa aagacagggg tactacaagg acactgtgta   11520
agagataagc agaaagttct tggagaacag caaaaaacaa aggaattgat agggattagg   11580
```

-continued

```
caaaaatcca aacttcccat aaaggccact tcaccaaaag ataccttccc accgaaccat    11640
atgtcaaaca ctaaagcaag taaaatgaag caggttagtc aatccgagaa aaccaaagcc    11700
cttactactt cttcatgtgt agatgtaaag tccagaattc cagtgaaaaa cacacacagg    11760
gataacataa ttgcagttag aaaagcatgt gccacacaaa agcaagggca gccagagaaa    11820
ggcaaggcca aacagcttcc atccaagttg ccagtaaagg taagatccac ctgtgtcact    11880
accaccacca ccactgccac caccaccacc actaccacca ctaccaccac caccagctgc    11940
acagttaaag ttaggaaaag tcagctcaag gaagtatgta acattccat tgaatatttt    12000
aagggaatta gtggtgagac cttaaagctt gtggaccgcc tctctgaaga agaaaaaaag    12060
atgcagtccg agttgtccga tgaggaagaa agtacctcaa gaaacacgtc gttgtccgag    12120
acttcccggg gtggccagcc ttcggttaca acgaagtctg ctagagataa gaaaacagag    12180
gcagcacctt taaaatcaaa gagtgaaaag gccggcagtg agaaaaggag cagtagaagg    12240
actggtccac agagtccatg tgaacggaca gatatcagga tggcaatagt agccgatcac    12300
ctgggactta gttggacaga actggcaagg gaactgaatt tttcagtgga tgaaatcaat    12360
caaatacgtg tggaaaatcc aaattcttta atttctcaga gcttcatgtt attaaaaaaa    12420
tgggttacca gagacggaaa aaatgccaca actgatgcct taacttcggt cttgacaaaa    12480
attaatcgaa tagatatagt gacactgcta gaaggaccaa tatttgatta tggaaatatt    12540
tcaggcacca gaagttttgc agatgagaac aatgttttcc atgaccctgt tgatggttgg    12600
cagaatgaga catcaagtgg aaacctagag tcctgcgctc aagctcgaag agtaactggt    12660
gggttactag atcgactgga tgacagccct gaccagtgta gagattccat tacctcatat    12720
ctcaaaggag aagctggcaa atttgaagca atggaagcc atacagaaat cactccagaa    12780
gcaaagacaa atcttactt tccagaatcc caaaatgatg taggaaaaca gagtaccaag    12840
gaaactctga aaccaaaaat acatggatct ggtcatgttg aagaaccagc atcaccacta    12900
gcagcatatc agaaatctct agaagaaacc agcaagctta taatagaaga gactaaaccc    12960
tgtgtgcctg tcagtatgaa aaagatgagt aggacttctc cagcagatgg caagccaagg    13020
cttagcctcc atgaagaaga ggggtccagt gggtctgagc aaaagcaggg agaaggtttt    13080
aaggtgaaaa cgaagaaaga aatccggcat gtggaaaaga gagccactc gtaa           13134
```

<210> SEQ ID NO 66
<211> LENGTH: 4377
<212> TYPE: PRT
<213> ORGANISM: Homo sapiens

<400> SEQUENCE: 66

```
Met Ala His Ala Ala Ser Gln Leu Lys Lys Asn Arg Asp Leu Glu Ile
1               5                   10                  15

Asn Ala Glu Glu Glu Pro Glu Lys Lys Arg His Arg Lys Arg Ser
            20                  25                  30

Arg Asp Arg Lys Lys Lys Ser Asp Ala Asn Ala Ser Tyr Leu Arg Ala
        35                  40                  45

Ala Arg Ala Gly His Leu Glu Lys Ala Leu Asp Tyr Ile Lys Asn Gly
    50                  55                  60

Val Asp Ile Asn Ile Cys Asn Gln Asn Gly Leu Asn Ala Leu His Leu
65                  70                  75                  80

Ala Ser Lys Glu Gly His Val Glu Val Val Ser Glu Leu Leu Gln Arg
                85                  90                  95

Glu Ala Asn Val Asp Ala Ala Thr Lys Lys Gly Asn Thr Ala Leu His
            100                 105                 110
```

-continued

Ile Ala Ser Leu Ala Gly Gln Ala Glu Val Lys Val Leu Val Thr
            115                 120                 125

Asn Gly Ala Asn Val Asn Ala Gln Ser Gln Asn Gly Phe Thr Pro Leu
    130                 135                 140

Tyr Met Ala Ala Gln Glu Asn His Leu Glu Val Val Lys Phe Leu Leu
145                 150                 155                 160

Asp Asn Gly Ala Ser Gln Ser Leu Ala Thr Glu Asp Gly Phe Thr Pro
                165                 170                 175

Leu Ala Val Ala Leu Gln Gln Gly His Asp Gln Val Val Ser Leu Leu
            180                 185                 190

Leu Glu Asn Asp Thr Lys Gly Lys Val Arg Leu Pro Ala Leu His Ile
        195                 200                 205

Ala Ala Arg Lys Asp Asp Thr Lys Ala Ala Leu Leu Leu Gln Asn
    210                 215                 220

Asp Asn Asn Ala Asp Val Glu Ser Lys Ser Gly Phe Thr Pro Leu His
225                 230                 235                 240

Ile Ala Ala His Tyr Gly Asn Ile Asn Val Ala Thr Leu Leu Leu Asn
                245                 250                 255

Arg Ala Ala Val Asp Phe Thr Ala Arg Asn Asp Ile Thr Pro Leu
            260                 265                 270

His Val Ala Ser Lys Arg Gly Asn Ala Asn Met Val Lys Leu Leu Leu
        275                 280                 285

Asp Arg Gly Ala Lys Ile Asp Ala Lys Thr Arg Asp Gly Leu Thr Pro
    290                 295                 300

Leu His Cys Gly Ala Arg Ser Gly His Glu Gln Val Val Glu Met Leu
305                 310                 315                 320

Leu Asp Arg Ala Ala Pro Ile Leu Ser Lys Thr Lys Asn Gly Leu Ser
                325                 330                 335

Pro Leu His Met Ala Thr Gln Gly Asp His Leu Asn Cys Val Gln Leu
            340                 345                 350

Leu Leu Gln His Asn Val Pro Val Asp Asp Val Thr Asn Asp Tyr Leu
        355                 360                 365

Thr Ala Leu His Val Ala Ala His Cys Gly His Tyr Lys Val Ala Lys
    370                 375                 380

Val Leu Leu Asp Lys Lys Ala Asn Pro Asn Ala Lys Ala Leu Asn Gly
385                 390                 395                 400

Phe Thr Pro Leu His Ile Ala Cys Lys Lys Asn Arg Ile Lys Val Met
                405                 410                 415

Glu Leu Leu Leu Lys His Gly Ala Ser Ile Gln Ala Val Thr Glu Ser
            420                 425                 430

Gly Leu Thr Pro Ile His Val Ala Ala Phe Met Gly His Val Asn Ile
        435                 440                 445

Val Ser Gln Leu Met His Gly Ala Ser Pro Asn Thr Thr Asn Val
    450                 455                 460

Arg Gly Glu Thr Ala Leu His Met Ala Ala Arg Ser Gly Gln Ala Glu
465                 470                 475                 480

Val Val Arg Tyr Leu Val Gln Asp Gly Ala Gln Val Glu Ala Lys Ala
                485                 490                 495

Lys Asp Asp Gln Thr Pro Leu His Ile Ser Ala Arg Leu Gly Lys Ala
            500                 505                 510

Asp Ile Val Gln Gln Leu Leu Gln Gln Gly Ala Ser Pro Asn Ala Ala
        515                 520                 525

Thr Thr Ser Gly Tyr Thr Pro Leu His Leu Ser Ala Arg Glu Gly His

-continued

```
            530                 535                 540
Glu Asp Val Ala Ala Phe Leu Leu Asp His Gly Ala Ser Leu Ser Ile
545                 550                 555                 560

Thr Thr Lys Lys Gly Phe Thr Pro Leu His Val Ala Ala Lys Tyr Gly
                    565                 570                 575

Lys Leu Glu Val Ala Asn Leu Leu Gln Lys Ser Ala Ser Pro Asp
                580                 585                 590

Ala Ala Gly Lys Ser Gly Leu Thr Pro Leu His Val Ala Ala His Tyr
                595                 600                 605

Asp Asn Gln Lys Val Ala Leu Leu Leu Asp Gln Gly Ala Ser Pro
            610                 615                 620

His Ala Ala Lys Asn Gly Tyr Thr Pro Leu His Ile Ala Ala Lys
625                 630                 635                 640

Lys Asn Gln Met Asp Ile Ala Thr Thr Leu Leu Glu Tyr Gly Ala Asp
                    645                 650                 655

Ala Asn Ala Val Thr Arg Gln Gly Ile Ala Ser Val His Leu Ala Ala
                660                 665                 670

Gln Glu Gly His Val Asp Met Val Ser Leu Leu Leu Gly Arg Asn Ala
                675                 680                 685

Asn Val Asn Leu Ser Asn Lys Ser Gly Leu Thr Pro Leu His Leu Ala
                690                 695                 700

Ala Gln Glu Asp Arg Val Asn Val Ala Glu Val Leu Val Asn Gln Gly
705                 710                 715                 720

Ala His Val Asp Ala Gln Thr Lys Met Gly Tyr Thr Pro Leu His Val
                    725                 730                 735

Gly Cys His Tyr Gly Asn Ile Lys Ile Val Asn Phe Leu Leu Gln His
                740                 745                 750

Ser Ala Lys Val Asn Ala Lys Thr Lys Asn Gly Tyr Thr Pro Leu His
                755                 760                 765

Gln Ala Ala Gln Gln Gly His Thr His Ile Ile Asn Val Leu Leu Gln
770                 775                 780

Asn Asn Ala Ser Pro Asn Glu Leu Thr Val Asn Gly Asn Thr Ala Leu
785                 790                 795                 800

Gly Ile Ala Arg Arg Leu Gly Tyr Ile Ser Val Val Asp Thr Leu Lys
                    805                 810                 815

Ile Val Thr Glu Glu Thr Met Thr Thr Thr Thr Val Thr Glu Lys His
                820                 825                 830

Lys Met Asn Val Pro Glu Thr Met Asn Glu Val Leu Asp Met Ser Asp
                835                 840                 845

Asp Glu Val Arg Lys Ala Asn Ala Pro Glu Met Leu Ser Asp Gly Glu
850                 855                 860

Tyr Ile Ser Asp Val Glu Glu Gly Glu Asp Ala Met Thr Gly Asp Thr
865                 870                 875                 880

Asp Lys Tyr Leu Gly Pro Gln Asp Leu Lys Glu Leu Gly Asp Asp Ser
                    885                 890                 895

Leu Pro Ala Glu Gly Tyr Met Gly Phe Ser Leu Gly Ala Arg Ser Ala
                900                 905                 910

Ser Leu Arg Ser Phe Ser Ser Asp Arg Ser Tyr Thr Leu Asn Arg Ser
                915                 920                 925

Ser Tyr Ala Arg Asp Ser Met Met Ile Glu Glu Leu Leu Val Pro Ser
                930                 935                 940

Lys Glu Gln His Leu Thr Phe Thr Arg Glu Phe Asp Ser Asp Ser Leu
945                 950                 955                 960
```

-continued

Arg His Tyr Ser Trp Ala Ala Asp Thr Leu Asp Asn Val Asn Leu Val
                965                 970                 975

Ser Ser Pro Ile His Ser Gly Phe Leu Val Ser Phe Met Val Asp Ala
            980                 985                 990

Arg Gly Gly Ser Met Arg Gly Ser Arg His His Gly Met Arg Ile Ile
        995                 1000                1005

Ile Pro Pro Arg Lys Cys Thr Ala Pro Thr Arg Ile Thr Cys Arg
    1010                1015                1020

Leu Val Lys Arg His Lys Leu Ala Asn Pro Pro Met Val Glu
    1025                1030                1035

Gly Glu Gly Leu Ala Ser Arg Leu Val Glu Met Gly Pro Ala Gly
    1040                1045                1050

Ala Gln Phe Leu Gly Pro Val Ile Val Glu Ile Pro His Phe Gly
    1055                1060                1065

Ser Met Arg Gly Lys Glu Arg Glu Leu Ile Val Leu Arg Ser Glu
    1070                1075                1080

Asn Gly Glu Thr Trp Lys Glu His Gln Phe Asp Ser Lys Asn Glu
    1085                1090                1095

Asp Leu Thr Glu Leu Leu Asn Gly Met Asp Glu Glu Leu Asp Ser
    1100                1105                1110

Pro Glu Glu Leu Gly Lys Lys Arg Ile Cys Arg Ile Ile Thr Lys
    1115                1120                1125

Asp Phe Pro Gln Tyr Phe Ala Val Val Ser Arg Ile Lys Gln Glu
    1130                1135                1140

Ser Asn Gln Ile Gly Pro Glu Gly Gly Ile Leu Ser Ser Thr Thr
    1145                1150                1155

Val Pro Leu Val Gln Ala Ser Phe Pro Glu Gly Ala Leu Thr Lys
    1160                1165                1170

Arg Ile Arg Val Gly Leu Gln Ala Gln Pro Val Pro Asp Glu Ile
    1175                1180                1185

Val Lys Lys Ile Leu Gly Asn Lys Ala Thr Phe Ser Pro Ile Val
    1190                1195                1200

Thr Val Glu Pro Arg Arg Arg Lys Phe His Lys Pro Ile Thr Met
    1205                1210                1215

Thr Ile Pro Val Pro Pro Pro Ser Gly Glu Gly Val Ser Asn Gly
    1220                1225                1230

Tyr Lys Gly Asp Thr Thr Pro Asn Leu Arg Leu Leu Cys Ser Ile
    1235                1240                1245

Thr Gly Gly Thr Ser Pro Ala Gln Trp Glu Asp Ile Thr Gly Thr
    1250                1255                1260

Thr Pro Leu Thr Phe Ile Lys Asp Cys Val Ser Phe Thr Thr Asn
    1265                1270                1275

Val Ser Ala Arg Phe Trp Leu Ala Asp Cys His Gln Val Leu Glu
    1280                1285                1290

Thr Val Gly Leu Ala Thr Gln Leu Tyr Arg Glu Leu Ile Cys Val
    1295                1300                1305

Pro Tyr Met Ala Lys Phe Val Val Phe Ala Lys Met Asn Asp Pro
    1310                1315                1320

Val Glu Ser Ser Leu Arg Cys Phe Cys Met Thr Asp Asp Lys Val
    1325                1330                1335

Asp Lys Thr Leu Glu Gln Gln Glu Asn Phe Glu Glu Val Ala Arg
    1340                1345                1350

Ser Lys Asp Ile Glu Val Leu Glu Gly Lys Pro Ile Tyr Val Asp
    1355                1360                1365

```
Cys Tyr Gly Asn Leu Ala Pro Leu Thr Lys Gly Gln Gln Leu
    1370            1375                1380

Val Phe Asn Phe Tyr Ser Phe Lys Glu Asn Arg Leu Pro Phe Ser
1385            1390                1395

Ile Lys Ile Arg Asp Thr Ser Gln Glu Pro Cys Gly Arg Leu Ser
1400            1405                1410

Phe Leu Lys Glu Pro Lys Thr Thr Lys Gly Leu Pro Gln Thr Ala
1415            1420                1425

Val Cys Asn Leu Asn Ile Thr Leu Pro Ala His Lys Lys Glu Thr
1430            1435                1440

Glu Ser Asp Gln Asp Asp Glu Ile Glu Lys Thr Asp Arg Arg Gln
1445            1450                1455

Ser Phe Ala Ser Leu Ala Leu Arg Lys Arg Tyr Ser Tyr Leu Thr
1460            1465                1470

Glu Pro Gly Met Ile Glu Arg Ser Thr Gly Ala Thr Arg Ser Leu
1475            1480                1485

Pro Thr Thr Tyr Ser Tyr Lys Pro Phe Phe Ser Thr Arg Pro Tyr
1490            1495                1500

Gln Ser Trp Thr Thr Ala Pro Ile Thr Val Pro Gly Pro Ala Lys
1505            1510                1515

Ser Gly Phe Thr Ser Leu Ser Ser Ser Ser Asn Thr Pro Ser
1520            1525                1530

Ala Ser Pro Leu Lys Ser Ile Trp Ser Val Ser Thr Pro Ser Pro
1535            1540                1545

Ile Lys Ser Thr Leu Gly Ala Ser Thr Thr Ser Ser Val Lys Ser
1550            1555                1560

Ile Ser Asp Val Ala Ser Pro Ile Arg Ser Phe Arg Thr Met Ser
1565            1570                1575

Ser Pro Ile Lys Thr Val Val Ser Gln Ser Pro Tyr Asn Ile Gln
1580            1585                1590

Val Ser Ser Gly Thr Leu Ala Arg Ala Pro Ala Val Thr Glu Ala
1595            1600                1605

Thr Pro Leu Lys Gly Leu Ala Ser Asn Ser Thr Phe Ser Ser Arg
1610            1615                1620

Thr Ser Pro Val Thr Thr Ala Gly Ser Leu Leu Glu Arg Ser Ser
1625            1630                1635

Ile Thr Met Thr Pro Pro Ala Ser Pro Lys Ser Asn Ile Asn Met
1640            1645                1650

Tyr Ser Ser Ser Leu Pro Phe Lys Ser Ile Ile Thr Ser Ala Ala
1655            1660                1665

Pro Leu Ile Ser Ser Pro Leu Lys Ser Val Val Ser Pro Val Lys
1670            1675                1680

Ser Ala Val Asp Val Ile Ser Ser Ala Lys Ile Thr Met Ala Ser
1685            1690                1695

Ser Leu Ser Ser Pro Val Lys Gln Met Pro Gly His Ala Glu Val
1700            1705                1710

Ala Leu Val Asn Gly Ser Ile Ser Pro Leu Lys Tyr Pro Ser Ser
1715            1720                1725

Ser Thr Leu Ile Asn Gly Cys Lys Ala Thr Ala Thr Leu Gln Glu
1730            1735                1740

Lys Ile Ser Ser Ala Thr Asn Ser Val Ser Ser Val Ser Ala
1745            1750                1755

Ala Thr Asp Thr Val Glu Lys Val Phe Ser Thr Thr Thr Ala Met
```

```
                1760                1765                1770

Pro Phe Ser Pro Leu Arg Ser Tyr Val Ser Ala Ala Pro Ser Ala
    1775                1780                1785

Phe Gln Ser Leu Arg Thr Pro Ser Ala Ser Ala Leu Tyr Thr Ser
    1790                1795                1800

Leu Gly Ser Ser Ile Ser Ala Thr Thr Ser Ser Val Thr Ser Ser
    1805                1810                1815

Ile Ile Thr Val Pro Val Tyr Ser Val Val Asn Val Leu Pro Glu
    1820                1825                1830

Pro Ala Leu Lys Lys Leu Pro Asp Ser Asn Ser Phe Thr Lys Ser
    1835                1840                1845

Ala Ala Ala Leu Leu Ser Pro Ile Lys Thr Leu Thr Thr Glu Thr
    1850                1855                1860

His Pro Gln Pro His Phe Ser Arg Thr Ser Ser Pro Val Lys Ser
    1865                1870                1875

Ser Leu Phe Leu Ala Pro Ser Ala Leu Lys Leu Ser Thr Pro Ser
    1880                1885                1890

Ser Leu Ser Ser Ser Gln Glu Ile Leu Lys Asp Val Ala Glu Met
    1895                1900                1905

Lys Glu Asp Leu Met Arg Met Thr Ala Ile Leu Gln Thr Asp Val
    1910                1915                1920

Pro Glu Glu Lys Pro Phe Gln Pro Glu Leu Pro Lys Glu Gly Arg
    1925                1930                1935

Ile Asp Asp Glu Glu Pro Phe Lys Ile Val Glu Lys Val Lys Glu
    1940                1945                1950

Asp Leu Val Lys Val Ser Glu Ile Leu Lys Lys Asp Val Cys Val
    1955                1960                1965

Asp Asn Lys Gly Ser Pro Lys Ser Pro Lys Ser Asp Lys Gly His
    1970                1975                1980

Ser Pro Glu Asp Asp Trp Ile Glu Phe Ser Glu Glu Ile Arg
    1985                1990                1995

Glu Ala Arg Gln Gln Ala Ala Ala Ser Gln Ser Pro Ser Leu Pro
    2000                2005                2010

Glu Arg Val Gln Val Lys Ala Lys Ala Ala Ser Glu Lys Asp Tyr
    2015                2020                2025

Asn Leu Thr Lys Val Ile Asp Tyr Leu Thr Asn Asp Ile Gly Ser
    2030                2035                2040

Ser Ser Leu Thr Asn Leu Lys Tyr Lys Phe Glu Asp Ala Lys Lys
    2045                2050                2055

Asp Gly Glu Glu Arg Gln Lys Arg Val Leu Lys Pro Ala Ile Ala
    2060                2065                2070

Leu Gln Glu His Lys Leu Lys Met Pro Pro Ala Ser Met Arg Thr
    2075                2080                2085

Ser Thr Ser Gly Lys Glu Leu Cys Lys Met Ala Asp Ser Phe Phe
    2090                2095                2100

Gly Thr Asp Thr Ile Leu Glu Ser Pro Asp Asp Phe Ser Gln His
    2105                2110                2115

Asp Gln Asp Lys Ser Pro Leu Ser Asp Ser Gly Phe Glu Thr Arg
    2120                2125                2130

Ser Glu Lys Thr Pro Ser Ala Pro Gln Ser Ala Glu Ser Thr Gly
    2135                2140                2145

Pro Lys Pro Leu Phe His Glu Val Pro Ile Pro Pro Val Ile Thr
    2150                2155                2160
```

-continued

| | | | | | | | | | | | |
|---|---|---|---|---|---|---|---|---|---|---|---|
| Glu | Thr | Arg | Thr | Glu | Val | Val | His | Val | Ile | Arg | Ser | Tyr | Asp | Pro |
| | 2165 | | | | 2170 | | | | 2175 | | |

Ser Ala Gly Asp Val Pro Gln Thr Gln Pro Glu Glu Pro Val Ser
    2180                2185                2190

Pro Lys Pro Ser Pro Thr Phe Met Glu Leu Glu Pro Lys Pro Thr
    2195                2200                2205

Thr Ser Ser Ile Lys Glu Lys Val Lys Ala Phe Gln Met Lys Ala
    2210                2215                2220

Ser Ser Glu Glu Asp Asp His Asn Arg Val Leu Ser Lys Gly Met
    2225                2230                2235

Arg Val Lys Glu Glu Thr His Ile Thr Thr Thr Arg Met Val
    2240                2245                2250

Tyr His Ser Pro Pro Gly Gly Glu Gly Ala Ser Glu Arg Ile Glu
    2255                2260                2265

Glu Thr Met Ser Val His Asp Ile Met Lys Ala Phe Gln Ser Gly
    2270                2275                2280

Arg Asp Pro Ser Lys Glu Leu Ala Gly Leu Phe Glu His Lys Ser
    2285                2290                2295

Ala Val Ser Pro Asp Val His Lys Ser Ala Ala Glu Thr Ser Ala
    2300                2305                2310

Gln His Ala Glu Lys Asp Asn Gln Met Lys Pro Lys Leu Glu Arg
    2315                2320                2325

Ile Ile Glu Val His Ile Glu Lys Gly Asn Gln Ala Glu Pro Thr
    2330                2335                2340

Glu Val Ile Ile Arg Glu Thr Lys Lys His Pro Glu Lys Glu Met
    2345                2350                2355

Tyr Val Tyr Gln Lys Asp Leu Ser Arg Gly Asp Ile Asn Leu Lys
    2360                2365                2370

Asp Phe Leu Pro Glu Lys His Asp Ala Phe Pro Cys Ser Glu Glu
    2375                2380                2385

Gln Gly Gln Gln Glu Glu Glu Leu Thr Ala Glu Glu Ser Leu
    2390                2395                2400

Pro Ser Tyr Leu Glu Ser Ser Arg Val Asn Thr Pro Val Ser Gln
    2405                2410                2415

Glu Glu Asp Ser Arg Pro Ser Ser Ala Gln Leu Ile Ser Asp Asp
    2420                2425                2430

Ser Tyr Lys Thr Leu Lys Leu Leu Ser Gln His Ser Ile Glu Tyr
    2435                2440                2445

His Asp Asp Glu Leu Ser Glu Leu Arg Gly Glu Ser Tyr Arg Phe
    2450                2455                2460

Ala Glu Lys Met Leu Leu Ser Glu Lys Leu Asp Val Ser His Ser
    2465                2470                2475

Asp Thr Glu Glu Ser Val Thr Asp His Ala Gly Pro Pro Ser Ser
    2480                2485                2490

Glu Leu Gln Gly Ser Asp Lys Arg Ser Arg Glu Lys Ile Ala Thr
    2495                2500                2505

Ala Pro Lys Lys Glu Ile Leu Ser Lys Ile Tyr Lys Asp Val Ser
    2510                2515                2520

Glu Asn Gly Val Gly Lys Val Ser Lys Asp Glu His Phe Asp Lys
    2525                2530                2535

Val Thr Val Leu His Tyr Ser Gly Asn Val Ser Ser Pro Lys His
    2540                2545                2550

Ala Met Trp Met Arg Phe Thr Glu Asp Arg Leu Asp Arg Gly Arg
    2555                2560                2565

```
Glu Lys Leu Ile Tyr Glu Asp Arg Val Asp Arg Thr Val Lys Glu
    2570            2575                2580

Ala Glu Glu Lys Leu Thr Glu Val Ser Gln Phe Phe Arg Asp Lys
    2585            2590                2595

Thr Glu Lys Leu Asn Asp Glu Leu Gln Ser Pro Glu Lys Lys Ala
    2600            2605                2610

Arg Pro Lys Asn Gly Lys Glu Tyr Ser Ser Gln Ser Pro Thr Ser
    2615            2620                2625

Ser Ser Pro Glu Lys Val Leu Leu Thr Glu Leu Leu Ala Ser Asn
    2630            2635                2640

Asp Glu Trp Val Lys Ala Arg Gln His Gly Pro Asp Gly Gln Gly
    2645            2650                2655

Phe Pro Lys Ala Glu Lys Ala Pro Ser Leu Pro Ser Ser Pro
    2660            2665                2670

Glu Lys Met Val Leu Ser Gln Gln Thr Glu Asp Ser Lys Ser Thr
    2675            2680                2685

Val Glu Ala Lys Gly Ser Ile Ser Gln Ser Lys Ala Pro Asp Gly
    2690            2695                2700

Pro Gln Ser Gly Phe Gln Leu Lys Gln Ser Lys Leu Ser Ser Ile
    2705            2710                2715

Arg Leu Lys Phe Glu Gln Gly Thr His Ala Lys Ser Lys Asp Met
    2720            2725                2730

Ser Gln Glu Asp Arg Lys Ser Asp Gly Gln Ser Arg Ile Pro Val
    2735            2740                2745

Lys Lys Ile Gln Glu Ser Lys Leu Pro Val Tyr Gln Val Phe Ala
    2750            2755                2760

Arg Glu Lys Gln Gln Lys Ala Ile Asp Leu Pro Asp Glu Ser Val
    2765            2770                2775

Ser Val Gln Lys Asp Phe Met Val Leu Lys Thr Lys Asp Glu His
    2780            2785                2790

Ala Gln Ser Asn Glu Ile Val Val Asn Asp Ser Gly Ser Asp Asn
    2795            2800                2805

Val Lys Lys Gln Arg Thr Glu Met Ser Ser Lys Ala Met Pro Asp
    2810            2815                2820

Ser Phe Ser Glu Gln Gln Ala Lys Asp Leu Ala Cys His Ile Thr
    2825            2830                2835

Ser Asp Leu Ala Thr Arg Gly Pro Trp Asp Lys Lys Val Phe Arg
    2840            2845                2850

Thr Trp Glu Ser Ser Gly Ala Thr Asn Asn Lys Ser Gln Lys Glu
    2855            2860                2865

Lys Leu Ser His Val Leu Val His Asp Val Arg Glu Asn His Ile
    2870            2875                2880

Gly His Pro Glu Ser Lys Ser Val Asp Gln Lys Asn Glu Phe Met
    2885            2890                2895

Ser Val Thr Glu Arg Glu Arg Lys Leu Leu Thr Asn Gly Ser Leu
    2900            2905                2910

Ser Glu Ile Lys Glu Met Thr Val Lys Ser Pro Ser Lys Lys Val
    2915            2920                2925

Leu Tyr Arg Glu Tyr Val Val Lys Glu Gly Asp His Pro Gly Gly
    2930            2935                2940

Leu Leu Asp Gln Pro Ser Arg Arg Ser Glu Ser Ser Ala Val Ser
    2945            2950                2955

His Ile Pro Val Arg Val Ala Asp Glu Arg Arg Met Leu Ser Ser
```

-continued

```
                2960                2965                2970

Asn Ile Pro Asp Gly Phe Cys Glu Gln Ser Ala Phe Pro Lys His
    2975                2980                2985

Glu Leu Ser Gln Lys Leu Ser Gln Ser Ser Met Ser Lys Glu Thr
    2990                2995                3000

Val Glu Thr Gln His Phe Asn Ser Ile Glu Asp Glu Lys Val Thr
    3005                3010                3015

Tyr Ser Glu Ile Ser Lys Val Ser Lys His Gln Ser Tyr Val Gly
    3020                3025                3030

Leu Cys Pro Pro Leu Glu Glu Thr Glu Thr Ser Pro Thr Lys Ser
    3035                3040                3045

Pro Asp Ser Leu Glu Phe Ser Pro Gly Lys Glu Ser Pro Ser Ser
    3050                3055                3060

Asp Val Phe Asp His Ser Pro Ile Asp Gly Leu Glu Lys Leu Ala
    3065                3070                3075

Pro Leu Ala Gln Thr Glu Gly Gly Lys Glu Ile Lys Thr Leu Pro
    3080                3085                3090

Val Tyr Val Ser Phe Val Gln Val Gly Lys Gln Tyr Glu Lys Glu
    3095                3100                3105

Ile Gln Gln Gly Gly Val Lys Lys Ile Ile Ser Gln Glu Cys Lys
    3110                3115                3120

Thr Val Gln Glu Thr Arg Gly Thr Phe Tyr Thr Thr Arg Gln Gln
    3125                3130                3135

Lys Gln Pro Pro Ser Pro Gln Gly Ser Pro Glu Asp Asp Thr Leu
    3140                3145                3150

Glu Gln Val Ser Phe Leu Asp Ser Ser Gly Lys Ser Pro Leu Thr
    3155                3160                3165

Pro Glu Thr Pro Ser Ser Glu Glu Val Ser Tyr Glu Phe Thr Ser
    3170                3175                3180

Lys Thr Pro Asp Ser Leu Ile Ala Tyr Ile Pro Gly Lys Pro Ser
    3185                3190                3195

Pro Ile Pro Glu Val Ser Glu Glu Ser Glu Glu Glu Gln Ala
    3200                3205                3210

Lys Ser Thr Ser Leu Lys Gln Thr Thr Val Glu Glu Thr Ala Val
    3215                3220                3225

Glu Arg Glu Met Pro Asn Asp Val Ser Lys Asp Ser Asn Gln Arg
    3230                3235                3240

Pro Lys Asn Asn Arg Val Ala Tyr Ile Glu Phe Pro Pro Pro Pro
    3245                3250                3255

Pro Leu Asp Ala Asp Gln Ile Glu Ser Asp Lys Lys His His Tyr
    3260                3265                3270

Leu Pro Glu Lys Glu Val Asp Met Ile Glu Val Asn Leu Gln Asp
    3275                3280                3285

Glu His Asp Lys Tyr Gln Leu Ala Glu Pro Val Ile Arg Val Gln
    3290                3295                3300

Pro Pro Ser Pro Val Pro Gly Ala Asp Val Ser Asp Ser Ser
    3305                3310                3315

Asp Asp Glu Ser Ile Tyr Gln Pro Val Pro Val Lys Lys Tyr Thr
    3320                3325                3330

Phe Lys Leu Lys Glu Val Asp Asp Glu Gln Lys Glu Lys Pro Lys
    3335                3340                3345

Ala Ser Ala Glu Lys Ala Ser Asn Gln Lys Glu Leu Glu Ser Asn
    3350                3355                3360
```

-continued

```
Gly Ser Gly Lys Asp Asn Glu Phe Gly Leu Gly Leu Asp Ser Pro
3365                3370                3375

Gln Asn Glu Ile Ala Gln Asn Gly Asn Asn Asp Gln Ser Ile Thr
3380                3385                3390

Glu Cys Ser Ile Ala Thr Thr Ala Glu Phe Ser His Asp Thr Asp
3395                3400                3405

Ala Thr Glu Ile Asp Ser Leu Asp Gly Tyr Asp Leu Gln Asp Glu
3410                3415                3420

Asp Asp Gly Leu Thr Glu Ser Asp Ser Lys Leu Pro Ile Gln Ala
3425                3430                3435

Met Glu Ile Lys Lys Asp Ile Trp Asn Thr Glu Gly Ile Leu Lys
3440                3445                3450

Pro Ala Asp Arg Ser Phe Ser Gln Ser Lys Leu Glu Val Ile Glu
3455                3460                3465

Glu Glu Gly Lys Val Gly Pro Asp Glu Asp Lys Pro Pro Ser Lys
3470                3475                3480

Ser Ser Ser Ser Glu Lys Thr Pro Asp Lys Thr Asp Gln Lys Ser
3485                3490                3495

Gly Ala Gln Phe Phe Thr Leu Glu Gly Arg His Pro Asp Arg Ser
3500                3505                3510

Val Phe Pro Asp Thr Tyr Phe Ser Tyr Lys Val Asp Glu Glu Phe
3515                3520                3525

Ala Thr Pro Phe Lys Thr Val Ala Thr Lys Gly Leu Asp Phe Asp
3530                3535                3540

Pro Trp Ser Asn Asn Arg Gly Asp Asp Glu Val Phe Asp Ser Lys
3545                3550                3555

Ser Arg Glu Asp Glu Thr Lys Pro Phe Gly Leu Ala Val Glu Asp
3560                3565                3570

Arg Ser Pro Ala Thr Thr Pro Asp Thr Thr Pro Ala Arg Thr Pro
3575                3580                3585

Thr Asp Glu Ser Thr Pro Thr Ser Glu Pro Asn Pro Phe Pro Phe
3590                3595                3600

His Glu Gly Lys Met Phe Glu Met Thr Arg Ser Gly Ala Ile Asp
3605                3610                3615

Met Ser Lys Arg Asp Phe Val Glu Glu Arg Leu Gln Phe Phe Gln
3620                3625                3630

Ile Gly Glu His Thr Ser Glu Gly Lys Ser Gly Asp Gln Gly Glu
3635                3640                3645

Gly Asp Lys Ser Met Val Thr Ala Thr Pro Gln Pro Gln Ser Gly
3650                3655                3660

Asp Thr Thr Val Glu Thr Asn Leu Glu Arg Asn Val Glu Thr Pro
3665                3670                3675

Thr Val Glu Pro Asn Pro Ser Ile Pro Thr Ser Gly Glu Cys Gln
3680                3685                3690

Glu Gly Thr Ser Ser Ser Gly Ser Leu Glu Lys Ser Ala Ala Ala
3695                3700                3705

Thr Asn Thr Ser Lys Val Asp Pro Lys Leu Arg Thr Pro Ile Lys
3710                3715                3720

Met Gly Ile Ser Ala Ser Thr Met Thr Met Lys Lys Glu Gly Pro
3725                3730                3735

Gly Glu Ile Thr Asp Lys Ile Glu Ala Val Met Thr Ser Cys Gln
3740                3745                3750

Gly Leu Glu Asn Glu Thr Ile Thr Met Ile Ser Asn Thr Ala Asn
3755                3760                3765
```

-continued

Ser Gln Met Gly Val Arg Pro His Glu Lys His Asp Phe Gln Lys
3770                    3775                    3780

Asp Asn Phe Asn Asn Asn Asn Leu Asp Ser Ser Thr Ile Gln
3785                    3790                    3795

Thr Asp Asn Ile Met Ser Asn Ile Val Leu Thr Glu His Ser Ala
3800                    3805                    3810

Pro Thr Cys Thr Thr Glu Lys Asp Asn Pro Val Lys Val Ser Ser
3815                    3820                    3825

Gly Lys Lys Thr Gly Val Leu Gln Gly His Cys Val Arg Asp Lys
3830                    3835                    3840

Gln Lys Val Leu Gly Glu Gln Gln Lys Thr Lys Glu Leu Ile Gly
3845                    3850                    3855

Ile Arg Gln Lys Ser Lys Leu Pro Ile Lys Ala Thr Ser Pro Lys
3860                    3865                    3870

Asp Thr Phe Pro Pro Asn His Met Ser Asn Thr Lys Ala Ser Lys
3875                    3880                    3885

Met Lys Gln Val Ser Gln Ser Glu Lys Thr Lys Ala Leu Thr Thr
3890                    3895                    3900

Ser Ser Cys Val Asp Val Lys Ser Arg Ile Pro Val Lys Asn Thr
3905                    3910                    3915

His Arg Asp Asn Ile Ile Ala Val Arg Lys Ala Cys Ala Thr Gln
3920                    3925                    3930

Lys Gln Gly Gln Pro Glu Lys Gly Lys Ala Lys Gln Leu Pro Ser
3935                    3940                    3945

Lys Leu Pro Val Lys Val Arg Ser Thr Cys Val Thr Thr Thr Thr
3950                    3955                    3960

Thr Thr Ala Thr Thr Thr Thr Thr Thr Thr Thr Thr Thr Thr Thr
3965                    3970                    3975

Ser Cys Thr Val Lys Val Arg Lys Ser Gln Leu Lys Glu Val Cys
3980                    3985                    3990

Lys His Ser Ile Glu Tyr Phe Lys Gly Ile Ser Gly Glu Thr Leu
3995                    4000                    4005

Lys Leu Val Asp Arg Leu Ser Glu Glu Lys Lys Met Gln Ser
4010                    4015                    4020

Glu Leu Ser Asp Glu Glu Glu Ser Thr Ser Arg Asn Thr Ser Leu
4025                    4030                    4035

Ser Glu Thr Ser Arg Gly Gly Gln Pro Ser Val Thr Thr Lys Ser
4040                    4045                    4050

Ala Arg Asp Lys Lys Thr Glu Ala Ala Pro Leu Lys Ser Lys Ser
4055                    4060                    4065

Glu Lys Ala Gly Ser Glu Lys Arg Ser Ser Arg Arg Thr Gly Pro
4070                    4075                    4080

Gln Ser Pro Cys Glu Arg Thr Asp Ile Arg Met Ala Ile Val Ala
4085                    4090                    4095

Asp His Leu Gly Leu Ser Trp Thr Glu Leu Ala Arg Glu Leu Asn
4100                    4105                    4110

Phe Ser Val Asp Glu Ile Asn Gln Ile Arg Val Glu Asn Pro Asn
4115                    4120                    4125

Ser Leu Ile Ser Gln Ser Phe Met Leu Leu Lys Lys Trp Val Thr
4130                    4135                    4140

Arg Asp Gly Lys Asn Ala Thr Thr Asp Ala Leu Thr Ser Val Leu
4145                    4150                    4155

Thr Lys Ile Asn Arg Ile Asp Ile Val Thr Leu Leu Glu Gly Pro

-continued

```
                  4160           4165                    4170
Ile Phe Asp Tyr Gly Asn Ile Ser Gly Thr Arg Ser Phe Ala Asp
    4175                4180                4185

Glu Asn Asn Val Phe His Asp Pro Val Asp Gly Trp Gln Asn Glu
    4190                4195                4200

Thr Ser Ser Gly Asn Leu Glu Ser Cys Ala Gln Ala Arg Arg Val
    4205                4210                4215

Thr Gly Gly Leu Leu Asp Arg Leu Asp Asp Ser Pro Asp Gln Cys
    4220                4225                4230

Arg Asp Ser Ile Thr Ser Tyr Leu Lys Gly Glu Ala Gly Lys Phe
    4235                4240                4245

Glu Ala Asn Gly Ser His Thr Glu Ile Thr Pro Glu Ala Lys Thr
    4250                4255                4260

Lys Ser Tyr Phe Pro Glu Ser Gln Asn Asp Val Gly Lys Gln Ser
    4265                4270                4275

Thr Lys Glu Thr Leu Lys Pro Lys Ile His Gly Ser Gly His Val
    4280                4285                4290

Glu Glu Pro Ala Ser Pro Leu Ala Ala Tyr Gln Lys Ser Leu Glu
    4295                4300                4305

Glu Thr Ser Lys Leu Ile Ile Glu Glu Thr Lys Pro Cys Val Pro
    4310                4315                4320

Val Ser Met Lys Lys Met Ser Arg Thr Ser Pro Ala Asp Gly Lys
    4325                4330                4335

Pro Arg Leu Ser Leu His Glu Glu Glu Gly Ser Ser Gly Ser Glu
    4340                4345                4350

Gln Lys Gln Gly Glu Gly Phe Lys Val Lys Thr Lys Lys Glu Ile
    4355                4360                4365

Arg His Val Glu Lys Lys Ser His Ser
    4370                4375

<210> SEQ ID NO 67
<211> LENGTH: 5298
<212> TYPE: DNA
<213> ORGANISM: Mus musculus

<400> SEQUENCE: 67
atgagtgaag agccaaagga gaagcccgcc aagcctgctc ataggaagag gaaaggaaaa      60
aagtctgatg ccaacgcaag ttacttaaga gcagctcggg cagggcacct ggaaaaggcc     120
cttgactaca tcaaaaatgg agtggacgtc aacatctgta accagaatgg attgaatgca     180
ctccatcttg cttccaaaga aggccatgtg gaagtggtct ctgagctgct gcagagggaa     240
gccaatgttg atgccgccac aaagaaagga aacacggcct acacatcgc atctttggct      300 gggcaagcgg aagtggtcaa ggtcttggtt acgaacggag cgaatgtcaa cgcacaatct     360
cagaatggct tcacaccatt gtatatggca gcccaggaga accacctgga agtcgtcagg     420
tttcttctgg acaatggcgc cagccaaagc ctggccacag aggacggctt cacgccattg     480
gccgtggctc tgcaacaagg tcatgaccaa gtcgtgtccc tcctgctcga gaacgacacg     540
aagggaaaag tgcgcctccc agccctccac atcgcagccc ggaaagacga caccaaggca     600
gcagctctgc tcctgcagaa tgacacaaac gcggacgtgg agtcaaagag tggcttcacc     660
ccgctccaca tagctgccca ctatgggaac atcaatgtgg ccacgttgct gttaaaccga     720
gcggctgctg tggacttcac cgcacggaat gacatcactc ccttacacgt tgcctcgaag     780
cgaggaaatg caaatatggt gaagctattg ctggaccggg tgcgaagat cgatgccaag     840
```

```
accagggacg gtctgactcc gttgcactgt ggggcgagaa gtggccatga gcaggtggta    900
gagatgttgc ttgacagatc cgcccccatc ctttcaaaaa ccaagaatgg attgtcgcca    960
ctgcacatgg ccacacaagg agaccattta aactgcgtcc aactcctcct ccagcacaac   1020
gtgcccgtgg acgacgtcac caacgactac ctgactgccc tccatgtggc tgcccactgc   1080
ggccattaca aagttgccaa ggttcttttg gataagaaag ctagccccaa tgccaaagcc   1140
ctgaatggct tcacccctct ccatatcgcc tgcaaaaaga accgcatccg agtaatggaa   1200
ctccttttga agcacggtgc atctattcaa gccgtaaccg agtcgggcct taccccaatc   1260
catgttgctg ccttcatggg acatgtaaat atcgtgtcac agctaatgca tcatggagcc   1320
tccccaaaca ccaccaatgt gagaggagag acggcattgc atatggcggc tcggtccgga   1380
caagcagaag tggtgcggta tctggtccaa gatggggctc aggtagaagc aaaagctaag   1440
gatgaccaga ctccactcca catctcagcc cgacttggga aagctgacat agtgcaacaa   1500
ctgttacagc aaggagcatc ccccaatgca gcaacaactt ctgggtacac ccccttcac    1560
cttgcggcca gagaggggca tgaggatgta gctgcgttcc tcctggatca tggagcatct   1620
ttatccataa caacaaagaa gggattcacc cctctgcacg tggcagccaa atacggaaag   1680
cttgaagtcg caagtctcct gctgcagaag agtgcgtctc ccgatgccgc agggaagagc   1740
gggctaactc cactgcatgt agcagcgcat tacgataatc agaaagtggc ccttctgctc   1800
ttggaccagg agcctcacc ccacgcagcc gcaaagaacg gctatacacc actgcacatc    1860
gcggccaaga agaaccagat ggacatagcc acgtccctgc tggagtacgg tgctgatgca   1920
aacgcggtta cccggcaagg gattgcgtcc gtccatcttg cggcacagga agggcacgtg   1980
gacatggtgt cgctgctcct gagtagaaac gcgaatgtca acctgagcaa taagagcggt   2040
ctcacccac tccacctggc tgctcaagaa gaccgagtga atgtggccga ggtccttgtc    2100
aaccagggg cccatgtgga tgctcagaca aagatgggct acaccccgct ccatgtgggc    2160
tgtcactatg gaaatatcaa aatagtcaat tttctgctgc agcattctgc aaaagttaat   2220
gccaagacga agaatggata cacagcactg caccaggctg ctcagcaggg ccacacgcat   2280
atcatcaatg tcttgcttca gaacaacgcc tcccccaatg aactcactgt gaatgggaac   2340
acagctctgg ccatcgcccg cgcccttggt tacatctcgg tggttgacac actgaaggtc   2400
gtgacggagg aaaattatgac caccactacc atcacggaga agcacaaaat gaatgtccca   2460
gaaacgatga atgaagtcct cgatatgtca gacgatgaag taaggaaagc cagcgcccccc  2520
gaaaagctca gtgatgggga atatatctca gacggtgaag aaggtgataa atgcacatgg   2580
ttcaaaattc ccaaagtaca ggaggttttg gtgaaaagtg aagatgccat cacaggggac   2640
actgacaagt atctcgggcc acaggacctt aaggagctag gtgatgactc cctgccagca   2700
gaaggttacg taggcttcag tcttggagcc cgttctgcca gcctccgctc cttcagttcg   2760
gataggtcct acaccttgaa cagaagctcc tacgcaaggg acagcatgat gatagaggaa   2820
cttctggtac catccaaaga gcagcacctg acgttcacga gggagtttga ttctgactcc   2880
ctcagacact acagttgggc agcggacacg ttagataatg tgaacctggt ctcaagcccg   2940
gtgcattctg ggtttctggt tagctttatg gtggacgcga gaggggctc catgcgagga    3000
agccgccacc acgggatgcg gatcatcatc cctcgcgcaa agtgtacggc ccccacccgc   3060
atcacgtgcc gcctggtaaa gagacataaa ctggccaacc cacccccat ggtggaagga    3120
gagggattag ccagtaggct ggtagaaatg ggtcctgcgg gggcacaatt tttaggcccc   3180
gtcattgtgg aaatccctca ttttgggtcc atgagggggga aggagagaga acttatcgtc   3240
```

```
cttcggagcg agaacggaga gacctggaag gaacatcagt ttgacagtaa aaacgaagac    3300
ctcgcggagc ttctcaatgg catggatgaa gaactcgaca gcccggaaga gttgggtaca    3360
aagcgcatct gcagaattat cacaaaggat ttcccccagt attttgccgt ggtttcccgg    3420
attaagcagg aaagcaacca gatcggtcct gagggtggga ttctgagcag caccaccgtg    3480
cccctcgtcc aggcctcctt cccagagggc gccttaacca agaggatccg tgtgggtctc    3540
caggctcagc ccgtgccaga ggaaacggta aaaaaaatcc ttgggaacaa agcaacattt    3600
agcccaattg tcacggtaga gccgaggaga aggaagttcc ataagccgat caccatgacc    3660
attccggtgc cccgccctc gggagaaggc gtgtccaatg ggtacaaggg ggatgccacg    3720
cccaacctgc ggctcctctg cagcatcaca ggaggcacct caccagctca atgggaagac    3780
atcacaggaa caaccctct gacgttcata aaggattgtg tgtctttcac aaccaacgtt    3840
tcagccagat tctggctggc ggactgccat caggtgttag agaccgtagg gctagcctcc    3900
cagctgtaca gagagctgat atgcgttccc tacatggcca agttcgttgt gtttgccaaa    3960
acaaacgacc cggtggagtc ctcgctgagg tgcttctgta tgacagacga cagggtggac    4020
aaaaccctgg agcagcagga gaacttcgag gaggttgcca gaagcaaaga cattgaggtt    4080
ctggaaggaa agcccatcta cgttgattgc tatggaaacc tggcccctct gaccaaagga    4140
ggacagcagc ttgttttttaa cttttattct ttcaaagaaa acagactgcc attttccatc    4200
aagatcagag acaccagtca agagccctgt ggccgcctgt ctttcctgaa ggagccaaag    4260
acaacaaagg gattaccccca aacagctgtt tgcaacttaa atattactct gccggcacat    4320
aaaaaggctg agaaggcaga cagacgccag agctttgcct ccctagcttt acgtaagcgc    4380
tacagctact tgactgaacc cagcatgagt ccgcagagtc cttgtgagcg gacggatatc    4440
aggatggcga tagtagccga tcacctggga cttagttgga cagagctggc aagggaactg    4500 aattttttcag tggatgaaat caaccaaata cgtgtggaaa atcccaattc tttaatttct    4560
cagagcttca tgttattaaa aaagtgggtg accagagacg gaaagaatgc cacaactgat    4620
gccttaactt cggtcttaac gaagattaac cggatagaca ttgtaactct gctggaagga    4680
ccaatatttg attatgggaa tatttcaggc accagaagct ttgcagatga aaacaatgtt    4740
ttccatgacc cagttgatgg ttggcagaac gagacgccaa gtggaagcct agagtcccca    4800
gcgcaagctc gaagactaac tggtgggtta ctggaccgtc tggatgacag ctctgaccag    4860
gctcgggatt ctattacctc atacctcacg ggagaacctg ggaagatcga agcaaatgga    4920
aaccacacag cggaagtcat tccagaagca aaggcaaaac cctacttccc ggaatcccaa    4980
aacgatatag ggaaacagag catcaaggag aacctgaaac caaaaacaca cggatgtggt    5040
cgcactgagg aaccagtgtc gccccctcaca gcctaccaga atctctggga gaaaccagc    5100 aagcttgtca tagaagacgc acctaaaccc tgtgtgcctg tcggcatgaa aaagatgacc    5160
aggactacgg ctgacggcaa agccaggctc aacctccagg aagaagaggg gtccaccagg    5220
tcagagccta agcagggaga aggctataag gtgaagacga agaaggaaat ccggaacgtg    5280
gagaagaaaa cccactag                                                   5298
```

<210> SEQ ID NO 68
<211> LENGTH: 1961
<212> TYPE: PRT
<213> ORGANISM: Mus musculus

<400> SEQUENCE: 68

Met Ser Glu Glu Pro Lys Glu Lys Pro Ala Lys Pro Ala His Arg Lys
1               5                   10                  15

```
Arg Lys Gly Lys Lys Ser Asp Ala Asn Ala Ser Tyr Leu Arg Ala Ala
            20                  25                  30

Arg Ala Gly His Leu Glu Lys Ala Leu Asp Tyr Ile Lys Asn Gly Val
        35                  40                  45

Asp Val Asn Ile Cys Asn Gln Asn Gly Leu Asn Ala Leu His Leu Ala
50                  55                  60

Ser Lys Glu Gly His Val Glu Val Val Ser Glu Leu Leu Gln Arg Glu
65                  70                  75                  80

Ala Asn Val Asp Ala Ala Thr Lys Lys Gly Asn Thr Ala Leu His Ile
            85                  90                  95

Ala Ser Leu Ala Gly Gln Ala Glu Val Val Lys Val Leu Val Thr Asn
            100                 105                 110

Gly Ala Asn Val Asn Ala Gln Ser Gln Asn Gly Phe Thr Pro Leu Tyr
            115                 120                 125

Met Ala Ala Gln Glu Asn His Leu Glu Val Val Arg Phe Leu Leu Asp
            130                 135                 140

Asn Gly Ala Ser Gln Ser Leu Ala Thr Glu Asp Gly Phe Thr Pro Leu
145                 150                 155                 160

Ala Val Ala Leu Gln Gln Gly His Asp Gln Val Val Ser Leu Leu Leu
            165                 170                 175

Glu Asn Asp Thr Lys Gly Lys Val Arg Leu Pro Ala Leu His Ile Ala
            180                 185                 190

Ala Arg Lys Asp Asp Thr Lys Ala Ala Leu Leu Leu Gln Asn Asp
            195                 200                 205

Thr Asn Ala Asp Val Glu Ser Lys Ser Gly Phe Thr Pro Leu His Ile
210                 215                 220

Ala Ala His Tyr Gly Asn Ile Asn Val Ala Thr Leu Leu Leu Asn Arg
225                 230                 235                 240

Ala Ala Ala Val Asp Phe Thr Ala Arg Asn Asp Ile Thr Pro Leu His
            245                 250                 255

Val Ala Ser Lys Arg Gly Asn Ala Asn Met Val Lys Leu Leu Leu Asp
            260                 265                 270

Arg Gly Ala Lys Ile Asp Ala Lys Thr Arg Asp Gly Leu Thr Pro Leu
            275                 280                 285

His Cys Gly Ala Arg Ser Gly His Glu Gln Val Val Glu Met Leu Leu
            290                 295                 300

Asp Arg Ser Ala Pro Ile Leu Ser Lys Thr Lys Asn Gly Leu Ser Pro
305                 310                 315                 320

Leu His Met Ala Thr Gln Gly Asp His Leu Asn Cys Val Gln Leu Leu
            325                 330                 335

Leu Gln His Asn Val Pro Val Asp Asp Val Thr Asn Asp Tyr Leu Thr
            340                 345                 350

Ala Leu His Val Ala Ala His Cys Gly His Tyr Lys Val Ala Lys Val
            355                 360                 365

Leu Leu Asp Lys Lys Ala Ser Pro Asn Ala Lys Ala Leu Asn Gly Phe
            370                 375                 380

Thr Pro Leu His Ile Ala Cys Lys Lys Asn Arg Ile Arg Val Met Glu
385                 390                 395                 400

Leu Leu Leu Lys His Gly Ala Ser Ile Gln Ala Val Thr Glu Ser Gly
            405                 410                 415

Leu Thr Pro Ile His Val Ala Ala Phe Met Gly His Val Asn Ile Val
            420                 425                 430

Ser Gln Leu Met His His Gly Ala Ser Pro Asn Thr Thr Asn Val Arg
```

```
                435                 440                 445
Gly Glu Thr Ala Leu His Met Ala Ala Arg Ser Gly Gln Ala Glu Val
            450                 455                 460

Val Arg Tyr Leu Val Gln Asp Gly Ala Gln Val Glu Ala Lys Ala Lys
465                 470                 475                 480

Asp Asp Gln Thr Pro Leu His Ile Ser Ala Arg Leu Gly Lys Ala Asp
                485                 490                 495

Ile Val Gln Gln Leu Leu Gln Gln Gly Ala Ser Pro Asn Ala Ala Thr
            500                 505                 510

Thr Ser Gly Tyr Thr Pro Leu His Leu Ala Ala Arg Glu Gly His Glu
        515                 520                 525

Asp Val Ala Ala Phe Leu Leu Asp His Gly Ala Ser Leu Ser Ile Thr
530                 535                 540

Thr Lys Lys Gly Phe Thr Pro Leu His Val Ala Ala Lys Tyr Gly Lys
545                 550                 555                 560

Leu Glu Val Ala Ser Leu Leu Leu Gln Lys Ser Ala Ser Pro Asp Ala
                565                 570                 575

Ala Gly Lys Ser Gly Leu Thr Pro Leu His Val Ala Ala His Tyr Asp
            580                 585                 590

Asn Gln Lys Val Ala Leu Leu Leu Asp Gln Gly Ala Ser Pro His
        595                 600                 605

Ala Ala Ala Lys Asn Gly Tyr Thr Pro Leu His Ile Ala Ala Lys Lys
610                 615                 620

Asn Gln Met Asp Ile Ala Thr Ser Leu Leu Glu Tyr Gly Ala Asp Ala
625                 630                 635                 640

Asn Ala Val Thr Arg Gln Gly Ile Ala Ser Val His Leu Ala Ala Gln
                645                 650                 655

Glu Gly His Val Asp Met Val Ser Leu Leu Leu Ser Arg Asn Ala Asn
            660                 665                 670

Val Asn Leu Ser Asn Lys Ser Gly Leu Thr Pro Leu His Leu Ala Ala
        675                 680                 685

Gln Glu Asp Arg Val Asn Val Ala Glu Val Leu Val Asn Gln Gly Ala
690                 695                 700

His Val Asp Ala Gln Thr Lys Met Gly Tyr Thr Pro Leu His Val Gly
705                 710                 715                 720

Cys His Tyr Gly Asn Ile Lys Ile Val Asn Phe Leu Leu Gln His Ser
                725                 730                 735

Ala Lys Val Asn Ala Lys Thr Lys Asn Gly Tyr Thr Ala Leu His Gln
            740                 745                 750

Ala Ala Gln Gln Gly His Thr His Ile Ile Asn Val Leu Leu Gln Asn
        755                 760                 765

Asn Ala Ser Pro Asn Glu Leu Thr Val Asn Gly Asn Thr Ala Leu Ala
770                 775                 780

Ile Ala Arg Arg Leu Gly Tyr Ile Ser Val Val Asp Thr Leu Lys Val
785                 790                 795                 800

Val Thr Glu Glu Ile Met Thr Thr Thr Ile Thr Glu Lys His Lys
                805                 810                 815

Met Asn Val Pro Glu Thr Met Asn Glu Val Leu Asp Met Ser Asp Asp
            820                 825                 830

Glu Val Arg Lys Ala Ser Ala Pro Glu Lys Leu Ser Asp Gly Glu Tyr
        835                 840                 845

Ile Ser Asp Gly Glu Glu Gly Asp Lys Cys Thr Trp Phe Lys Ile Pro
850                 855                 860
```

```
Lys Val Gln Glu Val Leu Val Lys Ser Glu Asp Ala Ile Thr Gly Asp
865                 870                 875                 880

Thr Asp Lys Tyr Leu Gly Pro Gln Asp Leu Lys Glu Leu Gly Asp Asp
                885                 890                 895

Ser Leu Pro Ala Glu Gly Tyr Val Gly Phe Ser Leu Gly Ala Arg Ser
            900                 905                 910

Ala Ser Leu Arg Ser Phe Ser Ser Asp Arg Ser Tyr Thr Leu Asn Arg
        915                 920                 925

Ser Ser Tyr Ala Arg Asp Ser Met Met Ile Glu Glu Leu Leu Val Pro
930                 935                 940

Ser Lys Glu Gln His Leu Thr Phe Thr Arg Glu Phe Asp Ser Asp Ser
945                 950                 955                 960

Leu Arg His Tyr Ser Trp Ala Ala Asp Thr Leu Asp Asn Val Asn Leu
                965                 970                 975

Val Ser Ser Pro Val His Ser Gly Phe Leu Val Ser Phe Met Val Asp
            980                 985                 990

Ala Arg Gly Gly Ser Met Arg Gly Ser Arg His His Gly Met Arg Ile
        995                 1000                1005

Ile Ile Pro Pro Arg Lys Cys Thr Ala Pro Thr Arg Ile Thr Cys
1010                1015                1020

Arg Leu Val Lys Arg His Lys Leu Ala Asn Pro Pro Met Val
1025                1030                1035

Glu Gly Glu Gly Leu Ala Ser Arg Leu Val Glu Met Gly Pro Ala
1040                1045                1050

Gly Ala Gln Phe Leu Gly Pro Val Ile Val Glu Ile Pro His Phe
1055                1060                1065

Gly Ser Met Arg Gly Lys Glu Arg Glu Leu Ile Val Leu Arg Ser
1070                1075                1080

Glu Asn Gly Glu Thr Trp Lys Glu His Gln Phe Asp Ser Lys Asn
1085                1090                1095

Glu Asp Leu Ala Glu Leu Leu Asn Gly Met Asp Glu Glu Leu Asp
1100                1105                1110

Ser Pro Glu Glu Leu Gly Thr Lys Arg Ile Cys Arg Ile Ile Thr
1115                1120                1125

Lys Asp Phe Pro Gln Tyr Phe Ala Val Val Ser Arg Ile Lys Gln
1130                1135                1140

Glu Ser Asn Gln Ile Gly Pro Glu Gly Gly Ile Leu Ser Ser Thr
1145                1150                1155

Thr Val Pro Leu Val Gln Ala Ser Phe Pro Glu Gly Ala Leu Thr
1160                1165                1170

Lys Arg Ile Arg Val Gly Leu Gln Ala Gln Pro Val Pro Glu Glu
1175                1180                1185

Thr Val Lys Lys Ile Leu Gly Asn Lys Ala Thr Phe Ser Pro Ile
1190                1195                1200

Val Thr Val Glu Pro Arg Arg Arg Lys Phe His Lys Pro Ile Thr
1205                1210                1215

Met Thr Ile Pro Val Pro Pro Ser Gly Glu Gly Val Ser Asn
1220                1225                1230

Gly Tyr Lys Gly Asp Ala Thr Pro Asn Leu Arg Leu Leu Cys Ser
1235                1240                1245

Ile Thr Gly Gly Thr Ser Pro Ala Gln Trp Glu Asp Ile Thr Gly
1250                1255                1260

Thr Thr Pro Leu Thr Phe Ile Lys Asp Cys Val Ser Phe Thr Thr
1265                1270                1275
```

```
Asn Val Ser Ala Arg Phe Trp Leu Ala Asp Cys His Gln Val Leu
    1280            1285            1290

Glu Thr Val Gly Leu Ala Ser Gln Leu Tyr Arg Glu Leu Ile Cys
    1295            1300            1305

Val Pro Tyr Met Ala Lys Phe Val Val Phe Ala Lys Thr Asn Asp
    1310            1315            1320

Pro Val Glu Ser Ser Leu Arg Cys Phe Cys Met Thr Asp Asp Arg
    1325            1330            1335

Val Asp Lys Thr Leu Glu Gln Gln Glu Asn Phe Glu Glu Val Ala
    1340            1345            1350

Arg Ser Lys Asp Ile Glu Val Leu Glu Gly Lys Pro Ile Tyr Val
    1355            1360            1365

Asp Cys Tyr Gly Asn Leu Ala Pro Leu Thr Lys Gly Gly Gln Gln
    1370            1375            1380

Leu Val Phe Asn Phe Tyr Ser Phe Lys Glu Asn Arg Leu Pro Phe
    1385            1390            1395

Ser Ile Lys Ile Arg Asp Thr Ser Gln Glu Pro Cys Gly Arg Leu
    1400            1405            1410

Ser Phe Leu Lys Glu Pro Lys Thr Thr Lys Gly Leu Pro Gln Thr
    1415            1420            1425

Ala Val Cys Asn Leu Asn Ile Thr Leu Pro Ala His Lys Lys Ala
    1430            1435            1440

Glu Lys Ala Asp Arg Arg Gln Ser Phe Ala Ser Leu Ala Leu Arg
    1445            1450            1455

Lys Arg Tyr Ser Tyr Leu Thr Glu Pro Ser Met Ser Pro Gln Ser
    1460            1465            1470

Pro Cys Glu Arg Thr Asp Ile Arg Met Ala Ile Val Ala Asp His
    1475            1480            1485

Leu Gly Leu Ser Trp Thr Glu Leu Ala Arg Glu Leu Asn Phe Ser
    1490            1495            1500

Val Asp Glu Ile Asn Gln Ile Arg Val Glu Asn Pro Asn Ser Leu
    1505            1510            1515

Ile Ser Gln Ser Phe Met Leu Leu Lys Lys Trp Val Thr Arg Asp
    1520            1525            1530

Gly Lys Asn Ala Thr Thr Asp Ala Leu Thr Ser Val Leu Thr Lys
    1535            1540            1545

Ile Asn Arg Ile Asp Ile Val Thr Leu Leu Glu Gly Pro Ile Phe
    1550            1555            1560

Asp Tyr Gly Asn Ile Ser Gly Thr Arg Ser Phe Ala Asp Glu Asn
    1565            1570            1575

Asn Val Phe His Asp Pro Val Asp Gly His Pro Ser Phe Gln Val
    1580            1585            1590

Glu Leu Glu Thr Pro Met Gly Leu Tyr Trp Thr Pro Pro Asn Pro
    1595            1600            1605

Phe Gln Gln Asp Asp His Phe Ser Asp Ile Ser Ser Ile Glu Ser
    1610            1615            1620

Pro Phe Arg Thr Pro Ser Arg Leu Ser Asp Gly Leu Val Pro Ser
    1625            1630            1635

Gln Gly Asn Ile Glu His Pro Thr Gly Gly Pro Pro Val Val Thr
    1640            1645            1650

Ala Glu Asp Thr Ser Leu Glu Asp Ser Lys Met Asp Asp Ser Val
    1655            1660            1665

Thr Val Thr Asp Pro Ala Asp Pro Leu Asp Val Asp Glu Ser Gln
```

| | | | | |
|---|---|---|---|---|
| | 1670 | | 1675 | 1680 |

Leu Lys Asp Leu Cys Gln Ser Glu Cys Ala Gln Cys Trp Ala Ser
1685              1690              1695

Val Pro Gly Ile Pro Asn Asp Gly Arg Gln Ala Glu Pro Leu Arg
1700              1705              1710

Pro Gln Thr Arg Lys Val Gly Met Ser Ser Glu Gln Gln Glu Lys
1715              1720              1725

Gly Lys Ser Gly Pro Asp Glu Glu Val Thr Glu Asp Lys Val Lys
1730              1735              1740

Ser Leu Phe Glu Asp Ile Gln Leu Glu Glu Val Glu Ala Glu Glu
1745              1750              1755

Met Thr Glu Asp Gln Gly Gln Ala Met Leu Asn Arg Val Gln Arg
1760              1765              1770

Ala Glu Leu Ala Met Ser Ser Leu Ala Gly Trp Gln Asn Glu Thr
1775              1780              1785

Pro Ser Gly Ser Leu Glu Ser Pro Ala Gln Ala Arg Arg Leu Thr
1790              1795              1800

Gly Gly Leu Leu Asp Arg Leu Asp Asp Ser Ser Asp Gln Ala Arg
1805              1810              1815

Asp Ser Ile Thr Ser Tyr Leu Thr Gly Glu Pro Gly Lys Ile Glu
1820              1825              1830

Ala Asn Gly Asn His Thr Ala Glu Val Ile Pro Glu Ala Lys Ala
1835              1840              1845

Lys Pro Tyr Phe Pro Glu Ser Gln Asn Asp Ile Gly Lys Gln Ser
1850              1855              1860

Ile Lys Glu Asn Leu Lys Pro Lys Thr His Gly Cys Gly Arg Thr
1865              1870              1875

Glu Glu Pro Val Ser Pro Leu Thr Ala Tyr Gln Lys Ser Leu Glu
1880              1885              1890

Glu Thr Ser Lys Leu Val Ile Glu Asp Ala Pro Lys Pro Cys Val
1895              1900              1905

Pro Val Gly Met Lys Lys Met Thr Arg Thr Thr Ala Asp Gly Lys
1910              1915              1920

Ala Arg Leu Asn Leu Gln Glu Glu Glu Gly Ser Thr Arg Ser Glu
1925              1930              1935

Pro Lys Gln Gly Glu Gly Tyr Lys Val Lys Thr Lys Lys Glu Ile
1940              1945              1950

Arg Asn Val Glu Lys Lys Thr His
1955              1960

<210> SEQ ID NO 69
<211> LENGTH: 2466
<212> TYPE: DNA
<213> ORGANISM: Homo sapiens

<400> SEQUENCE: 69

```
atggtcagct ggggtcgttt catctgcctg gtcgtggtca ccatggcaac cttgtccctg      60
gcccggcccc ccttcagttt agttgaggat accacattag agccagaaga gccaccaacc     120
aaataccaaa tctctcaacc agaagtgtac gtggctgcgc caggggagtc gctagaggtg     180
cgctgcctgt tgaaagatgc cgccgtgatc agttggacta aggatggggt gcacttgggg     240
cccaacaata ggacagtgct tattgggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
```

```
gaagattttg tcagtgagaa cagtaacaac aagagagcac catactgac caacacagaa      480 aagatggaaa agcggctcca tgctgtgcct gcggccaaca ctgtcaagtt tcgctgccca      540
gccgggggga acccaatgcc aaccatgcgg tggctgaaaa acgggaagga gtttaagcag      600
gagcatcgca ttggaggcta caaggtacga aaccagcact ggagcctcat tatggaaagt      660
gtggtcccat ctgacaaggg aaattatacc tgtgtggtgg agaatgaata cgggtccatc      720
aatcacacgt accacctgga tgttgtggag cgatcgcctc accggcccat cctccaagcc      780
ggactgccgg caaatgcctc cacagtggtc ggaggagacg tagagtttgt ctgcaaggtt      840
tacagtgatg cccagcccca catccagtgg atcaagcacg tggaaaagaa cggcagtaaa      900
tacgggcccg acgggctgcc ctacctcaag gttctcaagg ccgccggtgt taacaccacg      960
gacaaagaga ttgaggttct ctatattcgg aatgtaactt ttgaggacgc tggggaatat     1020
acgtgcttgg cgggtaattc tattgggata tcctttcact ctgcatggtt gacagttctg     1080
ccagcgcctg aagagaaaaa ggagattaca gcttccccag actacctgga gatagccatt     1140
tactgcatag gggtcttctt aatcgcctgt atggtggtaa cagtcatcct gtgccgaatg     1200
aagaacacga ccaagaagcc agacttcagc agccagccgg ctgtgcacaa gctgaccaaa     1260
cgtatccccc tgcggagaca ggtaacagtt tcggctgagt ccagctcctc catgaactcc     1320 aacacccgc tggtgaggat aacaacacgc ctctcttcaa cggcagacac ccccatgctg     1380 gcagggtct ccgagtatga acttccagag acccaaaat gggagtttcc aagagataag     1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
ccacccggga tggagtactc ctatgacatt aaccgtgttc ctgaggagca gatgaccttc     1800
aaggacttgg tgtcatgcac ctaccagctg gccagaggca tggagtactt ggcttcccaa     1860
aaatgtattc atcgagattt agcagccaga atgttttgg taacagaaaa caatgtgatg     1920
aaaatagcag actttggact cgccagagat atcaacaata tagactatta caaaagacc     1980 accaatgggc ggcttccagt caagtggatg gctccagaag ccctgtttga tagagtatac     2040
actcatcaga gtgatgtctg gtccttcggg gtgttaatgt gggagatctt cactttaggg     2100
ggctcgccct acccagggat tcccgtggag gaacttttta gctgctgaa ggaaggacac     2160 agaatggata gccagccaa ctgcaccaac gaactgtaca tgatgatgag ggactgttgg     2220
catgcagtgc cctcccagag accaacgttc aagcagttgg tagaagactt ggatcgaatt     2280
ctcactctca caaccaatga ggaatacttg gacctcagcc aacctctcga acagtattca     2340
cctagttacc ctgacacaag aagttcttgt tcttcaggag atgattctgt tttttctcca     2400
gaccccatgc cttacgaacc atgccttcct cagtatccac acataaacgg cagtgttaaa     2460
acatga                                                                2466
```

<210> SEQ ID NO 70
<211> LENGTH: 821
<212> TYPE: PRT
<213> ORGANISM: Homo sapiens

<400> SEQUENCE: 70

Met Val Ser Trp Gly Arg Phe Ile Cys Leu Val Val Val Thr Met Ala

-continued

```
1               5                  10                 15
Thr Leu Ser Leu Ala Arg Pro Ser Phe Ser Leu Val Glu Asp Thr Thr
                20                 25                 30

Leu Glu Pro Glu Glu Pro Pro Thr Lys Tyr Gln Ile Ser Gln Pro Glu
                35                 40                 45

Val Tyr Val Ala Ala Pro Gly Glu Ser Leu Glu Val Arg Cys Leu Leu
     50                 55                 60

Lys Asp Ala Ala Val Ile Ser Trp Thr Lys Asp Gly Val His Leu Gly
 65                 70                 75                 80

Pro Asn Asn Arg Thr Val Leu Ile Gly Glu Tyr Leu Gln Ile Lys Gly
                85                 90                 95

Ala Thr Pro Arg Asp Ser Gly Leu Tyr Ala Cys Thr Ala Ser Arg Thr
               100                105                110

Val Asp Ser Glu Thr Trp Tyr Phe Met Val Asn Val Thr Asp Ala Ile
               115                120                125

Ser Ser Gly Asp Asp Glu Asp Asp Thr Asp Gly Ala Glu Asp Phe Val
               130                135                140

Ser Glu Asn Ser Asn Asn Lys Arg Ala Pro Tyr Trp Thr Asn Thr Glu
145                150                155                160

Lys Met Glu Lys Arg Leu His Ala Val Pro Ala Ala Asn Thr Val Lys
               165                170                175

Phe Arg Cys Pro Ala Gly Gly Asn Pro Met Pro Thr Met Arg Trp Leu
               180                185                190

Lys Asn Gly Lys Glu Phe Lys Gln Glu His Arg Ile Gly Gly Tyr Lys
               195                200                205

Val Arg Asn Gln His Trp Ser Leu Ile Met Glu Ser Val Val Pro Ser
     210                215                220

Asp Lys Gly Asn Tyr Thr Cys Val Val Glu Asn Glu Tyr Gly Ser Ile
225                230                235                240

Asn His Thr Tyr His Leu Asp Val Val Glu Arg Ser Pro His Arg Pro
               245                250                255

Ile Leu Gln Ala Gly Leu Pro Ala Asn Ala Ser Thr Val Val Gly Gly
               260                265                270

Asp Val Glu Phe Val Cys Lys Val Tyr Ser Asp Ala Gln Pro His Ile
     275                280                285

Gln Trp Ile Lys His Val Glu Lys Asn Gly Ser Lys Tyr Gly Pro Asp
     290                295                300

Gly Leu Pro Tyr Leu Lys Val Leu Lys Ala Ala Gly Val Asn Thr Thr
305                310                315                320

Asp Lys Glu Ile Glu Val Leu Tyr Ile Arg Asn Val Thr Phe Glu Asp
               325                330                335

Ala Gly Glu Tyr Thr Cys Leu Ala Gly Asn Ser Ile Gly Ile Ser Phe
               340                345                350

His Ser Ala Trp Leu Thr Val Leu Pro Ala Pro Gly Arg Glu Lys Glu
               355                360                365

Ile Thr Ala Ser Pro Asp Tyr Leu Glu Ile Ala Ile Tyr Cys Ile Gly
     370                375                380

Val Phe Leu Ile Ala Cys Met Val Val Thr Val Ile Leu Cys Arg Met
385                390                395                400

Lys Asn Thr Thr Lys Lys Pro Asp Phe Ser Ser Gln Pro Ala Val His
               405                410                415

Lys Leu Thr Lys Arg Ile Pro Leu Arg Arg Gln Val Thr Val Ser Ala
               420                425                430
```

Glu Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 71
<211> LENGTH: 2124
<212> TYPE: DNA
<213> ORGANISM: Mus musculus

```
<400> SEQUENCE: 71
atggtcagct gggggcgctt catctgcctg gtcttggtca ccatggcaac cttgtccctg      60
gcccggccct ccttcagttt agttgaggat accactttag aaccagaagg agcaccgtac     120
tggaccaaca ccgagaagat ggagaagcgg ctccacgctg tccctgccgc caacactgtg     180
aagttccgct gtccggctgg ggggaatcca acgcccacaa tgaggtggtt aaaaaacggg     240
aaggagttta agcaggagca tcgcattgga ggctataagg tacgaaacca gcactggagc     300
cttattatgg aaagtgtggt cccgtcagac aaaggcaact acacctgcct ggtggagaat     360
gaatacgggt ccatcaacca cacctaccac ctcgatgtcg ttgaacggtc accacaccgg     420
cccatcctcc aagctggact gcctgcaaat gcctccacgg tggtcggagg ggatgtggag     480
tttgtctgca aggtttacag cgatgcccag ccccacatcc agtggatcaa gcacgtggaa     540
agaacggca gtaaatacgg gcctgatggg ctgccctacc tcaaggtcct gaagcactcg     600
gggataaata gctccaatgc agaagtgctg gctctgttca atgtgacgga gatggatgct     660
gggaatatat atgtaaggt ctccaattat atagggcagg ccaaccagtc tgcctggctc     720
actgtcctgc ccaaacagca gcgcctgtg agagagaagg agatcacggc ttccccagat     780
tatctggaga tagctatta ctgcataggg gtcttcttaa tcgcctgcat ggtggtgaca     840
gtcatcttt gccgaatgaa gaccacgacc aagaagccag acttcagcag ccagccagct     900
gtgcacaagc tgaccaagcg catccccctg cggagacagg taacagtttc ggccgagtcc     960
agctcctcca tgaactccaa caccccgctg gtgaggataa caacgcgtct gtcctcaaca    1020
gcggacaccc cgatgctagc agggtctcc gagtatgagt tgccagagga tccaaagtgg    1080
gaattcccca gagataagct gacgctgggc aaaccccgtgg gggaaggttg cttcgggcaa    1140
gtagtcatgg ctgaagcagt gggaatcgat aaagacaaac ccaaggaggc ggtcaccgtg    1200
gcagtgaaga tgttgaaga tgatgccaca gagaaggacc tgtctgatct ggtatcagag    1260
atggagatga tgaagatgat tgggaaacat aagaacatta tcaacctcct gggggcctgc    1320
acgcaggatg gacctctcta cgtcatagtt gaatatgcat cgaaaggcaa cctccgggaa    1380
tacctccgag cccggaggcc acctggcatg gagtactcct atgacattaa ccgtgtcccc    1440
gaggagcaga tgaccttcaa ggacttggtg tcctgcacct accagctggc tagaggcatg    1500
gagtacttgg cttcccaaaa atgtatccat cgagatttgg ctgccagaaa cgtgttggta    1560
acagaaaaca atgtgatgaa gatagcagac tttggcctgg ccaggatat caacaacata    1620
gactactata aaaagaccac aaatgggcga cttccagtca agtggatggc tcctgaagcc    1680
cttttgata gagtttacac tcatcagagc gatgtctggt ccttcggggt gttaatgtgg    1740
gagatcttta ctttaggggg ctcaccctac ccagggattc cgtggagga acttttaag    1800
ctgctcaaag agggacacag gatggacaag cccaccaact gcaccaatga actgtacatg    1860
atgatgaggg attgctggca tgctgtaccc tcacagagac ccacattcaa gcagttggtc    1920
gaagacttgg atcgaattct gactctcaca accaatgagg aatacttgga tctcacccag    1980
cctctcgaac agtattctcc tagttacccc gacacaagga gctcttgttc ttcagggac    2040
gattctgtgt tttctccaga ccccatgcct tatgaaccct gtctgcctca gtatccacac    2100
ataaacggca gtgttaaaac atga                                          2124

<210> SEQ ID NO 72
<211> LENGTH: 707
<212> TYPE: PRT
<213> ORGANISM: Mus musculus
```

<400> SEQUENCE: 72

```
Met Val Ser Trp Gly Arg Phe Ile Cys Leu Val Leu Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
50                  55                  60

Pro Ala Gly Gly Asn Pro Thr Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Leu Val Glu Asn Glu Tyr Gly Ser Ile Asn His Thr
        115                 120                 125

Tyr His Leu Asp Val Val Glu Arg Ser Pro His Arg Pro Ile Leu Gln
130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys His Ser Gly Ile Asn Ser Ser Asn Ala Glu
        195                 200                 205

Val Leu Ala Leu Phe Asn Val Thr Glu Met Asp Ala Gly Glu Tyr Ile
210                 215                 220

Cys Lys Val Ser Asn Tyr Ile Gly Gln Ala Asn Gln Ser Ala Trp Leu
225                 230                 235                 240

Thr Val Leu Pro Lys Gln Gln Ala Pro Val Arg Glu Lys Glu Ile Thr
                245                 250                 255

Ala Ser Pro Asp Tyr Leu Glu Ile Ala Ile Tyr Cys Ile Gly Val Phe
            260                 265                 270

Leu Ile Ala Cys Met Val Val Thr Val Ile Phe Cys Arg Met Lys Thr
        275                 280                 285

Thr Thr Lys Lys Pro Asp Phe Ser Ser Gln Pro Ala Val His Lys Leu
290                 295                 300

Thr Lys Arg Ile Pro Leu Arg Arg Gln Val Thr Val Ser Ala Glu Ser
305                 310                 315                 320

Ser Ser Ser Met Asn Ser Asn Thr Pro Leu Val Arg Ile Thr Thr Arg
                325                 330                 335

Leu Ser Ser Thr Ala Asp Thr Pro Met Leu Ala Gly Val Ser Glu Tyr
            340                 345                 350

Glu Leu Pro Glu Asp Pro Lys Trp Glu Phe Pro Arg Asp Lys Leu Thr
        355                 360                 365

Leu Gly Lys Pro Leu Gly Glu Gly Cys Phe Gly Gln Val Val Met Ala
370                 375                 380

Glu Ala Val Gly Ile Asp Lys Asp Lys Pro Lys Glu Ala Val Thr Val
385                 390                 395                 400

Ala Val Lys Met Leu Lys Asp Asp Ala Thr Glu Lys Asp Leu Ser Asp
                405                 410                 415
```

```
Leu Val Ser Glu Met Glu Met Met Lys Met Ile Gly Lys His Lys Asn
            420                 425                 430
Ile Ile Asn Leu Leu Gly Ala Cys Thr Gln Asp Gly Pro Leu Tyr Val
            435                 440                 445
Ile Val Glu Tyr Ala Ser Lys Gly Asn Leu Arg Glu Tyr Leu Arg Ala
            450                 455                 460
Arg Arg Pro Pro Gly Met Glu Tyr Ser Tyr Asp Ile Asn Arg Val Pro
465                 470                 475                 480
Glu Glu Gln Met Thr Phe Lys Asp Leu Val Ser Cys Thr Tyr Gln Leu
                485                 490                 495
Ala Arg Gly Met Glu Tyr Leu Ala Ser Gln Lys Cys Ile His Arg Asp
            500                 505                 510
Leu Ala Ala Arg Asn Val Leu Val Thr Glu Asn Asn Val Met Lys Ile
            515                 520                 525
Ala Asp Phe Gly Leu Ala Arg Asp Ile Asn Asn Ile Asp Tyr Tyr Lys
            530                 535                 540
Lys Thr Thr Asn Gly Arg Leu Pro Val Lys Trp Met Ala Pro Glu Ala
545                 550                 555                 560
Leu Phe Asp Arg Val Tyr Thr His Gln Ser Asp Val Trp Ser Phe Gly
                565                 570                 575
Val Leu Met Trp Glu Ile Phe Thr Leu Gly Gly Ser Pro Tyr Pro Gly
            580                 585                 590
Ile Pro Val Glu Glu Leu Phe Lys Leu Leu Lys Glu Gly His Arg Met
            595                 600                 605
Asp Lys Pro Thr Asn Cys Thr Asn Glu Leu Tyr Met Met Met Arg Asp
            610                 615                 620
Cys Trp His Ala Val Pro Ser Gln Arg Pro Thr Phe Lys Gln Leu Val
625                 630                 635                 640
Glu Asp Leu Asp Arg Ile Leu Thr Leu Thr Thr Asn Glu Glu Tyr Leu
                645                 650                 655
Asp Leu Thr Gln Pro Leu Glu Gln Tyr Ser Pro Ser Tyr Pro Asp Thr
            660                 665                 670
Arg Ser Ser Cys Ser Ser Gly Asp Asp Ser Val Phe Ser Pro Asp Pro
            675                 680                 685
Met Pro Tyr Glu Pro Cys Leu Pro Gln Tyr Pro His Ile Asn Gly Ser
            690                 695                 700
Val Lys Thr
705

<210> SEQ ID NO 73
<211> LENGTH: 1707
<212> TYPE: DNA
<213> ORGANISM: Homo sapiens

<400> SEQUENCE: 73
atgtggctcc gtgcctttat cctggccact ctctctgctt ccgcggcttg ggcagggcat      60
ccgtcctcgc cacctgtggt ggacaccgtg catggcaaag tgctggggaa gttcgtcagc     120
ttagaaggat ttgcacagcc tgtggccatt ttcctgggaa tccctttgc caagccgcct      180 cttggacccc tgaggtttac tccaccgcag cctgcagaac catggagctt gtgtgaagaat    240 gccacctcgt accctcctat gtgcacccaa gatcccaagg cggggcagtt actctcagag     300
ctatttacaa accgaaagga gaacattcct ctcaagcttt ctgaagactg tctttacctc     360
aatatttaca ctcctgctga cttgaccaag aaaaacaggc tgccggtgat ggtgtggatc     420
```

```
cacggagggg ggctgatggt gggtgcggca tcaacctatg atgggctggc ccttgctgcc    480
catgaaaacg tggtggtggt gaccattcaa tatcgcctgg gcatctgggg attcttcagc    540
acagggatg  aacacagccg ggggaactgg ggtcacctgg accaggtggc tgccctgcgc    600
tgggtccagg acaacattgc cagctttgga gggaacccag gctctgtgac catctttgga    660
gagtcagcgg gaggagaaag tgtctctgtt cttgttttgt ctccattggc caagaacctc    720
ttccaccggg ccatttctga gagtggcgtg gccctcactt ctgttctggt gaagaaaggt    780
gatgtcaagc ccttggctga gcaaattgct atcactgctg ggtgcaaaac caccacctct    840
gctgtcatgg ttcactgcct gcgacagaag acggaagagg agctcttgga gacgacattg    900
aaaatgaaat tcttatctct ggacttacag ggagacccca gagagagtca acccettctg    960
ggcactgtga ttgatgggat gctgctgctg aaaacacctg aagagcttca agctgaaagg   1020
aatttccaca ctgtccccta catggtcgga attaacaagc aggagtttgg ctggttgatt   1080
ccaatgcagt tgatgagcta tccactctcc gaagggcaac tggaccagaa acagccatg    1140
tcactcctgt ggaagtccta tccccttgtt tgcattgcta aggaactgat tccagaagcc   1200
actgagaaat acttaggagg aacagacgac actgtcaaaa agaaagacct gttcctggac   1260
ttgatagcag atgtgatgtt tggtgtccca tctgtgattg tggcccggaa ccacagagat   1320
gctggagcac ccacctacat gtatgagttt cagtaccgtc caagcttctc atcagacatg   1380
aaacccaaga cggtgatagg agaccacggg gatgagctct ctccgtcttt ggggcccca    1440
tttttaaaag agggtgcctc agaagaggag atcagactta gcaagatggt gatgaaattc   1500
tgggccaact tgctcgcaa tggaaacccc aatggggaag ggctgcccca ctggccagag    1560
tacaaccaga aggaagggta tctgcagatt ggtgccaaca cccaggcggc ccagaagctg   1620
aaggacaaag aagtagcttt ctggaccaac ctctttgcca gaaggcagt ggagaagcca    1680
ccccagacag aacacataga gctgtga                                       1707
```

<210> SEQ ID NO 74
<211> LENGTH: 568
<212> TYPE: PRT
<213> ORGANISM: Homo sapiens

<400> SEQUENCE: 74

```
Met Trp Leu Arg Ala Phe Ile Leu Ala Thr Leu Ser Ala Ser Ala Ala
 1               5                  10                  15

Trp Ala Gly His Pro Ser Ser Pro Val Val Asp Thr Val His Gly
            20                  25                  30

Lys Val Leu Gly Lys Phe Val Ser Leu Glu Gly Phe Ala Gln Pro Val
        35                  40                  45

Ala Ile Phe Leu Gly Ile Pro Phe Ala Lys Pro Leu Gly Pro Leu
    50                  55                  60

Arg Phe Thr Pro Pro Gln Pro Ala Glu Pro Trp Ser Phe Val Lys Asn
 65                  70                  75                  80

Ala Thr Ser Tyr Pro Pro Met Cys Thr Gln Asp Pro Lys Ala Gly Gln
                85                  90                  95

Leu Leu Ser Glu Leu Phe Thr Asn Arg Lys Glu Asn Ile Pro Leu Lys
            100                 105                 110

Leu Ser Glu Asp Cys Leu Tyr Leu Asn Ile Tyr Thr Pro Ala Asp Leu
        115                 120                 125

Thr Lys Lys Asn Arg Leu Pro Val Met Val Trp Ile His Gly Gly Gly
    130                 135                 140

Leu Met Val Gly Ala Ala Ser Thr Tyr Asp Gly Leu Ala Leu Ala Ala
```

```
                145                 150                 155                 160
His Glu Asn Val Val Val Thr Ile Gln Tyr Arg Leu Gly Ile Trp
                    165                 170                 175

Gly Phe Phe Ser Thr Gly Asp Glu His Ser Arg Gly Asn Trp Gly His
                180                 185                 190

Leu Asp Gln Val Ala Ala Leu Arg Trp Val Gln Asp Asn Ile Ala Ser
                195                 200                 205

Phe Gly Gly Asn Pro Gly Ser Val Thr Ile Phe Gly Glu Ser Ala Gly
            210                 215                 220

Gly Glu Ser Val Ser Val Leu Val Leu Ser Pro Leu Ala Lys Asn Leu
225                 230                 235                 240

Phe His Arg Ala Ile Ser Glu Ser Gly Val Ala Leu Thr Ser Val Leu
                245                 250                 255

Val Lys Lys Gly Asp Val Lys Pro Leu Ala Glu Gln Ile Ala Ile Thr
                260                 265                 270

Ala Gly Cys Lys Thr Thr Thr Ser Ala Val Met Val His Cys Leu Arg
            275                 280                 285

Gln Lys Thr Glu Glu Glu Leu Leu Glu Thr Thr Leu Lys Met Lys Phe
        290                 295                 300

Leu Ser Leu Asp Leu Gln Gly Asp Pro Arg Glu Ser Gln Pro Leu Leu
305                 310                 315                 320

Gly Thr Val Ile Asp Gly Met Leu Leu Leu Lys Thr Pro Glu Glu Leu
                325                 330                 335

Gln Ala Glu Arg Asn Phe His Thr Val Pro Tyr Met Val Gly Ile Asn
                340                 345                 350

Lys Gln Glu Phe Gly Trp Leu Ile Pro Met Gln Leu Met Ser Tyr Pro
            355                 360                 365

Leu Ser Glu Gly Gln Leu Asp Gln Lys Thr Ala Met Ser Leu Leu Trp
        370                 375                 380

Lys Ser Tyr Pro Leu Val Cys Ile Ala Lys Glu Leu Ile Pro Glu Ala
385                 390                 395                 400

Thr Glu Lys Tyr Leu Gly Gly Thr Asp Asp Thr Val Lys Lys Lys Asp
                405                 410                 415

Leu Phe Leu Asp Leu Ile Ala Asp Val Met Phe Gly Val Pro Ser Val
                420                 425                 430

Ile Val Ala Arg Asn His Arg Asp Ala Gly Ala Pro Thr Tyr Met Tyr
            435                 440                 445

Glu Phe Gln Tyr Arg Pro Ser Phe Ser Ser Asp Met Lys Pro Lys Thr
        450                 455                 460

Val Ile Gly Asp His Gly Asp Glu Leu Phe Ser Val Phe Gly Ala Pro
465                 470                 475                 480

Phe Leu Lys Glu Gly Ala Ser Glu Glu Glu Ile Arg Leu Ser Lys Met
                485                 490                 495

Val Met Lys Phe Trp Ala Asn Phe Ala Arg Asn Gly Asn Pro Asn Gly
            500                 505                 510

Glu Gly Leu Pro His Trp Pro Glu Tyr Asn Gln Lys Glu Gly Tyr Leu
        515                 520                 525

Gln Ile Gly Ala Asn Thr Gln Ala Ala Gln Lys Leu Lys Asp Lys Glu
    530                 535                 540

Val Ala Phe Trp Thr Asn Leu Phe Ala Lys Lys Ala Val Glu Lys Pro
545                 550                 555                 560

Pro Gln Thr Glu His Ile Glu Leu
                565
```

<210> SEQ ID NO 75
<211> LENGTH: 1698
<212> TYPE: DNA
<213> ORGANISM: Mus musculus

<400> SEQUENCE: 75

```
atgtggctct gtgctttgag tctgatctct ctcactgctt gcttgagtct gggacaccca      60
tccttaccgc ctgtggtaca caccgttcat ggcaaagtcc tggggaagta tgtcaccta     120
gaaggattct cacagcctgt ggccgtcttc ctgggagtcc cctttgccaa gcccctctt     180
ggatctctga ggtttgctcc accagagcct gcagagccct ggagcttcgt gaagcacacc    240
acttcctacc ctcctttgtg ctaccaaaac ccagaggcag cattgaggct cgctgagcgc    300
ttcaccaacc aaaggaagat cattccccac aaattttctg aggactgtct ctacctcaac    360
atttatactc ctgctgactt aacacagaac agcaggttgc ccgtgatggt gtggatacat    420
ggaggtggac ttgtgataga tggagcatca acctatgatg gagtgcccct ggctgtccat    480
gaaaatgtgg ttgtagtggt cattcagtat cgcctgggca tctggggatt cttcagcaca    540
gaggatgaac acagccgggg gaactggggt cacttggacc aggtggctgc actacattgg    600
gtccaagaca acattgccaa cttttggggc aacccaggat ctgtgactat cttcggcgag    660
tcagcaggag gtgaaagtgt ctctgttctt gtgttaagcc cactggccaa gaacctcttc    720
cacagggcca tcgctcagag tagtgtcatt ttcaatcctt gccttttttgg gagagctgcc    780
agacccttgg ctaagaaaat tgctgctctt gctggctgta aaaccaccac ctccgctgcc    840
atggttcact gcctgcgcca aagactgaa gatgagctct ggaggtctc actgaaaatg     900
aaatttggga ctgttgattt tcttggagac cccagagaga gctatccctt cctcctact     960
gtgattgatg gagtgttgct gccaaaggca ccagaagaga ttctggctga aagagtttc    1020
aacactgtcc cctacatggt gggcatcaac aagcatgagt ttggctggat cattccaatg    1080
tttttggact tcccactctc tgaaagaaaa ctggaacaga agacagctgc atccatcctg    1140
tggcaggcct acccaattct taacatctct gaaaagctga ttccagcagc tattgaaaag    1200
tatttaggag ggacagaaga ccctgccaca atgacagacc tgttcctgga cttgattgga    1260
gacattatgt tcggtgtccc atctgtaatc gtgtcccgta gtcacagaga tgctggagcc    1320
ccaacctaca tgtatgaata tcagtatcgc ccaagttttg tatcagacga tagaccccag    1380
gaattgttag agaccacgc tgatgaactc ttttctgtat ggggagcccc gttttttaaaa    1440
gagggtgctt cagaagaaga gatcaacctc agcaacatgg tgatgaaatt ctgggccaac    1500
tttgctcgga atgggaaccc taatggtgaa gggctgcctc attggccaga atatgaccag    1560
aaggaaggat accttcagat tggagtccca gcacaggcag cccataggct gaaagacaag    1620
gaagtggact tttggactga gctcagagcc aaggaaacag cagagaggtc atcccatagg    1680
gaacatgttg aactgtga                                                  1698
```

<210> SEQ ID NO 76
<211> LENGTH: 565
<212> TYPE: PRT
<213> ORGANISM: Mus musculus

<400> SEQUENCE: 76

```
Met Trp Leu Cys Ala Leu Ser Leu Ile Ser Leu Thr Ala Cys Leu Ser
1               5                   10                  15

Leu Gly His Pro Ser Leu Pro Pro Val Val His Thr Val His Gly Lys
            20                  25                  30
```

```
Val Leu Gly Lys Tyr Val Thr Leu Glu Gly Phe Ser Gln Pro Val Ala
         35                  40                  45

Val Phe Leu Gly Val Pro Phe Ala Lys Pro Pro Leu Gly Ser Leu Arg
 50                  55                  60

Phe Ala Pro Pro Glu Pro Ala Glu Pro Trp Ser Phe Val Lys His Thr
 65                  70                  75                  80

Thr Ser Tyr Pro Pro Leu Cys Tyr Gln Asn Pro Glu Ala Ala Leu Arg
                 85                  90                  95

Leu Ala Glu Arg Phe Thr Asn Gln Arg Lys Ile Ile Pro His Lys Phe
                100                 105                 110

Ser Glu Asp Cys Leu Tyr Leu Asn Ile Tyr Thr Pro Ala Asp Leu Thr
            115                 120                 125

Gln Asn Ser Arg Leu Pro Val Met Val Trp Ile His Gly Gly Gly Leu
130                 135                 140

Val Ile Asp Gly Ala Ser Thr Tyr Asp Gly Val Pro Leu Ala Val His
145                 150                 155                 160

Glu Asn Val Val Val Val Ile Gln Tyr Arg Leu Gly Ile Trp Gly
                165                 170                 175

Phe Phe Ser Thr Glu Asp Glu His Ser Arg Gly Asn Trp Gly His Leu
                180                 185                 190

Asp Gln Val Ala Ala Leu His Trp Val Gln Asp Asn Ile Ala Asn Phe
                195                 200                 205

Gly Gly Asn Pro Gly Ser Val Thr Ile Phe Gly Glu Ser Ala Gly Gly
210                 215                 220

Glu Ser Val Ser Val Leu Val Leu Ser Pro Leu Ala Lys Asn Leu Phe
225                 230                 235                 240

His Arg Ala Ile Ala Gln Ser Ser Val Ile Phe Asn Pro Cys Leu Phe
                245                 250                 255

Gly Arg Ala Ala Arg Pro Leu Ala Lys Lys Ile Ala Ala Leu Ala Gly
                260                 265                 270

Cys Lys Thr Thr Thr Ser Ala Ala Met Val His Cys Leu Arg Gln Lys
            275                 280                 285

Thr Glu Asp Glu Leu Leu Glu Val Ser Leu Lys Met Lys Phe Gly Thr
            290                 295                 300

Val Asp Phe Leu Gly Asp Pro Arg Glu Ser Tyr Pro Phe Leu Pro Thr
305                 310                 315                 320

Val Ile Asp Gly Val Leu Leu Pro Lys Ala Pro Glu Glu Ile Leu Ala
                325                 330                 335

Glu Lys Ser Phe Asn Thr Val Pro Tyr Met Val Gly Ile Asn Lys His
                340                 345                 350

Glu Phe Gly Trp Ile Ile Pro Met Phe Leu Asp Phe Pro Leu Ser Glu
            355                 360                 365

Arg Lys Leu Glu Gln Lys Thr Ala Ala Ser Ile Leu Trp Gln Ala Tyr
370                 375                 380

Pro Ile Leu Asn Ile Ser Glu Lys Leu Ile Pro Ala Ala Ile Glu Lys
385                 390                 395                 400

Tyr Leu Gly Gly Thr Glu Asp Pro Ala Thr Met Thr Asp Leu Phe Leu
                405                 410                 415

Asp Leu Ile Gly Asp Ile Met Phe Gly Val Pro Ser Val Ile Val Ser
                420                 425                 430

Arg Ser His Arg Asp Ala Gly Ala Pro Thr Tyr Met Tyr Glu Tyr Gln
            435                 440                 445

Tyr Arg Pro Ser Phe Val Ser Asp Asp Arg Pro Gln Glu Leu Leu Gly
450                 455                 460
```

-continued

```
Asp His Ala Asp Glu Leu Phe Ser Val Trp Gly Ala Pro Phe Leu Lys
465                 470                 475                 480

Glu Gly Ala Ser Glu Glu Ile Asn Leu Ser Asn Met Val Met Lys
                485                 490                 495

Phe Trp Ala Asn Phe Ala Arg Asn Gly Asn Pro Asn Gly Glu Gly Leu
                500                 505                 510

Pro His Trp Pro Glu Tyr Asp Gln Lys Glu Gly Tyr Leu Gln Ile Gly
            515                 520                 525

Val Pro Ala Gln Ala Ala His Arg Leu Lys Asp Lys Glu Val Asp Phe
        530                 535                 540

Trp Thr Glu Leu Arg Ala Lys Glu Thr Ala Glu Arg Ser Ser His Arg
545                 550                 555                 560

Glu His Val Glu Leu
                565
```